United States Patent
Shemesh et al.

(10) Patent No.: US 12,351,615 B2
(45) Date of Patent: Jul. 8, 2025

(54) CELL BODY TARGETED SENSORS

(71) Applicant: Massachusetts Institute of Technology, Cambridge, MA (US)

(72) Inventors: Or A. Shemesh, Cambridge, MA (US); Changyang Linghu, Cambridge, MA (US); Kiryl D. Piatkevich, Cambridge, MA (US); Edward S. Boyden, Cambridge, MA (US); Won Min Park, Cambridge, MA (US)

(73) Assignee: Massachuetts Institute of Technology, Cambridge, MA (US)

( * ) Notice: Subject to any disclaimer, the term of this patent is extended or adjusted under 35 U.S.C. 154(b) by 940 days.

(21) Appl. No.: 17/312,445

(22) PCT Filed: Dec. 11, 2019

(86) PCT No.: PCT/US2019/065773
§ 371 (c)(1),
(2) Date: Jun. 10, 2021

(87) PCT Pub. No.: WO2020/123688
PCT Pub. Date: Jun. 18, 2020

(65) Prior Publication Data
US 2022/0048970 A1 Feb. 17, 2022

Related U.S. Application Data

(60) Provisional application No. 62/778,004, filed on Dec. 11, 2018.

(51) Int. Cl.
| | |
|---|---|
| C07K 14/705 | (2006.01) |
| A61B 5/00 | (2006.01) |
| C12N 13/00 | (2006.01) |
| G01N 33/50 | (2006.01) |
| A61B 1/04 | (2006.01) |

(52) U.S. Cl.
CPC ............ *C07K 14/705* (2013.01); *C12N 13/00* (2013.01); *G01N 33/5091* (2013.01); *A61B 1/043* (2013.01); *A61B 5/0071* (2013.01); *G01N 2500/10* (2013.01)

(58) Field of Classification Search
CPC .............. C07K 14/705; C07K 2319/50; C07K 14/4702; C07K 2319/60; C07K 14/4728; C12N 13/00; G01N 33/5091; G01N 2500/10; G01N 33/5058; A61B 1/043; A61B 5/0071
See application file for complete search history.

(56) References Cited

FOREIGN PATENT DOCUMENTS

WO 2017/210664 A1 12/2017

OTHER PUBLICATIONS

Zhang and Bennett J. Cell Biology, 1998, 142, 1571-1581 (Year: 1998).*
Moll et al Protein Science, 2001, 10, 649-655 (Year: 2001).*
Jun et al. J. Neurochem., 2016, 139, 1102-1112 (Year: 2016).*
Mukamel, E.A. et al., "Automated analysis of cellular signals from large-scale calcium imaging data." Neuron 63, 747-760 (2009).
Nguyen, J.P. et al., "Whole-brain calcium imaging ,vith cellular resolution in freely behaving Caenorhabditis elegans." Proc. Natl. Acad. Sci. 113, E1074-E1081 (2016).
Oakley, M.G. et al., "A buried polar interaction can direct the relative orientation of helices in a coiled coil." Biochemistry 37, 12603-12610 (1998).
Patel, T.P. et al., "Automated quantification of neuronal networks and single-cell calcium dynamics using calcium maging." J. Neurosci. Methods 243, 26-38 (2015).
Pedelacq, J.-D. et al., "Engineering and characterization of a superfolder green fluorescent protein." Nat. Biotechnol. 24, 79-88 (2006).
Pegard, N.C. et al. "Three-dimensional scanless holographic optogenetics with temporal focusing (3D-Shot)." Nat. Commun. 8, 1228 (2017).
Peron, S.P. et al., "A Cellular Resolution Map of Barrel Cortex Activity during Tactile Behavior." Neuron 86, 783-799 (2015).
Pinto, L. et al., "Cell-Type-Specific Activity in Prefrontal Cortex during GoalA-Directed Behavior." Neuron 87, 437-450 (2015).
Pneumatikakis, E.A, et al., "A structured matrix factorization framework for large scale calcium imaging data analysis." arXiv:1409.2903v1 [q-bio.NC] Sep. 9, 2014.
Pneumatikakis, E.A. et al., "Simultaneous Denoising, Deconvolution, and Demixing of Calcium Imaging Data." Neuron 89, 285-299 (2016).
Pneumatikakis, E.A., et al., "NoRMCorre: An online algorithm for piecewise rigid motion correction of calcium imaging data." Journal of Neuroscience Methods 291 (2017) 83-94.
Raichle, M.E. "Behind the scenes of functional brain imaging: a historical and physiological perspective." Proc. Natl. Acad. Sci. U. S. A 95, 765-772 (1998).
Ramirez, O.A. et al., "Location matters: the endoplasmic reticulum and protein trafficking in dendrites." Biol. Res. 44, 17-23 (2011).
Resendez, S.L. et al., "Visualization of cortical, subcortical and deep brain neural circuit dynamics during naturalistic mammalian behavior \vith head-mounted microscopes and chronically implanted lenses." Nat Protoc. 11, 566-597 (2016).
Romano, S.A. et al., "An integrated calcium imaging processing toolbox for the analysis of neuronal population dynamics." PLoS Comput Biol. 13, el005526 (2017).
Ruffinatti, F.A. et al., "Spatial Wavelet Analysis of Calcium Oscillations in Developing Neurons." PLoS One 8, e75986 (2013).
Schafer, M.K.E. et al., "LI syndrome mutations impair neuronal LI function at different levels by divergent mechanisms. Neurobiol. Dis." 40, 222-20 237 (2010).
Schrodel, T.et al., Brain-wide 3D imaging of neuronal activity in Caenorhabditis elegans with sculpted light Nat Methods 10, 1013-1020 (2013).
Sekiguchi, K.J. et al., "Imaging large-scale cellular activity in spinal cord of freely behaving mice." Nat. Commun. 7, 11450 (2016).

(Continued)

*Primary Examiner* — Olga N Chernyshev
(74) *Attorney, Agent, or Firm* — Pierce Atwood LLP

(57) ABSTRACT

The invention, in some aspects, relates to polypeptide molecules and their encoding nucleic acid molecules and use of such molecules to direct and localize sensor molecules in the soma of cells in which they are expressed. Compositions of the invention may be delivered to cells and subjects and used in methods to determine activity in cells in which they are expressed.

8 Claims, 58 Drawing Sheets

Specification includes a Sequence Listing.

(56) References Cited

OTHER PUBLICATIONS

Selgrade, D.F. et al., "Protein scaffold activated protein trans-splicing in mammalian cells." J. Am. Chem. Soc. 135, 7713-7719 (2013).

Shekhawat et al., "An Autoinhibited Coiled-Coil Design Strategy for Split-Protein Protease Sensors." J Am Chem Soc. Oct. 28, 2009; 131(42): 15284-15290.

Shemesh et al."Precision Calcium Imaging of Dense Neural Populations via a Cell Body-Targeted Calcium Indicator." bioRxiv preprint, Sep. 17, 2017; pp. 1-85.

Shemesh, O.A. et al., "Temporally precise single-cell-resolution optogenetics." Nat Neurosci. 20, 1796-1806 (2017).

Shen, S.P. et al., Automatic Cell Segmentation by Adaptive Thresholding (ACSAT) for large scale calcium imaging datasets. bioRxiv 260075 (2018).

Siciliano, C.A. etal., Leveraging calcium imaging to illuminate circuit dysfunction in addiction. Alcohol 74, 47-63 (2019).

Streit, A.K. et al., "Calcium Imaging of Neuronal Activity in Drosophila Can Identify Anticonvulsive Compounds." PLoS One 11, e0148461 (2016).

Sun, C. et al., "Distinct speed dependence of entorhinal island and ocean cells, including respective grid cells." Proc. Natl. Acad. Sci. 112, 9466-9471 (2015).

Tang, Shen et al., "Fast Kinetics of Calcium Signaling and Sensor Design." Curr Opin Chem Biol. 2015, Aug. 27:90-97.

Tian, C. et al., "Molecular identity of axonal sodium channels in human cortical pyramidal cells." Front. Cell. Neurosci. 3, 297 (2014).

Valluru, L. et al., "Ligand binding is a critical requirement for plasma membrane expression of heteromeric kainate receptors." J. Biol. Chem 280, 6085-6093 (2005).

Vander Weele, C.M. et al., "Dopamine enhances signal-to-noise ratio in cortical-brainstem encoding of aversive stimuli." Nature 563, 397-401 (2018).

Vladimirov, N. et al., "Light-sheet functional imaging in fictively behaving zebrafish." Nat. Methods 11, 883-884 (2014).

Wu, C. et al., "rAAV-mediated subcellular targeting of optogenetic tools in retinal ganglion cells in vivo." PLoS One 8, e66332 (2013).

Xia, L., et al., "Dorsal-CA1 Hippocampal Neuronal Ensembles Encode Nicotine-Reward Contextual Associations." Cell Rep. 19, 2143-2156 (2017).

Yamada, Yoshiyuki et al., "Quantitative comparison of novel GCaMP-type genetically encoded Ca2+ indicators in mammalian neurons." Frontiers in Cellular Neuroscience, Oct. 2012, vol. 6, Article 41(1).

Yu, Y. et al., "P/Q and N channels control baseline and spike-triggered calcium levels in neocortical axons and synaptic boutons." J. Neurosci. 30, 11858-11869 (2010).

Zhang, X. et al., "Restriction of 480/270-kD ankyrin G to axon proximal segments requires multiple ankyrin G-specific domains." J. Cell Biol. 142, 1571-1581 (1998).

Zhou, P. et al., "Efficient and accurate extraction of in vivo calcium signals from microendoscopic video data." eLife 2018;7:e28728, p. 1-37 (2016).

Ziv, Y. et al., "Long-term dynamics of CA1 hippocampal place codes." Nat. Neurosci. 16, 264-266 (2013).

Ahrens, M.B., et al., "Whole brain functional imaging at cellular resolution using light-sheet microscopy." Nat. Methods 10, 413-420 (2013).

Alivisatos, AP. Et al., "Nanotools for Neuroscience and Brain Activity Mapping." ACS Nano 7, 1850-1866 (2013).

Alonso, J.-M., and Martinez, L.M. (1998). Functional connectivity between simple cells and complex cells in cat striate cortex. Nat. Neurosci. 1, 395-403.

Andilla, F.D. et al., "Sparse Space-Time Deconvolution for Calcium Image Analysis." 64-72 (2014).

Baker, C.A. et al., "Cellular resolution circuit mapping with temporal-focused excitation of soma-targeted channelrhodopsin." Elife 5, p. 1-15 (2016).

Barbera, G., et al., "Spatially Compact Neural Clusters in the Dorsal Striatum Encode Locomotion Relevant Information." Neuron 92, 202-213(2016).

Bengtson, C.P. et al., "Nuclear Calcium Sensors Reveal that Repetition of Trains of Synaptic Stimuli Boosts Nuclear Calcium Signaling in CAI Pyramidal Neurons." Biophys. J. 99, 4066-4077 (2010).

Berdyyeva, T. et al., "Zolpidem Reduces Hippocampal Neuronal Activity in Freely Behaving Mice: A Large Scale Calcium Imaging Study \with Miniaturized Fluorescence Microscope." PLoS One 9, el 12068, p. 1-13 (2014).

Berdyyeva, T.K. et al., "Direct Imaging of Hippocampal Epileptiform Calcium Motifs Following Kainic Acid Administration in Freely Behaving Mice." Front. Neurosci. 10, 53, p. 1-10 (2016).

Bowden, S.E.H. et al., "Somatic Colocalization of Rat SKI and D class (Cav 1.2) L-type Calcium Channels in Rat CAI Hippocampal Pyramidal Neurons." J. Neurosci. 21, p. 1-6 (2001).

Cai, D.J. et al., "A shared neural ensemble links distinct contextual memories encoded close in time." Nature 534, 115-118 (2016).

Chen, T.-W. et al., "Ultrasensitive fluorescent proteins for imaging neuronal activity." Nature 499, 295-300 (2013).

Dana, H. et al., "High-performance calcium sensors for imaging activity in neuronal populations and microcompartments." Nat. Methods 16, 649-657 (2019).

Dana, H. et al., "Sensitive red protein calcium indicators for imaging neural activity." eLife 2016; 5:e 12727.

Deneux, T. et al., "Accurate spike estimation from noisy calcium signals for ultrafast three-dimensional imaging oflarge neuronal populations in vivo." Nat. Commun. 7, 12190, p. 1-17 (2016).

Dombeck, Daniel A., et al. "Imaging Large-Scale Neural Activity with Cellular Resolution in Awake, Mobile Mice." Neuron. 56(1):43-57 (2007).

Dunn T.W. et al., "Brain-wide mapping of neural activity controlling zebrafish exploratory locomotion." Elife 5, e12741, 6.1-29 (2016).

Fletcher, S. etal., "False interaction of syntaxin IA with a Ca2+-activated K + channel revealed by co-Immunoprecipitation and pull-down assays: implications for identification of protein-protein interactions." Neuropharmacology 44, 817-827 (2003).

Flusberg, B.A. et al., "High-speed, miniaturized fluorescence microscopy in freely moving mice." Nat. Methods 5, 935-938 (2008).

Forli, A. et al. "Two-Photon Bidirectional Control and Imaging of Neuronal Excitability with High Spatial Resolution In Vivo." Cell Rep. 22, 3087-3098 (2018).

Freeman, J. et al. "Mapping brain activity at scale with cluster computing." Nat. Methods 11, 941-950 (2014).

Garrido, J.J. et al. A targeting motif involved in sodium channel clustering at the axonal initial segment.: Science 300, 2091-2094 (2003).

Garrido, J.J. et al., "Identification of an axonal determinant in the C-terminus of the sodium channel Na(v)I.2." EMBO J. 20, 5950-5961 (2001).

Greenberg, K.P. et al., "Differential targeting of optical neuromodulators to ganglion cell soma and dendrites allows dynamic control of center-surround antagonism." Neuron 69, 713-720 (2011).

Greschner, M. et al., "Correlated firing among major ganglion cell types in primate retina." J. Physiol. 589, 75-86 (2011).

Grewe, B.F. et al., "Neural ensemble dynamics underlying a long-term associative memory." Nature 543, 670-675 (2017).

Grienberger, C. et al., "Imaging Calcium in Neurons." Neuron 73, 862-885 (2012).

Grubb, M.S. et al., "Channelrhodopsin-2 Localised to the Axon Initial Segment." PLoS One 5, e13761 (2010).

Harris, K.D. et al., "Improving data quality in neuronal population recordings." Nat. Neurosci. 19, 1165-1174 (2016).

Helmchen, F. et al., "Deep tissue two-photon microscopy." Nat. Methods 2, 932-940 (2005).

Hofherr, A. et al., Selective Golgi export of Kir2. I controls the stoichiometry of functional Kir2.x channel heteromers. J. Cell Sci. 118, 1935-1943(2005).

Horikawa, Kazuki et al. "Recent progress in the development of genetically encoded Ca2+ indicators." The Journal of Medical Investigation, vol. 62, 2015.

(56) References Cited

OTHER PUBLICATIONS

International Search Report and Written Opinon of the International Searching Authority from corresponding International Patent Application No. PCT/US2019/065773 filed on Dec. 11, 2019.
Jennings, J.H. et al., "Visualizing Hypothalamic Network Dynamics for Appetitive and Consummatory Behaviors." Cell 160, 516-527 (2015).
Jensen, C.S. et al., "Trafficking of Kv2.1 Channels to the Axon Initial Segment by a Novel Nonconventional Secretory Pathway." J. Neurosci. 37, 11523-11536 (2017).
Jiang, M. et al., "High Ca2+-phosphate transfection efficiency in low-density neuronal cultures." Nat. Protoc. 1, 695-700 (2006).
Keller, P.J. et al., "Light-sheet imaging for systems neuroscience." Nat. Methods 12, 27-29 (2015).
Kim, C.K. et al., "Prolonged, brain-wide expression of nuclear-localized GCaMP3 for functional circuit mapping." Front. Neural Circuits 8, 138, p. 1-12 (2014).
Kim, T.H. et al., "Long-Term Optical Access to an Estimated One Million Neurons in the Live Mouse Cortex." Cell Rep. 17, 3385-3394 (2016).
Kitamura, T. et al., "Entorhinal Cortical Ocean Cells Encode Specific Contexts and Drive Context-Specific Fear Memory." Neuron 87, 1317-1331 (2015).
Klapoetke, N.C. et al., "Independent optical excitation of distinct neural populations." Nat. Methods 11, 338-346 (2014).
Klaus et al., "The Spatiotemporal Organization of the Striatum Encodes Action Space." Neuron 95, p. 1171-1180 (2017).
Kosugi, S. et al., "Six classes of nuclear localization signals specific to different binding grooves of importin alpha." J. Biol. Chem. 284, 478-485(2009).
Kumar, J., Schuck, P., and Mayer, M.L. Structure and assembly mechanism for heteromeric kainate receptors. Neuron 71, 319-331. (2011).
Lim, S.T. et al., "A Novel Targeting Signal for Proximal Clustering of the Kv2. I K + Channel in Hippocampal Neurons." Neuron 25, 385-397 (2000).
Ma, D., Zerangue, N., Lin, Y.F., Collins, A, Yu, M., Jan, Y.N., and Jan, L.Y. (2001). Role of ER export signals in controlling surface potassium channel numbers. Science 291, 316-319.
Mahn et al., "High-Efficiency Optogenetic Silencing With Soma-targeted Anion-Conducting Channel Rhodopsins." Nature Communications, Oct. 8, 2018; 9:4125, pp. 1-15; abstract.
Mohammed, A.I. et al., "An integrative approach for analyzing hundreds of neurons in task performing mice using wide-field calcium imaging." Sci. Rep. 6, 20986 (2016).
Moll et al., "Designed heterodimerizing leucine zippers with a ranger of pls and stabilities up to 10-15 M." Protein Sci. 10, 649-655 (2001).
Moruno Manchon, J.F. et al., "Cytoplasmic sphingosine-1-phosphate pathway modulates neuronal autophagy." Sci. Rep. 5, 15213 (2015).

* cited by examiner

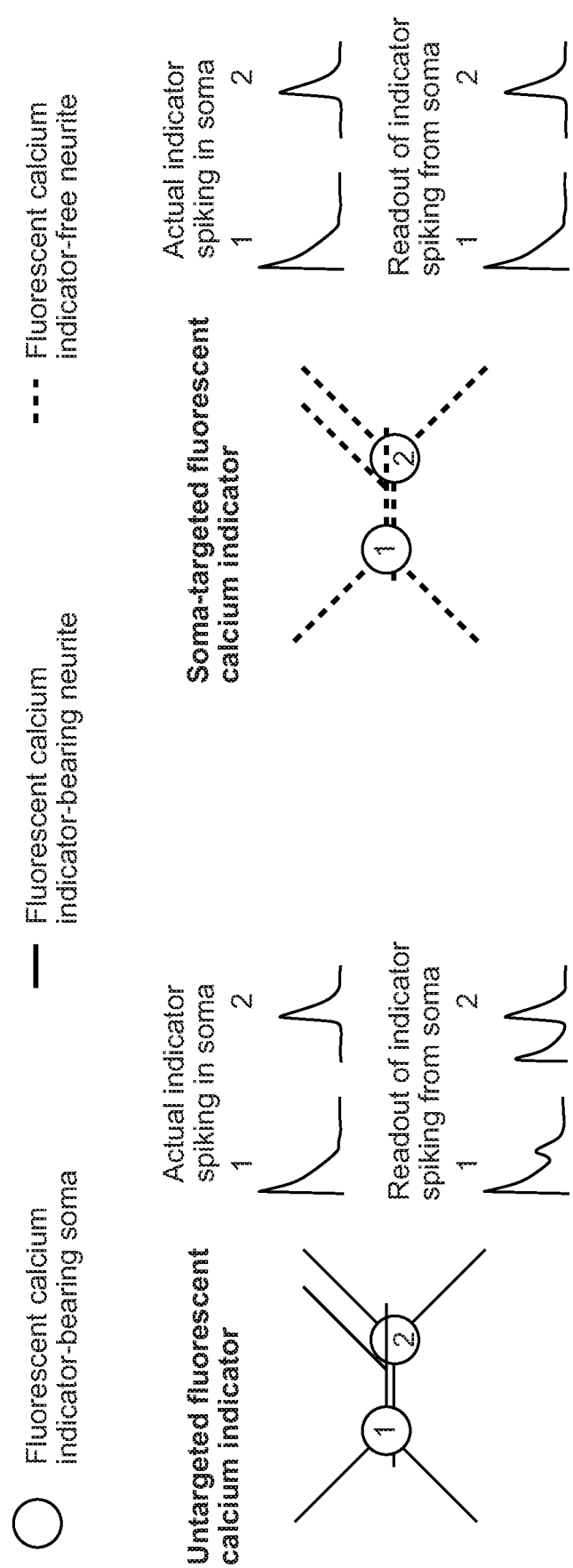

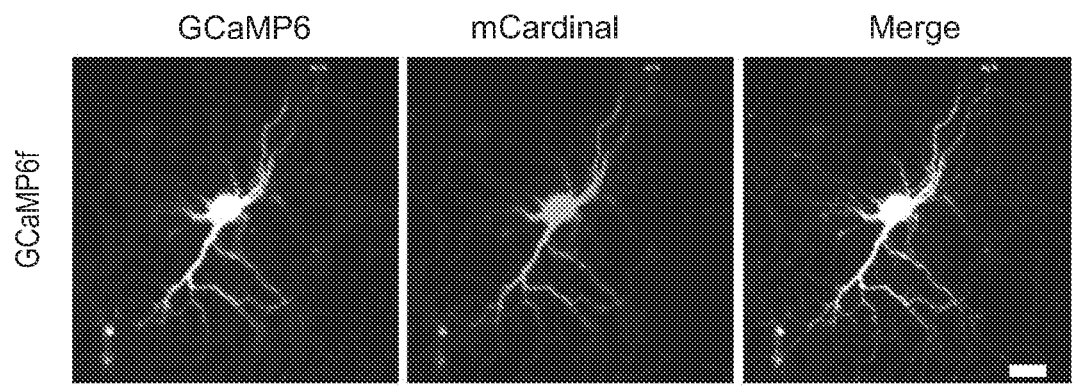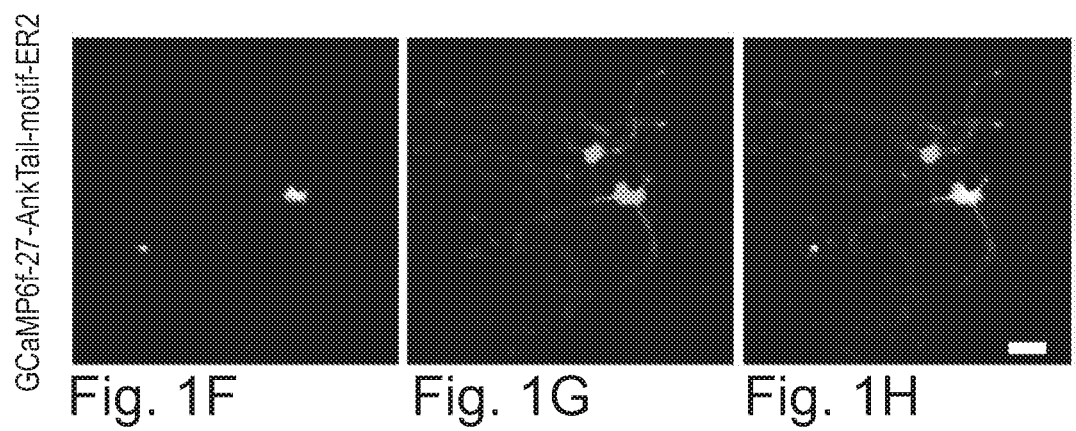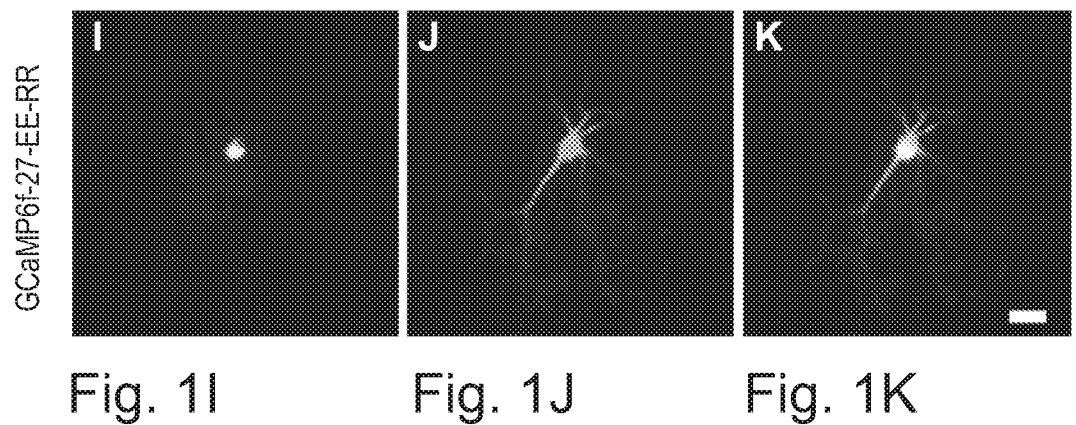

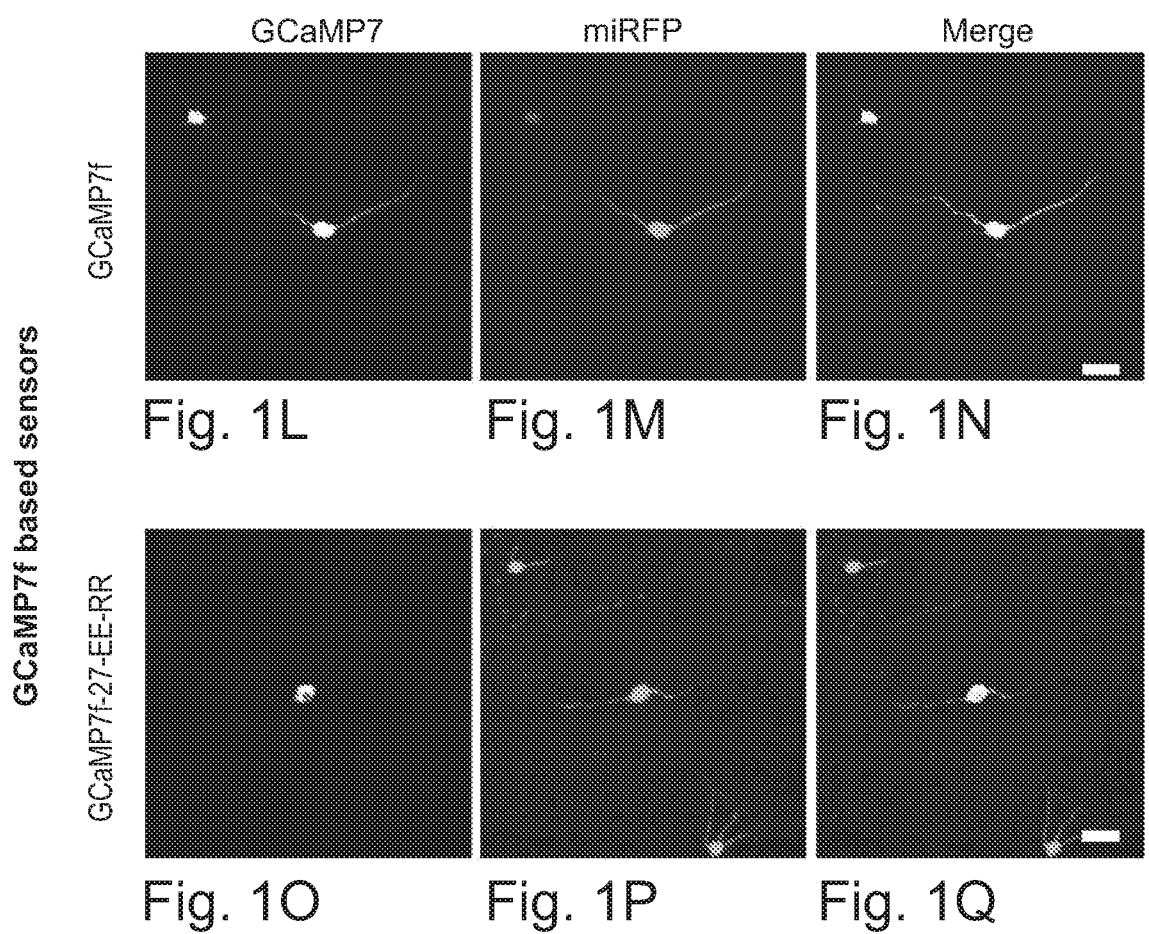

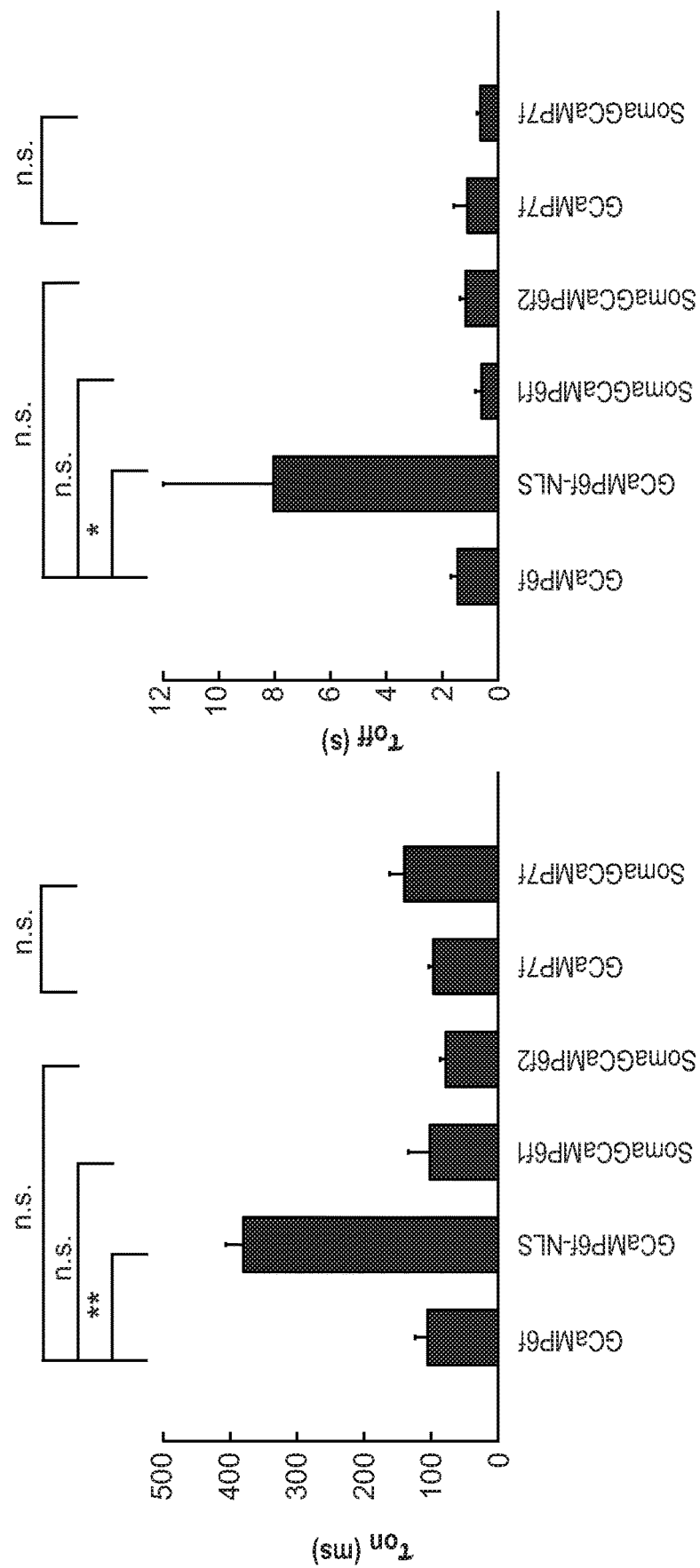

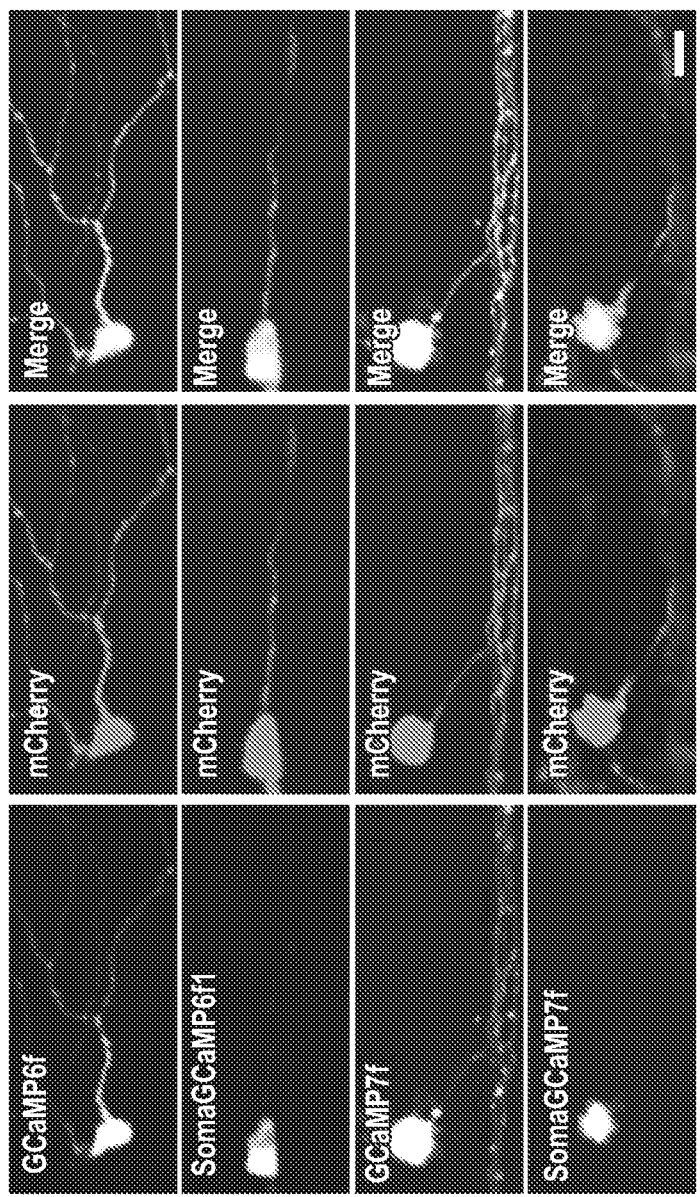
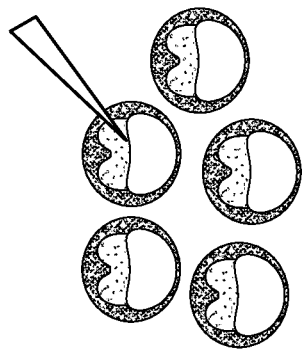
Fig. 4A
Fig. 4B

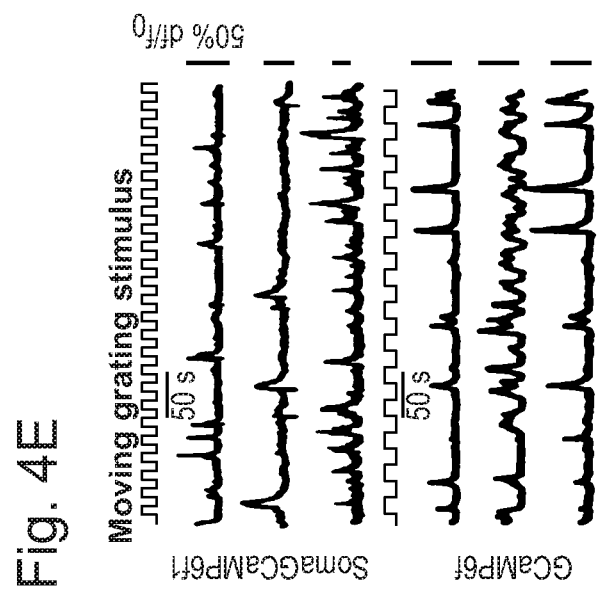
Fig. 4D Two-photon microscope
Fig. 4E
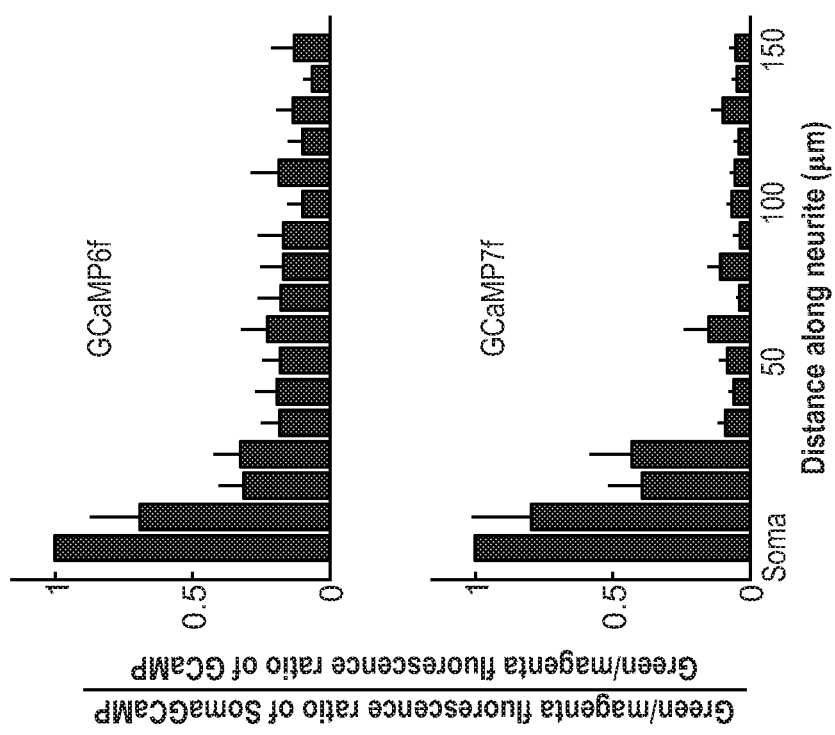
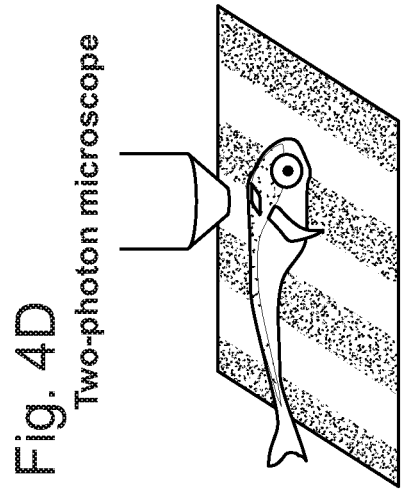
Fig. 4C

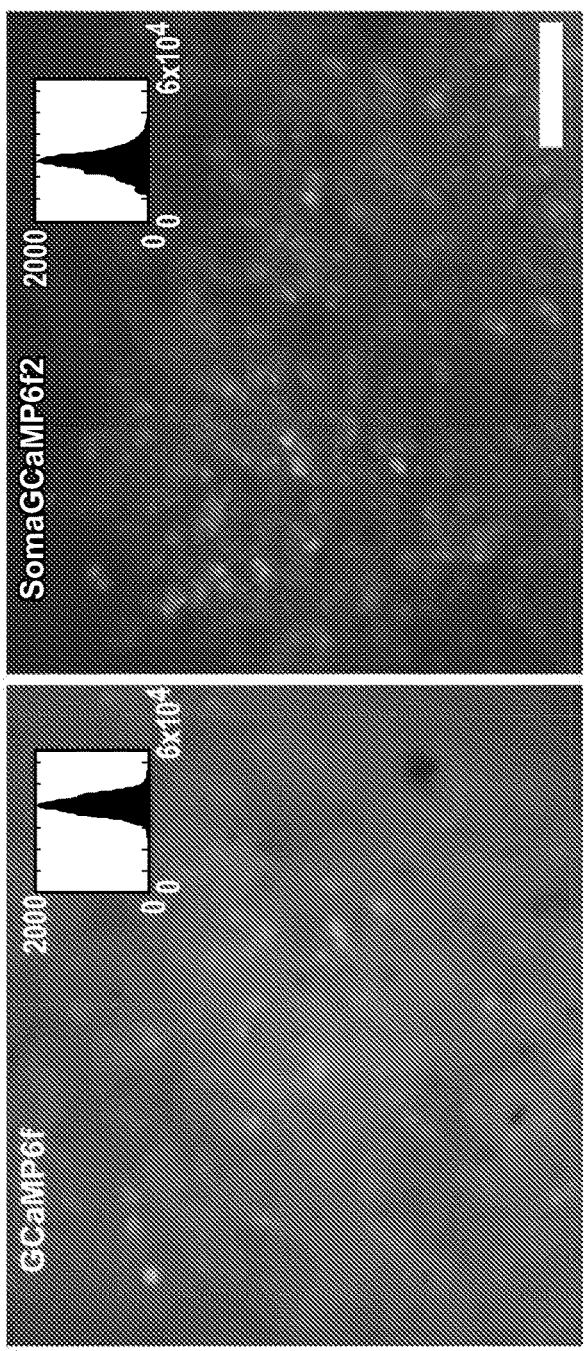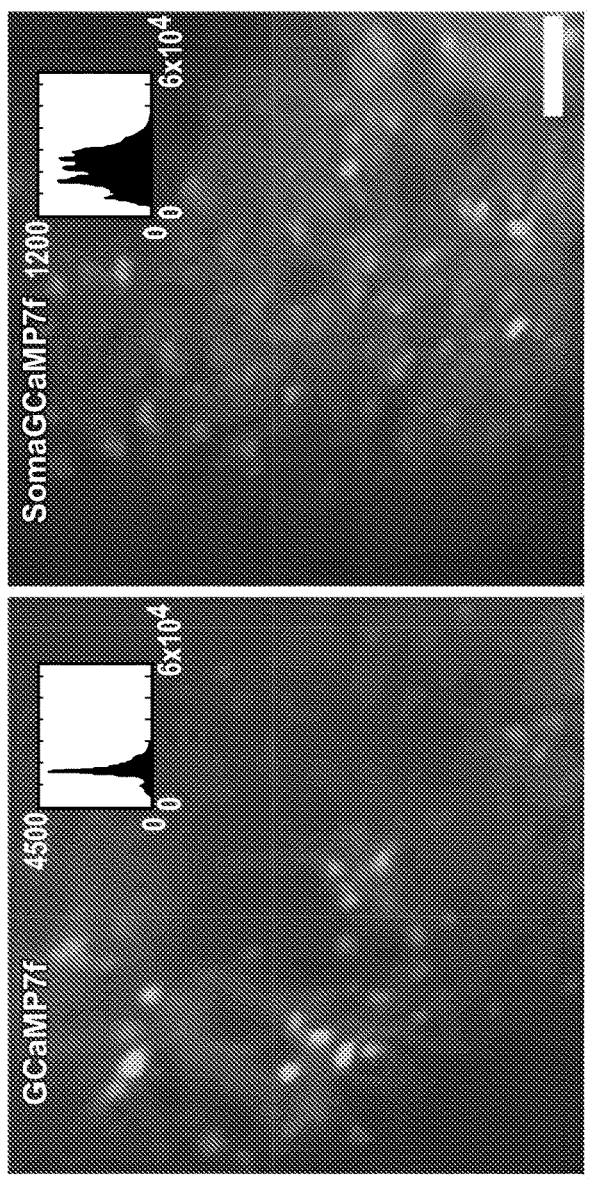

GCaMP6f

SomaGCaMP6f2

100% df/f$_0$
100 s

Fig. 7A
GCaMP6f
Fig. 7B
GCaMP6f-27-AnkTail-motif-ER2
Fig. 7C
GCaMP6f-27-EE-RR
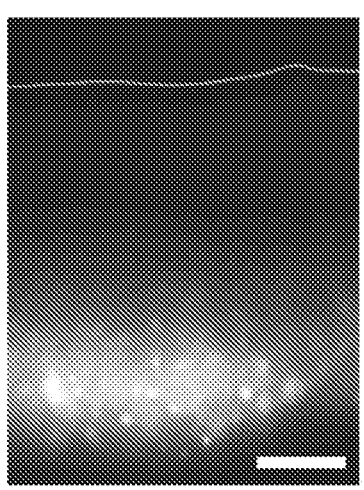
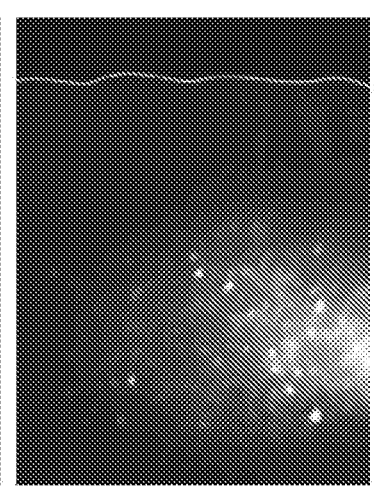
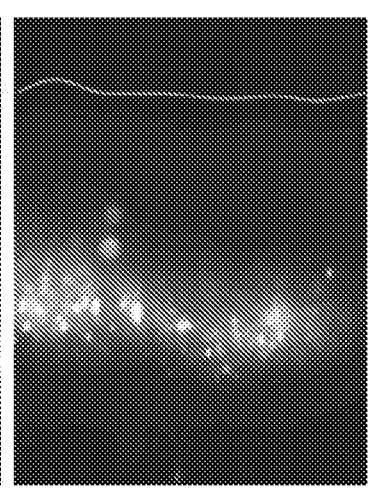
Fig. 7D
nullCoChR-12-GCaMP6f-Kv2.1-motif
Fig. 7E
GCaMP6f-27-Nav1.2(I-II)-ER2
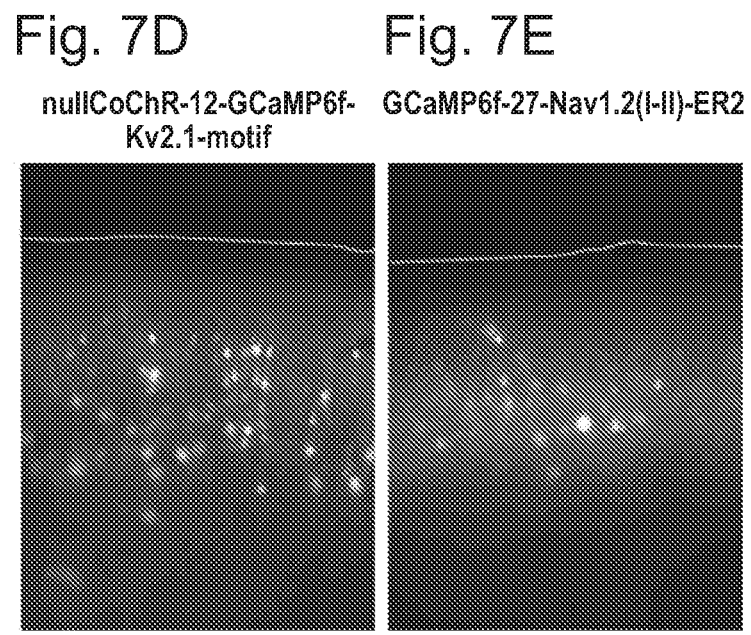

— Soma
---- Neuropil
GCaMP6f

GCaMP6f-27-AnkTail-motif-ER2

GCaMP6f-27-EE-RR nullCoChR-12-GCaMP6f-Kv2.1-motif

GCaMP6f-27-Nav1.2(I-II)-ER2

50% df/f
20 s

Membrane properties

Action potential properties

Fig. 9A
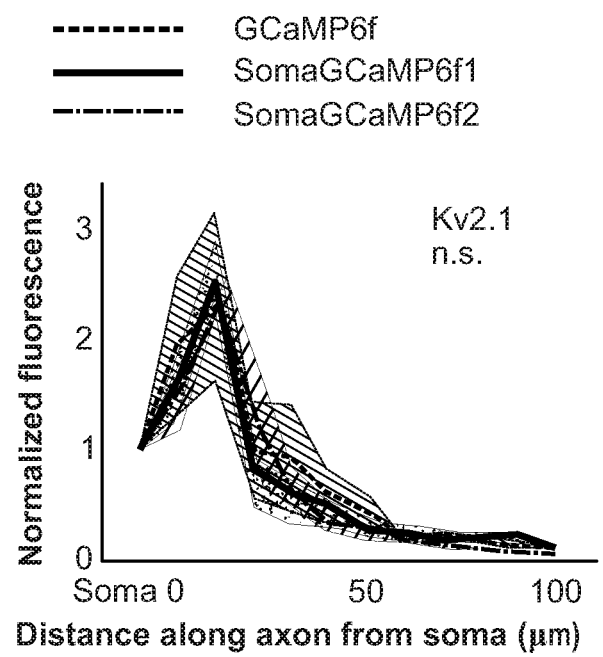
Fig. 9B
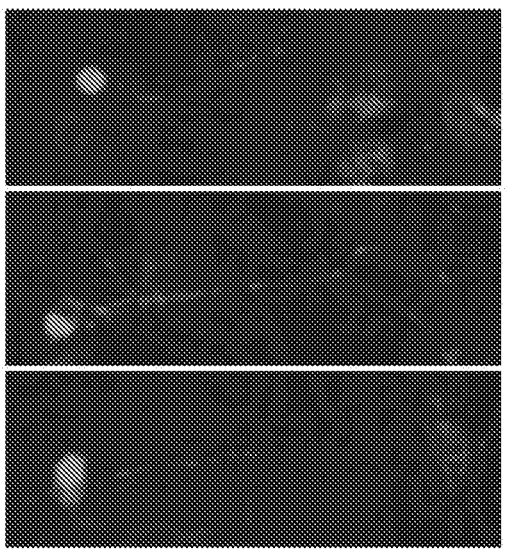
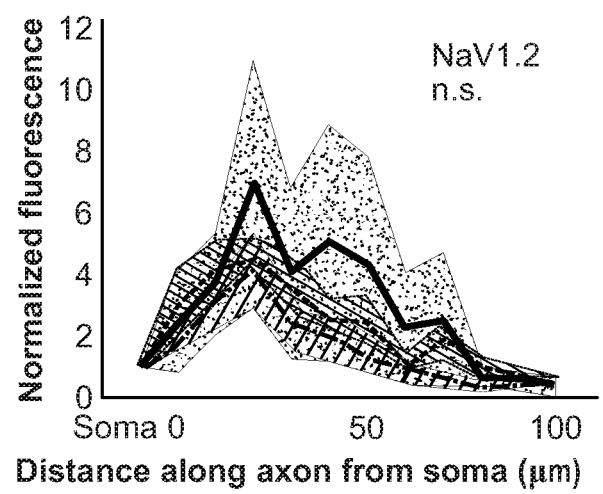

Fig. 9C
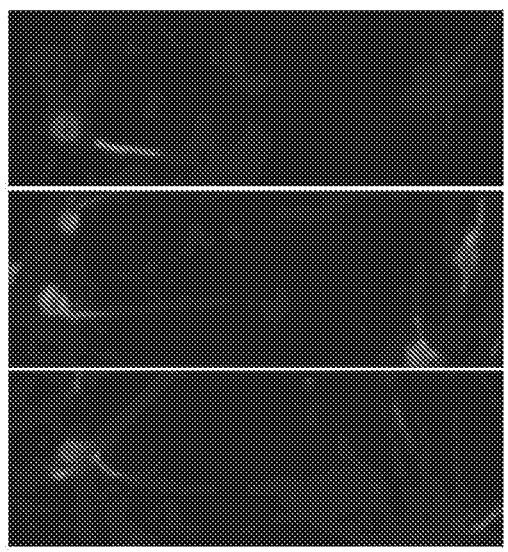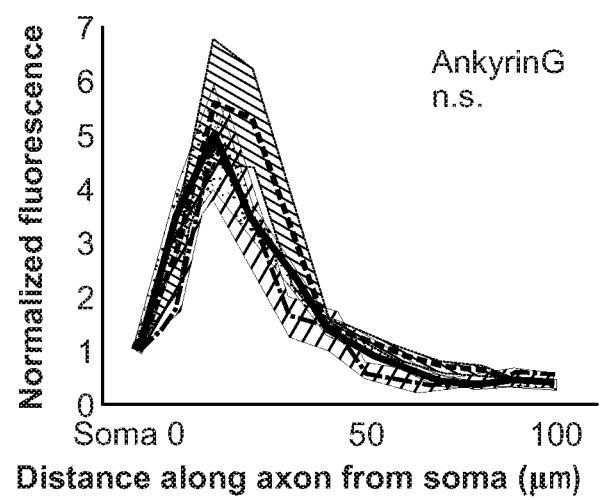
Fig. 9D
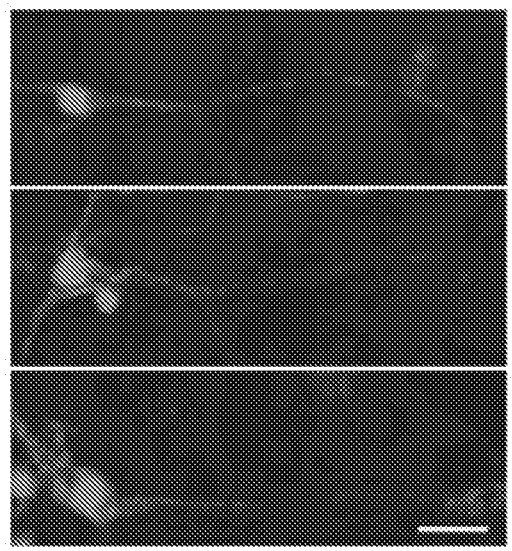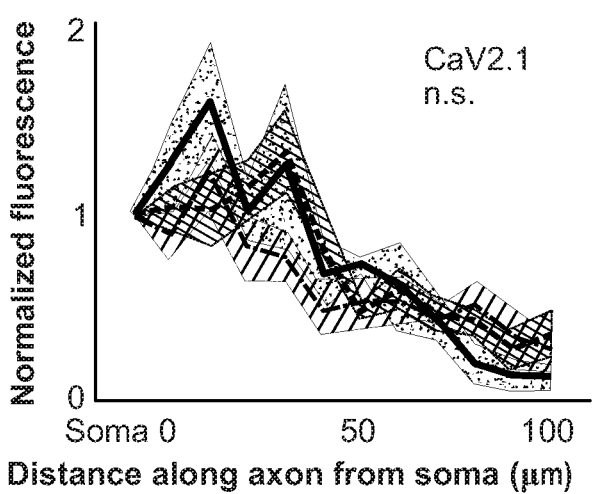

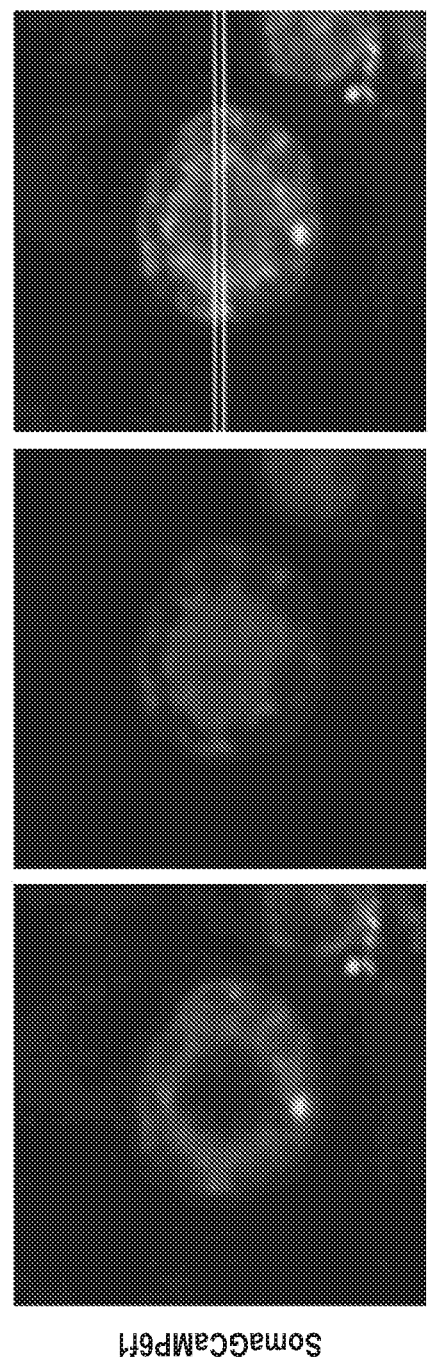
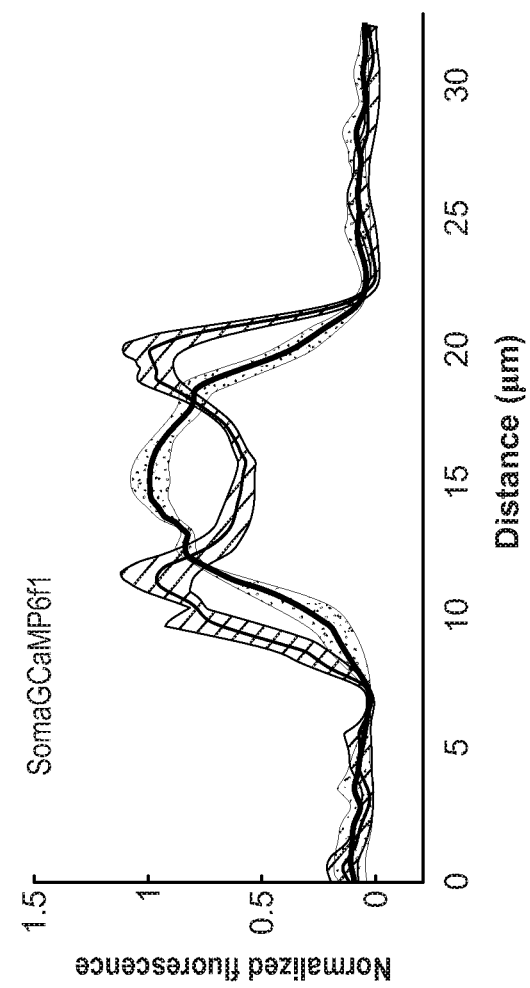
Fig. 10B

Distance along neurite from soma (µm)

Fig. 19

| Name of Protein | Was the protein fused to a fluorescent protein, a luminescent protein, or an immunoepitope tag? If yes, was it an N-terminal or a C-terminal fusion? | If any, what was the soma targeting motif or peptide found? | Was the soma-targeting fragment fused to a fluorescent protein or an immuno-epitope tag? If yes, was it an N-terminal or a C-terminal fusion? | How far from the soma, approximately, was the fluorescence detected using visual inspection, in this study? | Did the sequence target an opsin or (in the current study) GCaMP6f to the soma or to the axon initial segment? If yes, what was the construct used? | Linker used between GCaMP6f and the localization sequence |
|---|---|---|---|---|---|---|
| $Na_V1.6$ | Yes. C-terminal fusion with GFP (Garrido et al., 2003) | $Na_V1.6$(II-III) (Garrido et al., 2003), a 27 amino acid sequence, from the intracellular loop between transmembrane domains II and III. | Yes. C-terminal (Garrido et al., 2003). A C-terminal fusion was made. | 20-70 μm | Yes, to the axon hillock; ChR2-GFP-$Na_V$1.6(II-III) (Wu et al., 2013b). A somatic GCaMP6f-27-$Na_V$1.6(II-III)-ER2 was made. The 27 refers to the linker of such length (see Table 2 for linker definitions). | (ggggsggt) x3 (SEQ ID NO: 23) |
| $Na_V1.2$ | Yes. C-terminal fusion with GFP (Garrido et al., 2003) | $Na_V1.2$(I-II) (Garrido et al., 2001), a 326 amino acid sequence, from the intracellular loop between transmembrane domains I and II. | Yes. C-terminal (Garrido et al., 2003). A C-terminal fusion was made. | 20-50 μm | Yes, to the axon hillock; ChR2-YFP-$Na_V$1.2(I-II) (Grubb and Burrone, 2010). A somatic GCaMP6f-27-$Na_V$1.2(I-II)-ER2 was made. | (ggggsggt) x3 (SEQ ID NO: 23) |

Fig. 19, continued

| | | | | |
|---|---|---|---|---|
| Calcium-activated potassium channel SK1 from rat brain (rSK1) | Yes, N-terminal with GFP (Moruno Manchon et al., 2015) | Amino acids 351–411 (Fletcher et al., 2003), named rSK1-tail in that paper. | Yes. N-terminal with a FLAG tag (Fletcher et al., 2003) | 80-100 μm | Yes, to the soma and proximal neurites. A fusion was made between GCaMP6f and the tail region of rSK1 (see Table 17 for rSK1-tail sequence). GCaMP6f-rSK1-tail-ER2 was somatic, but had a lower baseline fluorescence compared with GCaMP6f. | ggsggt (SEQ ID NO: 27) |
| Ankyring | Yes. N-terminal with GFP (Zhang and Bennett, 1998). | Ankyring(1-837) (Greenberg et al., 2011), from the N-terminal fragment of Ankyring. | No. N-terminal fusions were made with ChR2 or with eNpHR (Greenberg et al., 2011). Both N- and C-terminal fusions were made for the present study. | 20-50 μm. The C-terminal fusion had ~10-fold higher expression than the N-terminal one. | Yes, to the soma. Ankyring(1-837)-ChR2-mCherry and AnkyrinG(1-837)-eNpHR–GFP (Greenberg et al., 2011). GCaMP6f-27-AnkTail-motif-ER2 and AnkTail-motif-27-GCaMP6f-ER2 were made, which were both somatic and reported spikes. A fusion between nullCoChR, the most N-terminal fragment of AnkyrinG (denoted here as Ank(1-334), and described before (Zhang and Bennett, 1998)) and GCaMP6f ws made, resulting in null CoChR-Ank(1-334)-GCaMP6f, however, this was toxic to neurons (see Table 2). | (ggsggsggt) x3 (SEQ ID NO: 23) or no linker |

Fig. 19, continued

| $K_V2.1$ | Yes, an HA-tag was fused to the N-terminus of $K_V2.1$ (Lim et al., 2000). | $K_V2.1$-motif, a 65 amino acid sequence (Wu et al., 2013b) from the intracellular loop between transmembrane domains IV and V of $K_V2.1$. | No. C-terminal fusions were made with ChR2 (Wu et al., 2013b). A C-terminal fusion with GFP was made for the present study. | 60-150μm | Yes. To the soma. ChR2-YFP-$K_V2.1$-motif and NpHR-YFP-$K_V2.1$-motif (Wu et al., 2013b). nullCoChR-12-KA2-(1-150)-GCaMP6f-$K_V2.1$-motif (somatic), nullCoChR-12-GCaMP6f-$K_V2.1$-motif (somatic), and GCaMP6f-12-$K_V2.1$-motif-ER2 (non-somatic) were made. | (ggsggt) x2 (SEQ ID NO: 21) or no linker |

Fig. 19, continued

| | | | | |
|---|---|---|---|---|
| KA2 | Yes, a myc-tag was fused to the N-terminus of KA2. Both N- and C- fusions with GFP were made. | KA2(1-150). To find it, KA2 was fragmented (from N- to C- terminus) into: KA2_PART1 (360 amino acids), KA2_PART2 (360 amino acids) and KA2_PART3 (259 amino acids), as previously described (Shemesh et al., 2017). After identifying that KA2 (1-150) was soma-targeting, it was further fragmented into KA2 (1-75), which was not soma-targeting, and KA2 (1-100), which was soma-targeting. | Yes, C- and N-terminal fusions of KA2(1-150) were made with GFP, and of KA2 (1-100) with GFP. | 20-50 μm | Yes, both the opsin CoChR and GCaMP6f to the soma. Both KA2(1-150)-CoChR-GFP and CoChR-KA2(1-150)-GFP, which was named soCoChR, were cloned (Shemesh et al., 2017). Additionally, GCaMP was fused to KA2(1-100) using different linker sizes (see right), as well as with null sfGFP, in both N- and C-terminal fusion form (see Table 2). | (ggsggt) x2 (SEQ ID NO: 21), (ggsggtggsggt)x2 (SEQ ID NO: 22), (ggsggtggsggt)x4 (SEQ ID NO: 24), (ggsggtggsggt)x8 (SEQ ID NO: 25), (ggsggtggsggt)x16 (SEQ ID NO: 26) |

Fig. 19, continued

| EE-RR | Yes. EE and RR were fused to two separate proteins for a split-intein assay (Selgrade et al., 2013) in which the splicing of a self-splicing protein fragment would lead a split luciferase to become whole and generate luminescence. | EE and RR are de-novo designed heterodimers (Moll et al., 2001). | No. A tandem fusion of EE to RR was made in order for them to self-assemble. A C-terminal fusion to GCaMP6f was made first, which appeared to be soma-targeted; an N-terminal fusion to GCaMP6f was not made. | 0-40 μm | Yes. The construct used was GCaMP6f-27-EE-RR. | ggsggsggtggsggs ggtggsggsggt (SEQ ID NO: 23) |

Fig. 19, continued

| AcidP1-BaseP1 | No. | AcidP1 and BaseP1 are de-novo designed heterodimers (Oakley and Kim, 1998). | No. The tandem fusion of AcidP1-BaseP1 was made as a self-assembling protein fragment. A C-terminal fusion to GCaMP6f was made first, which appeared to be soma-targeted; an N-terminal fusion to GCaMP6f was not made. | 50-100 μm | Yes. The construct used was GCaMP6f-27-AcidP1-BaseP1. | ggsggsgtggsggs ggtggsggsggt (SEQ ID NO: 23) |

SEQUENCE LISTING

<160> NUMBER OF SEQ ID NOS: 27

<210> SEQ ID NO 1
<211> LENGTH: 400
<212> TYPE: PRT
<213> ORGANISM: Artificial Sequence
<220> FEATURE:
<223> OTHER INFORMATION: Synthetic polypeptide

<400> SEQUENCE: 1

```
Arg Glu Gly Arg Ile Asp Asp Glu Pro Phe Lys Ile Val Glu Lys
1               5                   10                  15

Val Lys Glu Asp Leu Val Lys Val Ser Glu Ile Leu Lys Lys Asp Val
            20                  25                  30

Cys Val Glu Ser Lys Gly Pro Pro Lys Ser Pro Lys Ser Asp Lys Gly
        35                  40                  45

His Ser Pro Glu Asp Asp Trp Thr Glu Phe Ser Ser Glu Glu Ile Arg
    50                  55                  60

Glu Ala Arg Gln Ala Ala Ala Ser His Ala Pro Ser Leu Pro Glu Arg
65                  70                  75                  80

Val His Gly Lys Ala Asn Leu Thr Arg Val Ile Asp Tyr Leu Thr Asn
                85                  90                  95

Asp Ile Gly Ser Ser Ser Leu Thr Asn Leu Lys Tyr Lys Phe Glu Glu
                100                 105                 110

Ala Lys Lys Asp Gly Glu Glu Arg Gln Lys Arg Ile Leu Lys Pro Ala
            115                 120                 125

Met Ala Leu Gln Glu His Lys Leu Lys Met Pro Pro Ala Ser Met Arg
    130                 135                 140

Pro Ser Thr Ser Glu Lys Glu Leu Cys Lys Met Ala Asp Ser Phe Phe
145                 150                 155                 160

Gly Ala Asp Ala Ile Leu Glu Ser Pro Asp Asp Phe Ser Gln His Asp
                165                 170                 175

Gln Asp Lys Ser Pro Leu Ser Asp Ser Gly Phe Glu Thr Arg Ser Glu
            180                 185                 190

Lys Thr Pro Ser Ala Pro Gln Ser Ala Glu Ser Thr Gly Pro Lys Pro
    195                 200                 205

Leu Phe His Glu Val Pro Ile Pro Pro Val Ile Thr Glu Thr Arg Thr
210                 215                 220

Glu Val Val His Val Ile Arg Ser Tyr Glu Pro Ser Ser Gly Glu Ile
225                 230                 235                 240

Pro Gln Ser Gln Pro Glu Asp Pro Val Ser Pro Lys Pro Ser Pro Thr
                245                 250                 255

Phe Met Glu Leu Glu Pro Lys Pro Thr Thr Ser Ser Ile Lys Glu Lys
            260                 265                 270

Val Lys Ala Phe Gln Met Lys Ala Ser Ser Glu Glu Glu Asp His Ser
    275                 280                 285

Arg Val Leu Ser Lys Gly Met Arg Val Lys Glu Glu Thr His Ile Thr
290                 295                 300

Thr Thr Thr Arg Met Val Tyr His Ser Pro Pro Gly Gly Glu Cys Ala
305                 310                 315                 320

Ser Glu Arg Ile Glu Glu Thr Met Ser Val His Asp Ile Met Lys Ala
                325                 330                 335

Phe Gln Ser Gly Arg Asp Pro Ser Lys Glu Leu Ala Gly Leu Phe Glu
            340                 345                 350

His Lys Ser Ala Met Ser Pro Asp Val Ala Lys Ser Ala Ala Glu Thr
    355                 360                 365

Ser Ala Gln His Ala Glu Lys Asp Ser Gln Met Lys Pro Lys Leu Glu
370                 375                 380

Arg Ile Ile Glu Val His Ile Glu Lys Gly Pro Gln Ser Pro Cys Glu
385                 390                 395                 400
```

<210> SEQ ID NO 2

```
<211> LENGTH: 88
<212> TYPE: PRT
<213> ORGANISM: Artificial Sequence
<220> FEATURE:
<223> OTHER INFORMATION: Synthetic polypeptide

<400> SEQUENCE: 2

Leu Glu Ile Glu Ala Ala Phe Leu Glu Gln Glu Asn Thr Ala Leu Glu
1               5                   10                  15

Thr Glu Val Ala Glu Leu Glu Gln Glu Val Gln Arg Leu Glu Asn Ile
            20                  25                  30

Val Ser Gln Tyr Glu Thr Arg Tyr Gly Pro Leu Gly Ser Leu Glu Ile
        35                  40                  45

Arg Ala Ala Phe Leu Arg Arg Arg Asn Thr Ala Leu Arg Thr Arg Val
    50                  55                  60

Ala Glu Leu Arg Gln Arg Val Gln Arg Leu Arg Asn Ile Val Ser Gln
65                  70                  75                  80

Tyr Glu Thr Arg Tyr Gly Pro Leu
                85

<210> SEQ ID NO 3
<211> LENGTH: 64
<212> TYPE: PRT
<213> ORGANISM: Artificial Sequence
<220> FEATURE:
<223> OTHER INFORMATION: Synthetic polypeptide

<400> SEQUENCE: 3

Ala Gln Leu Glu Lys Glu Leu Gln Ala Leu Glu Lys Glu Asn Ala Gln
1               5                   10                  15

Leu Glu Trp Glu Leu Gln Ala Leu Glu Lys Glu Leu Ala Gln Gly Ser
            20                  25                  30

Gly Ser Ala Gln Leu Lys Lys Lys Leu Gln Ala Leu Lys Lys Lys Asn
        35                  40                  45

Ala Gln Leu Lys Trp Lys Leu Gln Ala Leu Lys Lys Lys Leu Ala Gln
    50                  55                  60

<210> SEQ ID NO 4
<211> LENGTH: 238
<212> TYPE: PRT
<213> ORGANISM: Artificial Sequence
<220> FEATURE:
<223> OTHER INFORMATION: Synthetic polypeptide

<400> SEQUENCE: 4

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Gly Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
                100                 105                 110
```

```
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Phe Asn Ser His Asn Val Tyr Ile Thr Ala Asp Lys Gln Lys Asn Gly
145                 150                 155                 160

Ile Lys Ala Asn Phe Lys Ile Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 5
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 5

Arg Lys Arg Pro Ser Asp Leu Val His Val Phe Ser Pro Arg Lys
1               5                   10                  15

Lys

<210> SEQ ID NO 6
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 6

Lys Ser Arg Ile Thr Ser Glu Gly Glu Tyr Ile Pro Leu Asp Gln Ile
1               5                   10                  15

Asp Ile Asn Val
            20

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

Phe Cys Tyr Glu Asn Glu Val
1               5

<210> SEQ ID NO 8
<211> LENGTH: 288
<212> TYPE: PRT
<213> ORGANISM: Artificial Sequence
<220> FEATURE:
<223> OTHER INFORMATION: Synthetic polypeptide
```

<400> SEQUENCE: 8

```
Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Val
50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
    130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Ala Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
        275                 280                 285
```

<210> SEQ ID NO 9
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 9

```
Met Pro Ala Glu Leu Leu Leu Leu Ile Val Ala Phe Ala Asn Pro
1               5                   10                  15

Ser Cys Gln Val Leu Ser Ser Leu Arg Met Ala Ala Ile Leu Asp Asp
            20                  25                  30

Gln Thr Val Cys Gly Arg Gly Glu Arg Leu Ala Leu Ala Leu Ala Arg
        35                  40                  45

Glu Gln Ile Asn Gly Ile Ile Glu Val Pro Ala Lys Ala Arg Val Glu
    50                  55                  60
```

```
Val Asp Ile Phe Glu Leu Gln Arg Asp Ser Gln Tyr Glu Thr Thr Asp
 65                  70                  75                  80

Thr Met Cys Gln Ile Leu Pro Lys Gly Val Val Ser Val Leu Gly Pro
                 85                  90                  95

Ser Ser Ser Pro Ala Ser Ala Ser Thr Val Ser His Ile Cys Gly Glu
             100                 105                 110

Lys Glu Ile Pro His Ile Lys Val Gly Pro Glu Glu Thr Pro Arg Leu
         115                 120                 125

Gln Tyr Leu Arg Phe Ala Ser Val Ser Leu Tyr Pro Ser Asn Glu Asp
     130                 135                 140

Val Ser Leu Ala Val Ser
145                 150

<210> SEQ ID NO 10
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 10

Met Pro Ala Glu Leu Leu Leu Leu Ile Val Ala Phe Ala Asn Pro
1                5                  10                  15

Ser Cys Gln Val Leu Ser Ser Leu Arg Met Ala Ala Ile Leu Asp Asp
                 20                  25                  30

Gln Thr Val Cys Gly Arg Gly Glu Arg Leu Ala Leu Ala Leu Ala Arg
             35                  40                  45

Glu Gln Ile Asn Gly Ile Ile Glu Val Pro Ala Lys Ala Arg Val Glu
 50                  55                  60

Val Asp Ile Phe Glu Leu Gln Arg Asp Ser Gln Ala Glu Thr Thr Asp
 65                  70                  75                  80

Thr Met Cys Gln Ile Leu Pro Lys Gly Val Val Ser Val Leu Gly Pro
                 85                  90                  95

Ser Ser Ser Pro Ala Ser Ala Ser Thr Val Ser His Ile Cys Gly Glu
             100                 105                 110

Lys Glu Ile Pro His Ile Lys Val Gly Pro Glu Glu Thr Pro Arg Leu
         115                 120                 125

Gln Tyr Leu Arg Phe Ala Ser Val Ser Leu Tyr Pro Ser Asn Glu Asp
     130                 135                 140

Val Ser Leu Ala Val Ser
145                 150

<210> SEQ ID NO 11
<211> LENGTH: 100
<212> TYPE: PRT
<213> ORGANISM: Artificial Sequence
<220> FEATURE:
<223> OTHER INFORMATION: Synthetic polypeptide

<400> SEQUENCE: 11

Met Pro Ala Glu Leu Leu Leu Leu Ile Val Ala Phe Ala Asn Pro
1                5                  10                  15

Ser Cys Gln Val Leu Ser Ser Leu Arg Met Ala Ala Ile Leu Asp Asp
                 20                  25                  30

Gln Thr Val Cys Gly Arg Gly Glu Arg Leu Ala Leu Ala Leu Ala Arg
             35                  40                  45

Glu Gln Ile Asn Gly Ile Ile Glu Val Pro Ala Lys Ala Arg Val Glu
 50                  55                  60
```

Val Asp Ile Phe Glu Leu Gln Arg Asp Ser Gln Tyr Glu Thr Thr Asp
65                  70                  75                  80

Thr Met Cys Gln Ile Leu Pro Lys Gly Val Ser Val Leu Gly Pro
            85                  90                  95

Ser Ser Ser Pro
            100

<210> SEQ ID NO 12
<211> LENGTH: 334
<212> TYPE: PRT
<213> ORGANISM: Artificial Sequence
<220> FEATURE:
<223> OTHER INFORMATION: Synthetic polypeptide

<400> SEQUENCE: 12

Met Ala His Ala Ala Ser Gln Leu Lys Lys Asn Arg Asp Leu Glu Ile
1               5                   10                  15

Asn Ala Glu Glu Glu Thr Glu Lys Lys Lys His Arg Lys Arg Ser
            20                  25                  30

Arg Asp Arg Lys Lys Lys Ser Asp Ala Asn Ala Ser Tyr Leu Arg Ala
        35                  40                  45

Ala Arg Ala Gly His Leu Glu Lys Ala Leu Asp Tyr Ile Lys Asn Gly
    50                  55                  60

Val Asp Val Asn Ile Cys Asn Gln Asn Gly Leu Asn Ala Leu His Leu
65                  70                  75                  80

Ala Ser Lys Glu Gly His Val Glu Val Val Ser Glu Leu Leu Gln Arg
            85                  90                  95

Glu Ala Asn Val Asp Ala Ala Thr Lys Lys Gly Asn Thr Ala Leu His
            100                 105                 110

Ile Ala Ser Leu Ala Gly Gln Ala Glu Val Val Lys Val Leu Val Thr
            115                 120                 125

Asn Gly Ala Asn Val Asn Ala Gln Ser Gln Asn Gly Phe Thr Pro Leu
130                 135                 140

Tyr Met Ala Ala Gln Glu Asn His Leu Glu Val Val Arg Phe Leu Leu
145                 150                 155                 160

Asp Asn Gly Ala Ser Gln Ser Leu Ala Thr Glu Asp Gly Phe Thr Pro
            165                 170                 175

Leu Ala Val Ala Leu Gln Gln Gly His Asp Gln Val Val Ser Leu Leu
            180                 185                 190

Leu Glu Asn Asp Thr Lys Gly Lys Val Arg Leu Pro Ala Leu His Ile
            195                 200                 205

Ala Ala Arg Lys Asp Asp Thr Lys Ala Ala Ala Leu Leu Leu Gln Asn
210                 215                 220

Asp Thr Asn Ala Asp Ile Glu Ser Lys Met Val Val Asn Arg Ala Thr
225                 230                 235                 240

Glu Ser Gly Phe Thr Ser Leu His Ile Ala His Tyr Gly Asn Ile
            245                 250                 255

Asn Val Ala Thr Leu Leu Leu Asn Arg Ala Ala Val Asp Phe Thr
            260                 265                 270

Ala Arg Asn Asp Ile Thr Pro Leu His Val Ala Ser Lys Arg Gly Asn
    275                 280                 285

Ala Asn Met Val Lys Leu Leu Leu Asp Arg Gly Ala Lys Ile Asp Ala
    290                 295                 300

Lys Thr Arg Asp Gly Leu Thr Pro Leu His Cys Gly Ala Arg Ser Gly
305                 310                 315                 320

His Glu Gln Val Val Glu Met Leu Leu Asp Arg Ala Ala Pro
                    325                 330

<210> SEQ ID NO 13
<211> LENGTH: 289
<212> TYPE: PRT
<213> ORGANISM: Artificial Sequence
<220> FEATURE:
<223> OTHER INFORMATION: Synthetic polypeptide

<400> SEQUENCE: 13

Arg Thr Asp Ile Arg Met Ala Ile Val Ala Asp His Leu Gly Leu Ser
1               5                   10                  15

Trp Thr Glu Leu Ala Arg Glu Leu Asn Phe Ser Val Asp Glu Ile Asn
            20                  25                  30

Gln Ile Arg Val Glu Asn Pro Asn Ser Leu Ile Ser Gln Ser Phe Met
        35                  40                  45

Leu Leu Lys Lys Trp Val Thr Arg Asp Gly Lys Asn Ala Thr Thr Asp
50                  55                  60

Ala Leu Thr Ser Val Leu Thr Lys Ile Asn Arg Ile Asp Ile Val Thr
65                  70                  75                  80

Leu Leu Glu Gly Pro Ile Phe Asp Tyr Gly Asn Ile Ser Gly Thr Arg
                85                  90                  95

Ser Phe Ala Asp Glu Asn Asn Val Phe His Asp Pro Val Asp Gly Trp
            100                 105                 110

Gln Asn Glu Thr Pro Ser Gly Ser Leu Glu Ser Pro Ala Gln Ala Arg
        115                 120                 125

Arg Leu Thr Gly Gly Leu Leu Asp Arg Leu Asp Asp Ser Ser Asp Gln
130                 135                 140

Ala Arg Asp Ser Ile Thr Ser Tyr Leu Thr Gly Glu Pro Gly Lys Ile
145                 150                 155                 160

Glu Ala Asn Gly Asn His Thr Ala Glu Val Ile Pro Glu Ala Lys Ala
                165                 170                 175

Lys Pro Tyr Phe Pro Glu Ser Gln Asn Asp Ile Gly Lys Gln Ser Ile
            180                 185                 190

Lys Glu Asn Leu Lys Pro Lys Thr His Gly Cys Gly Arg Thr Glu Glu
        195                 200                 205

Pro Val Ser Pro Leu Thr Ala Tyr Gln Lys Ser Leu Glu Glu Thr Ser
210                 215                 220

Lys Leu Val Ile Glu Asp Ala Pro Lys Pro Cys Val Pro Val Gly Met
225                 230                 235                 240

Lys Lys Met Thr Arg Thr Thr Ala Asp Gly Lys Ala Arg Leu Asn Leu
                245                 250                 255

Gln Glu Glu Glu Gly Ser Thr Arg Ser Glu Pro Lys Gln Gly Glu Gly
            260                 265                 270

Tyr Lys Val Lys Thr Lys Lys Glu Ile Arg Asn Val Glu Lys Lys Thr
        275                 280                 285

His

<210> SEQ ID NO 14
<211> LENGTH: 800
<212> TYPE: PRT
<213> ORGANISM: Artificial Sequence
<220> FEATURE:
<223> OTHER INFORMATION: Synthetic polypeptide

<400> SEQUENCE: 14

```
Met Ala His Ala Ala Ser Gln Leu Lys Lys Asn Arg Asp Leu Glu Ile
1               5                   10                  15

Asn Ala Glu Glu Glu Thr Glu Lys Lys Arg Lys His Arg Lys Arg Ser
            20                  25                  30

Arg Asp Arg Lys Lys Lys Ser Asp Ala Asn Ala Ser Tyr Leu Arg Ala
        35                  40                  45

Ala Arg Ala Gly His Leu Glu Lys Ala Leu Asp Tyr Ile Lys Asn Gly
    50                  55                  60

Val Asp Val Asn Ile Cys Asn Gln Asn Gly Leu Asn Ala Leu His Leu
65                  70                  75                  80

Ala Ser Lys Glu Gly His Val Glu Val Val Ser Glu Leu Leu Gln Arg
                85                  90                  95

Glu Ala Asn Val Asp Ala Ala Thr Lys Lys Gly Asn Thr Ala Leu His
            100                 105                 110

Ile Ala Ser Leu Ala Gly Gln Ala Glu Val Val Lys Val Leu Val Thr
        115                 120                 125

Asn Gly Ala Asn Val Asn Ala Gln Ser Gln Asn Gly Phe Thr Pro Leu
130                 135                 140

Tyr Met Ala Ala Gln Glu Asn His Leu Glu Val Val Arg Phe Leu Leu
145                 150                 155                 160

Asp Asn Gly Ala Ser Gln Ser Leu Ala Thr Glu Asp Gly Phe Thr Pro
                165                 170                 175

Leu Ala Val Ala Leu Gln Gln Gly His Asp Gln Val Val Ser Leu Leu
            180                 185                 190

Leu Glu Asn Asp Thr Lys Gly Lys Val Arg Leu Pro Ala Leu His Ile
        195                 200                 205

Ala Ala Arg Lys Asp Asp Thr Lys Ala Ala Leu Leu Leu Gln Asn
    210                 215                 220

Asp Thr Asn Ala Asp Val Glu Ser Lys Ser Gly Phe Thr Pro Leu His
225                 230                 235                 240

Ile Ala Ala His Tyr Gly Asn Ile Asn Val Ala Thr Leu Leu Leu Asn
                245                 250                 255

Arg Ala Ala Ala Val Asp Phe Thr Ala Arg Asn Asp Ile Thr Pro Leu
            260                 265                 270

His Val Ala Ser Lys Arg Gly Asn Ala Asn Met Val Lys Leu Leu Leu
        275                 280                 285

Asp Arg Gly Ala Lys Ile Asp Ala Lys Thr Arg Asp Gly Leu Thr Pro
290                 295                 300

Leu His Cys Gly Ala Arg Ser Gly His Glu Gln Val Val Glu Met Leu
305                 310                 315                 320

Leu Asp Arg Ser Ala Pro Ile Leu Ser Lys Thr Lys Asn Gly Leu Ser
                325                 330                 335

Pro Leu His Met Ala Thr Gln Gly Asp His Leu Asn Cys Val Gln Leu
            340                 345                 350

Leu Leu Gln His Asn Val Pro Val Asp Asp Val Thr Asn Asp Tyr Leu
        355                 360                 365

Thr Ala Leu His Val Ala His Cys Gly His Tyr Lys Val Ala Lys
    370                 375                 380

Val Leu Leu Asp Lys Lys Ala Ser Pro Asn Ala Lys Ala Leu Asn Gly
385                 390                 395                 400
```

```
Phe Thr Pro Leu His Ile Ala Cys Lys Lys Asn Arg Ile Arg Val Met
                405                 410                 415

Glu Leu Leu Leu Lys His Gly Ala Ser Ile Gln Ala Val Thr Glu Ser
            420                 425                 430

Gly Leu Thr Pro Ile His Val Ala Ala Phe Met Gly His Val Asn Ile
        435                 440                 445

Val Ser Gln Leu Met His His Gly Ala Ser Pro Asn Thr Thr Asn Val
    450                 455                 460

Arg Gly Glu Thr Ala Leu His Met Ala Ala Arg Ser Gly Gln Ala Glu
465                 470                 475                 480

Val Val Arg Tyr Leu Val Gln Asp Gly Ala Gln Val Glu Ala Lys Ala
                485                 490                 495

Lys Asp Asp Gln Thr Pro Leu His Ile Ser Ala Arg Leu Gly Lys Ala
            500                 505                 510

Asp Ile Val Gln Gln Leu Leu Gln Gln Gly Ala Ser Pro Asn Ala Ala
        515                 520                 525

Thr Thr Ser Gly Tyr Thr Pro Leu His Leu Ala Ala Arg Glu Gly His
    530                 535                 540

Glu Asp Val Ala Ala Phe Leu Leu Asp His Gly Ala Ser Leu Ser Ile
545                 550                 555                 560

Thr Thr Lys Lys Gly Phe Thr Pro Leu His Val Ala Ala Lys Tyr Gly
                565                 570                 575

Lys Leu Glu Val Ala Ser Leu Leu Leu Gln Lys Ser Ala Ser Pro Asp
            580                 585                 590

Ala Ala Gly Lys Ser Gly Leu Thr Pro Leu His Val Ala His Tyr
        595                 600                 605

Asp Asn Gln Lys Val Ala Leu Leu Leu Asp Gln Gly Ala Ser Pro
    610                 615                 620

His Ala Ala Ala Lys Asn Gly Tyr Thr Pro Leu His Ile Ala Ala Lys
625                 630                 635                 640

Lys Asn Gln Met Asp Ile Ala Thr Ser Leu Leu Glu Tyr Gly Ala Asp
                645                 650                 655

Ala Asn Ala Val Thr Arg Gln Gly Ile Ala Ser Val His Leu Ala Ala
            660                 665                 670

Gln Glu Gly His Val Asp Met Val Ser Leu Leu Leu Ser Arg Asn Ala
        675                 680                 685

Asn Val Asn Leu Ser Asn Lys Ser Gly Leu Thr Pro Leu His Leu Ala
    690                 695                 700

Ala Gln Glu Asp Arg Val Asn Val Ala Glu Val Leu Val Asn Gln Gly
705                 710                 715                 720

Ala His Val Asp Ala Gln Thr Lys Met Gly Tyr Thr Pro Leu His Val
                725                 730                 735

Gly Cys His Tyr Gly Asn Ile Lys Ile Val Asn Phe Leu Leu Gln His
            740                 745                 750

Ser Ala Lys Val Asn Ala Lys Thr Lys Asn Gly Tyr Thr Ala Leu His
        755                 760                 765

Gln Ala Ala Gln Gln Gly His Thr His Ile Ile Asn Val Leu Leu Gln
    770                 775                 780

Asn Asn Ala Ser Pro Asn Glu Leu Thr Val Asn Gly Asn Thr Ala Leu
785                 790                 795                 800

<210> SEQ ID NO 15
<211> LENGTH: 733
```

```
<212> TYPE: PRT
<213> ORGANISM: Artificial Sequence
<220> FEATURE:
<223> OTHER INFORMATION: Synthetic polypeptide

<400> SEQUENCE: 15
```

| | | | | | | | | | | | | |
|---|---|---|---|---|---|---|---|---|---|---|---|---|
| Ala | Ile | Ala | Arg | Arg | Leu | Gly | Tyr | Ile | Ser | Val | Val | Asp | Thr | Leu | Lys |
| 1 | | | | 5 | | | | | 10 | | | | | 15 | |

| Val | Val | Thr | Glu | Glu | Ile | Met | Thr | Thr | Thr | Ile | Thr | Glu | Lys | His |
|---|---|---|---|---|---|---|---|---|---|---|---|---|---|---|
| | | | 20 | | | | | 25 | | | | | 30 | |

| Lys | Met | Asn | Val | Pro | Glu | Thr | Met | Asn | Glu | Val | Leu | Asp | Met | Ser | Asp |
|---|---|---|---|---|---|---|---|---|---|---|---|---|---|---|---|
| | | 35 | | | | | 40 | | | | | 45 | | | |

| Asp | Glu | Val | Arg | Lys | Ala | Ser | Ala | Pro | Glu | Lys | Leu | Ser | Asp | Gly | Glu |
| | 50 | | | | | 55 | | | | | 60 | | | | |

| Tyr | Ile | Ser | Asp | Gly | Glu | Glu | Gly | Asp | Ala | Ile | Thr | Gly | Asp | Thr |
| 65 | | | | | 70 | | | | | 75 | | | | 80 |

| Asp | Lys | Tyr | Leu | Gly | Pro | Gln | Asp | Leu | Lys | Glu | Leu | Gly | Asp | Ser |
| | | | | 85 | | | | | 90 | | | | | 95 |

| Leu | Pro | Ala | Glu | Gly | Tyr | Val | Gly | Phe | Ser | Leu | Gly | Ala | Arg | Ser | Ala |
| | | | 100 | | | | | 105 | | | | | 110 | | |

| Ser | Leu | Arg | Ser | Phe | Ser | Ser | Asp | Arg | Ser | Tyr | Thr | Leu | Asn | Arg | Ser |
| | | | 115 | | | | | 120 | | | | | 125 | | |

| Ser | Tyr | Ala | Arg | Asp | Ser | Met | Met | Ile | Glu | Glu | Leu | Leu | Val | Pro | Ser |
| | 130 | | | | | 135 | | | | | 140 | | | | |

| Lys | Glu | Gln | His | Leu | Thr | Phe | Thr | Arg | Glu | Phe | Asp | Ser | Asp | Ser | Leu |
| 145 | | | | | 150 | | | | | 155 | | | | | 160 |

| Arg | His | Tyr | Ser | Trp | Ala | Ala | Asp | Thr | Leu | Asp | Asn | Val | Asn | Leu | Val |
| | | | | 165 | | | | | 170 | | | | | 175 | |

| Ser | Ser | Pro | Val | His | Ser | Gly | Phe | Leu | Val | Ser | Phe | Met | Val | Asp | Ala |
| | | | 180 | | | | | 185 | | | | | 190 | | |

| Arg | Gly | Gly | Ser | Met | Arg | Gly | Ser | Arg | His | His | Gly | Met | Arg | Ile | Ile |
| | | 195 | | | | | 200 | | | | | 205 | | | |

| Ile | Pro | Pro | Arg | Lys | Cys | Thr | Ala | Pro | Thr | Arg | Ile | Thr | Cys | Arg | Leu |
| 210 | | | | | 215 | | | | | 220 | | | | | |

| Val | Lys | Arg | His | Lys | Leu | Ala | Asn | Pro | Pro | Met | Val | Glu | Gly | Glu |
| 225 | | | | | 230 | | | | | 235 | | | | | 240 |

| Gly | Leu | Ala | Ser | Arg | Leu | Val | Glu | Met | Gly | Pro | Ala | Gly | Ala | Gln | Phe |
| | | | | 245 | | | | | 250 | | | | | 255 | |

| Leu | Gly | Pro | Val | Ile | Val | Glu | Ile | Pro | His | Phe | Gly | Ser | Met | Arg | Gly |
| | | | 260 | | | | | 265 | | | | | 270 | | |

| Lys | Glu | Arg | Glu | Leu | Ile | Val | Leu | Arg | Ser | Glu | Asn | Gly | Glu | Thr | Trp |
| | | 275 | | | | | 280 | | | | | 285 | | | |

| Lys | Glu | His | Gln | Phe | Asp | Ser | Lys | Asn | Glu | Asp | Leu | Ala | Glu | Leu | Leu |
| 290 | | | | | 295 | | | | | 300 | | | | | |

| Asn | Gly | Met | Asp | Glu | Glu | Leu | Asp | Ser | Pro | Glu | Glu | Leu | Gly | Thr | Lys |
| 305 | | | | | 310 | | | | | 315 | | | | | 320 |

| Arg | Ile | Cys | Arg | Ile | Ile | Thr | Lys | Asp | Phe | Pro | Gln | Tyr | Phe | Ala | Val |
| | | | | 325 | | | | | 330 | | | | | 335 | |

| Val | Ser | Arg | Ile | Lys | Gln | Glu | Ser | Asn | Gln | Ile | Gly | Pro | Glu | Gly | Gly |
| | | | 340 | | | | | 345 | | | | | 350 | | |

| Ile | Leu | Ser | Ser | Thr | Thr | Val | Pro | Leu | Val | Gln | Ala | Ser | Phe | Pro | Glu |
| | | | 355 | | | | | 360 | | | | | 365 | | |

| Gly | Ala | Leu | Thr | Lys | Arg | Ile | Arg | Val | Gly | Leu | Gln | Ala | Gln | Pro | Val |
| | | | 370 | | | | | 375 | | | | | 380 | | |

```
Pro Glu Glu Thr Val Lys Lys Ile Leu Gly Asn Lys Ala Thr Phe Ser
385                 390                 395                 400

Pro Ile Val Thr Val Glu Pro Arg Arg Lys Phe His Lys Pro Ile
            405                 410                 415

Thr Met Thr Ile Pro Val Pro Pro Ser Gly Glu Gly Val Ser Asn
            420                 425                 430

Gly Tyr Lys Gly Asp Ala Thr Pro Asn Leu Arg Leu Leu Cys Ser Ile
            435                 440                 445

Thr Gly Gly Thr Ser Pro Ala Gln Trp Glu Asp Ile Thr Gly Thr Thr
450                 455                 460

Pro Leu Thr Phe Ile Lys Asp Cys Val Ser Phe Thr Thr Asn Val Ser
465                 470                 475                 480

Ala Arg Phe Trp Leu Ala Asp Cys His Gln Val Leu Glu Thr Val Gly
            485                 490                 495

Leu Ala Ser Gln Leu Tyr Arg Glu Leu Ile Cys Val Pro Tyr Met Ala
            500                 505                 510

Lys Phe Val Val Phe Ala Lys Thr Asn Asp Pro Val Glu Ser Ser Leu
            515                 520                 525

Arg Cys Phe Cys Met Thr Asp Asp Arg Val Asp Lys Thr Leu Glu Gln
530                 535                 540

Gln Glu Asn Phe Glu Glu Val Ala Arg Ser Lys Asp Ile Glu Val Leu
545                 550                 555                 560

Glu Gly Lys Pro Ile Tyr Val Asp Cys Tyr Gly Asn Leu Ala Pro Leu
            565                 570                 575

Thr Lys Gly Gly Gln Gln Leu Val Phe Asn Phe Tyr Ser Phe Lys Glu
            580                 585                 590

Asn Arg Leu Pro Phe Ser Ile Lys Ile Arg Asp Thr Ser Gln Glu Pro
            595                 600                 605

Cys Gly Arg Leu Ser Phe Leu Lys Glu Pro Lys Thr Thr Lys Gly Leu
610                 615                 620

Pro Gln Thr Ala Val Cys Asn Leu Asn Ile Thr Leu Pro Ala His Lys
625                 630                 635                 640

Lys Glu Thr Glu Ser Asp Gln Asp Asp Ala Glu Lys Ala Asp Arg Arg
            645                 650                 655

Gln Ser Phe Ala Ser Leu Ala Leu Arg Lys Arg Tyr Ser Tyr Leu Thr
            660                 665                 670

Glu Pro Ser Met Lys Thr Val Glu Arg Ser Ser Gly Thr Ala Arg Ser
            675                 680                 685

Leu Pro Thr Thr Tyr Ser His Lys Pro Phe Phe Ser Thr Arg Pro Tyr
            690                 695                 700

Gln Ser Trp Thr Thr Ala Pro Ile Thr Val Pro Gly Pro Ala Lys Ser
705                 710                 715                 720

Gly Ser Leu Ser Ser Ser Pro Ser Asn Thr Pro Ser Ala
                725                 730

<210> SEQ ID NO 16
<211> LENGTH: 400
<212> TYPE: PRT
<213> ORGANISM: Artificial Sequence
<220> FEATURE:
<223> OTHER INFORMATION: Synthetic polypeptide

<400> SEQUENCE: 16

Ser Pro Leu Lys Ser Ile Trp Ser Val Ser Thr Pro Pro Ile Lys
1               5                   10                  15
```

```
Ser Thr Leu Gly Ala Ser Thr Ser Ser Val Lys Ser Ile Ser Asp
             20                  25                  30

Val Ala Ser Pro Ile Arg Ser Phe Arg Thr Val Ser Pro Ile Lys
         35                  40                  45

Thr Val Val Ser Pro Ser Pro Tyr Asn Pro Gln Val Ala Ser Gly Thr
     50                  55                  60

Leu Gly Arg Val Pro Thr Ile Thr Glu Ala Thr Pro Ile Lys Gly Leu
65                  70                  75                  80

Ala Pro Asn Ser Thr Phe Ser Ser Arg Thr Ser Pro Val Thr Thr Ala
                 85                  90                  95

Gly Ser Leu Leu Glu Arg Ser Ser Ile Thr Met Thr Pro Pro Ala Ser
                100                 105                 110

Pro Lys Ser Asn Ile Thr Met Tyr Ser Ser Ser Leu Pro Phe Lys Ser
            115                 120                 125

Ile Ile Thr Ser Ala Thr Pro Leu Ile Ser Ser Pro Leu Lys Ser Val
    130                 135                 140

Val Ser Pro Thr Lys Ser Ala Ala Asp Val Ile Ser Thr Ala Lys Ala
145                 150                 155                 160

Thr Met Ala Ser Ser Leu Ser Ser Pro Leu Lys Gln Met Ser Gly His
                165                 170                 175

Ala Glu Val Ala Leu Val Asn Gly Ser Val Ser Pro Leu Lys Tyr Pro
            180                 185                 190

Ser Ser Ser Ala Leu Ile Asn Gly Cys Lys Ala Thr Ala Thr Leu Gln
        195                 200                 205

Asp Lys Ile Ser Thr Ala Thr Asn Ala Val Ser Val Val Ser Ala
    210                 215                 220

Ala Ser Asp Thr Val Glu Lys Ala Leu Ser Thr Thr Thr Ala Met Pro
225                 230                 235                 240

Phe Ser Pro Leu Arg Ser Tyr Val Ser Ala Ala Pro Ser Ala Phe Gln
                245                 250                 255

Ser Leu Arg Thr Pro Ser Ala Ser Ala Leu Tyr Thr Ser Leu Gly Ser
            260                 265                 270

Ser Ile Ala Ala Thr Thr Ser Ser Val Thr Ser Ser Ile Ile Thr Val
    275                 280                 285

Pro Val Tyr Ser Val Val Asn Val Leu Pro Glu Pro Ala Leu Lys Lys
290                 295                 300

Leu Pro Asp Ser Asn Ser Phe Thr Lys Ser Ala Ala Leu Leu Ser
305                 310                 315                 320

Pro Ile Lys Thr Leu Thr Thr Glu Thr Arg Pro Gln Pro His Phe Asn
            325                 330                 335

Arg Thr Ser Ser Pro Val Lys Ser Ser Leu Phe Leu Ala Ser Ser Ala
                340                 345                 350

Leu Lys Pro Ser Val Pro Ser Ser Leu Ser Ser Ser Gln Glu Ile Leu
            355                 360                 365

Lys Asp Val Ala Glu Met Lys Glu Asp Leu Met Arg Met Thr Ala Ile
    370                 375                 380

Leu Gln Thr Asp Val Pro Glu Glu Lys Pro Phe Gln Thr Asp Leu Pro
385                 390                 395                 400

<210> SEQ ID NO 17
<211> LENGTH: 65
<212> TYPE: PRT
<213> ORGANISM: Artificial Sequence
<220> FEATURE:
<223> OTHER INFORMATION: Synthetic polypeptide
```

<400> SEQUENCE: 17

Gln Ser Gln Pro Ile Leu Asn Thr Lys Glu Met Ala Pro Gln Ser Lys
1               5                   10                  15

Pro Pro Glu Glu Leu Glu Met Ser Ser Met Pro Ser Pro Val Ala Pro
            20                  25                  30

Leu Pro Ala Arg Thr Glu Gly Val Ile Asp Met Arg Ser Met Ser Ser
        35                  40                  45

Ile Asp Ser Phe Ile Ser Cys Ala Thr Asp Phe Pro Glu Ala Thr Arg
    50                  55                  60

Phe
65

<210> SEQ ID NO 18
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 18

Gln Ala Gln Lys Leu Arg Thr Val Lys Ile Glu Gln Gly Lys Val Asn
1               5                   10                  15

Asp Gln Ala Asn Thr Leu Ala Asp Leu Ala Lys Ala Gln Ser Ile Ala
            20                  25                  30

Tyr Glu Val Val Ser Glu Leu Gln Ala Gln Gln Glu Leu Glu Ala
        35                  40                  45

Arg Leu Ala Ala Leu Glu Ser Arg Leu Asp Val Leu Gly Ala Ser Leu
    50                  55                  60

Gln Ala Leu Pro Ser Leu Ile Ala Gln Ala Ile Cys Pro Leu Pro Pro
65                  70                  75                  80

Pro Trp Pro Gly Pro Ser His Leu Thr Thr Ala Ala Gln Ser Pro Gln
            85                  90                  95

Ser His Trp Leu Pro Thr Thr Ala Ser Asp Cys Gly
        100                 105

<210> SEQ ID NO 19
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 19

Thr Val Arg Val Pro Ile Ala Val Gly Glu Ser Asp Phe Glu Asn Leu
1               5                   10                  15

Asn Thr Glu Asp Val Ser Ser Glu Ser Asp Pro
            20                  25

<210> SEQ ID NO 20
<211> LENGTH: 326
<212> TYPE: PRT
<213> ORGANISM: Artificial Sequence
<220> FEATURE:
<223> OTHER INFORMATION: Synthetic polypeptide

<400> SEQUENCE: 20

Tyr Glu Glu Gln Asn Gln Ala Thr Leu Glu Glu Ala Glu Gln Lys Glu
1               5                   10                  15

```
Ala Glu Phe Gln Gln Met Leu Glu Gln Leu Lys Lys Gln Gln Glu Glu
            20                  25                  30

Ala Gln Ala Ala Ala Ala Ala Ser Ala Glu Ser Arg Asp Phe Ser
        35                  40                  45

Gly Ala Gly Gly Ile Gly Val Phe Ser Glu Ser Ser Val Ala Ser
    50                  55                  60

Lys Leu Ser Ser Lys Ser Glu Lys Glu Leu Lys Asn Arg Arg Lys Lys
 65                  70                  75                  80

Lys Lys Gln Lys Glu Gln Ala Gly Glu Glu Lys Glu Asp Ala Val
                85                  90                  95

Arg Lys Ser Ala Ser Glu Asp Ser Ile Arg Lys Lys Gly Phe Gln Phe
                    100                 105                 110

Ser Leu Glu Gly Ser Arg Leu Thr Tyr Glu Lys Arg Phe Ser Ser Pro
            115                 120                 125

His Gln Ser Leu Leu Ser Ile Arg Gly Ser Leu Phe Ser Pro Arg Arg
    130                 135                 140

Asn Ser Arg Ala Ser Leu Phe Asn Phe Lys Gly Arg Val Lys Asp Ile
145                 150                 155                 160

Gly Ser Glu Asn Asp Phe Ala Asp Glu His Ser Thr Phe Glu Asp
                165                 170                 175

Asn Asp Ser Arg Arg Asp Ser Leu Phe Val Pro His Arg His Gly Glu
            180                 185                 190

Arg Arg Pro Ser Asn Val Ser Gln Ala Ser Arg Ala Ser Arg Gly Ile
        195                 200                 205

Pro Thr Leu Pro Met Asn Gly Lys Met His Ser Ala Val Asp Cys Asn
    210                 215                 220

Gly Val Val Ser Leu Val Gly Pro Ser Ala Leu Thr Ser Pro Val
225                 230                 235                 240

Gly Gln Leu Leu Pro Glu Gly Thr Thr Thr Glu Thr Glu Ile Arg Lys
                245                 250                 255

Arg Arg Ser Ser Ser Tyr His Val Ser Met Asp Leu Leu Glu Asp Pro
                260                 265                 270

Ser Arg Gln Arg Ala Met Ser Met Ala Ser Ile Leu Thr Asn Thr Met
            275                 280                 285

Glu Glu Leu Glu Glu Ser Arg Gln Lys Cys Pro Pro Cys Trp Tyr Lys
290                 295                 300

Phe Ala Asn Met Cys Leu Ile Trp Asp Cys Cys Lys Pro Trp Leu Lys
305                 310                 315                 320

Val Lys His Val Val Asn
                325

<210> SEQ ID NO 21
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 21

Gly Gly Ser Gly Gly Thr Gly Gly Ser Gly Gly Thr
1               5                   10

<210> SEQ ID NO 22
<211> LENGTH: 24
<212> TYPE: PRT
<213> ORGANISM: Artificial Sequence
```

<220> FEATURE:
<223> OTHER INFORMATION: Synthetic polypeptide

<400> SEQUENCE: 22

Gly Gly Ser Gly Gly Thr Gly Gly Ser Gly Gly Thr Gly Gly Ser Gly
1               5                   10                  15
Gly Thr Gly Gly Ser Gly Gly Thr
            20

<210> SEQ ID NO 23
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 23

Gly Gly Ser Gly Gly Ser Gly Gly Thr Gly Gly Ser Gly Gly Ser Gly
1               5                   10                  15
Gly Thr Gly Gly Ser Gly Gly Ser Gly Gly Thr
            20                  25

<210> SEQ ID NO 24
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 24

Gly Gly Ser Gly Gly Thr Gly Gly Ser Gly Gly Thr Gly Gly Ser Gly
1               5                   10                  15
Gly Thr Gly Gly Ser Gly Gly Thr Gly Gly Ser Gly Gly Thr Gly Gly
            20                  25                  30
Ser Gly Gly Thr Gly Gly Ser Gly Gly Thr Gly Gly Ser Gly Gly Thr
        35                  40                  45

<210> SEQ ID NO 25
<211> LENGTH: 96
<212> TYPE: PRT
<213> ORGANISM: Artificial Sequence
<220> FEATURE:
<223> OTHER INFORMATION: Synthetic polypeptide

<400> SEQUENCE: 25

Gly Gly Ser Gly Gly Thr Gly Gly Ser Gly Gly Thr Gly Gly Ser Gly
1               5                   10                  15
Gly Thr Gly Gly Ser Gly Gly Thr Gly Gly Ser Gly Gly Thr Gly Gly
            20                  25                  30
Ser Gly Gly Thr Gly Gly Ser Gly Gly Thr Gly Gly Ser Gly Gly Thr
        35                  40                  45
Gly Gly Ser Gly Gly Thr Gly Gly Ser Gly Gly Thr Gly Gly Ser Gly
    50                  55                  60
Gly Thr Gly Gly Ser Gly Gly Thr Gly Gly Ser Gly Gly Thr Gly Gly
65                  70                  75                  80
Ser Gly Gly Thr Gly Gly Ser Gly Gly Thr Gly Gly Ser Gly Gly Thr
                85                  90                  95

<210> SEQ ID NO 26
<211> LENGTH: 192
<212> TYPE: PRT
<213> ORGANISM: Artificial Sequence
<220> FEATURE:
<223> OTHER INFORMATION: Synthetic polypeptide

<400> SEQUENCE: 26

Gly Gly Ser Gly Gly Thr Gly Gly Ser Gly Gly Thr Gly Gly Ser Gly
1               5                   10                  15
Gly Thr Gly Gly Ser Gly Gly Thr Gly Gly Ser Gly Gly Thr Gly Gly
                20                  25                  30
Ser Gly Gly Thr Gly Gly Ser Gly Gly Thr Gly Gly Ser Gly Gly Thr
            35                  40                  45
Gly Gly Ser Gly Gly Thr Gly Gly Ser Gly Gly Thr Gly Gly Ser Gly
        50                  55                  60
Gly Thr Gly Gly Ser Gly Gly Thr Gly Gly Ser Gly Gly Thr Gly Gly
65                  70                  75                  80
Ser Gly Gly Thr Gly Gly Ser Gly Gly Thr Gly Gly Ser Gly Gly Thr
            85                  90                  95
Gly Gly Ser Gly Gly Thr Gly Gly Ser Gly Gly Thr Gly Gly Ser Gly
        100                 105                 110
Gly Thr Gly Gly Ser Gly Gly Thr Gly Gly Ser Gly Gly Thr Gly Gly
        115                 120                 125
Ser Gly Gly Thr Gly Gly Ser Gly Gly Thr Gly Gly Ser Gly Gly Thr
        130                 135                 140
Gly Gly Ser Gly Gly Thr Gly Gly Ser Gly Gly Thr Gly Gly Ser Gly
145                 150                 155                 160
Gly Thr Gly Gly Ser Gly Gly Thr Gly Gly Ser Gly Gly Thr Gly Gly
            165                 170                 175
Ser Gly Gly Thr Gly Gly Ser Gly Gly Thr Gly Gly Ser Gly Gly Thr
            180                 185                 190

<210> SEQ ID NO 27
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 27

Gly Gly Ser Gly Gly Thr
1               5

CELL BODY TARGETED SENSORS

RELATED APPLICATIONS

This application claims priority under 35 U.S.C. § 371 to international application number PCT/US2019/065773, filed Dec. 11, 2019, which claims the benefit under 35 U.S.C. § 119 (e) of U.S. Provisional application Ser. No. 62/778,004 filed on Dec. 11, 2018, the disclosure of each of which is incorporated by reference herein in its entirety.

GOVERNMENT INTEREST

This invention was made with government support under Grant No(s) R01_EB024261, R01_MH103910, R24_MH106075, NS087724 and R44_EB021054, awarded by the National Institutes of Health (NIH). The government has certain rights in the invention.

FIELD OF THE INVENTION

The invention, in some aspects, relates to polypeptide molecules and their encoding nucleic acid molecules and use of such molecules, to target molecules such as calcium sensors, to the soma of cells in which they are expressed. Compositions of the invention may be delivered to cells and subjects and used in methods to assess activity sensors in living cells, tissues, and organisms.

BACKGROUND OF THE INVENTION

Conventional calcium sensors are not-targeted, meaning they are expressed through the entirety of neurons, in the cell body and in cellular processes, because the cell body is covered with multiple cellular processes. Thus existing calcium sensors don not permit determination of whether a signal that is read at a cell body of interest really originated from that cell body, or from other cells. This "noise" is called neuropil contamination, and leads to multiple kinds of artifact that hinder imaging the "ground truth" spiking of neurons, such as non-physiological correlations, spikes being read out in the cell body while originating from cellular processes of a neighboring cells, and poor, multi-cellular resolution. Thus, there remain difficulties that negatively impact the ability to determine activity at a level of single cell resolution.

In recent years, methods for one-photon fluorescent imaging of calcium dynamics in vivo, including epifluorescent, endoscopic, and light-sheet methods, have become popular techniques for neural activity mapping in living larval zebrafish, mice, and other species. In conjunction with fluorescent calcium indicators, these techniques capture, at high speeds (e.g., 20 Hz or more), the dynamics of hundreds of neurons across large fields of view, at a low equipment complexity and cost (Alivisatos et al., 2013: Grienberger and Konnerth, 2012; Keller et al., 2015). For the purposes of neural spike extraction, neuroscientists typically focus on analyzing the data from cell bodies of neurons being imaged.

SUMMARY OF THE INVENTION

According to an aspect of the invention, compositions are provided that include a soma-targeting polypeptide, wherein the soma-targeting polypeptide includes at least one of an EE-RR polypeptide or functional variant thereof; and an Anktail motif polypeptide or functional variant thereof. In some embodiments, the soma-targeting polypeptide further includes a cargo polypeptide, and when the soma-targeting and cargo polypeptides are expressed in a cell, the cargo polypeptide is positioned within 60 microns of the cell soma. In certain embodiments, when the soma-targeting and cargo polypeptides are expressed in a cell, the cargo polypeptide is positioned within 50 microns, 40 microns, 30 microns, 20 microns, 10 microns, or 5 microns of the cell soma. In some embodiments, the cargo polypeptide includes an indicator polypeptide. In some embodiments, the indicator polypeptide includes a detectable label, the detectability of which is altered with activation of the indicator polypeptide. In certain embodiments, the indicator polypeptide is a calcium sensor. In some embodiments, the calcium sensor is a GCaMP polypeptide. In some embodiments the calcium sensor is a GCaMP6f polypeptide. In certain embodiments the calcium sensor is a GCaMP7f polypeptide. In certain embodiments, the calcium sensor includes a fluorescent detectable label and activating the calcium sensor alters the level of fluorescence of the detectable label. In some embodiments, the composition includes a fusion protein comprising the soma-targeting polypeptide and the indicator polypeptide. In some embodiments, the soma-targeting polypeptide includes an EE-RR polypeptide having the amino acid sequence set forth as SEQ ID NO: 2. In some embodiments, the EE-RR polypeptide functional variant includes the amino acid sequence of SEQ ID NO: 2 with 1, 2, 3, 4, 5, or more amino acid sequence modifications. In certain embodiments, the amino acid sequence of the EE-RR polypeptide functional variant has at least: 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence of SEQ ID NO: 2. In some embodiments, the soma-targeting polypeptide includes an Anktail motif polypeptide having the amino acid sequence set forth as SEQ ID NO: 1. In some embodiments, the Anktail motif polypeptide functional variant includes the amino acid sequence of SEQ ID NO: 1 with 1, 2, 3, 4, 5, or more amino acid sequence modifications. In certain embodiments, the amino acid sequence of the Anktail motif polypeptide functional variant has at least 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence of SEQ ID NO: 1. In some embodiments, the EE-RR polypeptide or functional variant thereof and the cargo polypeptide or the Anktail motif polypeptide or functional variant thereof and the cargo polypeptide are expressed in a cell. In some embodiments, the cell is a vertebrate cell and optionally a mammalian cell. In certain embodiments, the cell is an excitable cell. In some embodiments, the composition is a pharmaceutical composition and includes a pharmaceutically acceptable carrier. In some embodiments, the composition also includes one or more of a: trafficking agent molecule, targeting agent molecule, and detectable label molecule.

According to another aspect of the invention, a nucleic acid molecule comprising a sequence encoding the EE-RR polypeptide or a functional variant thereof; or an Anktail motif polypeptide or a functional variant thereof of any one of the aforementioned embodiments. In some embodiments, the nucleic acid molecule also includes a nucleic acid sequence encoding a cargo polypeptide. In certain embodiments, the cargo polypeptide includes an indicator polypeptide. In some embodiments, the nucleic acid sequence is a mammalian codon-optimized DNA sequence.

According to another aspect of the invention, a composition comprising the nucleic acid molecule of any of the forgoing embodiments is provided. In certain embodiments, the composition is a pharmaceutical composition and includes a pharmaceutically acceptable carrier. In some embodiments, the composition also includes one or more of a trafficking agent molecule, a targeting agent molecule, and a detectable label molecule.

According to another aspect of the invention, a vector comprising the nucleic acid molecule of any one of the aforementioned aspects and embodiments is provided. In some embodiments, the nucleic acid molecule is operatively linked to a promoter sequence. In certain embodiments, the vector also includes a nucleic acid molecule comprising a sequence encoding a cargo polypeptide, wherein the cargo polypeptide is optionally an indicator polypeptide. In some embodiments, when the encoded soma-targeting and cargo polypeptides are expressed together in a cell, the cargo polypeptide is positioned within 60 microns of the cell soma. In some embodiments, when the soma-targeting and cargo polypeptides are expressed together in a cell, the cargo polypeptide is positioned within 50 microns, 40 microns, 30 microns, 20 microns, 10 microns, or 5 microns of the cell soma. In certain embodiments, when the soma-targeting and cargo polypeptides are expressed together in a cell, the cargo polypeptide is positioned within the cell soma. In some embodiments, the indicator polypeptide includes a detectable label, the detectability of which is altered with activation of the indicator polypeptide. In some embodiments, the indicator polypeptide indicator polypeptide is a calcium sensor. In some embodiments, the calcium sensor includes a fluorescent detectable label and activating the calcium sensor alters the level of the fluorescence of the detectable label. In certain embodiments, an expression product of the vector is a fusion protein that includes the EE-RR polypeptide or functional variant thereof fused to the indicator polypeptide or that includes an Anktail motif polypeptide or functional variant thereof fused to the indicator polypeptide. In some embodiments, the vector also includes a nucleic acid sequence encoding one or more of a trafficking agent, a targeting agent, and a detectable label. In some embodiments, the vector is in a cell. In certain embodiments, the cell is a vertebrate cell, optionally is a mammalian cell, and optionally is an excitable cell. In some embodiments, the vector-encoded soma-targeting polypeptide includes an EE-RR polypeptide set forth as SEQ ID NO: 2. In some embodiments, the vector-encoded soma-targeting polypeptide includes an Anktail motif polypeptide set forth as SEQ ID NO: 1.

According to another aspect of the invention, a pharmaceutical composition that includes a vector of an embodiment of one of aforementioned aspects of the invention. In certain embodiments, the pharmaceutical composition also includes one or more of: a pharmaceutically acceptable carrier, a trafficking agent, a targeting agent, and a detectable label.

According to another aspect of the invention, a fusion protein that includes a soma-targeting polypeptide is provided, wherein the soma-targeting polypeptide agent includes at least one of an EE-RR polypeptide or functional variant thereof; and an Anktail motif polypeptide or functional variant thereof. In some embodiments, the fusion protein also includes a cargo polypeptide, wherein the cargo polypeptide is optionally an indicator polypeptide. In some embodiments, the cargo polypeptide includes a detectable label. In some embodiments, expressing the fusion protein in a cell, positions the cargo polypeptide within 60 microns of the cell soma. In certain embodiments, expressing the fusion protein positions the cargo polypeptide within 50 microns, 40 microns, 30 microns, 20 microns, 10 microns, or 5 microns of the cell soma. In some embodiments, expressing the fusion protein in a cell, positions the cargo polypeptide within the soma of the cell. In some embodiments, the indicator polypeptide includes a detectable label and activation of the indicator polypeptide alters the detectability of the detectable label, which indicates activation of the indicator polypeptide. In certain embodiments, the indicator polypeptide is a calcium sensor. In some embodiments, the calcium sensor includes a fluorescent detectable label and activating the indicator polypeptide alters the level of fluorescence of the detectable label. In some embodiments, the fusion protein is in a cell. In certain embodiments, the cell is a vertebrate cell, and optionally is a mammalian cell. In some embodiments, the cell is an excitable cell. In some embodiments, the soma-targeting polypeptide includes an EE-RR polypeptide sequence set forth as SEQ ID NO: 2. In some embodiments, the EE-RR polypeptide functional variant includes an amino acid sequence of SEQ ID NO: 2 with 1, 2, 3, 4, 5, or more amino acid sequence modifications. In certain embodiments, the amino acid sequence of the EE-RR polypeptide functional variant has at least: 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence of SEQ ID NO:2. In some embodiments, the soma-targeting polypeptide includes an Anktail motif polypeptide sequence set forth as SEQ ID NO: 1. In some embodiments, the Anktail motif polypeptide functional variant includes an amino acid sequence of SEQ ID NO: 1 with 1, 2, 3, 4, 5, or more amino acid sequence modifications. In certain embodiments, the amino acid sequence of the Anktail motif polypeptide functional variant has at least: 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence of SEQ ID NO: 1.

According to yet another aspect of the invention, a cell that includes an embodiment of any of the aforementioned aspects of a fusion protein is provided. In some embodiments, the cell is an in vitro cell.

According to another aspect of the invention, methods of identifying ion conductance activity in the soma of a cell are provided, the methods including: a) expressing in a host cell a fusion protein of an embodiment of any of the aforementioned fusion proteins, wherein the fusion protein includes a soma-targeting polypeptide and a cargo polypeptide: wherein the cargo polypeptide is an ion-conductance indicator polypeptide; and b) detecting a change in the ion-conductance indicator polypeptide, wherein a detected change identifies ion conductance activity in the cell. In some embodiments, the host cell is a vertebrate cell, optionally a mammalian cell. In certain embodiments, the host cell is a human cell. In some embodiments, the indicator polypeptide includes a calcium sensor. In some embodiments, the host cell is a neuron. In some embodiments, the host cell is a nervous system cell, a cardiac cell, a circulatory system cell, or an immune system cell. In certain embodiments, the neuron or nervous system cell is a visual system cell or an auditory system cell. In some embodiments, the soma-targeting polypeptide includes the amino acid sequence of an Anktail-motif polypeptide set forth as SEQ ID NO: 1 or a functional variant thereof, wherein the functional variant of SEQ ID NO: 1 includes the amino acid sequence of SEQ ID NO: 1 with 1, 2, 3, 4, 5, or more amino acid sequence modifications. In certain embodiments, the amino acid sequence of the functional variant of SEQ ID NO: 1 has at least: 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence of SEQ ID NO: 1. In some embodiments, the soma-targeting polypeptide includes the amino acid sequence of an EE-RR polypeptide set forth as SEQ ID NO: 2 or a functional variant thereof, wherein the functional variant of SEQ ID NO: 2 includes the amino acid sequence of SEQ ID NO: 2 with 1, 2, 3, 4, 5, or more amino acid sequence modifications. In some embodiments, the amino acid of the functional variant of SEQ ID NO: 2 has at least: 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence of SEQ ID NO: 2.

According to another aspect of the invention, methods of identifying an activity in the soma of a cell are provided, the methods including (a) expressing in a host cell, a fusion protein comprising a soma-targeting polypeptide and a cargo indicator polypeptide of an embodiment of any of the aforementioned aspects the invention, wherein the cargo polypeptide includes an indicator polypeptide and the expressed indicator polypeptide is positioned within 60 μM of the soma of the host cell: (b) stimulating the host cell; and (c) determining an alteration in an indicating characteristic of the indicator polypeptide, wherein an alteration indicates a change in an activity in the soma of the host cell. In certain embodiments, the presence of an alteration in the indicating characteristic of the indicator polypeptide is determined by: (d) detecting the indicating characteristic stimulated host cell: (e) comparing the detected indicating characteristic of (d) with a control of the indicating characteristic detected in a non-stimulated cell; and (f) determining a difference between the detection in (d) with the control detection, wherein an increase in the indicating characteristic in the host cell compared to the control, identifies an activity in the soma of the host cell. In some embodiments, the indicator polypeptide is an ion-conductance indicator polypeptide and an increase in ion-conductance increases the indicating characteristic. In some embodiments, the ion conduction is calcium conduction. In certain embodiments, the expressed indicator polypeptide includes a detectable label and activating the expressed indicator polypeptide increases the indicating characteristic of the detectable label, and an increase in the indicting characteristic indicates activation of the expressed indicator polypeptide. In some embodiments, the detectable label is fluorescence and an increase in the indicating characteristic is an increase in fluorescence. In some embodiments, the subject is a vertebrate, optionally a mammal. In certain embodiments, the subject is a human. In some embodiments, the soma-targeting polypeptide includes the amino acid sequence of an ankTail-motif polypeptide set forth as SEQ ID NO: 1 or a functional variant thereof, wherein the functional variant of SEQ ID NO: 1 includes the amino acid sequence of SEQ ID NO: 1 with 1, 2, 3, 4, 5, or more amino acid sequence modifications. In certain embodiments, the amino acid sequence of the functional variant of SEQ ID NO: 1 has at least: 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence of SEQ ID NO:1. In some embodiments, soma-targeting polypeptide includes the amino acid sequence of an EE-RR polypeptide set forth as SEQ ID NO: 2 or a functional variant thereof, wherein the functional variant of SEQ ID NO: 2 includes the amino acid sequence of SEQ ID NO: 2 with 1, 2, 3, 4, 5, or more amino acid sequence modifications. In some embodiments, the amino acid of the functional variant of SEQ ID NO: 2 has at least: 80%, 81%, 82%, 83%, 84%, 85%, 86%, 87%, 88%, 89%, 90%, 91%, 92%, 93%, 94%, 95%, 96%, 97%, 98%, or 99% sequence identity to the amino acid sequence of SEQ ID NO: 2.

The present invention is not intended to be limited to a system or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE DRAWINGS

FIG. 1A-V provides schematic diagrams, photomicrographic images and graphs relating to somatic GCaMP6f variants. Untargeted GCaMP expresses throughout the neural cytosol. One can image several cells, but each cell body is surrounded by GCaMP-bearing neurites from other cells (FIG. 1A), which can bleed into the signals attributed to a given cell body (compare "actual" to "readout"). Restricting GCaMP expression to the cell body would enable imaging at single cell resolution (FIG. 1B), because neurites cannot contribute bleed-through signal to a cell body of interest. FIG. 1C-K presents representative images for cultured hippocampal neurons expressing wild-type vs. selectively soma-targeted GCaMP6f variants, as well as the countermarker mCardinal. FIG. 1C shows a hippocampal neuron in culture expressing GCaMP6f and mCardinal, seen in the GFP channel. FIG. 1D, shows the neuron of FIG. 1C, seen in the mCardinal channel (magenta). FIG. 1E shows a merge of FIG. 1C and FIG. 1D. FIG. 1F-H, as in FIG. 1C-E, but for a neuron expressing GCaMP6f-27-AnkTail-motif-ER2 (termed SomaGCaMP6f1). For FIG. 1C, 1F, and 1I, look up tables (LUTs) were identically set to the range of 50-1000. (FIG. 1L-N) Representative max projection images are presented for cultured hippocampal neurons expressing wild-type vs. selectively soma-targeted GCaMP7f, as well as the countermarker miRFP. (FIG. 1L) A hippocampal neuron in culture expressing GCaMP7f and miRFP, seen in the GFP channel. (FIG. 1M) The neuron of FIG. 1L, seen in the miRFP channel (magenta). (FIG. 1N) Merge of FIG. 1L and FIG. 1M. (FIG. 1O-Q) As in FIG. 1L-N, for a neuron expressing GCaMP7f-27-EE-RR (termed SomaGCaMP7f). For FIG. 1L and FIG. 1O, look up tables (LUTs) were identically set to the range of 50-4500. FIG. 1I-K, as in FIG. 1C-E, except for a neuron expressing GCaMP6f-27-EE-RR (termed SomaGCaMP6f2). Scale bars for FIG. 1E, 1H, 1K, IN, IQ: 20 μm. FIG. 1V, as in FIG. 1R, for neurons expressing GCaMP7f-27-EE-RR (SomaGCaMP7f; n=6 neurites from 6 cells from 2 cultures).

*** P<0.001, Wilcoxon rank sum test of neurite brightness followed by post-hoc test via Steel's test with GCaMP6f as a control group: see Table 3 for full statistics for FIG. 1).

Figure 2A:
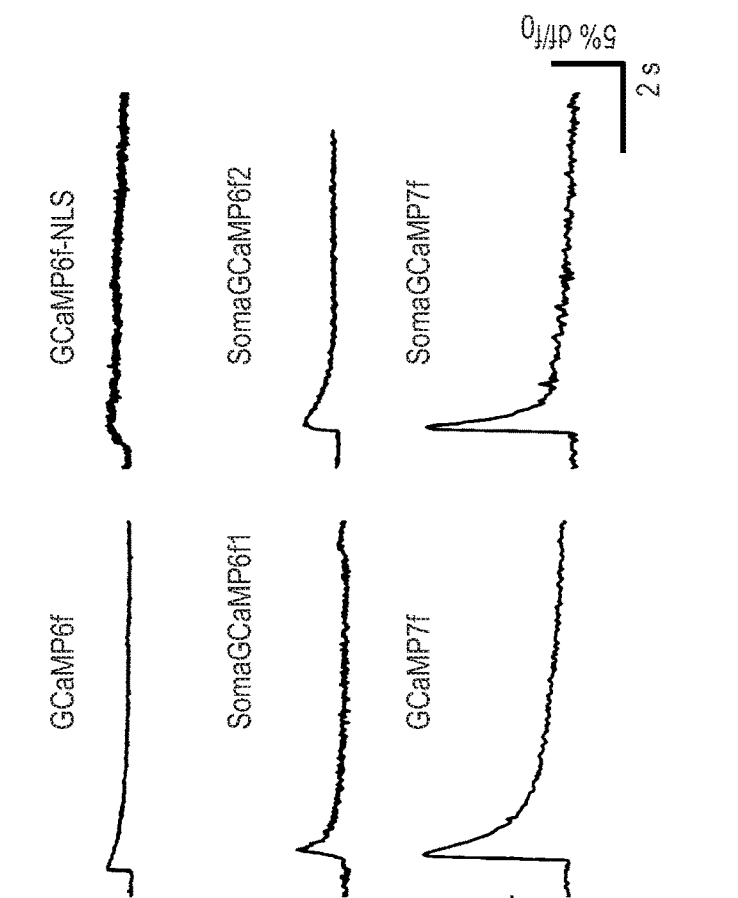
Figure 2B:
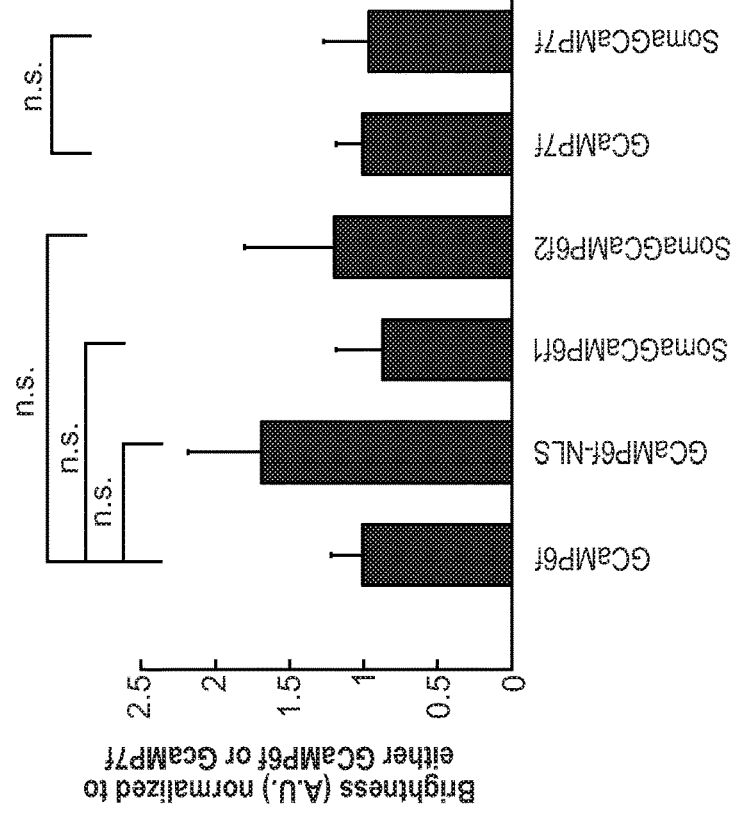
Figure 2C:
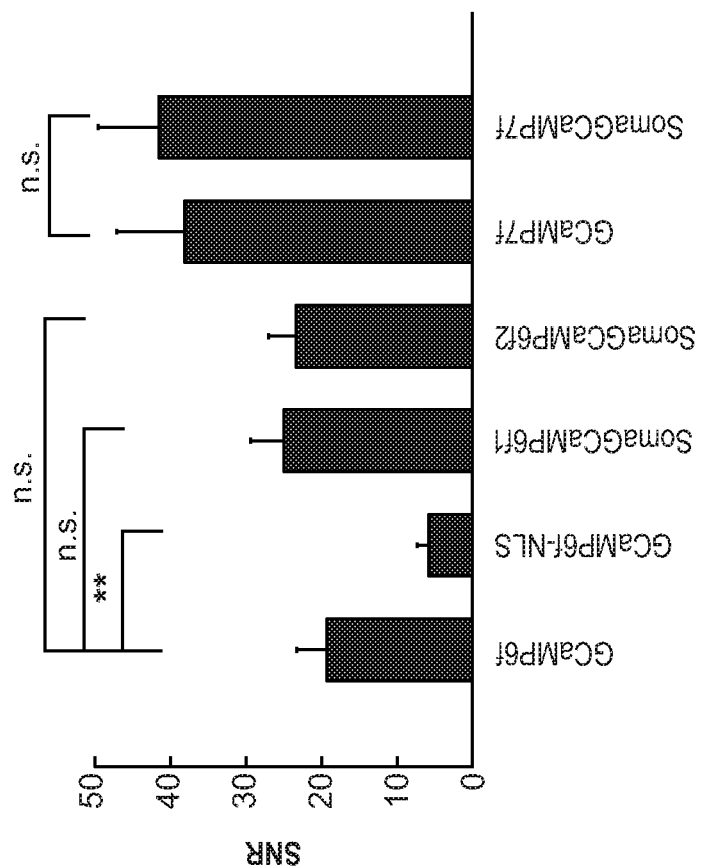
Figure 2D:
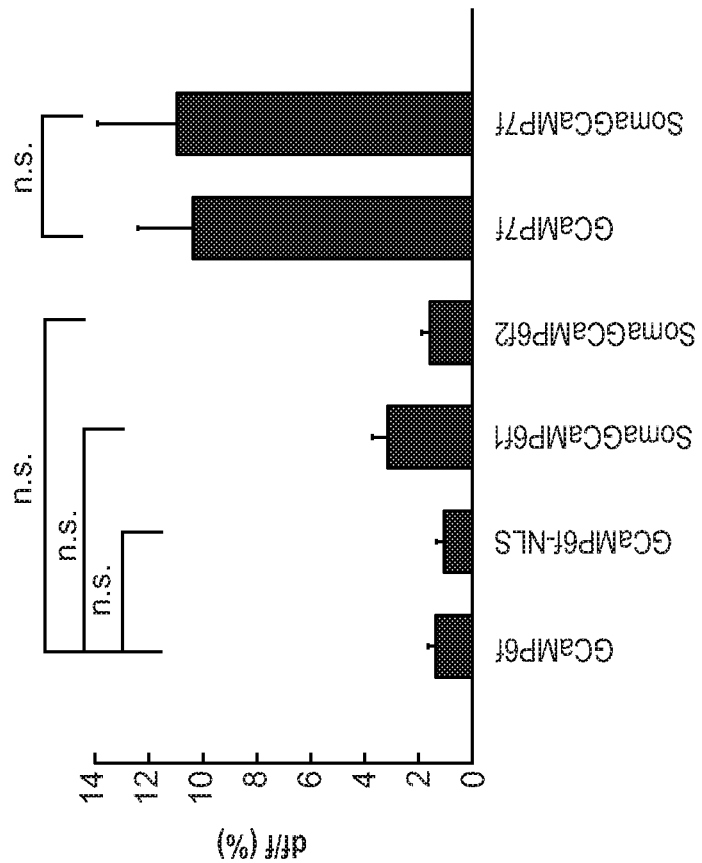

FIG. 2A-F provides graphs showing kinetics and sensitivity of SomaGCaMP6f1 and SomaGCaMP6f2, as compared to conventional and nuclear-targeted GCaMP6f, GCaMP6f. GCaMP6f-NLS (nuclear localization sequence), SomaGCaMP6f1, SomaGCaMP6f2, GCaMP7f and SomaGCaMP7f were transfected into hippocampal neurons for patch clamp and imaging. FIG. 2A shows average baseline brightness values for GCaMP6f, GCaMP6f-NLS, SomaGCaMP6f1, SomaGCaMP6f2, GCaMP7f and SomaGCaMP7f (n=8 cells from 2 cultures for GCaMP6f; n=7 cells from 2 cultures for SomaGCaMP6f1; n=5 cells from 2 cultures for SomaGCaMP6f2; n=7 cells from 2 cultures for GCaMP6f-NLS; n=6 cells from 2 cultures for GCaMP7f; n=7 cells from 3 cultures for SomaGCaMP7f). GCaMP6f. GCaMP6f-NLS, SomaGCaMP6f1, and SomaGCaMP6f2 brightness are normalized to GCaMP6f bightness. GCaMP7f and SomaGCaMP7f brightness are normalized to GCaMP7f bightness. n.s., not significant; for GCaMP6f, GCaMP6f-NLS, SomaGCaMP6f1, and SomaGCaMP6f2. Kruskal-Wallis analysis of variance followed by post-hoc test via Steel's test with GCaMP6f as control group; for GCaMP7f and SomaGCaMP7f. Wilcoxon rank sum test: see Table 4 for full statistics for FIG. 2. Plotted is mean plus or minus standard error throughout the figure. FIG. 2B shows a representative fluorescence response for one action potential in the cell body for cultured neurons expressing GCaMP6f, GCaMP6f-NLS. SomaGCaMP6f1, SomaGCaMP6f2, GCaMP7f and SomaGCaMP7f. FIG. 2C shows $df/f_0$ for GCaMP6f, GCaMP6f-NLS, SomaGCaMP6f1, SomaGCaMP6f2, GCaMP7f and SomaGCaMP7f (n=8 cells from 2 cultures for GCaMP6f; n=5 cells from 2 cultures for SomaGCaMP6f1; n=7 cells from 2 cultures for SomaGCaMP6f2; n=8 cells from 2 cultures for GCaMP6f-NLS; n=6 cells from 2 cultures for GCaMP7f; n=7 cells from 3 cultures for SomaGCaMP7f). n.s., not significant; for GCaMP6f, GCaMP6f-NLS, SomaGCaMP6f1, and SomaGCaMP6f2. Kruskal-Wallis analysis of variance followed by post-hoc test via Steel's test with GCaMP6f as control group; for GCaMP7f and SomaGCaMP7f. Wilcoxon rank sum test. FIG. 2D shows signal-to-noise ratio (SNR), defined as the magnitude of the fluorescence change caused by a single action potential divided by the standard deviation of the baseline fluorescence, for GCaMP6f, GCaMP6f-NLS, SomaGCaMP6f1, SomaGCaMP6f2, GCaMP7f and SomaGCaMP7f (n=8 cells from 2 cultures for GCaMP6f; n=5 cells from 2 cultures for SomaGCaMP6f1; n=7 cells from 2 cultures for SomaGCaMP6f2; n=8 cells from 2 cultures for GCaMP6f-NLS; n=6 cells from 2 cultures for GCaMP7f; n=7 cells from 3 cultures for SomaGCaMP7f).  P<0.01; n.s., not significant; for GCaMP6f, GCaMP6f-NLS, SomaGCaMP6f1, and SomaGCaMP6f2. Kruskal-Wallis analysis of variance followed by post-hoc test via Steel's test with GCaMP6f as control group; for GCaMP7f and SomaGCaMP7f. Wilcoxon rank sum test. FIG. 2E shows time constant for signal rise (Ton) during a single action potential for GCaMP6f, GCaMP6f-NLS, SomaGCaMP6f1. SomaGCaMP6f2, GCaMP7f and SomaGCaMP7f (n=8 cells from 2 cultures for GCaMP6f; n=5 cells from 2 cultures for SomaGCaMP6f1; n=6 cells from 2 cultures for SomaGCaMP6f2; n=8 cells from 2 cultures for GCaMP6f-NLS; n=6 cells from 2 cultures for GCaMP7f; n=7 cells from 3 cultures for SomaGCaMP7f). , P<0.01; n.s., not significant; for GCaMP6f, GCaMP6f-NLS, SomaGCaMP6f1, and SomaGCaMP6f2, Kruskal-Wallis analysis of variance followed by post-hoc test via Steel's test with GCaMP6f as control group; for GCaMP7f and SomaGCaMP7f, Wilcoxon rank sum test. FIG. 2F shows time constant for signal decay ($T_{off}$) after a single action potential for GCaMP6f, GCaMP6f-NLS, SomaGCaMP6f1, SomaGCaMP6f2, GCaMP7f and SomaGCaMP7f (n=7 cells from 2 cultures for GCaMP6f; n=5 cells from 2 cultures for SomaGCaMP6f1; n=7 cells from 2 cultures for SomaGCaMP6f2; n=8 cells from 2 cultures for GCaMP6f-NLS; n=6 cells from 2 cultures for GCaMP7f; n=7 cells from 3 cultures for SomaGCaMP7f.) *, P<0.05: n.s., not significant; for GCaMP6f, GCaMP6f-NLS, SomaGCaMP6f1, and SomaGCaMP6f2, Kruskal-Wallis analysis of variance followed by post-hoc test via Steel's test with GCaMP6f as control group; for GCaMP7f and SomaGCaMP7f, Wilcoxon rank sum test.

Figure 3B:
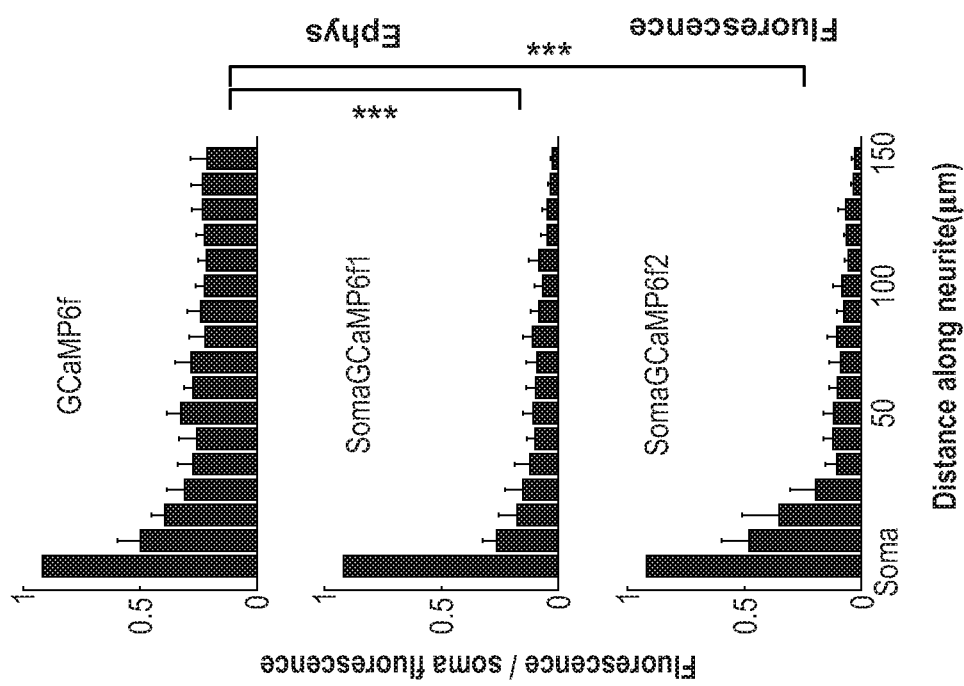
Figure 3A:
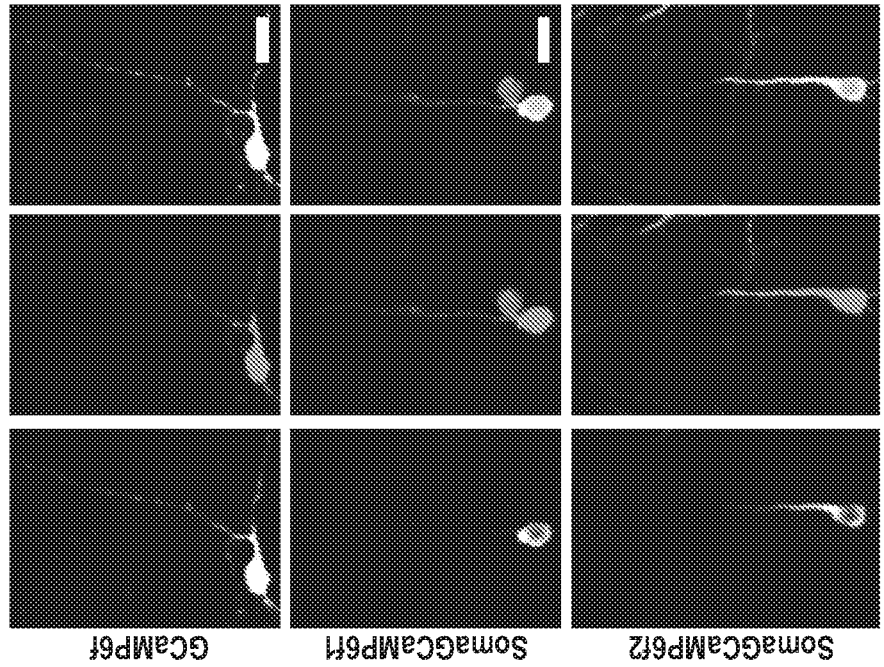
Figure 3C:
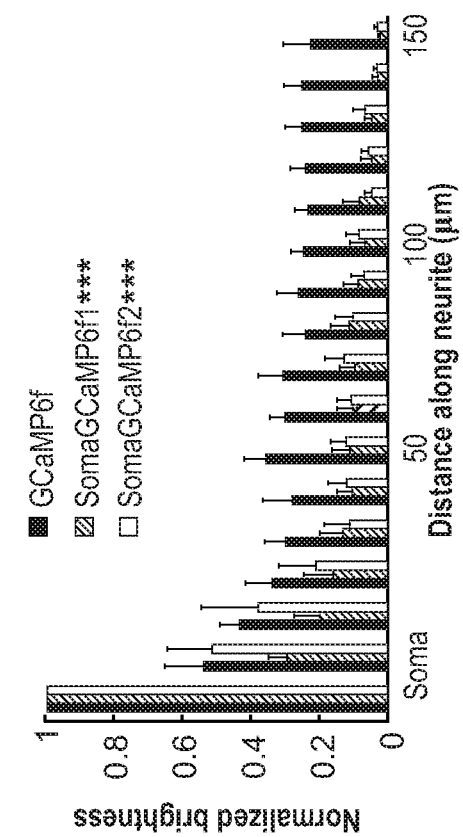
Figure 3D:
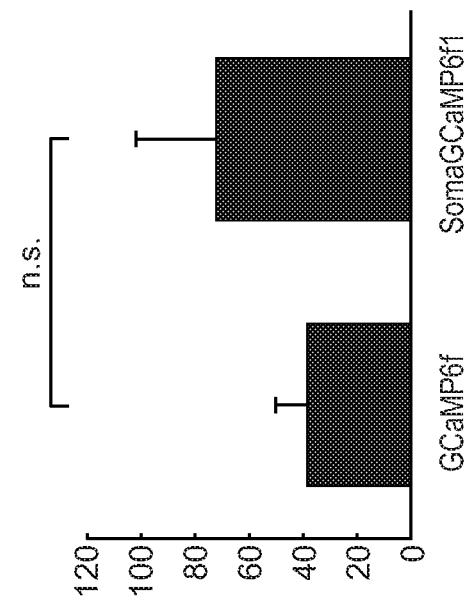
Figure 3E:
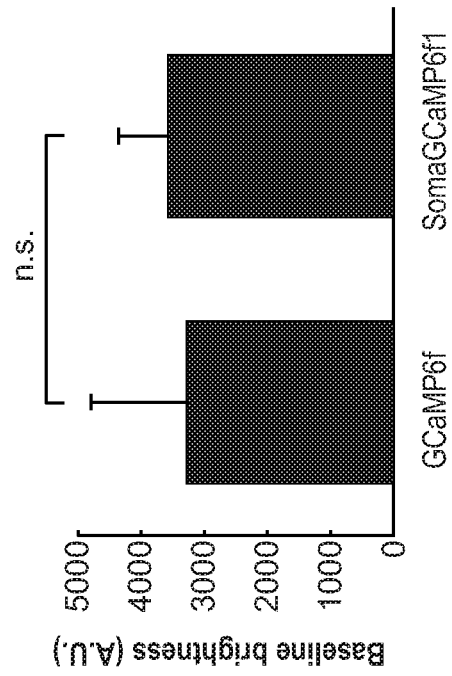
Figure 3F:
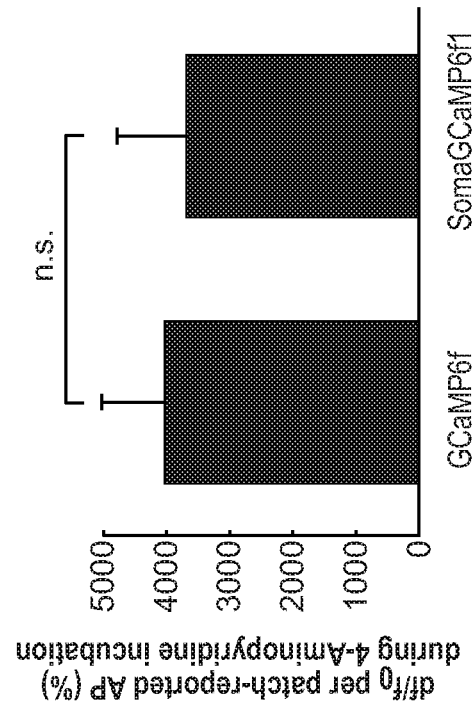

FIG. 3A-J provides photomicrographic images, bar charts, and traces that illustrate the decreased neuropil crosstalk in mouse brain slices expressing SomaGCaMP. FIG. 3A shows representative maximum intensity projections of confocal stacks of neurons expressing GCaMP6f, SomaGCaMP6f1, and SomaGCaMP6f2 in brain slices. GCaMP6f is presented in the left panels in green, mScarlet is given in magenta in the middle panels and the merged image is given in the right panels. Scale bar: 20 µm. Look up tables (LUTs) were identically set to the range of 0-450. FIG. 3B shows bar plots of GCaMP6f brightness/mScarlet brightness versus position along a neurite, normalized to GCaMP6f brightness/mScarlet brightness at the soma, extracted from neurites of neurons expressing GCaMP6f, SomaGCaMP6f1 or SomaGCaMP6f2 (for GCaMP6f, n=5 neurons from 4 slices from 2 mice: for SomaGCaMP6f1, n=9 neurons from 4 slices from 2 mice: for SomaGCaMP6f2, n=6, neurons from 3 slices from 2 mice.). * P<0.001, Kruskal-Wallis analysis of variance followed by post-hoc test via Steel's test: see Table 5 for full statistics for FIG. 3. Plotted is mean plus or minus standard error throughout this figure. FIG. 3C is a bar chart showing average baseline brightness values for cells expressing GCaMP6f or SomaGCaMP6f1 in brain slice, following light power tuning so that the baseline recorded brightness from GCaMP6f or SomaGCaMP6f1 slices were similar (n=7 neurons from 2 slices from 2 mice for GCaMP6f; n=22 neurons from 6 slices from 3 mice for SomaGCaMP6f1). n.s., not significant, Wilcoxon rank sum test of the brightness between GCaMP6f and SomaGCaMP6f1. FIG. 3D is a bar plot of brightness versus position along a neurite, normalized to brightness at the soma, extracted from neurites of neurons from slices expressing GCaMP6f, SomaGCaMP6f1 or SomaGCaMP6f2 (for GCaMP6f, n=5 neurons from 4 slices from 2 mice: for SomaGCaMP6f1, n=9 neurons from 4 slices from 2 mice: for SomaGCaMP6f2, n=6 neurons from 3 slices from 2 mice.). * P<0.001, Kruskal-Wallis analysis of variance followed by post-hoc test via Steel's test, comparing to GCaMP6f. FIG. 3E is a bar chart showing the average $df/f_0$ of somata of neurons in slices expressing GCaMP6f or SomaGCaMP6f1 during an action potential (n=14 APs from 3 neurons from 3 slices from 2 mice for GCaMP6f; n=6 APs from 3 neurons from 3 slices from 3 mice for SomaGCaMP6f1). n.s., not significant, Wilcoxon rank sum test of the $df/f_0$ between GCaMP6f and SomaGCaMP6f1. FIG. 3F is a bar chart showing the average SNR of somata of neurons in slices expressing GCaMP6f or somaGCaMP6f1 following an action potential (n=14 APs from 3 neurons from 3 slices from 2 mice for GCaMP6f; n=6

Figure 3H:
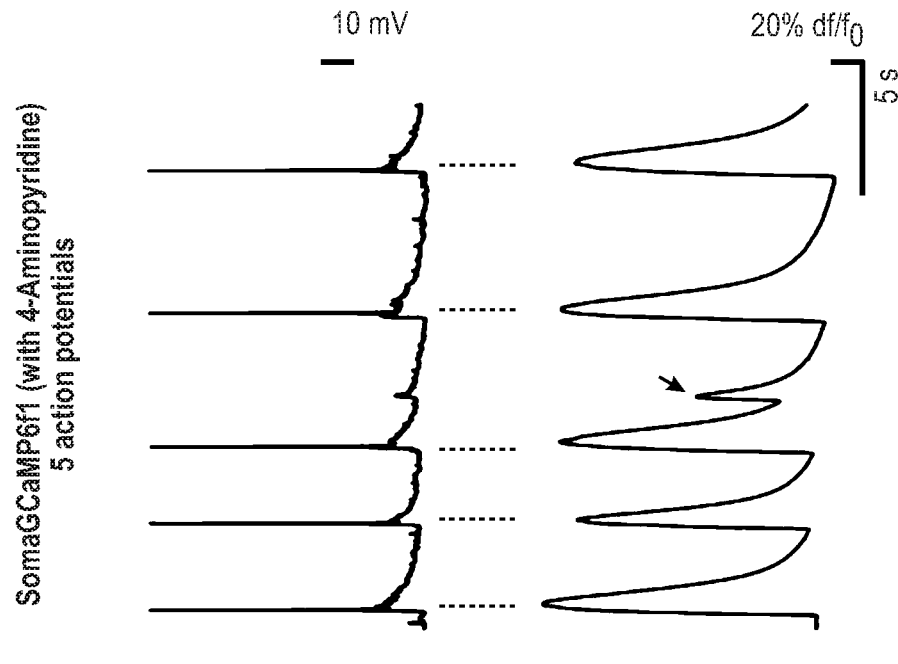
Figure 3G:
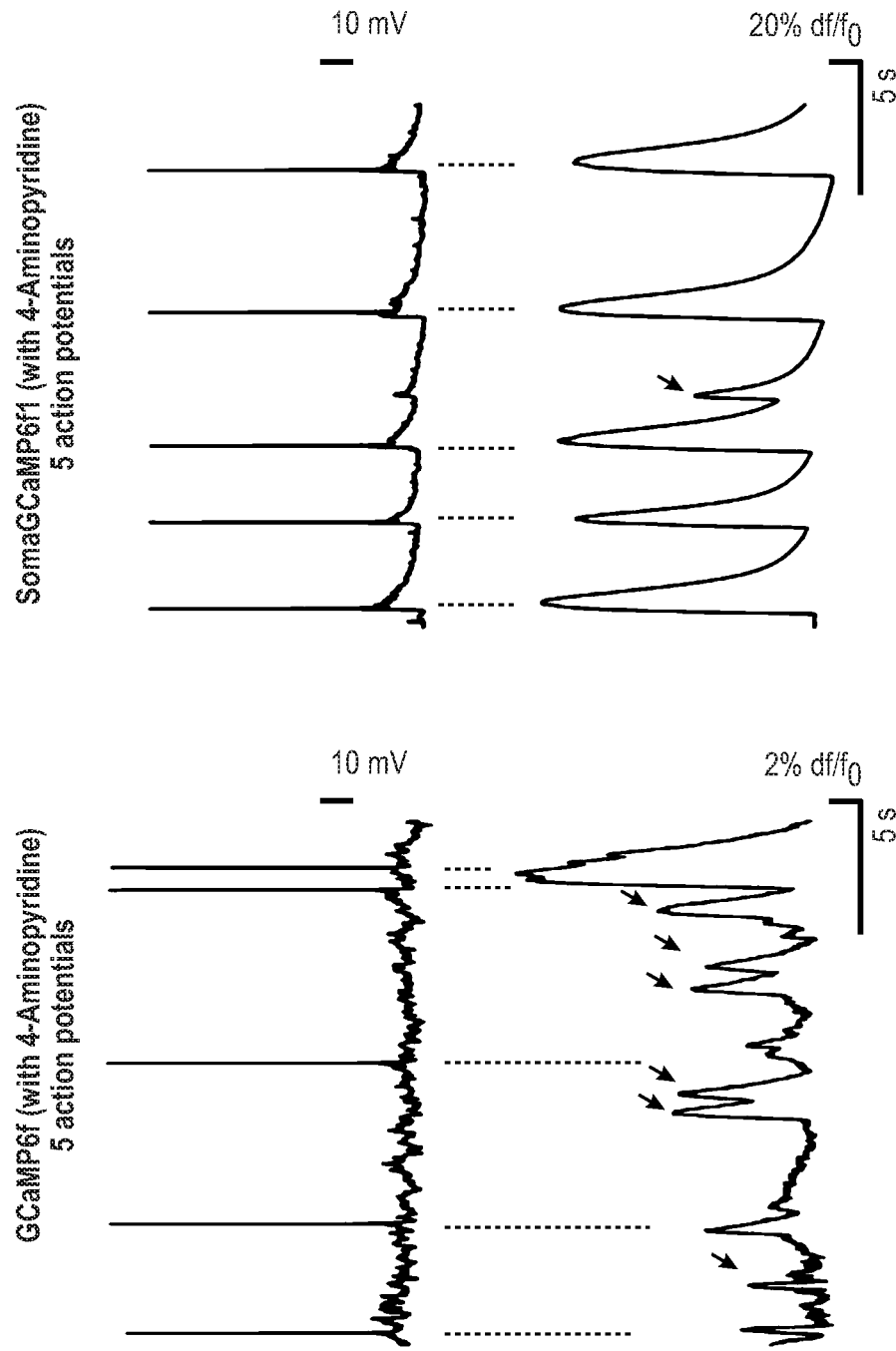
Figure 3I:
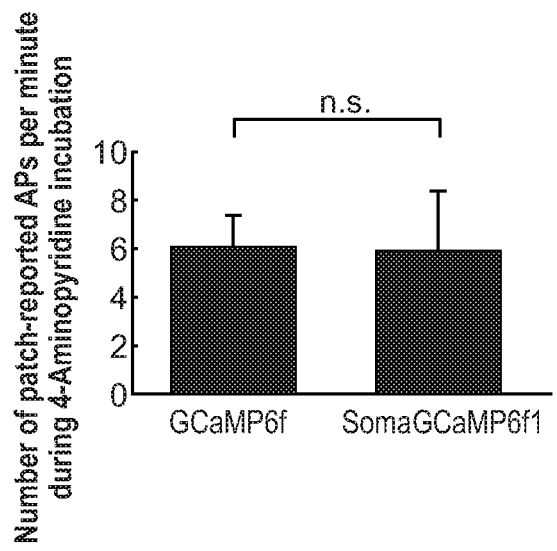
Figure 3J:
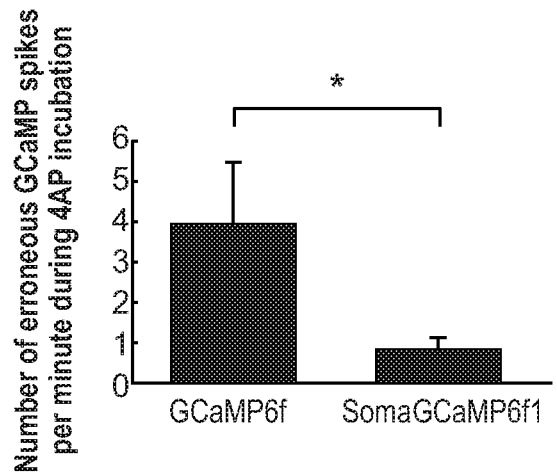

APs from 3 neurons from 3 slices from 3 mice for SomaGCaMP6f1). n.s., not significant, Wilcoxon rank sum test of the SNR between GCaMP6f and SomaGCaMP6f1. (FIG. G, top shows a representative electrophysiological recording of a cell expressing GCaMP6f in a slice, under 4-AP stimulation. FIG. 3G, bottom shows the GCaMP6f fluorescent signal in the cell recorded in FIG. 3G, top. Arrows denote peaks in the GCaMP fluorescent signal that do not have a corresponding patch-reported action potential (AP). FIG. 3H, top shows representative electrophysiological recording of a cell expressing SomaGCaMP6f1 in a slice, under 4-AP stimulation. FIG. 3H, bottom shows the SomaGCaMP6f1 fluorescent signal in the cell recorded from in FIG. 3H, top. Arrows denote peaks in the SomaGCaMP6f1 fluorescent signal that do not have a corresponding action potential. FIG. 3I is a bar chart showing the average number of patch-reported APs per minute in neurons in slices expressing GCaMP6f or somaGCaMP6f1 following an action potential (n=8 neurons from 8 slices for GCaMP6f from 4 mice: n=6 neurons from 6 slices for SomaGCaMP6f1 from 3 mice). n.s., not significant, Wilcoxon rank sum test of the average number of APs per minute between GCaMP6f and SomaGCaMP6f1. FIG. 3J is a bar chart showing the number of erroneous GCaMP-spikes per minute in neurons expressing either GCaMP6f or SomaGCaMP6f1 in slice (n=8 neurons from 8 slices from 4 mice for GCaMP6f; n=6 neurons from 6 slices from 3 mice for SomaGCaMP6f1). * P<0.05, Wilcoxon rank sum test of the number of fluorescent peaks minus the number of APs between GCaMP6f and SomaGCaMP6f1 expressing neurons.

Figure 4F:
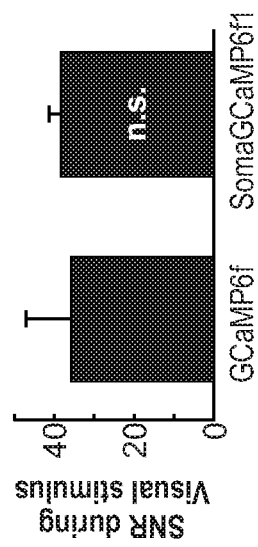
Figure 4H:
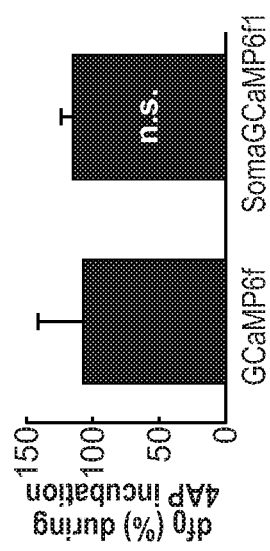
Figure 4G:
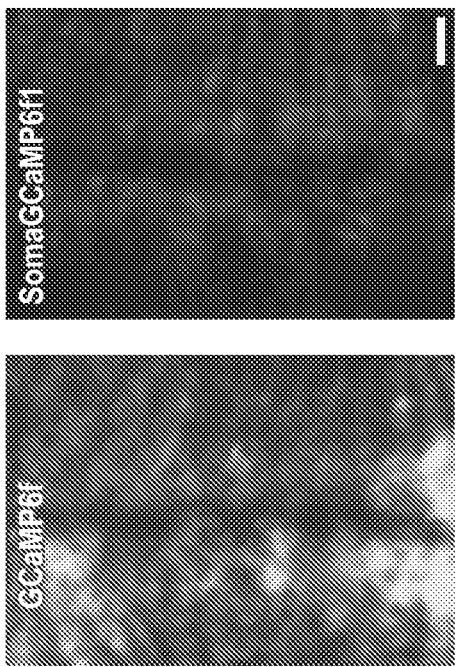
Figure 4I:
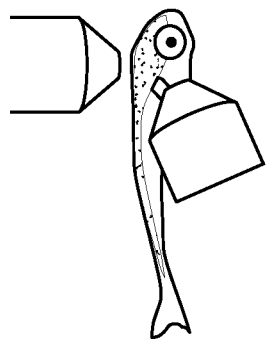
Figure 4J:
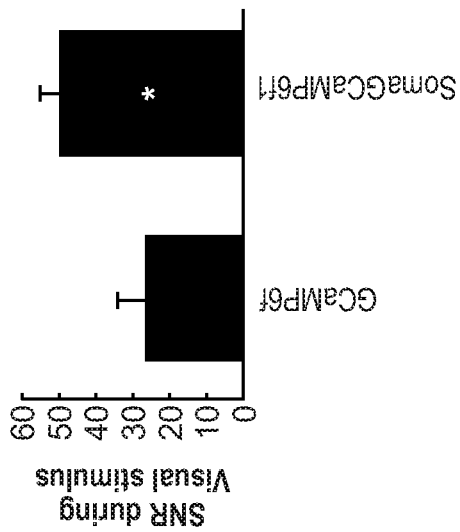
Figure 4K:
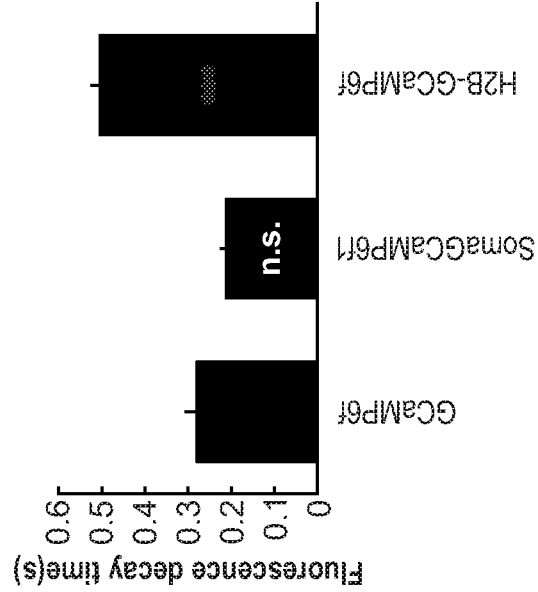
Figure 4L:
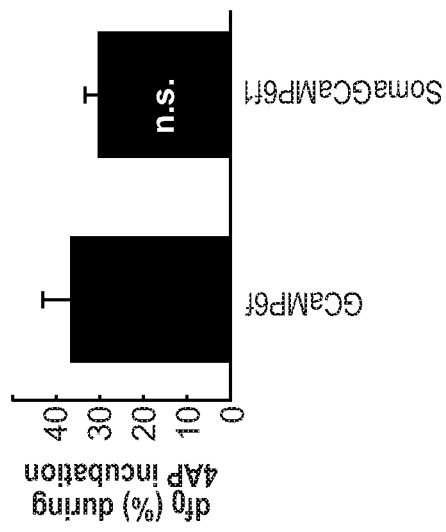
Figure 4M:
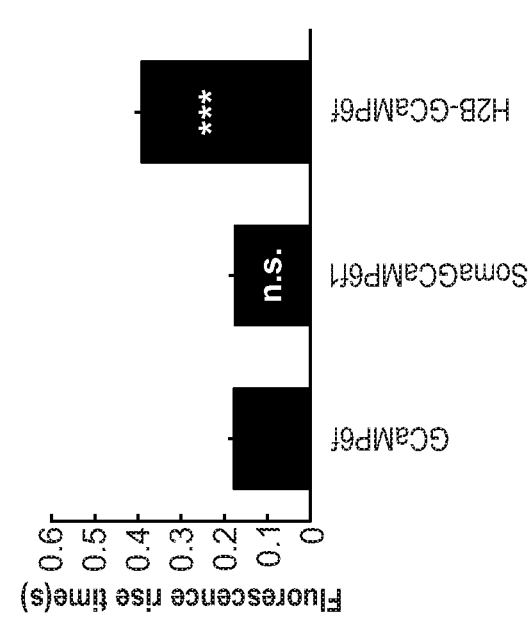
Figure 4N:
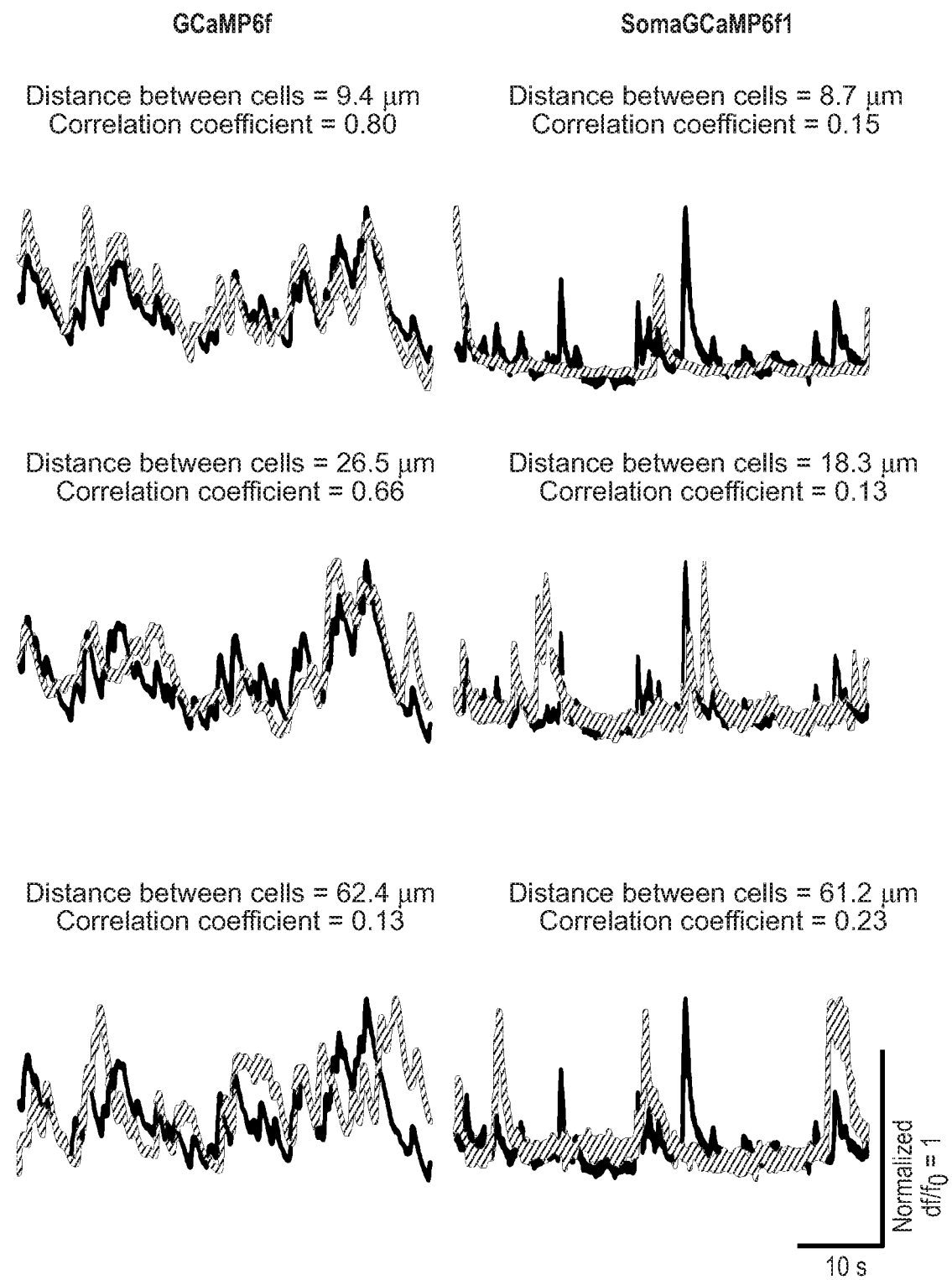
Figure 40:
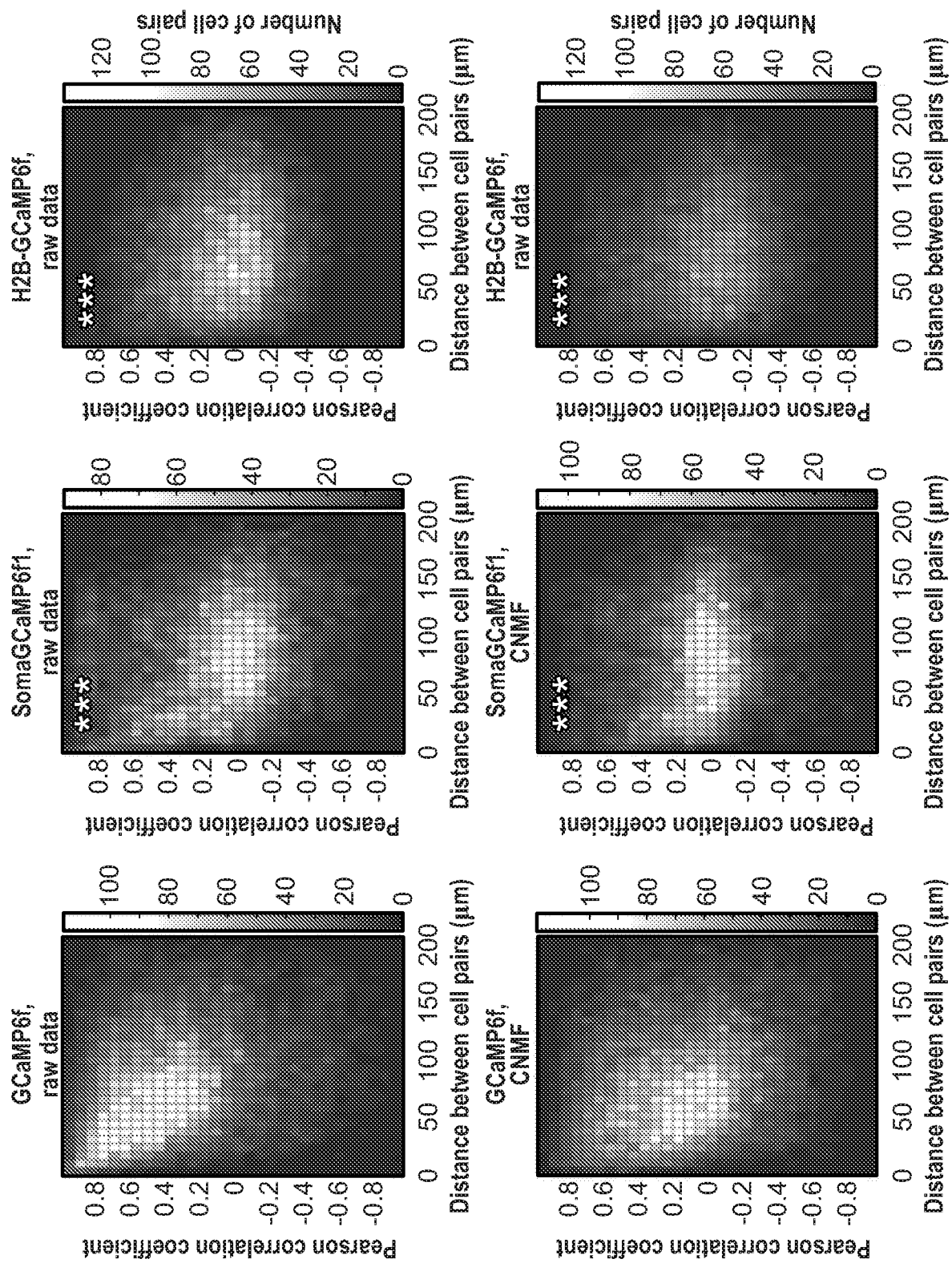

FIG. 4A-O provides schematic diagrams, photomicrographic images, bar charts, and traces illustrating decreased neuropil crosstalk in SomaGCaMP6f1-expressing larval zebrafish. FIG. 4A shows a schematic image of embryos (1-2 cell stage) that were injected with 20 ng/μl of elavl3: GCaMP6f, or elavl3: SomaGCaMP6f1, or elavl3: GCaMP7f, or elavl3: SomaGCaMP7f. FIG. 4B provides representative images of neurons transiently expressing GCaMP6f, SomaGCaMP6f1, GCaMP7f, SomaGCaMP7f in zebrafish larvae at 5 dpf. GCaMP6f is presented in the left panels in green, mCherry is given in magenta in the middle panels and the merged image is given in the right panels. Scale bar: 5 μm. Look up tables (LUTs) were identically set to the range of 30-3000. FIG. 4C, top provides bar plots of GCaMP brightness/mCherry brightness divided by SomaGCaMP brightness/mCherry versus position along a neurite, extracted from neurites of zebrafish neurons expressing GCaMP6f (n=8 neurons from 4 fishes) and SomaGCaMP6f1 (n=7 neurons from 6 fishes). FIG. 4C, bottom provides bar plots of GCaMP brightness/mCherry brightness divided by SomaGCaMP brightness/mCherry versus position along a neurite, extracted from neurites of zebrafish neurons expressing GCaMP7f (n=5 neurons from 3 fishes) and SomaGCaMP7f (n=5 neurons from 3 fishes). FIG. 4D shows a schematic of fish exhibiting transient expression in the brain that were selected and imaged under the 2-photon microscope. A forward moving grating was used as a stimulus as GCaMP6f or SomaGCaMP6f1 expressing cells were imaged at 15 Hz. For the two-photon experiments (FIG. 4E, FIG. 4F, and FIG. 4G): for GCaMP6f experiments, 20s on/20s off stimulus periods were used: for SomaGCaMP6f1, 10s on/10s off (the difference in frequencies between GCaMP6f and SomaGCaMP6f1 was inadvertent). FIG. 4E shows representative calcium traces for SomaGCaMP6f1-expressing cells and for GCaMP6f-expressing cells in response to the moving grating. FIG. 4F is a bar chart showing the average $df/f_0$ of somata of neurons in the optic tectum of zebrafish expressing GCaMP6f or SomaGCaMP6f1 in response to the moving grating (n=6 neurons from 3 fishes for GCaMP6f; n=5 neurons from 3 fishes for SomaGCaMP6f1). n.s., not significant, Wilcoxon rank sum test of the $df/f_0$ between GCaMP6f and SomaGCaMP6f1.FIG. 4G is a bar chart showing the average signal-to-noise ratio (SNR, see definition in Methods) of somata of neurons in the optic tectum of zebrafish expressing GCaMP6f or SomaGCaMP6f1 in response to the moving grating (n=6 neurons from 3 fishes for GCaMP6f; n=5 neurons from 3 fishes for SomaGCaMP6f1). n.s., not significant, Wilcoxon rank sum test of the SNR between GCaMP6f and SomaGCaMP6f1. FIG. 4H is a schematic image of one of the fish exhibiting stable pan-neuronal expression in the brain that were selected and imaged using a lightsheet microscope. 4-AP stimulation was used for the experiments described in panels FIG. 4J-M. FIG. 4I provides an image of neurons expressing GCaMP6f (left) taken at a depth of 70 μm from the top of the brain or SomaGCaMP6f1 (right) taken 70 μm from the top of the brain, in the midbrain of zebrafish. Scale bar: 10 μm. FIG. 4J is a bar chart showing the average $df/f_0$ of calcium events in the somata of zebrafish neurons in the forebrain expressing GCaMP6f or SomaGCaMP6f1 and stimulated with 4-AP (n=5 neurons from 2 fishes for GCaMP6f; n=5 neurons from 2 fishes for SomaGCaMP6f1). n.s., not significant, Wilcoxon rank sum test of the $df/f_0$ between GCaMP6f and SomaGCaMP6f1. FIG. 4K is a bar chart showing the average signal-to-noise ratio (SNR) of somata of zebrafish neurons in the forebrain expressing GCaMP6f or SomaGCaMP6f1 and stimulated with 4-AP (n=5 neurons from 2 fishes for GCaMP6f; n=5 neurons from 2 fishes for SomaGCaMP6f1) . * P<0.05, Wilcoxon rank sum test of the SNR between GCaMP6f and SomaGCaMP6f1. FIG. 4L is a bar chart showing the average fluorescence rise time (Ton) of somata of zebrafish neurons in the forebrain expressing GCaMP6f, SomaGCaMP6f1 or H2B-GCaMP6f and stimulated with 4-AP (n=101 neurons from 5 fishes for GCaMP6f; n=146 neurons from 4 fishes for SomaGCaMP6f1; n=513 neurons from 6 fishes for H2B-GCaMP6f). * P<0.001, Kruskal-Wallis analysis of variance followed by post-hoc test via Steel's test. FIG. 4M is a bar chart showing the average fluorescence decay time ($T_{off}$) of somata of zebrafish neurons in the forebrain expressing GCaMP6f, SomaGCaMP6f1 or H2B-GCaMP6f and stimulated with 4-AP (n=101 neurons from 5 fishes for GCaMP6f; n=146 neurons from 4 fishes for SomaGCaMP6f1; n=513 neurons from 6 fishes for H2B-GCaMP6f). * P<0.001, Kruskal-Wallis analysis of variance followed by post-hoc test via Steel's test. FIG. 4N shows traces, normalized to their respective maxima for clarity, of representative cell pairs in the forebrain expressing GCaMP6f (left) or SomaGCaMP6f1 (right) that are ~10 μm (top row), ~20 μm (middle row) and ~50 μm (bottom row) apart, during 4-AP stimulation. Pearson correlation coefficients between the traces are denoted above them. FIG. 4O provides a density plot showing the Pearson correlation coefficients of cell pairs in the forebrain as a function of the distance between cell pairs for GCaMP6f (n=426 cells from 5 fishes), SomaGCaMP6f1 (n=340) cells from 4 fishes) or H2B-GCaMP6f (n=676 cells from 6 fishes), during 4-AP stimulation. Top, analysis was performed using raw data: bottom, analysis was performed using data subjected to the neuropil contamination elimination algorithm CNMF. *** P<0.001, two-dimensional Kolmogorov-Smirnov test between GCaMP6f and SomaGCaMP6f1: two-dimensional Kolmogorov-Smirnov test between GCaMP6f and H2B-GCaMP6f.

Figure 5E:
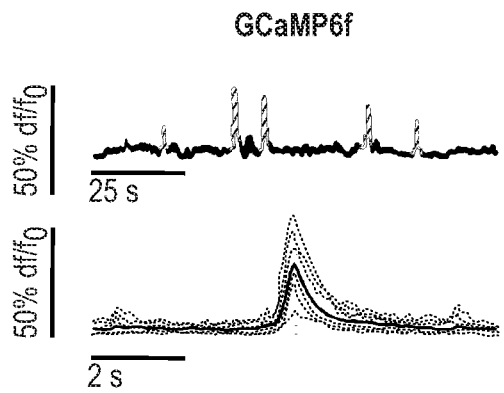
Figure 5F:
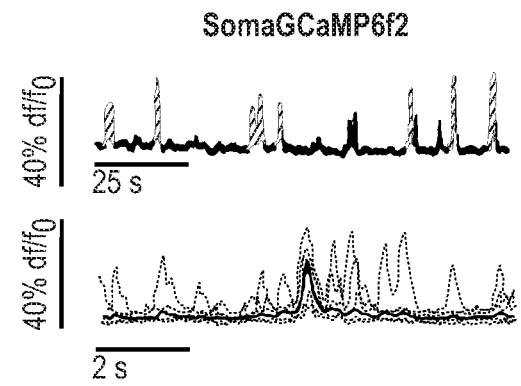
Figure 5G:
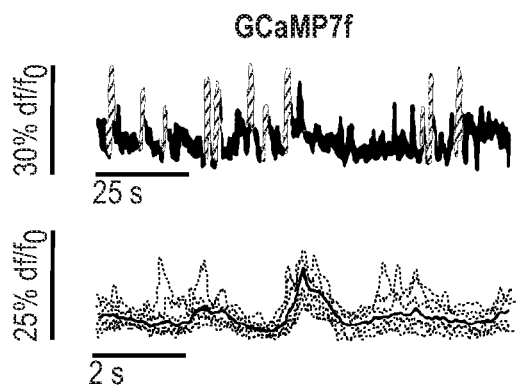
Figure 5H:
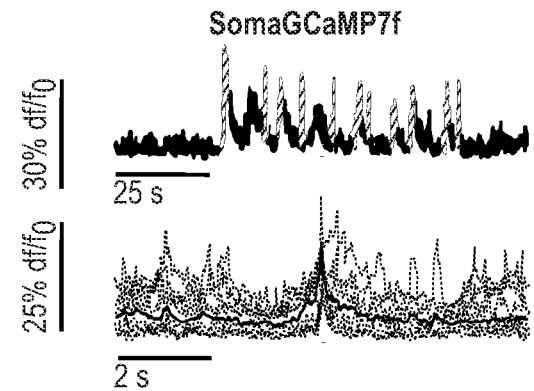
Figure 5I:
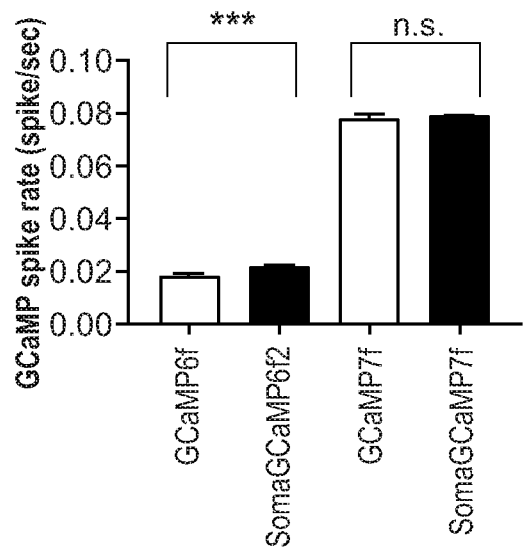
Figure 5J:
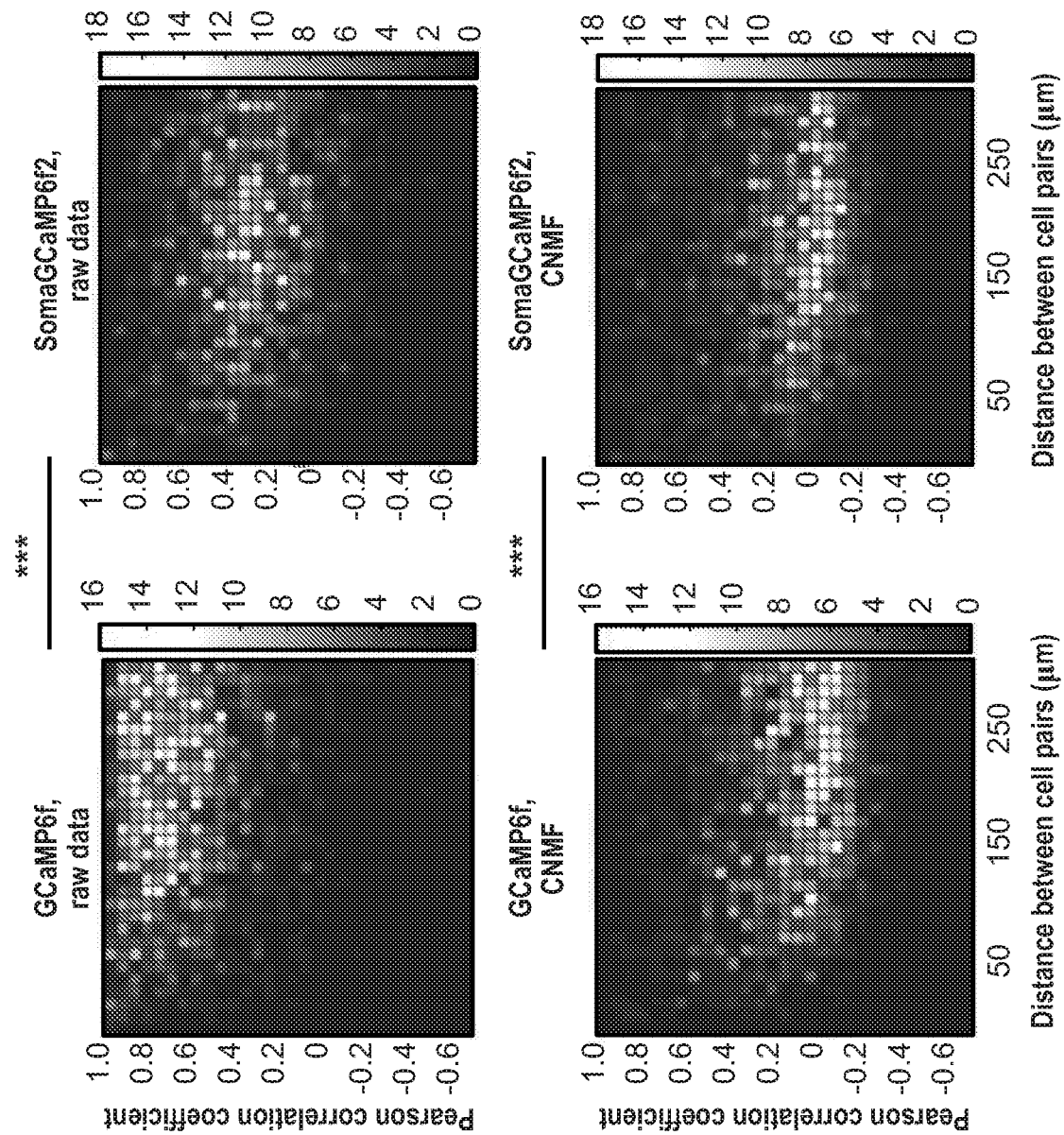
Figure 5K:
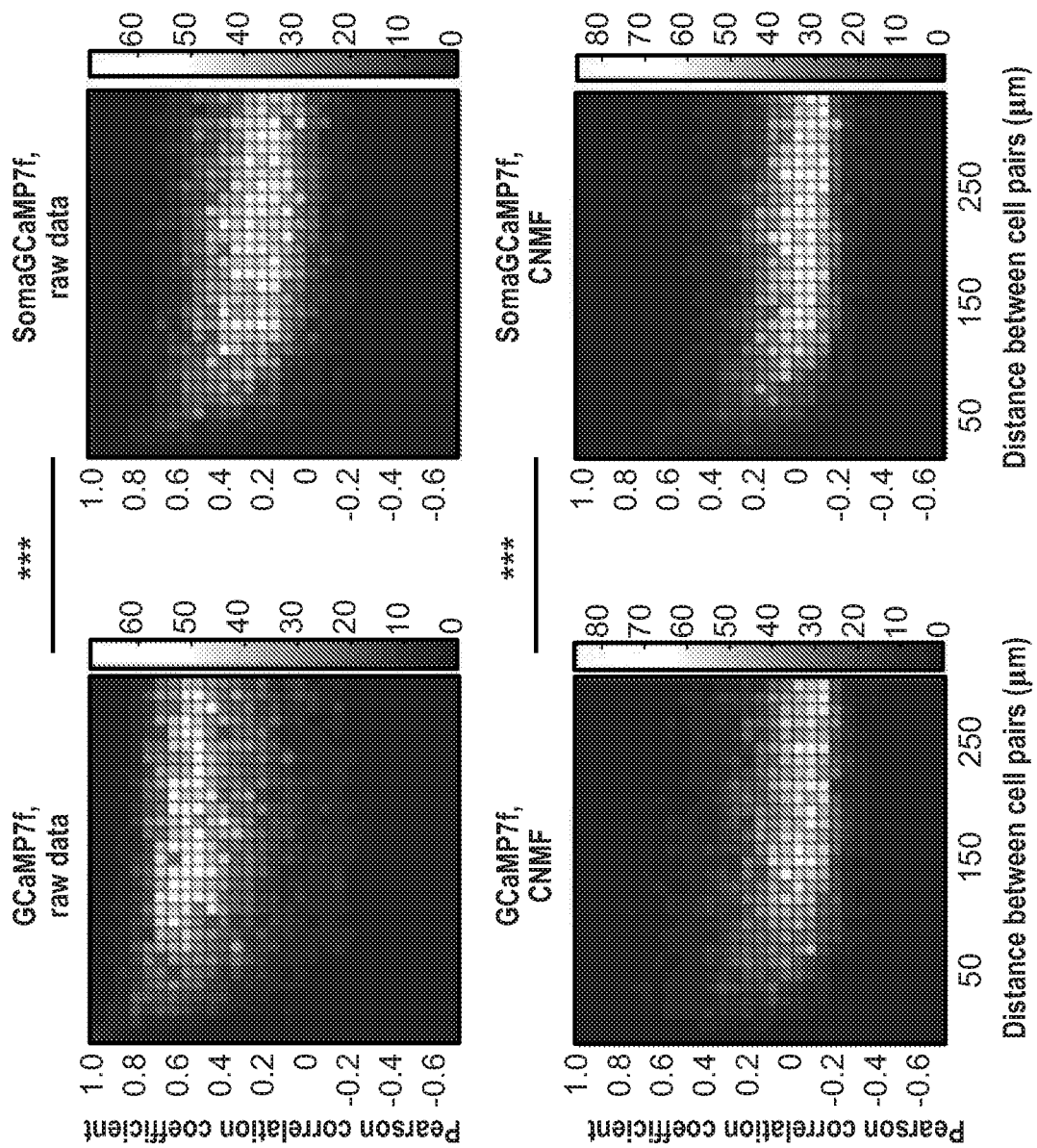
Figure 5L:
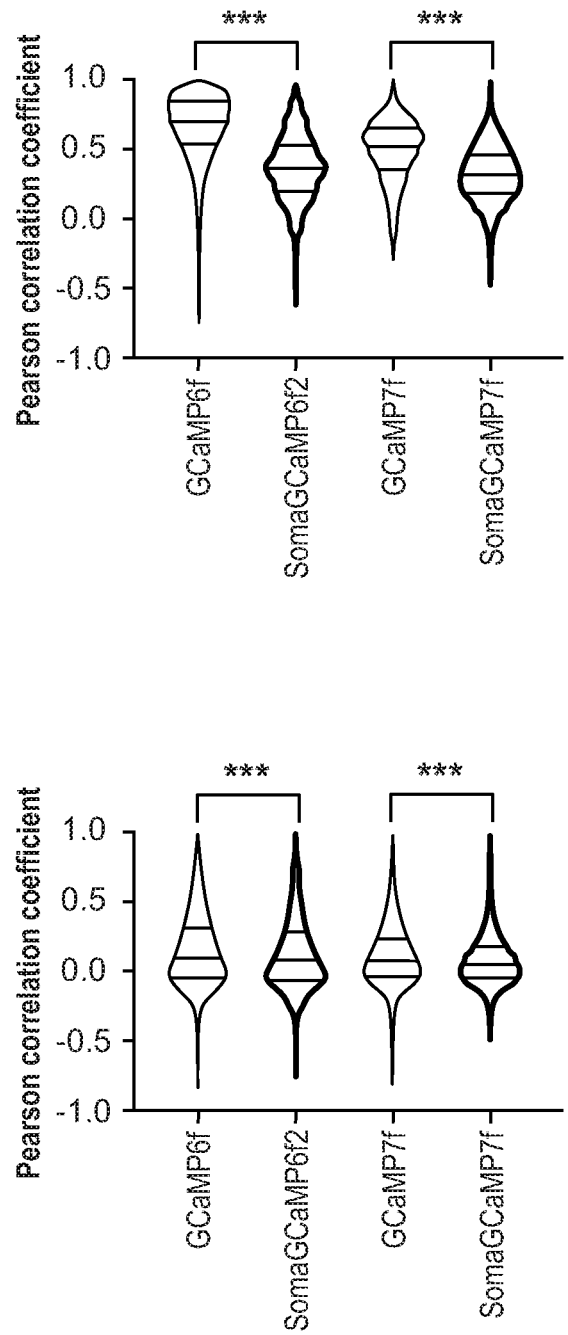

FIG. 5A-L provides photomicrographic images, traces, plots, and bar graphs of results indicating that SomaGCaMP6f2 reduces neuropil contamination in the striatum of behaving mice. FIGS. 5A and 5B provides representative projection images showing the summed fluorescence, across all frames acquired in an epifluorescent imaging session (i.e., so that any neuron active at any time can be visualized), from the dorsal striatum in GCaMP6f-(FIG. 5A) or SomaGCaMP6f2-(FIG. 5B) or GCaMP7f-(FIG. 5A) or SomaGCaMP7f-(FIG. 5B) expressing mice. Calcium imaging was performed using a 460 nm LED, with each imaging session lasting 5-12 minutes. Scale bar: 100 μm. Histogram of pixel values are given at the top-right corner of each image. For FIGS. 5A and 5B, look up tables (LUTs) were identically set to the range of 5000-65535. FIGS. 5C and 5D provide representative projection images showing the summed fluorescence, across all frames acquired in an epifluorescent imaging session (i.e., so that any neuron active at any time can be visualized), from the dorsal striatum in GCaMP7f-(FIG. 5C) or SomaGCaMP7f-(FIG. 5D) expressing mice. Calcium imaging was performed using a 460 nm LED, with each imaging session lasting 5-12 minutes. Scale bar: 100 μm. Histogram of pixel values are given at the top-right corner of each image. For FIG. 5C and FIG. 5D, look up tables (LUTs) were identically set to the range of 4000-50000. FIGS. 5E and 5F provide representative calcium traces from two neurons shown in the images above that reflect GCaMP6f (FIG. 5E), or SomaGCaMP6f2 (FIG. 5F), fluorescence over a two minute (top) window. Normalized calcium traces are shown in blue as changes in $df/f_0$. Calcium activation events were identified based on thresholding (see Methods) and detected individual events are highlighted in red. Note that smaller events were not always detected using this methodology. Bottom: traces show calcium signals from the full session traces shown above, aligned to their peak amplitude. Individual events are shown in gray and their averaged response is shown in black. (FIGS. 5G and 5H show representative calcium traces from two neurons shown in the images above that reflect GCaMP7f (FIG. 5G), or SomaGCaMP7f2 (FIG. 5H), fluorescence over a two minute (top) window: Normalized calcium traces are shown in blue as changes in $df/f_0$. Calcium activation events were identified based on thresholding (see Methods) and detected individual events are highlighted in red. Note that smaller events were not always detected using this methodology. Bottom: traces show calcium signals from the full session traces shown above, aligned to their peak amplitude. Individual events are shown in gray and their averaged response is shown in black. FIG. 5I is a bar chart showing mean GCaMP-spike rates for neurons expressing either SomaGCaMP6f2 or GCaMP6f, or GCaMP7f, or SomaGCaMP7f (n=594 neurons from 4 mice expressing SomaGCaMP6f2, n=930 neurons from 6 GCaMP6f mice, n=1098 neurons from 5 mice expressing SomaGCaMP7f, n=634 neurons from 4 GCaMP7f mice). *P<0).001, Kruskal-Wallis analysis of variance followed by post-hoc test via Dunn's test; see Table 6 for full statistics for FIG. 5A-L. Shown throughout this figure is mean plus or minus standard error. FIG. 5J provides correlograms denoting the relationship of distance to the strength of correlated fluorescence between cell pairs from mice expressing GCaMP6f (left: n=860 cells from 6 mice) or SomaGCaMP6f2 (right: n=149 cells from 4 mice). Distance distributions are shown on the x-axis and Pearson correlation coefficients are shown on the y-axis. (FIG. 5J, top row) Analysis was performed using raw data. (FIG. 5J, bottom row) Analysis was performed using data subjected to the neuropil contamination elimination algorithm CNMF. * P<0.001, two-dimensional Kolmogorov-Smirnov test between GCaMP6f and SomaGCaMP6f1. FIG. 5K provides correlograms denoting the relationship of distance to the strength of correlated fluorescence between cell pairs from mice expressing GCaMP7f (left: n=634 cells from 4 mice) or SomaGCaMP7f (right: n=1098 cells from 5 mice). Distance distributions are shown on the x-axis and Pearson correlation coefficients are shown on the y-axis. (FIG. 5K, top row) Analysis was performed using raw data. (FIG. 5K, bottom row) Analysis was performed using data subjected to the neuropil contamination elimination algorithm CNMF. *** P<0.001, two-dimensional Kolmogorov-Smirnov test between GCaMP7f and SomaGCaMP7f. FIG. 5L provides a violin plot showing the mean Pearson correlation coefficients from all SomaGCaMP6f2 or GCaMP6f or SomaGCaMP7f or GCaMP7f mice (n=44890 cell-pairs from 4 SomaGCaMP6f2 mice: n=67795 cell-pairs from 6 GCaMP6f mice, n=10420 cell-pairs from 5 SomaGCaMP7f mice: n=12582 cell-pairs from 4 GCaMP7f mice). FIG. 5L, top shows results from analysis that was performed using raw data. (FIG. 5L, bottom, shows results from analysis that was performed using data subjected to the neuropil contamination elimination algorithm CNMF. * P<0.05. *** p<0.001, Kruskal-Wallis analysis of variance followed by post-hoc test via Dunn's test.

Figure 6A:
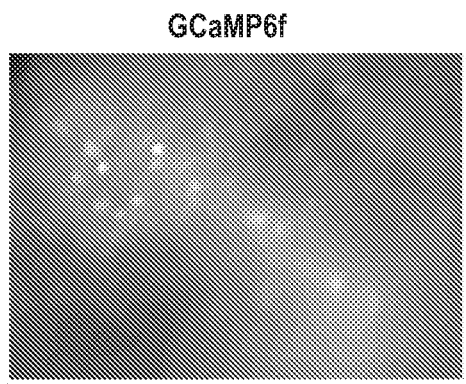
Figure 6B:
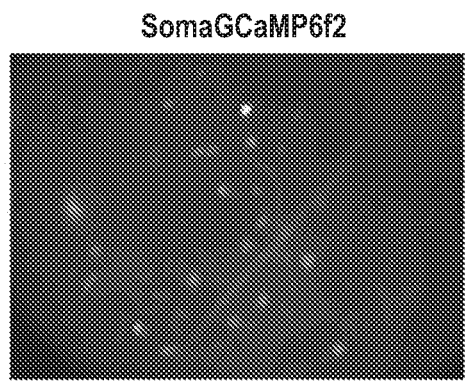
Figure 6C:
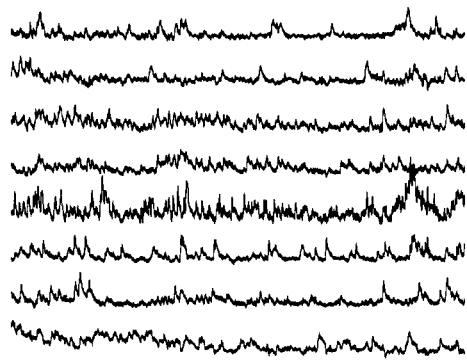
Figure 6D:
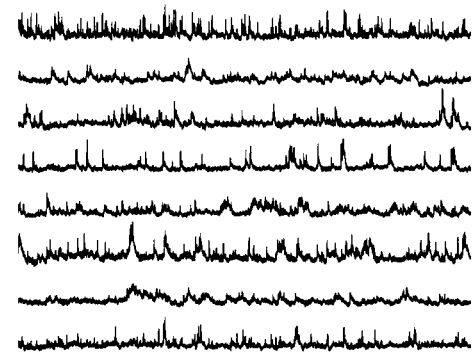
Figure 6E:
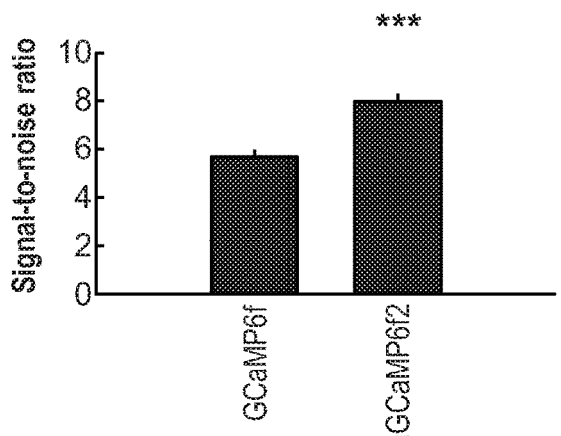
Figure 6F:
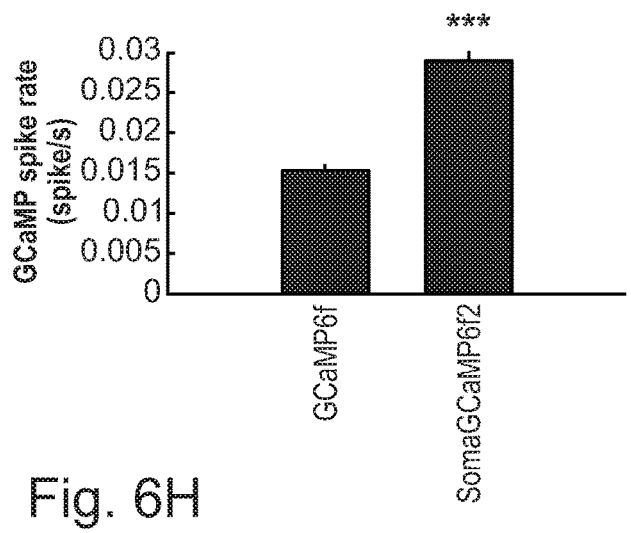
Figure 6G:
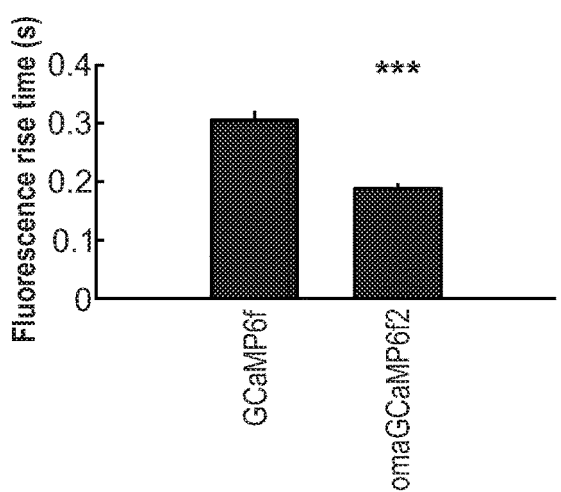
Figure 6H:
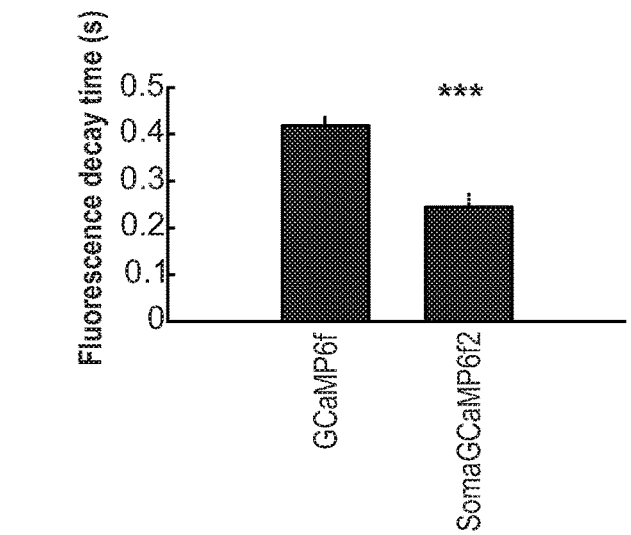

FIG. 6A-H shows images, traces and bar graphs showing results indicating that SomaGCaMP6f2 increases detectability of spiking neurons, SNR and speed of transients in the medial prefrontal cortex of awake mice. FIG. 6A, FIG. 6B show representative standard deviation images showing the fluctuation in fluorescence, across all frames acquired in an epifluorescent imaging session (i.e., so that any neuron active at any time can be visualized), from the medial prefrontal in GCaMP6f-(FIG. 6A) or SomaGCaMP6f2-(FIG. 6B) expressing mice. For FIG. 6A and FIG. 6B, look up tables (LUTs) were identically set to the range of 5-200. FIGS. 6C and 6D show representative calcium traces from ten neurons shown in the images above that reflect GCaMP6f (FIG. 6C), or SomaGCaMP6f2 (FIG. 6D), fluorescence over a 900s window. (FIG. 6E is a bar chart showing mean SNR for neurons expressing either SomaGCaMP6f2 or GCaMP6f (n=222 neurons from 4 mice expressing SomaGCaMP6f2, n=107 neurons from 2 GCaMP6f mice). * P<0.001, Wilcoxon rank sum test between the GCaMP-spike rates of SomaGCaMP6f2 and GCaMP6f expressing neurons: see Table 6 for full statistics for FIG. 6A-H. Plotted is mean plus or minus standard error throughout. FIG. 6F is a bar chart showing mean GCaMP-spike rates for neurons expressing either SomaGCaMP6f2 or GCaMP6f (n=222 neurons from 4 mice expressing SomaGCaMP6f2, n=107 neurons from 2 GCaMP6f mice). * P<0).001, Wilcoxon rank sum test between the GCaMP-spike rates of SomaGCaMP6f2 and GCaMP6f expressing neurons. FIG. 6G is a bar chart showing the mean fluorescence rise time (Ton) from all SomaGCaMP6f2 or GCaMP6f expressing cells (n=222 neurons from 4 SomaGCaMP6f2 expressing mice: n=107 neurons from 2 GCaMP6f expressing mice). *** P<0.001, Wilcoxon rank sum test between SomaGCaMP6f2 and GCaMP6f. FIG. 6H is a bar chart showing the mean fluorescence decay time ($T_{off}$) from all SomaGCaMP6f2 or GCaMP6f expressing cells (n=222 neurons from 4 SomaGCaMP6f2 expressing mice: n=107 neurons from 2 GCaMP6f expressing mice).

***P<0.001, Wilcoxon rank sum test between SomaGCaMP6f2 and GCaMP6f.

Figure 7F:
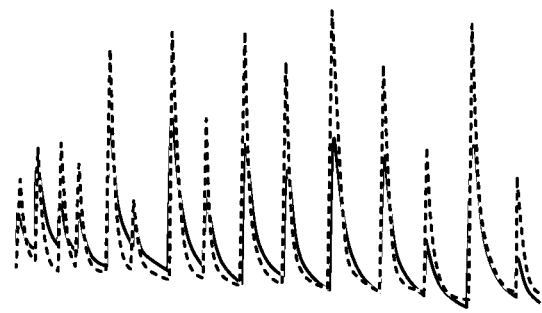
Figure 7G:
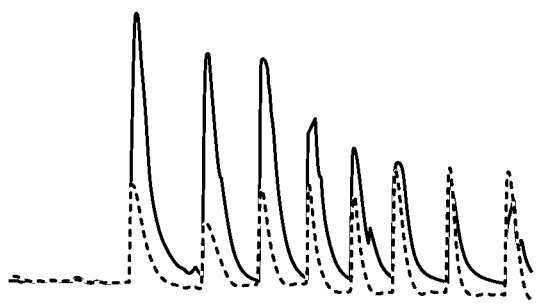
Figure 7H:
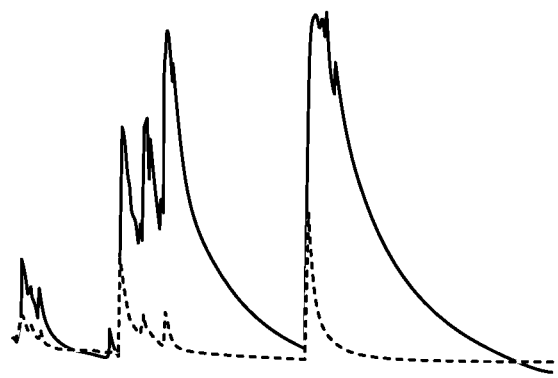
Figure 7I:
Figure 7J:
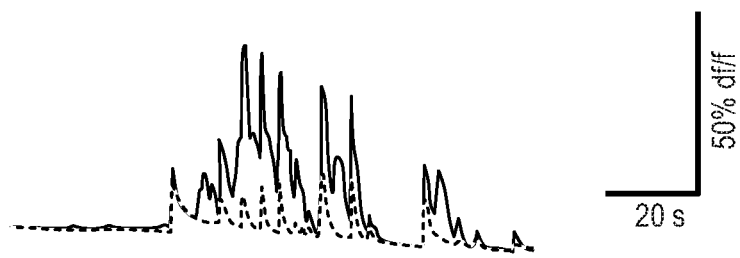
Figure 7K:
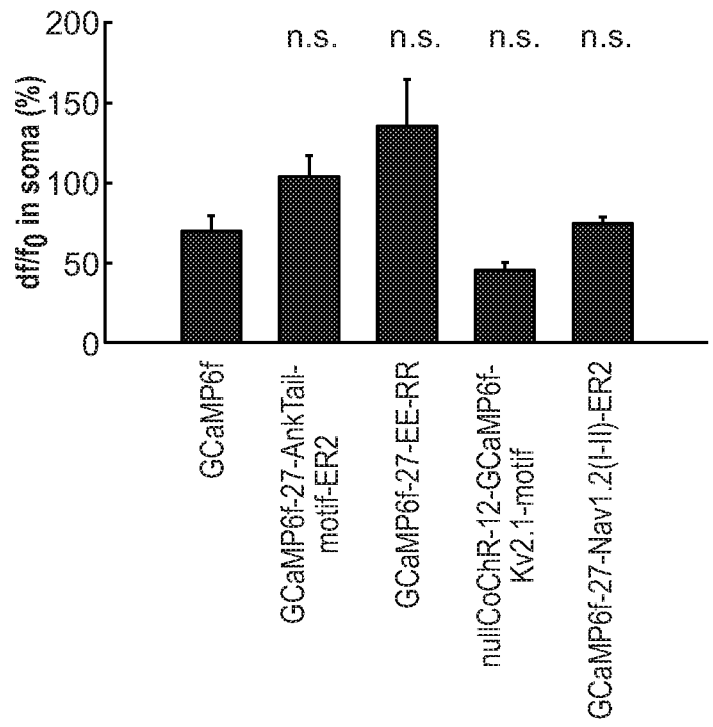
Figure 7L:
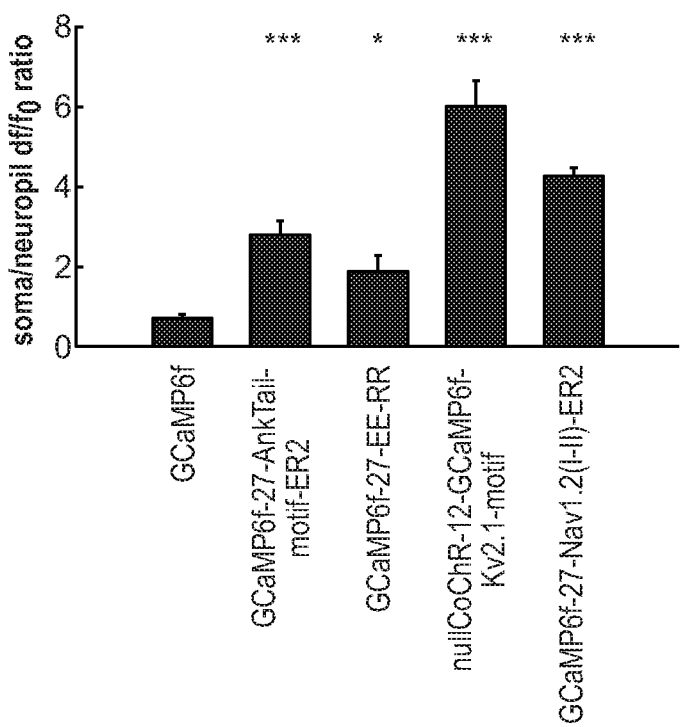
Figure 7M:
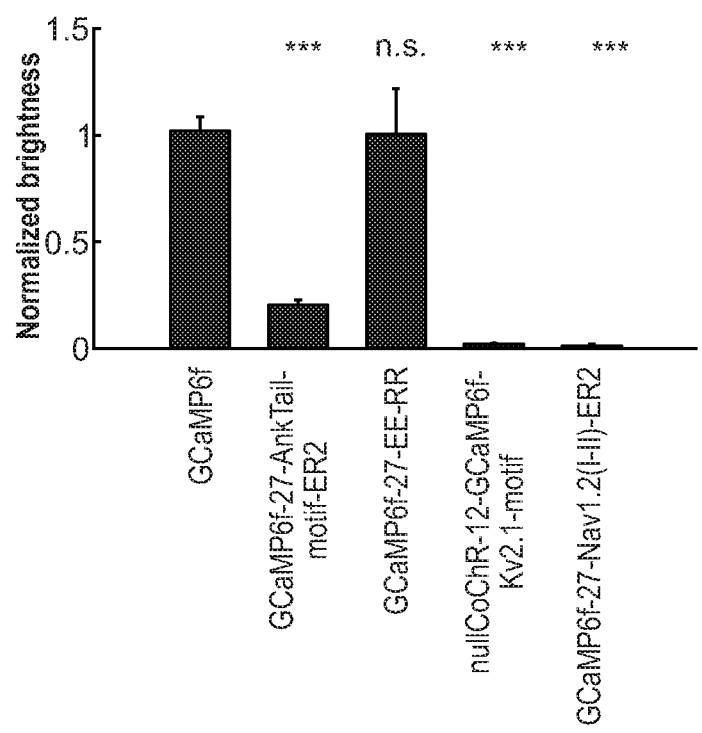

FIG. 7A-M shows slice imaging of soma-targeted GCaMP6f candidates during 4-Aminopyridine incubation. FIG. 7A-E shows representative epifluorescent images of slices expressing GCaMP6f targeting variants. Scale bar: 200 μm. Yellow line, edge of the brain. (FIG. 7A) GCaMP6f. (FIG. 7B) GCaMP6f-27-AnkTail-motif-ER2. (FIG. 7C) GCaMP6f-27-EE-RR. (FIG. 7D) nullCoChR-12-GCaMP6f-Kv2.1-motif. (FIG. 7E) GCaMP6f-27-Nav1.2 (I-II)-ER2. FIG. 7F-J shows representative traces of the GCaMP signals from the soma (magenta) and the neuropil (blue). (F) GCaMP6f. (G) GCaMP6f-27-AnkTail-motif-ER2. (H) GCaMP6f-27-EE-RR. (I) nullCoChR-12-GCaMP6f-Kv2.1-motif. (J) GCaMP6f-27-Nav1.2 (I-II)-ER2. FIG. 7K is a bar chart showing $df/f_0$ in the somata of neurons expressing different GCaMP6f targeting variants (n=20 cells from 2 slices from 2 mice for each variant). n.s., not significant, Kruskal-Wallis analysis of variance followed by post-hoc test via Steel's test with GCaMP6f as control group. Plotted is mean plus or minus standard error throughout. FIG. 7L is a bar chart showing the ratio between $df/f_0$ of the cell body and $df/f_0$ of the neuropil for different GCaMP6f targeting variants (n=20 cells from 2 slices from 2 mice for each variant). * $P<0.05$, * $P<0.001$, Kruskal-Wallis analysis of variance followed by post-hoc test via Steel's test with GCaMP6f as control group. FIG. 7M is a bar chart showing the baseline brightness of the cell body for different GCaMP6f targeting variants (n=20 cells from 2 slices from 2 mice for each variant). * $P<0.001$, n.s., not significant, Kruskal-Wallis analysis of variance followed by post-hoc test via Steel's test with GCaMP6f as control group: see Table 7 for full statistics for FIG. 7A-M.

Figure 8A:
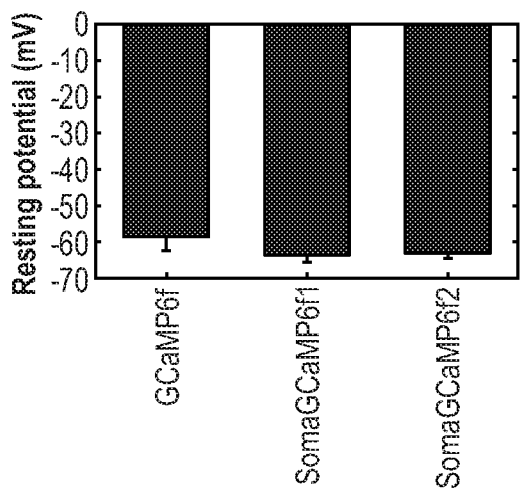
Figure 8B:
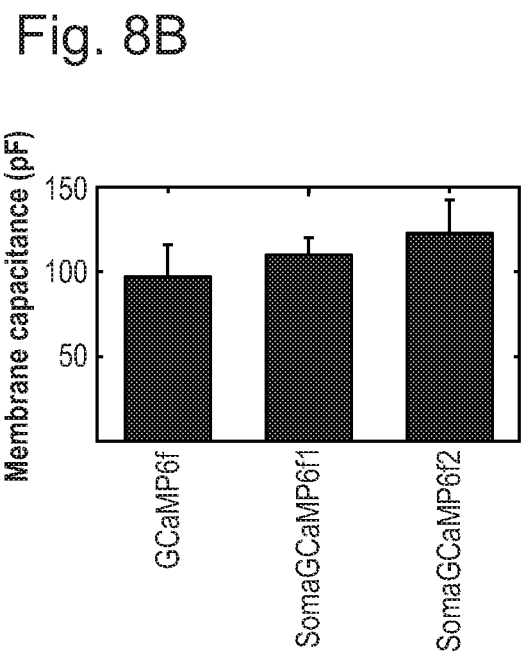
Figure 8C:
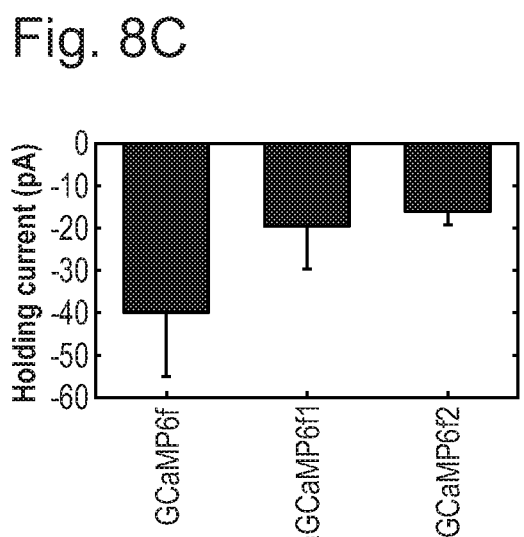
Figure 8D:
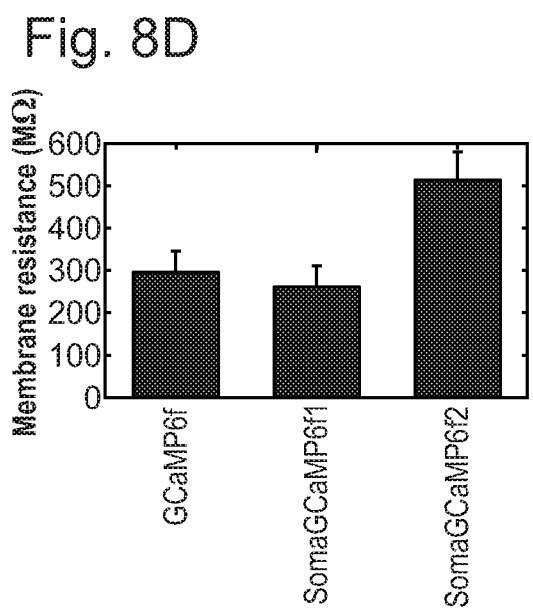
Figure 8E:
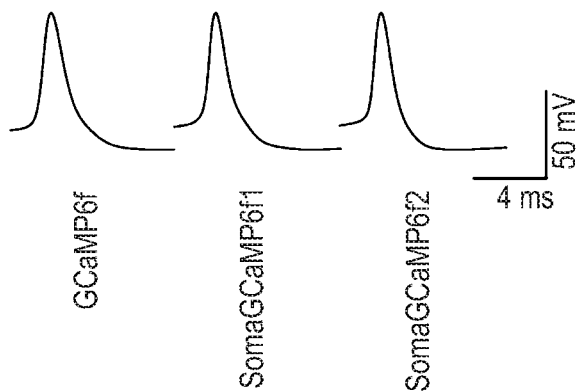
Figure 8F:
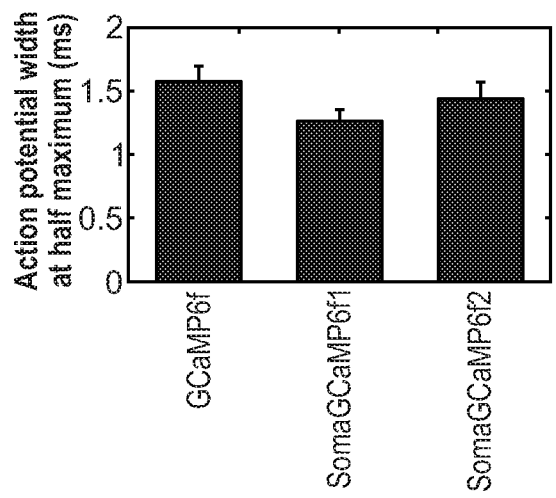
Figure 8G:
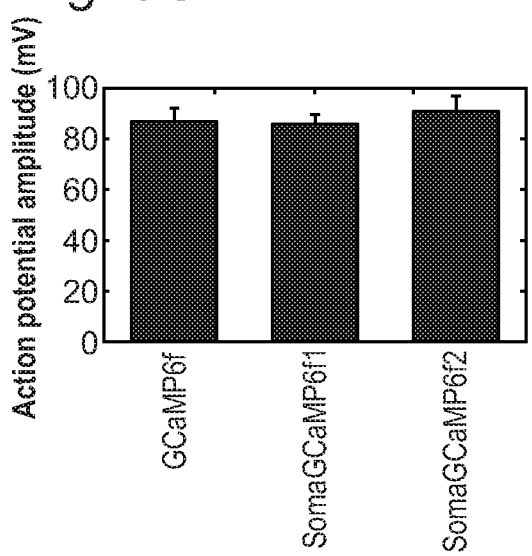
Figure 8H:
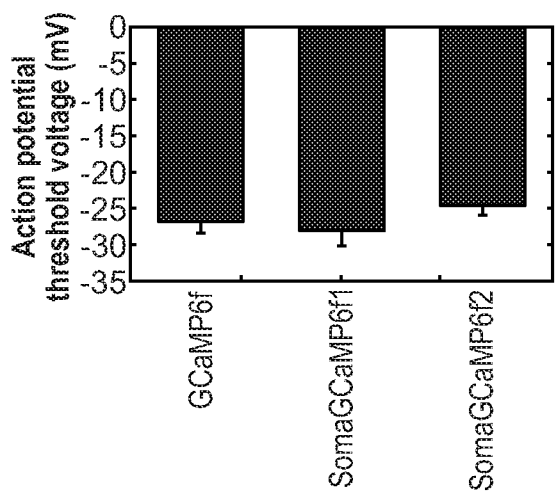

FIG. 8A-H shows bar charts and traces demonstrating membrane and action potential properties of neurons expressing somatic vs. untargeted forms of GCaMP6f. Cultured hippocampal neurons expressing GCaMP6f, SomaGCaMP6f1 and SomaGCaMP6f2 were patched and membrane properties recorded. FIG. 8A-D illustrate passive membrane properties. FIG. 8A shows resting potential (n=6 cells from 2 cultures for GCaMP6f; n=7 cells from 2 cultures for SomaGCaMP6f1; n=6 cells from 2 cultures for SomaGCaMP6f2). Plotted is mean plus or minus standard error throughout the figure. Not significant, Kruskal-Wallis analysis of variance followed by post-hoc test via Steel's test with GCaMP6f as control group. See Table 8 for full statistics for FIG. 8. FIG. 8B illustrates membrane capacitance (n=5 cells from 2 cultures for GCaMP6f; n=6 cells from 2 cultures for SomaGCaMP6f1; n=6 cells from 2 cultures for SomaGCaMP6f2). Not significant, Kruskal-Wallis analysis of variance followed by post-hoc test via Steel's test with GCaMP6f as control group. FIG. 8C shows holding current while held at −65 mV (n=5 cells from 2 cultures for GCaMP6f; n=6 cells from 2 cultures for SomaGCaMP6f1; n=6 cells from 2 cultures for SomaGCaMP6f2). Not significant, Kruskal-Wallis analysis of variance followed by post-hoc test via Steel's test with GCaMP6f as control group. FIG. 8D shows membrane resistance (n=5 cells from 2 cultures for GCaMP6f; n=6 cells from 2 cultures for SomaGCaMP6f1; n=6 cells from 2 cultures for SomaGCaMP6f2). Not significant, Kruskal-Wallis analysis of variance followed by post-hoc test via Steel's test with GCaMP6f as control group. FIG. 8E-H provides information on Action potential properties. FIG. 8E averages action potential waveforms for cells expressing GCaMP6f, SomaGCaMP6f1 and SomaGCaMP6f2 (n=12 cells from 2 cultures for GCaMP6f; n=12 cells from 2 cultures for SomaGCaMP6f1; n=12 cells from 2 cultures for SomaGCaMP6f2). FIG. 8F shows action potential width (n=12 cells from 2 cultures for GCaMP6f; n=12 cells from 2 cultures for SomaGCaMP6f1; n=12 cells from 2 cultures for SomaGCaMP6f2). Not significant, Kruskal-Wallis analysis of variance followed by post-hoc test via Steel's test with GCaMP6f as control group. FIG. 8G shows action potential amplitude (n=12 cells from 2 cultures for GCaMP6f; n=12 cells from 2 cultures for SomaGCaMP6f1; n=12 cells from 2 cultures for SomaGCaMP6f2). Not significant, Kruskal-Wallis analysis of variance followed by post-hoc test via Steel's test with GCaMP6f as control group. FIG. 8H shows action potential threshold (n=12 cells from 2 cultures for GCaMP6f; n=12 cells from 2 cultures for SomaGCaMP6f1; n=12 cells from 2 cultures for SomaGCaMP6f2). Not significant, Kruskal-Wallis analysis of variance followed by post-hoc test via Steel's test with GCaMP6f as control group.

FIG. 9A-D shows data demonstrating distribution of ion channels and $Ankyrin_G$ in neurons expressing GCaMP6f, SomaGCaMP6f1 or SomaGCaMP6f2. Cultured hippocampal neurons expressing GCaMP6f, SomaGCaMP6f1 and SomaGCaMP6f2 were immunostained using antibodies against ion channels or $Ankyrin_G$ epitopes. FIG. 9A, left, shows representative images (maximum intensity projections) of neurons expressing GCaMP6f, SomaGCaMP6f1 or SomaGCaMP6f2 (from top to bottom, respectively) and immunostained against Kv2.1 (blue). FIG. 9A, right, shows average fluorescent profiles down the axon of immunostained Kv2.1 in GCaMP6f (red), SomaGCaMP6f1 (blue) or SomaGCaMP6f2 (green) conditions (n=6 GCaMP6f expressing neurons from 3 cultures; n=6 SomaGCaMP6f1 expressing neurons from 2 cultures; n=6 SomaGCaMP6f2 expressing neurons from 4 cultures). Normalized to the soma value. n.s., not significant, Bonferroni-corrected Kruskal-Wallis analysis of variance; see Table 9 for full statistics for FIG. 9. Plotted is mean (solid line) plus or minus standard error (shaded area) throughout the figure. FIG. 9B shows results as in FIG. 9B, but for NaV1.2 (n=6 GCaMP6f expressing neurons from 3 cultures; n=6 SomaGCaMP6f1 expressing neurons from 4 cultures; n=6 SomaGCaMP6f2 expressing neurons from 2 cultures). FIG. 9C shows results as in FIG. 9A, but for $Ankyrin_G$ (n=6 GCaMP6f expressing neurons from 4 cultures; n=5 SomaGCaMP6f1 expressing neurons from 2 cultures; n=6 SomaGCaMP6f2 expressing neurons from 2 cultures). FIG. 9D shows results as in FIG. 9A, but for CaV2.1 (n=5 GCaMP6f expressing neurons from 2 cultures; n=5 SomaGCaMP6f1 expressing neurons from 2 cultures; n=5 SomaGCaMP6f2 expressing neurons from 5 cultures).

Figure 10A:
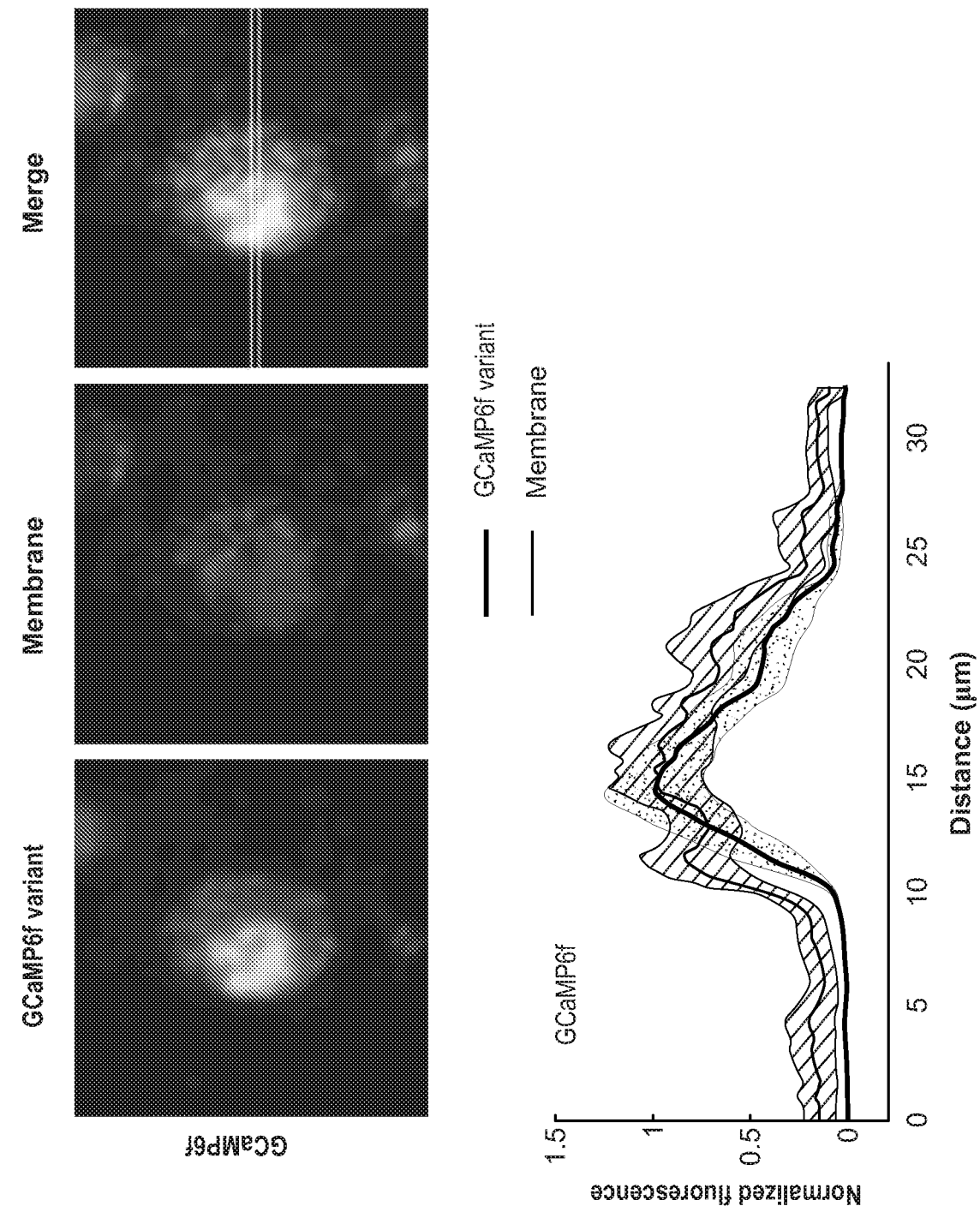
Figure 10C:
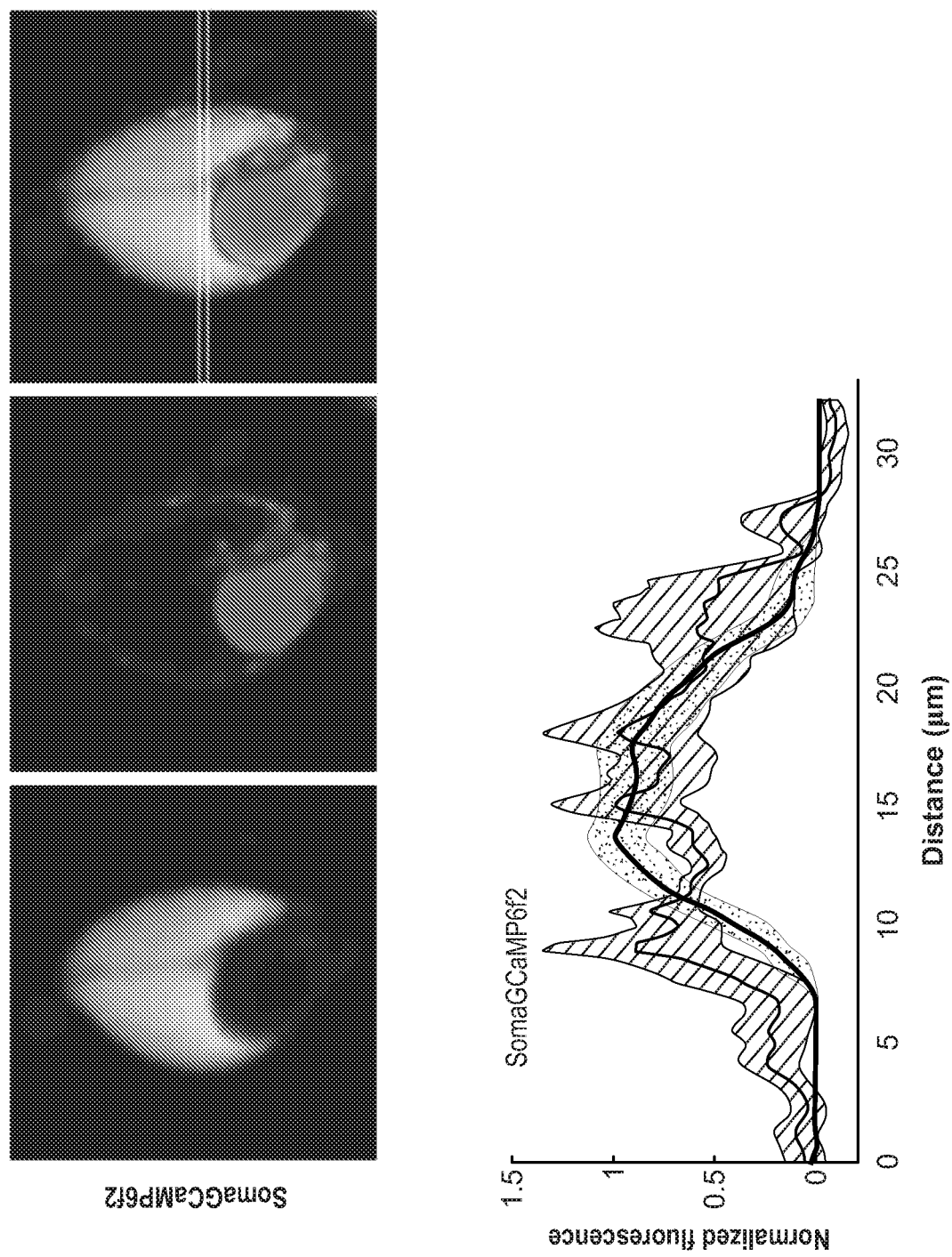

FIG. 10A-C provides fluorescent profiles of GCaMP6f, SomaGCaMP6f1 and SomaGCaMP6f2 in comparison to the fluorescent profile of the membrane in cell bodies of cultured neurons. FIG. 10A, left, provides an image (single confocal slice) of a hippocampal neural cell body expressing GCaMP6f (green, left panel) and stained with the membrane labeling dye WGA-647 (magenta, middle panel). Merge of the left and middle panels is presented on the right panel. The yellow rectangle indicates the region of interest for fluorescent profile analysis throughout this figure. FIG. 10A, right, shows average fluorescent profiles of GCaMP6f (black) and the membrane (red) (n=7 neurons from 2 cultures). Plotted is mean (solid line) plus or minus standard error (shaded area) throughout the figure. FIG. 10B shows, as in FIG. 10A, but for SomaGCaMP6f1 (n=4 neurons from 2 cultures). FIG. 10C shows, as in FIG. 10A, but for SomaGCaMP6f2 (n=6 neurons from 2 cultures).

Figure 11A:
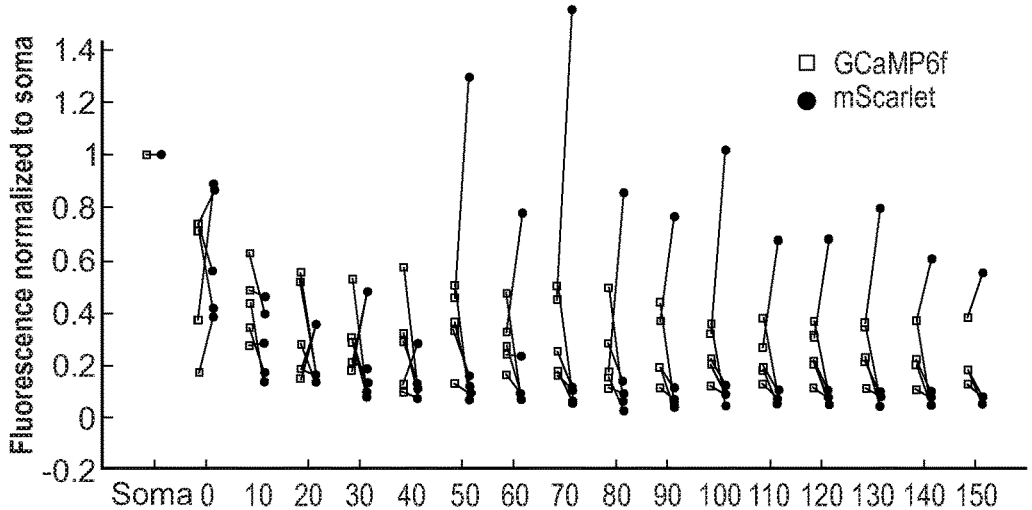
Figure 11B:
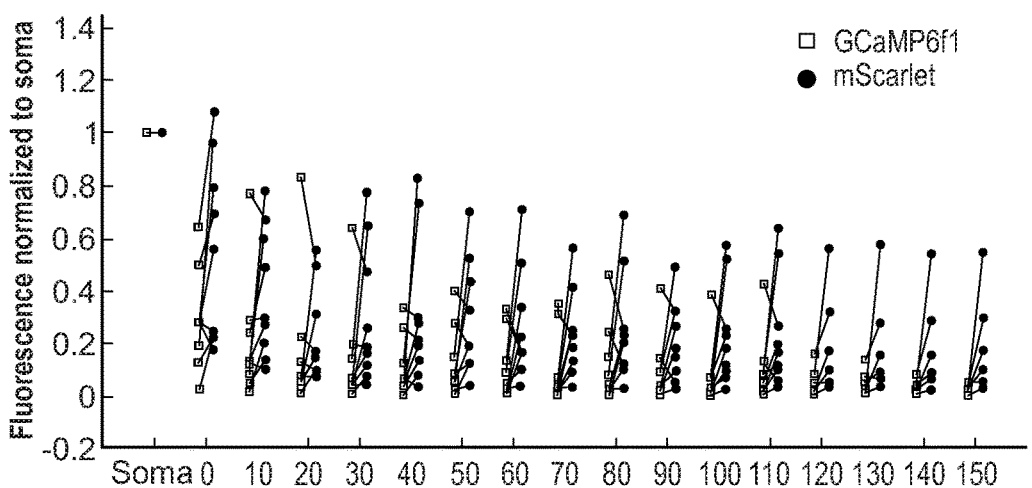
Figure 11C:
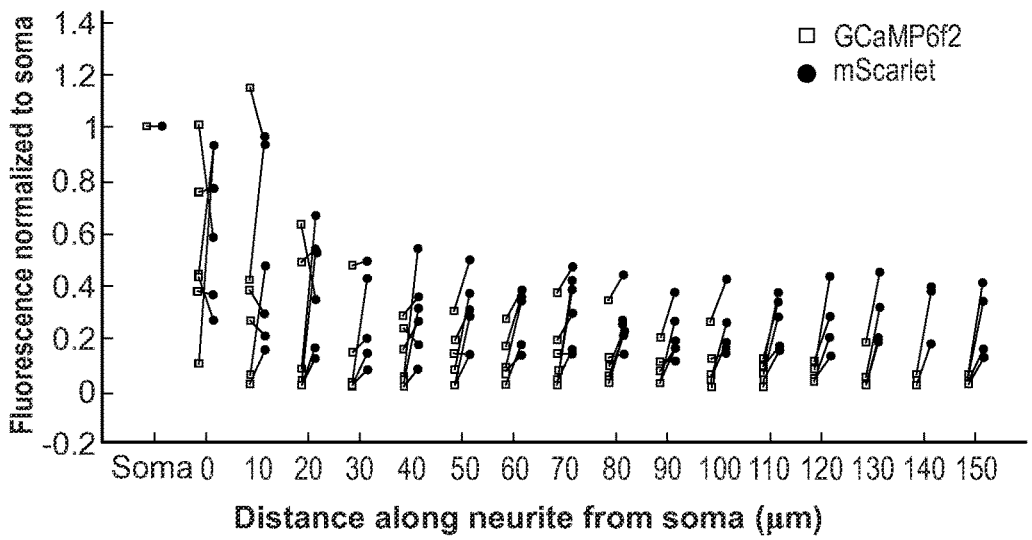

FIG. 11A-C provides fluorescent profiles of GCaMP6f, SomaGCaMP6f1, SomaGCaMP6f2 and mScarlet in fixed brain slices. FIG. 11A is a plot of GCaMP6f fluorescence (green dots) and mScarlet fluorescence (red dots), normalized to the fluorescence at the soma, versus position along a neurite (n=5 neurons from 2 mice). Dots represent individual cells: a line connects the GCaMP6f fluorescence value and the mScarlet fluorescence value originating from the same cell, throughout the figure. FIG. 11B is a plot of the SomaGCaMP6f1 fluorescence (green dots) and mScarlet fluorescence (red dots), normalized to the fluorescence at the soma versus position along a neurite (n=9 neurons from 2 mice). FIG. 11C is a plot of the SomaGCaMP6f2 fluorescence (green dots) and mScarlet fluorescence (red dots) normalized to the fluorescence at the soma versus position along a neurite (n=6 neurons from 2 mice).

Figure 12:
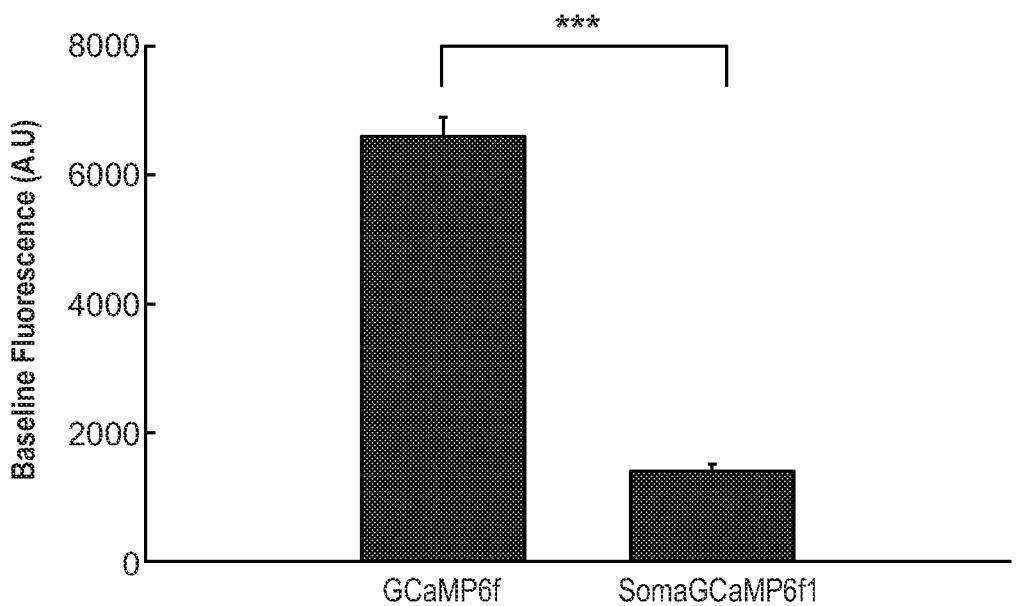

FIG. 12 shows bar chart of baseline fluorescence brightness of GCaMP6f and SomaGCaMP6f1 in living brain slices. Bars show average baseline brightness values for cells expressing GCaMP6f or SomaGCaMP6f1 in slice (n=42 neurons from 4 slices from 2 GCaMP6f mice: n=43 neurons from 8 slices from 3 SomaGCaMP6f1 mice). Error bars indicate standard error of the mean. *** $P<0.001$, Kolmogorov-Smirnov test of baseline fluorescence brightness between GCaMP6f and SomaGCaMP6f1; see Table 11 for full statistics for FIG. 12.

Figure 13A:
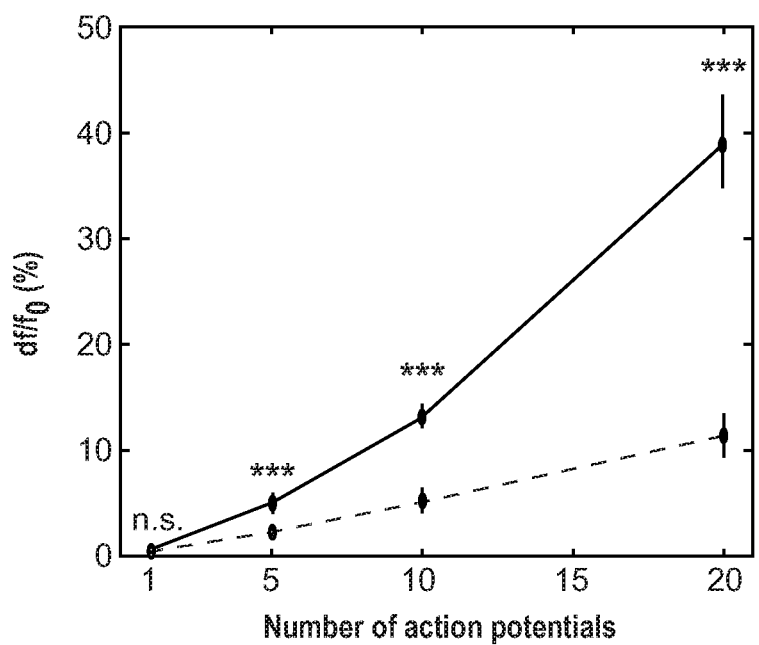
Figure 13B:
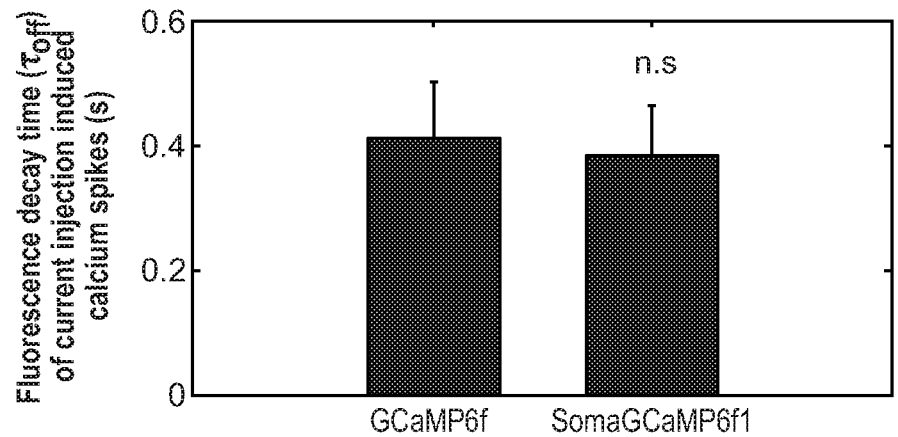
Figure 13C:
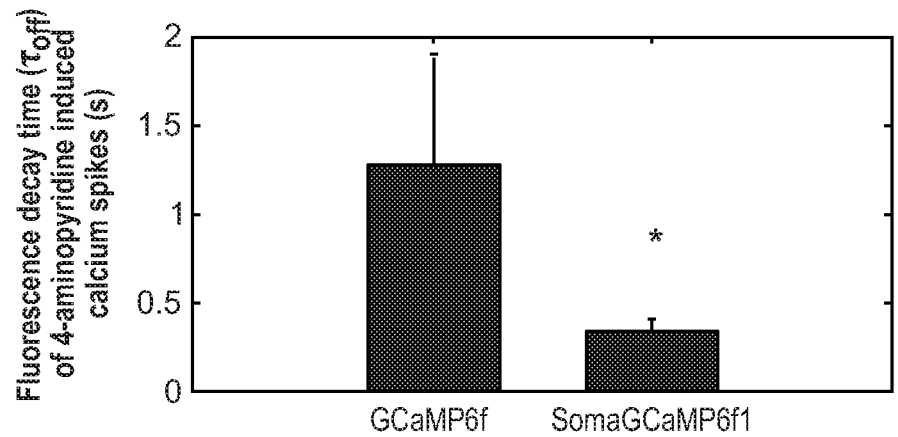
Figure 13D:
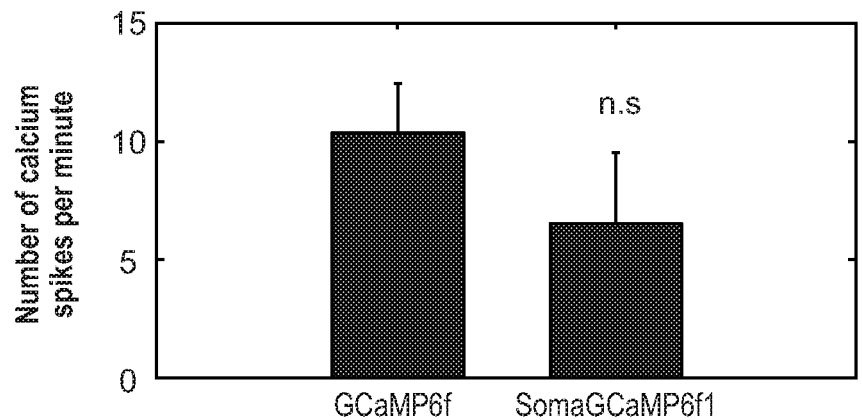

FIG. 13A-D provides a graph and bar charts showing sensitivity of multiple action potentials, temporal dynamics and event rate for GCaMP6f and SomaGCaMP6f1. (FIG. 13A is a graph showing the $df/f_0$ of the calcium transient elicited after a train of 1, 5, 10 and 20 current pulses (500 pA, 5 ms duration, 50 Hz) for neurons expressing GCaMP6f (dotted line) or SomaGCaMP6f1 (unbroken line, n=7 neurons from 5 slices from 2 mice for GCaMP6f; n=5 neurons from 3 slices from 2 mice for SomaGCaMP6f1). n.s., not significant, *** $P<0.001$, Bonferroni-corrected Wilcoxon rank sum test of the $df/f_0$ between GCaMP6f and SomaGCaMP6f1 expressing neurons: see Table 12 for full statistics for FIG. 13. Plotted is mean plus or minus standard error throughout the figure. FIG. 13B is a bar chart showing the mean $T_{off}$ of calcium spikes in slice, during electrophysiological inducement of single action potentials (n=3 neurons from 3 slices from 3 mice for GCaMP6f; n=3 neurons from 3 slices from 3 mice for SomaGCaMP6f1). n.s., not significant, Wilcoxon rank sum test between GCaMP6f and SomaGCaMP6f1. FIG. 13C is a bar chart showing the mean $T_{off}$ of calcium spikes in slice, during 4-aminopyridine inducement of single action potentials (n=5 neurons from 5 slices from 4 mice for GCaMP6f; n=5 neurons from 4 slices from 3 mice for SomaGCaMP6f1) . * $P<0.05$, Wilcoxon rank sum test between GCaMP6f and SomaGCaMP6f1. FIG. 13D is a bar chart showing the mean event rate of calcium spikes per minute in slice (n=8 neurons from 8 slices from 4 mice for GCaMP6f; n=6 neurons from 6 slices from 3 mice or SomaGCaMP6f1). n.s., not significant, Wilcoxon rank sum test between GCaMP6f and SomaGCaMP6f1.

Figure 14B:
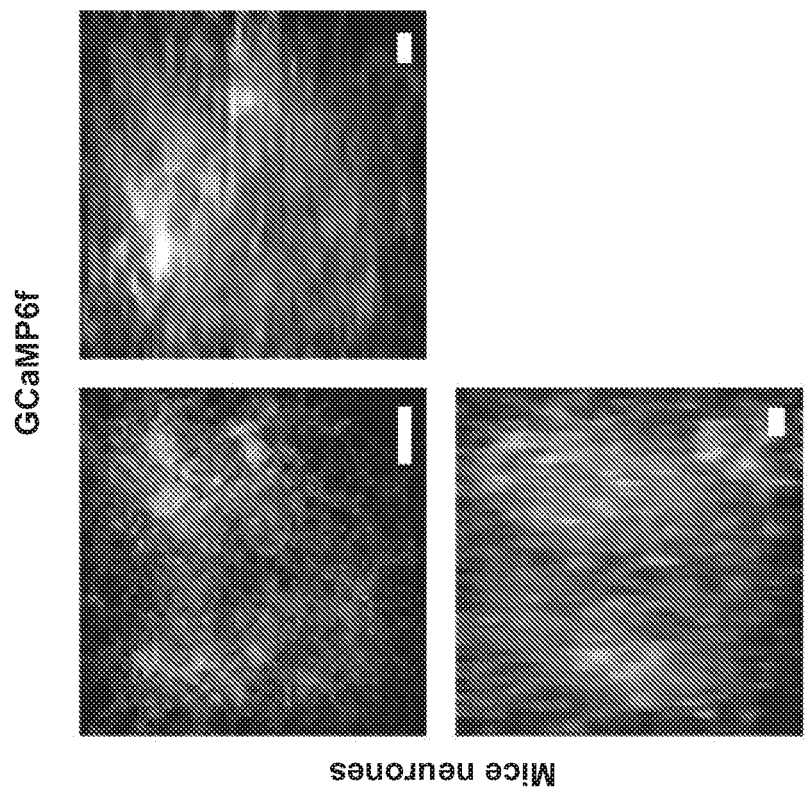
Figure 14A:
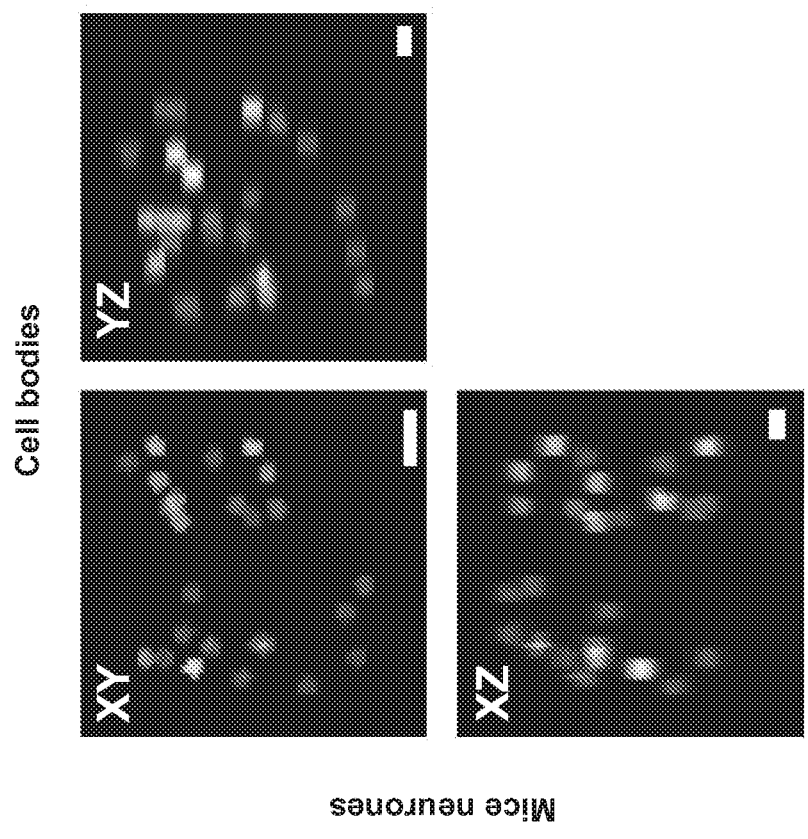
Figure 14D:
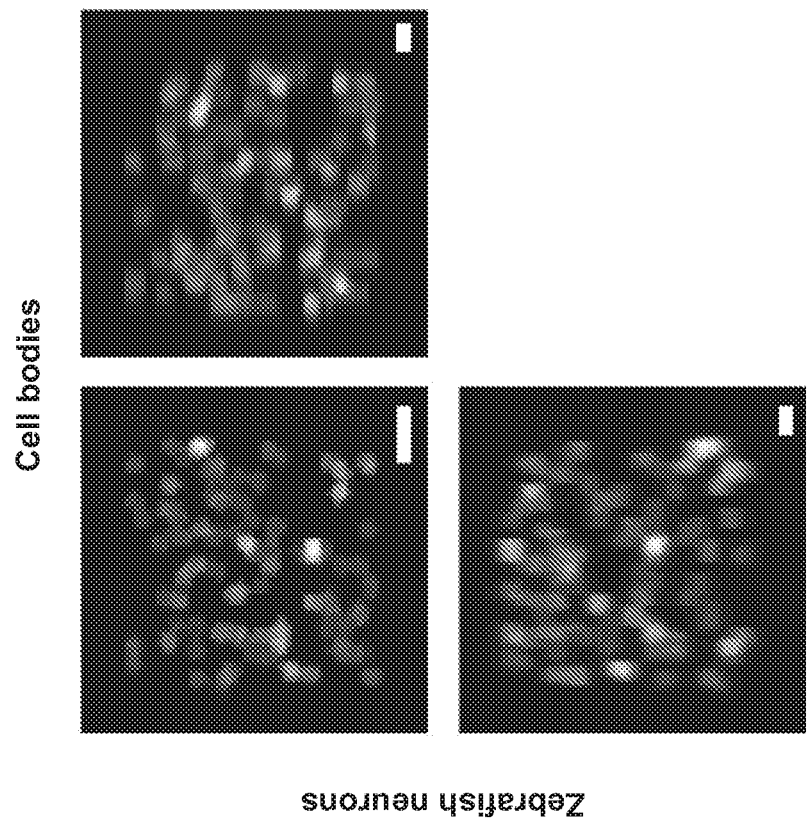
Figure 14C:
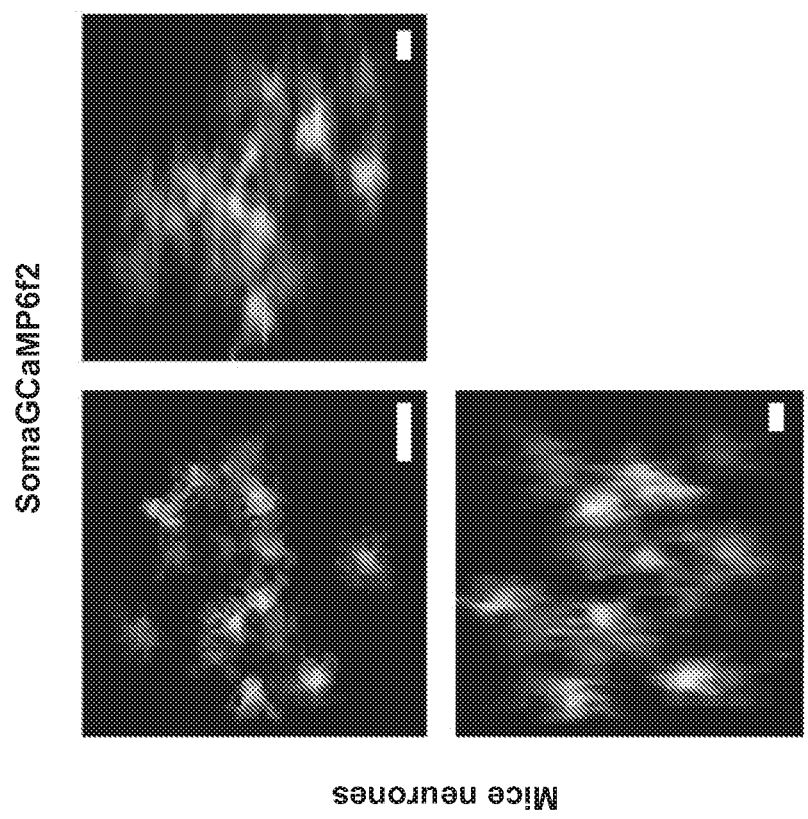
Figure 14F:
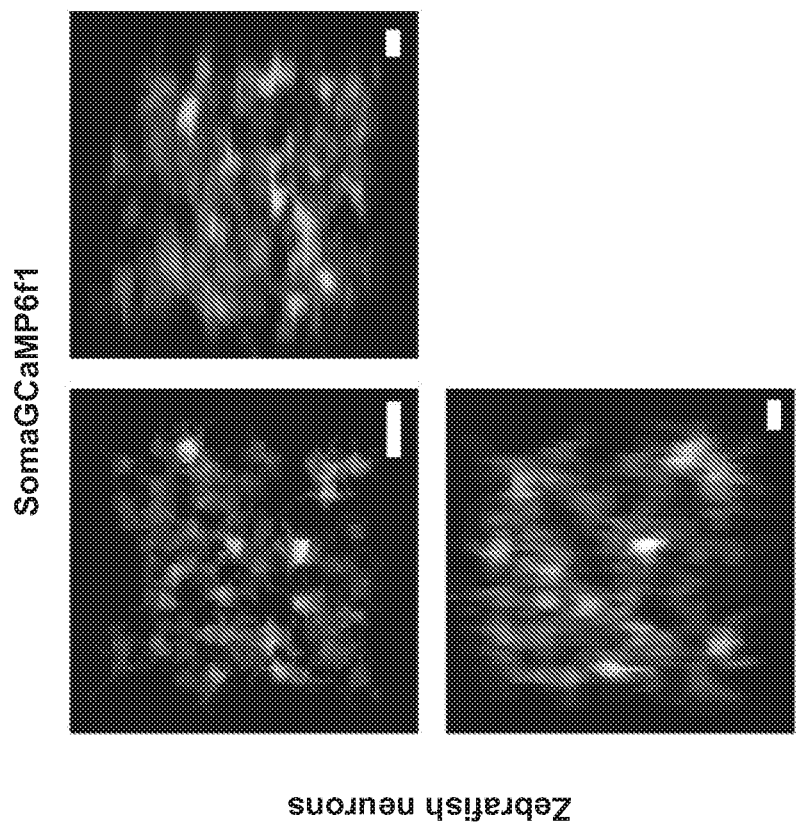
Figure 14E:
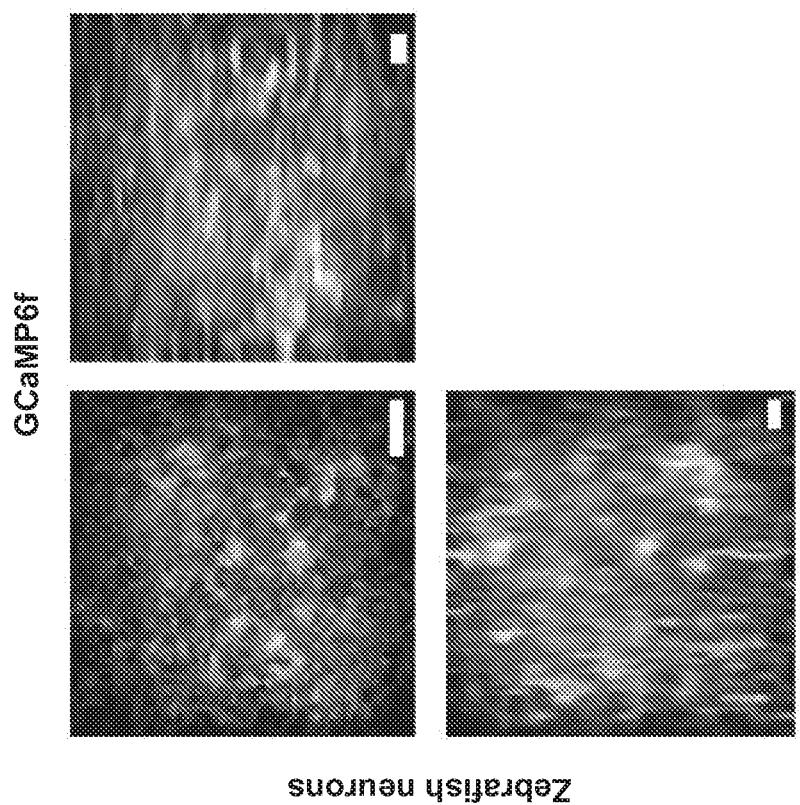
Figure 14G:
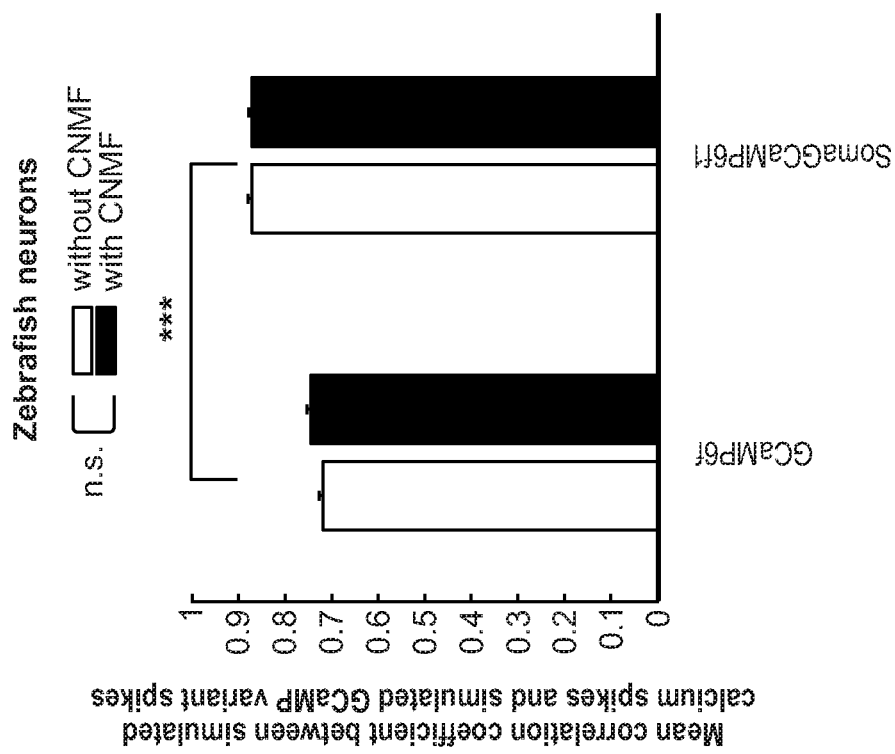
Figure 14H:
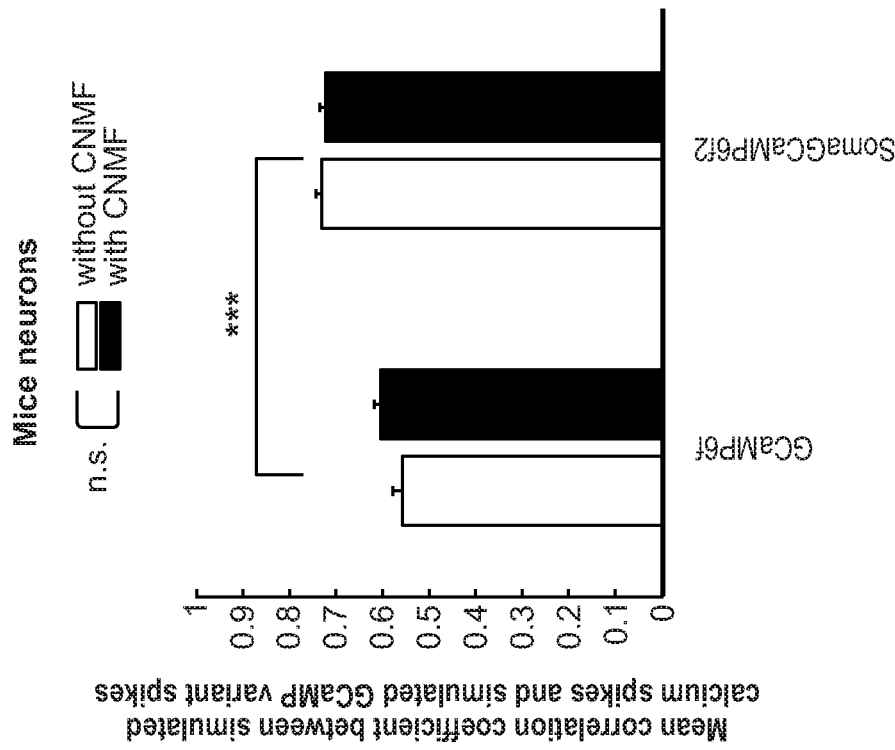

FIG. 14A-H provides simulation images indicating that simulation shows SomaGCaMP6f variants, compared to non-targeted GCaMP6f, report calcium spikes at a higher precision in population recording in mouse and zebrafish after post-hoc computational demixing using CNMF. FIG. 14A provides simulated images of cell bodies from mouse cortical in vivo imaging. Scale bars, 10 µm for XY images throughout the figure, 5 µm for XZ and YZ images throughout the figure. FIG. 14B provides simulated images of GCaMP6f from mouse in vivo imaging. FIG. 14C provides simulated images of SomaGCaMP6f2 from mouse in vivo imaging. FIG. 14D provides simulated images of the cell bodies from zebrafish midbrain in vivo imaging. FIG. 14E provides simulated images of GCaMP6f from zebrafish in vivo imaging. FIG. 14F provides simulated images of SomaGCaMP6f1 from zebrafish in vivo imaging. FIG. 14G shows mean correlation coefficient between the simulated ground-truth calcium dynamics and simulated recorded calcium dynamics from GCaMP variants in the simulation of mouse in vivo imaging, before CNMF (light gray) and after CNMF (dark gray; n=300 neurons from 10 simulations for SomaGCaMP6f2; n=300 neurons from 10 simulations for GCaMP6f). * $P<0.001$, Two-way analysis of variance (ANOVA) of the correlation coefficient between the ground-truth calcium dynamics and recorded calcium dynamics in the simulations, followed by post-hoc Tukey's HSD test: see Table 13 for full statistics for FIG. 14A-H. Plotted is mean plus or minus standard error in FIG. 14G and FIG. 14H. FIG. 14H provides mean correlation coefficient between the simulated ground-truth calcium dynamics and simulated recorded calcium dynamics from GCaMP variants in the simulation of zebrafish in vivo imaging before CNMF (light gray) and after CNMF (dark gray; n=1200 neurons from 10 simulations for SomaGCaMP6f1; n=1200 neurons from 10) simulations for GCaMP6f). * $P<0.001$, Two-way analysis of variance (ANOVA) of the correlation coefficient between the ground-truth calcium dynamics and recorded calcium dynamics in the simulations, followed by post-hoc Tukey's HSD test.

Figure 15A:
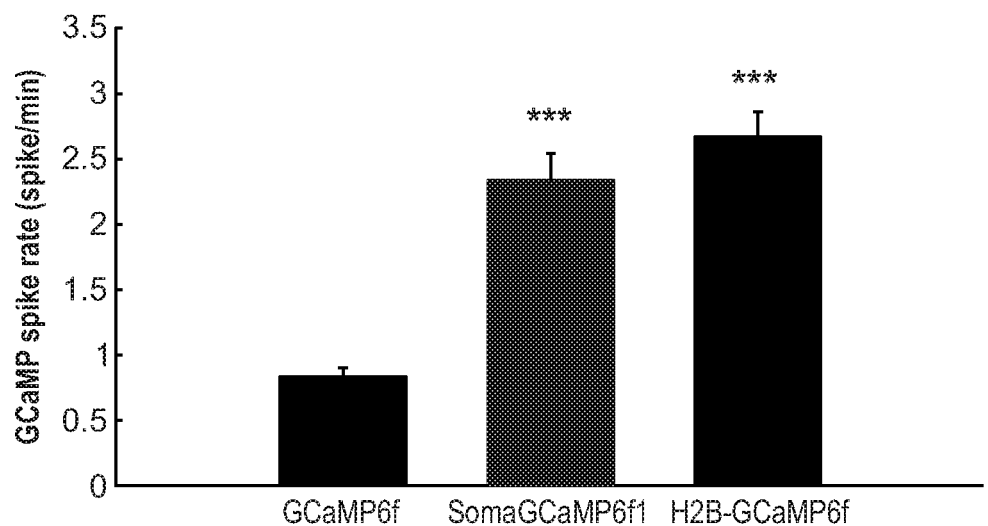
Figure 15B:
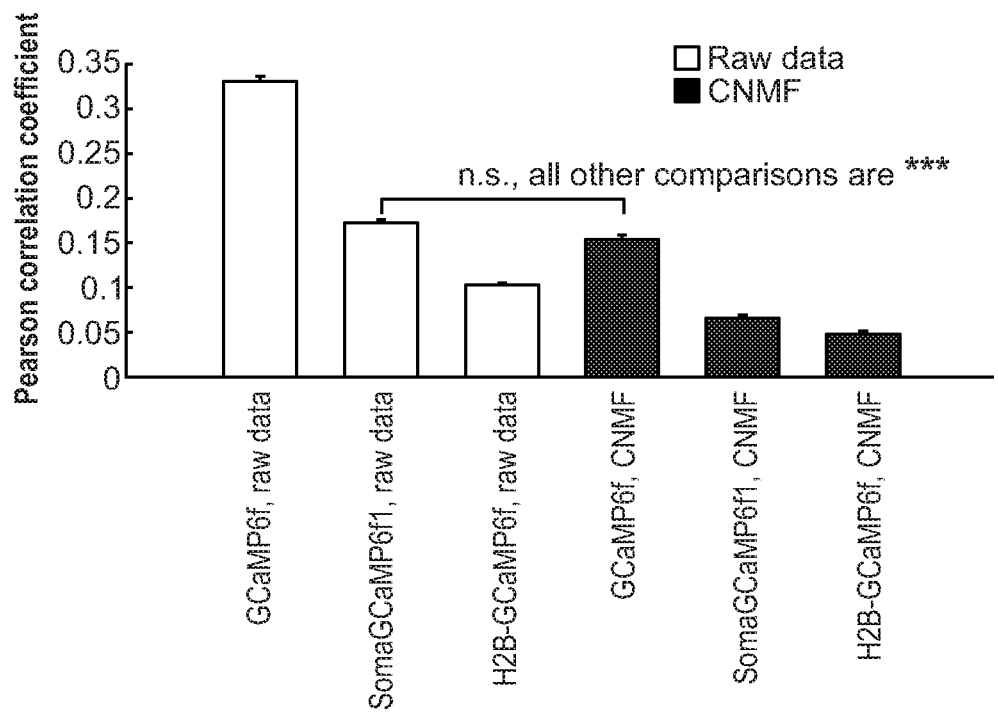
Figure 15C:
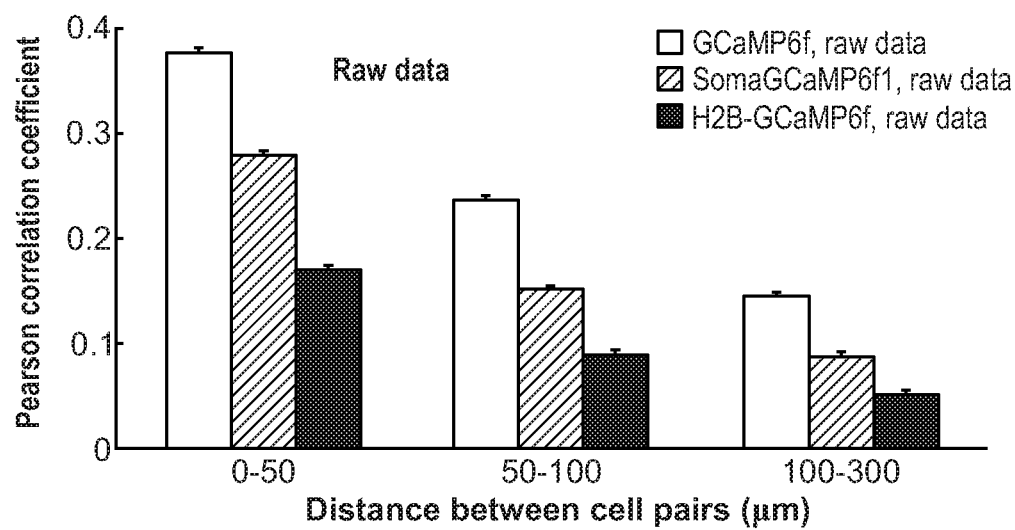
Figure 15D:
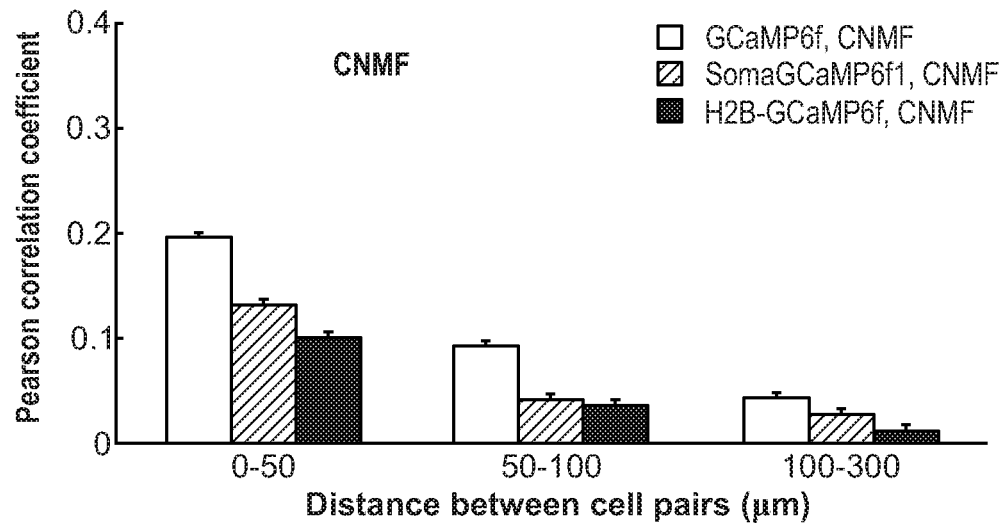

FIG. 15A-D provides bar charts illustrating temporal dynamics and calcium spike count for GCaMP6f and SomaGCaMP6f1 expressing neurons in zebrafish larvae, driven by 4-AP. FIG. 15A is a bar chart showing the mean GCaMP-spike rates for neurons in regions of the larval zebrafish forebrain expressing either GCaMP6f, SomaGCaMP6f1 or H2B-GCaMP6f (n=101 neurons from 5 fishes for GCaMP6f; n=146 neurons from 4 fishes for SomaGCaMP6f1; n=513 neurons from 6 fishes for H2B-GCaMP6f). * $P<0).001$, Kruskal-Wallis analysis of variance followed by post-hoc test via Steel's test. Plotted is mean plus or minus standard error. FIG. 15B is a bar chart showing the mean Pearson correlation coefficient between cell pairs in the larval zebrafish forebrain expressing either GCaMP6f, SomaGCaMP6f1 or H2B-GCaMP6f (n=426 neurons from 5 fishes for GCaMP6f; n=340) neurons from 4 fishes for SomaGCaMP6f1; n=676 neurons from 6 fishes for H2B-GCaMP6f). White bars are for correlation coefficients calculated from raw data. Black bars are for correlation coefficients calculated after CNMF was applied to the raw data. n.s., not significant. * $P<0.001$, Kruskal-Wallis analysis of variance followed by post-hoc Tukey's HSD test. Plotted is mean plus or minus standard error. FIG. 15C is a bar chart showing the mean Pearson correlation coefficient between cell pairs in the larval zebrafish forebrain expressing either GCaMP6f (white), SomaGCaMP6f1 (gray) or H2B-GCaMP6f (black), in three distance ranges from the soma: 0-50 µm, 50-100 µm and 100-300 µm (n=426 neurons from 5 fishes for GCaMP6f; n=340 neurons from 4 fishes for SomaGCaMP6f1; n=676 neurons from 6 fishes for H2B-GCaMP6f). Correlation coefficient was calculated from raw data. Plotted is mean plus or minus standard error. FIG. 15D is a bar chart showing the mean Pearson correlation coefficient between cell pairs in the larval zebrafish forebrain expressing either GCaMP6f (white), SomaGCaMP6f1 (gray) or H2B-GCaMP6f (black), in three distance ranges from the soma: 0-50 µm, 50-100 µm and 100-300 µm (n=426 neurons from 5 fishes for GCaMP6f; n=340 neurons from 4 fishes for SomaGCaMP6f1; n=676 neurons from 6 fishes for H2B-GCaMP6f). Correlation coefficient was calculated after CNMF was applied to raw data. See Table 14 for statistics for FIG. 15A-D. Plotted is mean plus or minus standard error.

Figure 16A:
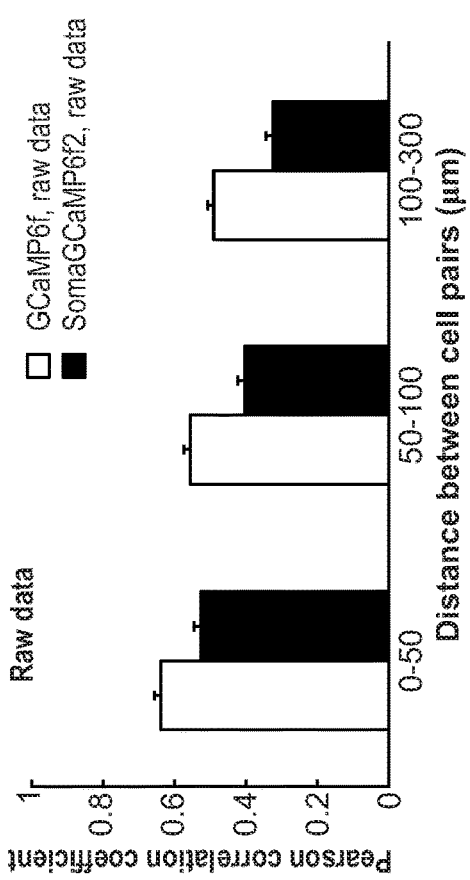
Figure 16B:
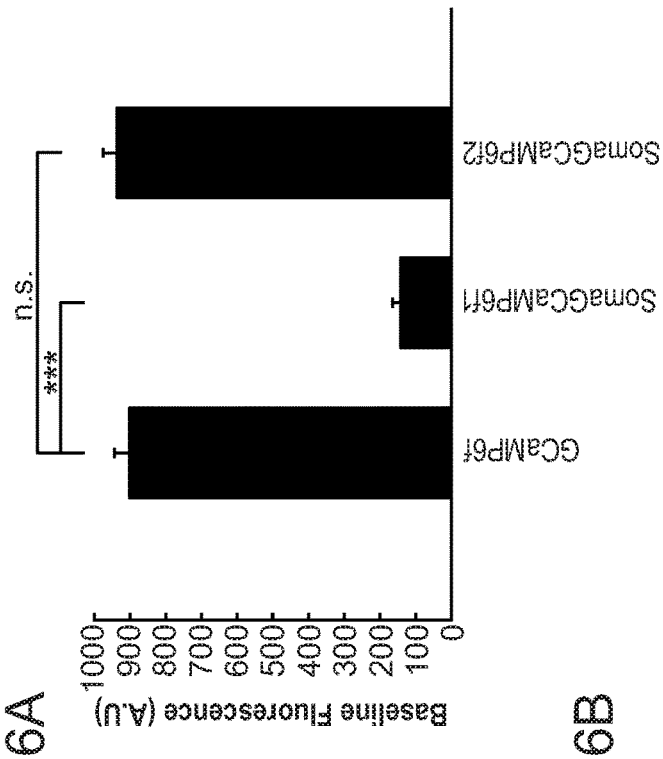
Figure 16C:
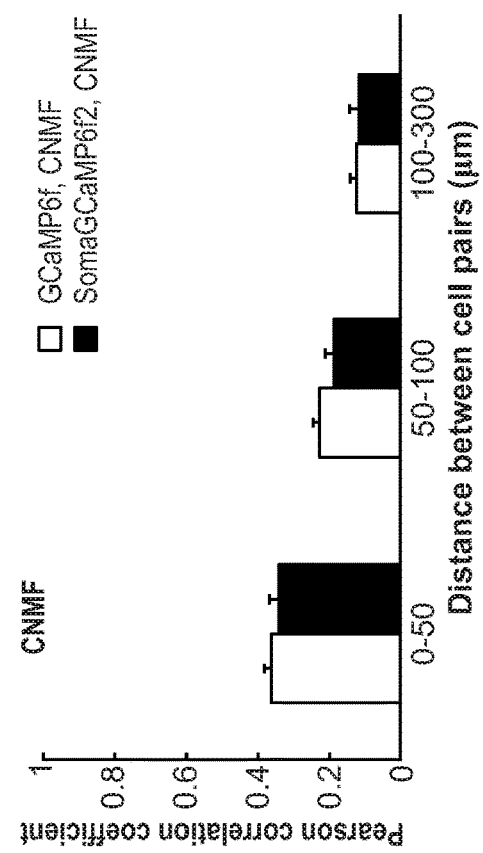
Figure 16D:
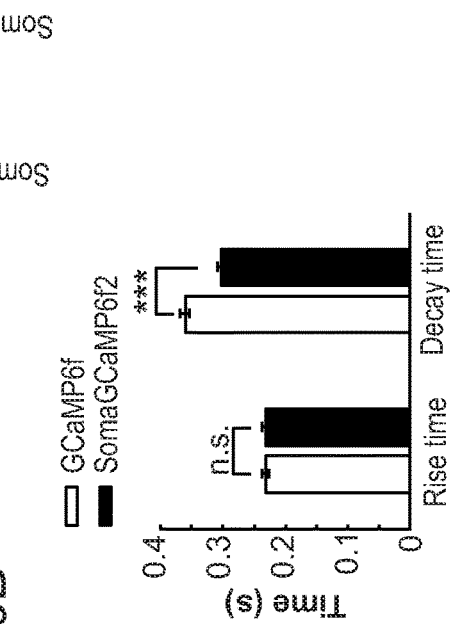

FIG. 16A-D provides bar charts/graphs showing baseline fluorescence brightness, kinetics and pairwise correlations of GCaMP6f and SomaGCaMP6f variants in mouse striatum in vivo. FIG. 16A is a bar chart showing the baseline fluorescence in vivo in the dorsal striatum for GCaMP6f, SomaGCaMP6f1 and SomaGCaMP6f2 (n=75 neurons from 5 mice for GCaMP6f; n=50 neurons from 2 mice for SomaGCaMP6f1; n=80 neurons from 4 mice for SomaGCaMP6f2). * P<0.001, Kruskal-Wallis analysis of variance followed by post-hoc test via Steel's test with GCaMP6f as control group. n.s., not significant, Kruskal-Wallis analysis of variance followed by post-hoc test via Steel's test with GCaMP6f as control group. Plotted is mean plus or minus standard error throughout the figure. FIG. 16B is a bar chart showing the average rise time (Ton) and the average decay time ($T_{off}$) for neurons expressing either SomaGCaMP6f2 or GCaMP6f (n=594 neurons from 4 mice expressing SomaGCaMP6f2, n=930 neurons from 6 GCaMP6f mice). n.s., not significant, Wilcoxon rank sum test between the rise times of SomaGCaMP6f2 and GCaMP6f expressing neurons: * P<0.001, Wilcoxon rank sum test between the decay times of SomaGCaMP6f2 and GCaMP6f expressing neurons. FIG. 16C is a bar chart showing the mean Pearson correlation coefficient between cell pairs in the mouse striatum expressing either GCaMP6f (white) or SomaGCaMP6f2 (gray), in three distance ranges from the soma: 0-50 µm, 50-100 µm and 100-300 µm (n=860 neurons from 6 mice for GCaMP6f; n=149 neurons from 4 mice for SomaGCaMP6f2). Correlation coefficient was calculated from raw data. Plotted is mean plus or minus standard error. FIG. 16D is a bar chart showing the mean Pearson correlation coefficient between cell pairs in the mouse striatum expressing either GCaMP6f (white) or SomaGCaMP6f2 (gray), in three distance ranges from the soma: 0-50 µm, 50-100 µm and 100-300 µm (n=860 neurons from 6 mice for GCaMP6f; n=149 neurons from 4 mice for SomaGCaMP6f2). Correlation coefficient was calculated from CNMF applied to raw data. See Table 15 for statistics for FIG. 16A-D. Plotted is mean plus or minus standard error.

Figure 17A:
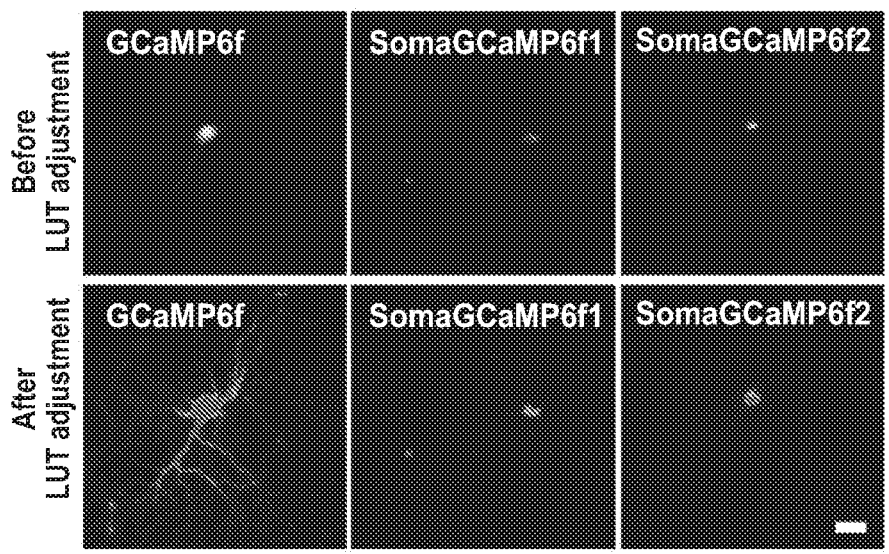
Figure 17B:
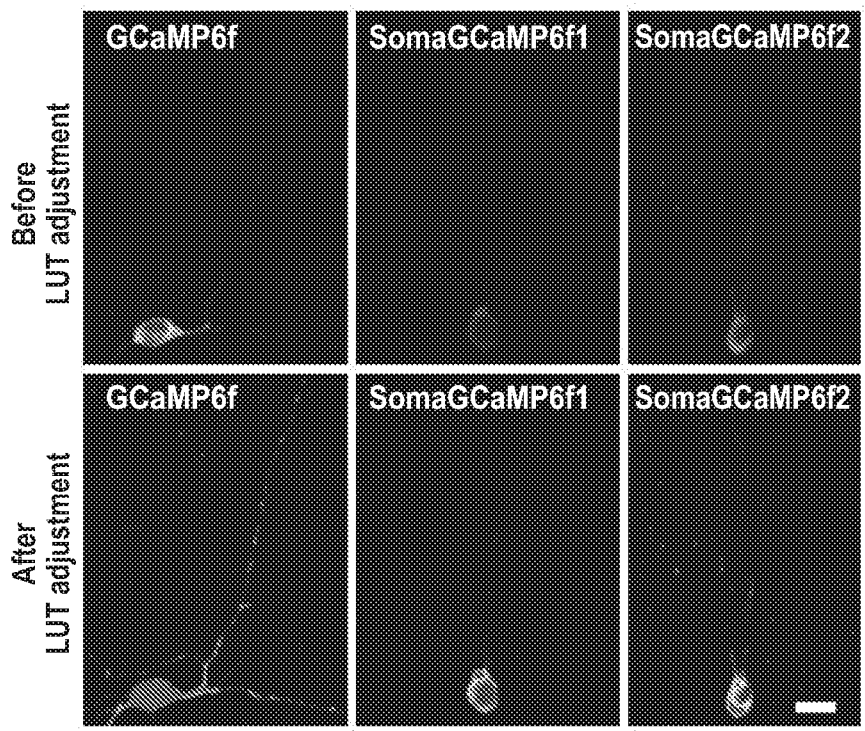
Figure 17C:
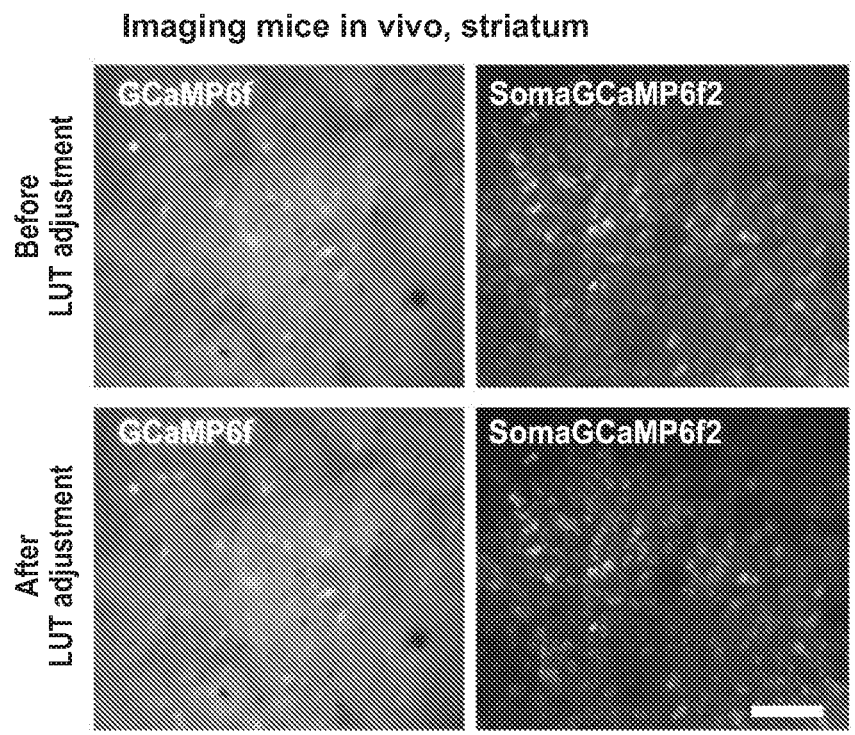
Figure 17D:
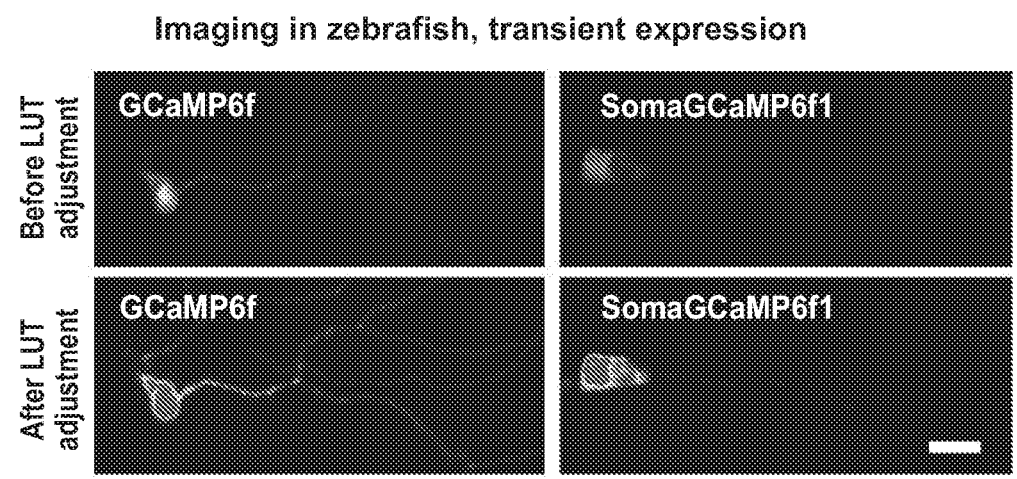
Figure 17E:
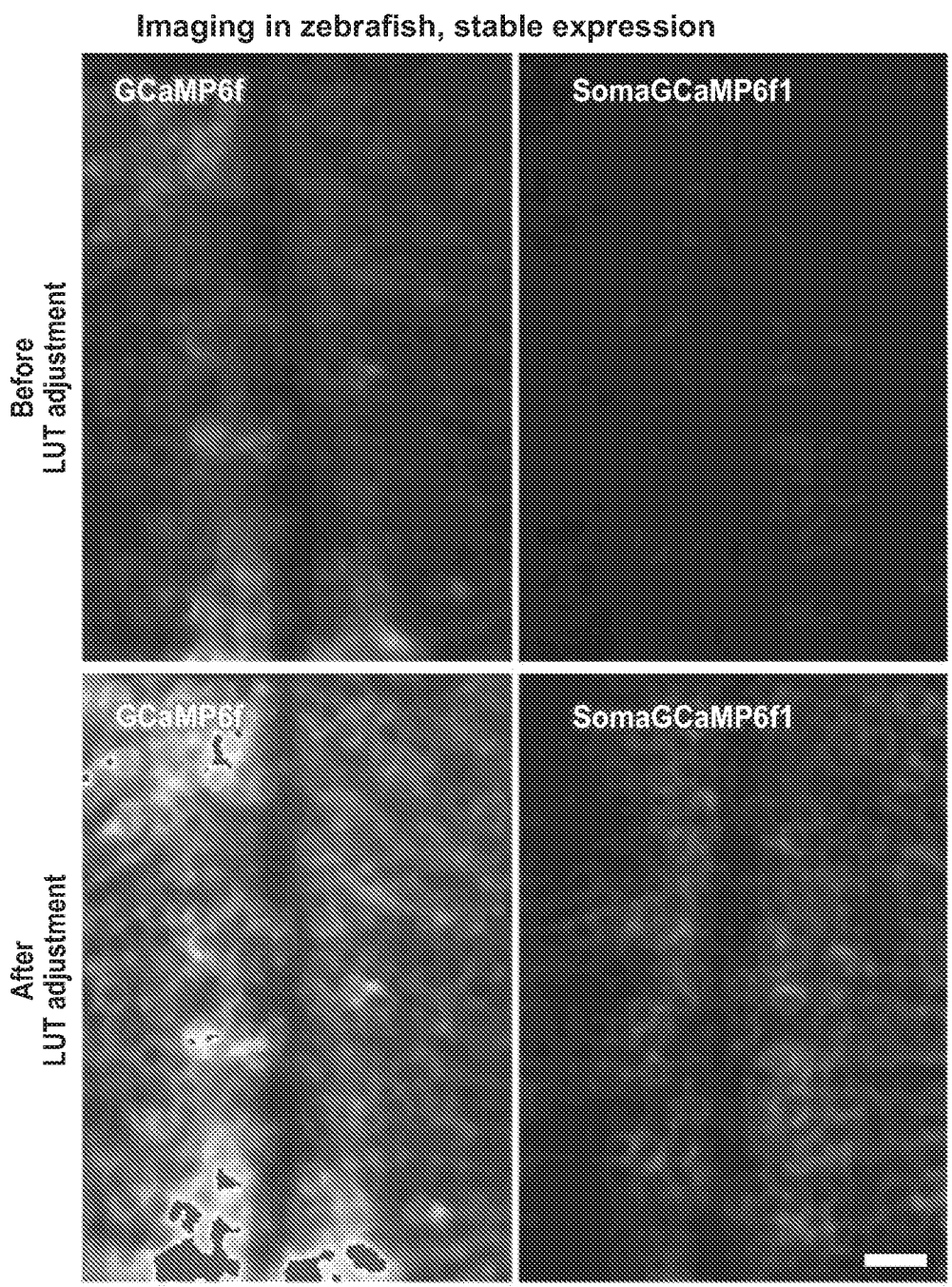
Figure 17F:
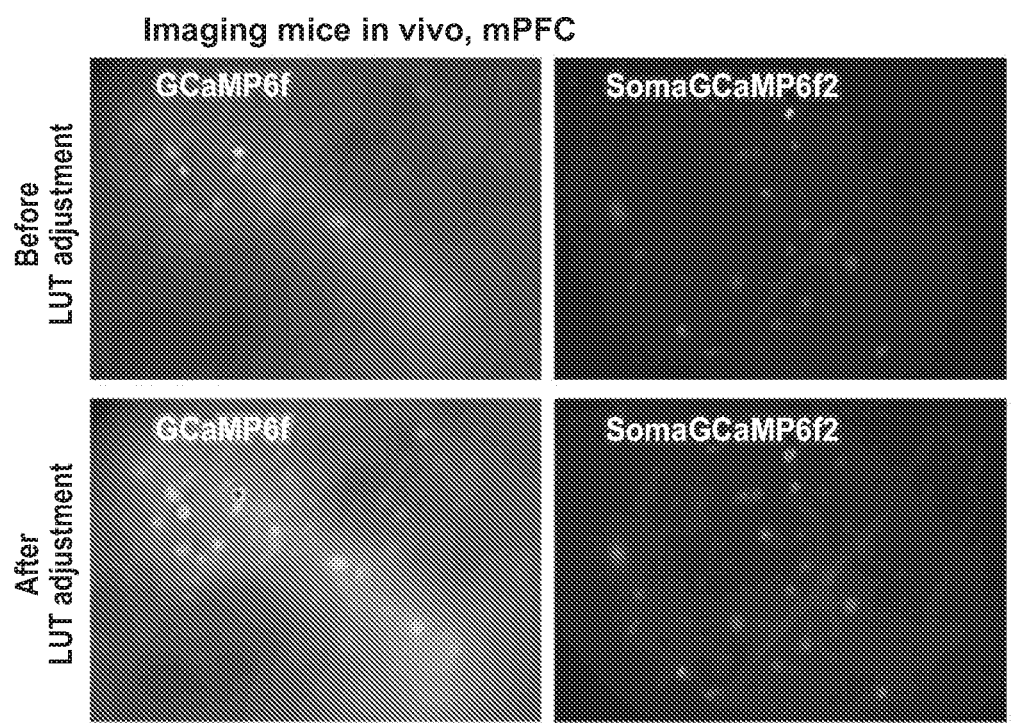

FIG. 17A-F provides images presented before and after look-up-table (LUT) adjustments. FIG. 17A provides images presented in FIGS. 1C, 1F and 1I of neurons expressing GCaMP6f, SomaGCaMP6f1 and SomaGCaMP6f2 respectively before and after LUT adjustment to maximize the brightness of the cell body. Scale bar, 20 µm. FIG. 17B provides images presented in FIG. 3A of neurons expressing GCaMP6f and SomaGCaMP6f1 before and after LUT adjustment. Scale bar, 20 µm. FIG. 17C provides images presented in FIGS. 5A and 5B of neurons expressing GCaMP6f and SomaGCaMP6f2 respectively before and after LUT adjustment. Scale bar, 100 µm. FIG. 17D provides images presented in FIG. 4B of neurons expressing GCaMP6f and SomaGCaMP6f1 before and after LUT adjustment. Scale bar, 5 µm. FIG. 17E provides images presented in FIG. 4I of neurons expressing GCaMP6f and SomaGCaMP6f1 before and after LUT adjustment. Scale bar, 10 µm. FIG. 17F provides images presented in FIGS. 6A and 6B of neurons expressing GCaMP6f and SomaGCaMP6f2 respectively before and after LUT adjustment.

Figure 18A:
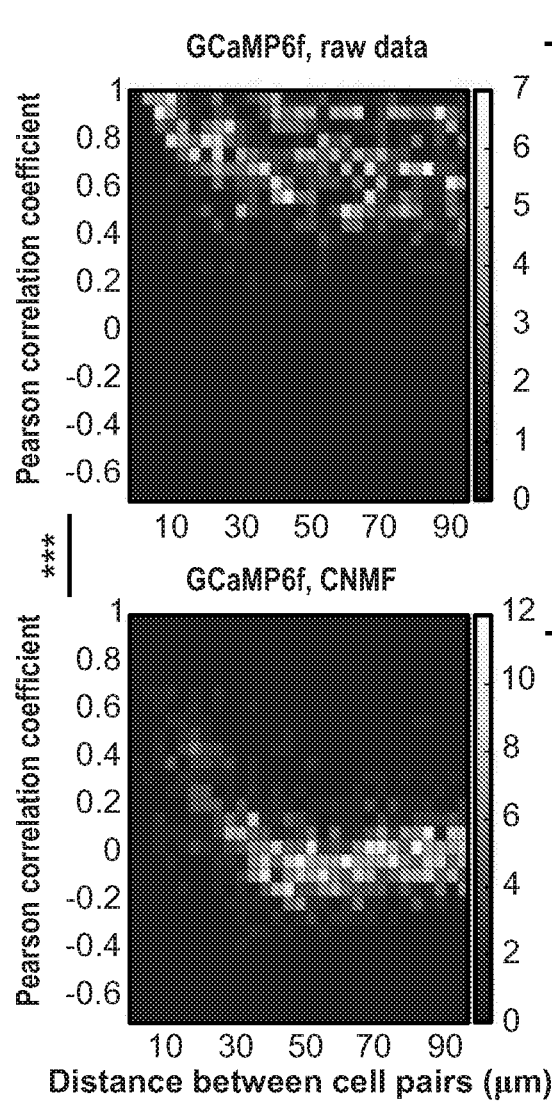
Figure 18B:
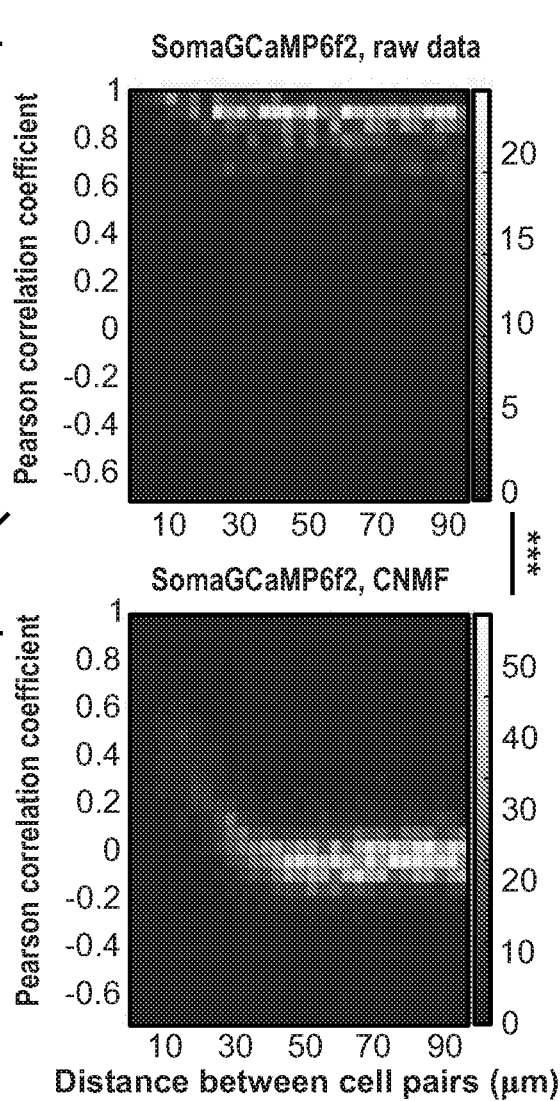
Figure 18C:
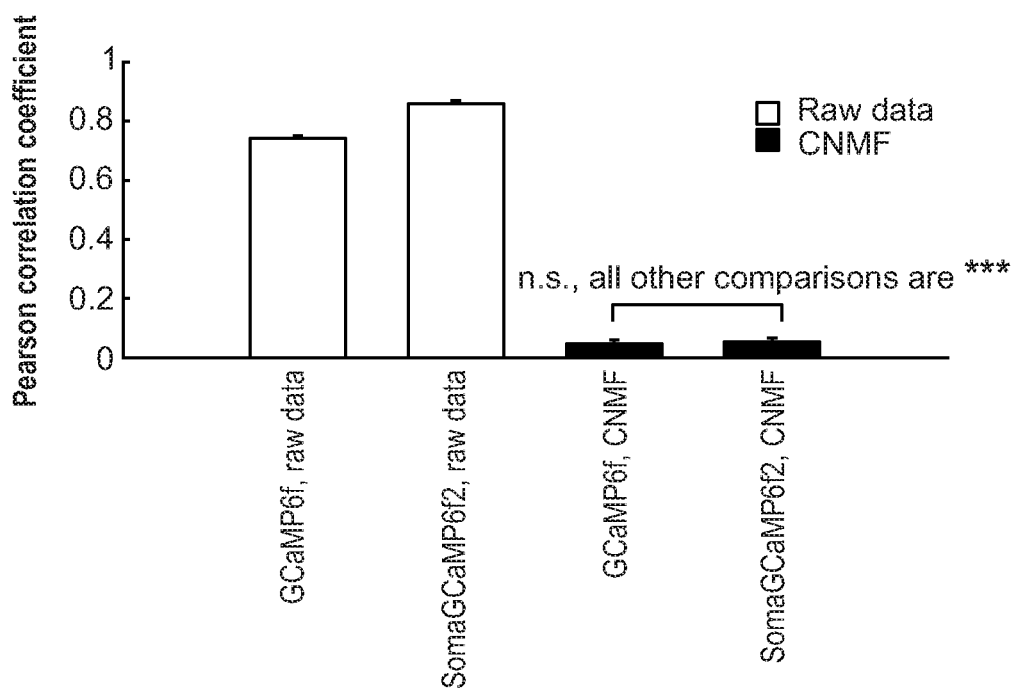
Figure 18D:
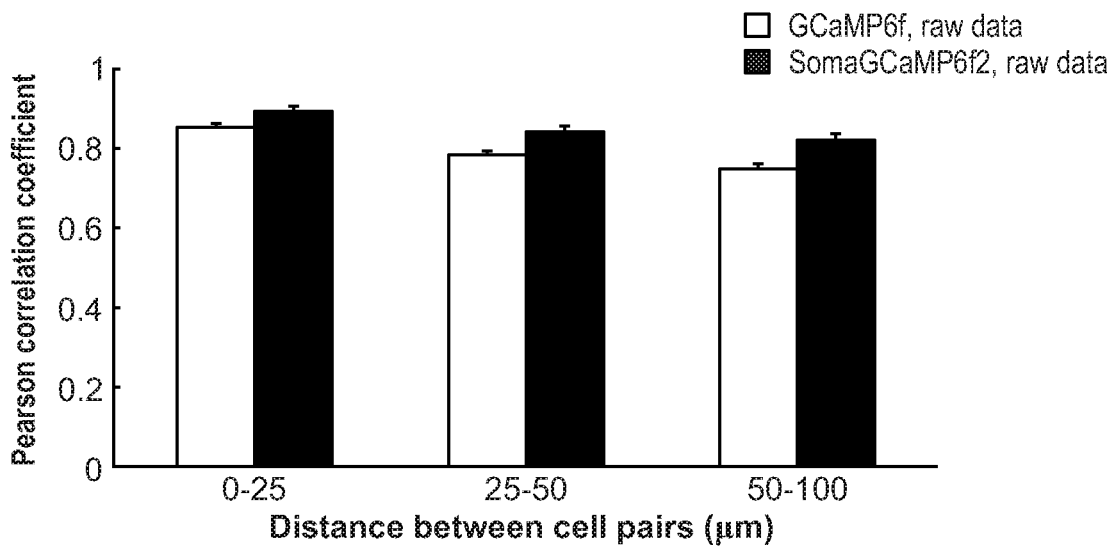
Figure 18E:
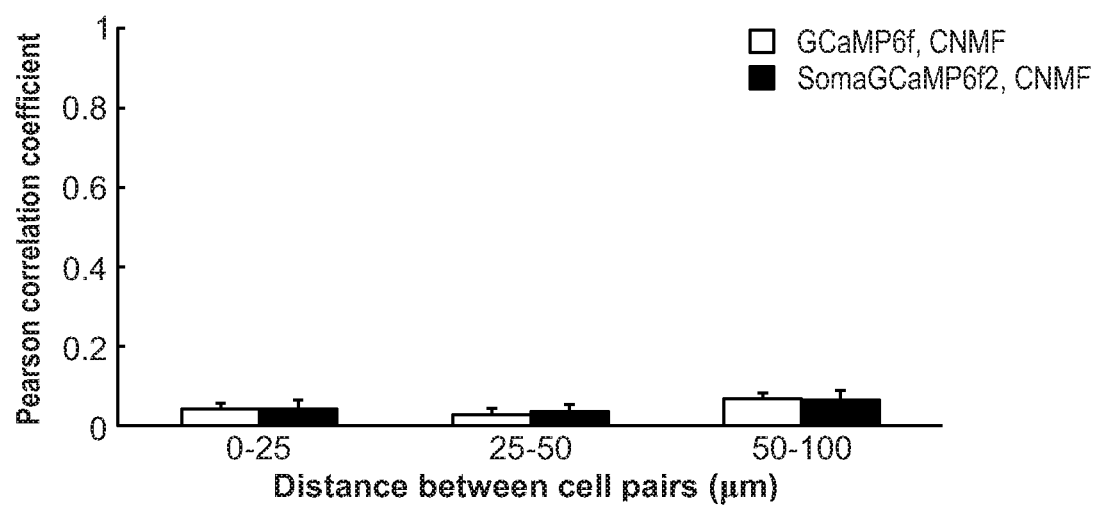

FIG. 18A-E shows correlograms based on neurons expressing GCaMP6f or SomaGCaMP6f2 imaged with a GRIN lens in the medial prefrontal cortex. FIGS. 18A and 18B provide correlograms denoting the relationship of distance to the strength of correlated fluorescence between cell pairs from mice expressing GCaMP6f (FIG. 18A; n=107 neurons from 2 mice) or SomaGCaMP6f2 (FIG. 18B; n=222 neurons from 4 mice). Distance distributions are shown on the x-axis and Pearson correlation coefficients are shown on the y-axis. (top row) Analysis was performed using raw data. (bottom row) Analysis was performed using data subjected to the neuropil contamination elimination algorithm CNMF. * P<0.001, two-dimensional Kolmogorov-Smirnov test between GCaMP6f and SomaGCaMP6f1. FIG. 18C is a bar chart showing the mean Pearson correlation coefficient between cell pairs in the mouse medial prefrontal cortex expressing either GCaMP6f or SomaGCaMP6f2 (n=107 neurons from 2 mice for GCaMP6f; n=222 neurons from 4 mice for SomaGCaMP6f2). White bars are for correlation coefficients calculated from raw data. Black bars are for correlation coefficients calculated from CNMF applied to the raw data. n.s., not significant. * P<0.001, Kruskal-Wallis analysis of variance followed by post-hoc Tukey's HSD test. Plotted is mean plus or minus standard error. FIG. 18D is a bar chart showing the mean Pearson correlation coefficient between cell pairs in the mouse medial prefrontal cortex expressing either GCaMP6f (white) or SomaGCaMP6f2 (gray), in three distance ranges from the soma: 0-25 µm, 25-50 µm and 50-100 µm (n=107 neurons from 2 mice for GCaMP6f; n=222 neurons from 4 mice for SomaGCaMP6f2). Correlation coefficient was calculated from raw data. Plotted is mean plus or minus standard error. FIG. 18E is a bar chart showing the mean Pearson correlation coefficient between cell pairs in the mouse medial prefrontal cortex expressing either GCaMP6f (white) or SomaGCaMP6f2 (gray), in three distance ranges from the soma: 0-25 µm, 25-50 µm and 50-100 µm (n=107 neurons from 2 mice for GCaMP6f; n=222 neurons from 4 mice for SomaGCaMP6f2). Correlation coefficient was calculated after CNMF was applied to raw data. See Table 16 for full statistics for FIG. 18A-E. Plotted is mean plus or minus standard error.

FIG. 19 provides proteins that were considered and certain of which were used in studies described herein. Information provided include protein names, targeting motifs, distance, constructs, and linkers.

BRIEF DESCRIPTION OF THE SEQUENCES

SEQ ID NO: 1 AnkTail-motif (AnkyrinG (1934-2333)):
REGRIDDEEPFKIVEKVKEDLVKV-
SEILKKDVCVESKGPPKSPKSDKGHSPEDDWTEF
SSEEIREARQAAASHAPSLPERVHGKANL-
TRVIDYLTNDIGSSSLTNLKYKFEEAKKD GEER-
QKRILKPAMALQEHKLKMPPASMRPSTSEKELCK-
MADSFFGADAILESPDDFS
QHDQDKSPLSDSGFETRSEKTPSAPQ-
SAESTGPKPLFHEVPIPPVITETRTEVVHVIRSY
EPSSGEIPQSQPEDPVSPKPSPTFMELEPKPTTSSIKE-
KVKAFQMKASSEEEDHSRVLS KGMRVKEETHITTT-
TRMVYHSPPGGECASERIEETMSVHDIMKAFQS-
GRDPSKELAG LFEHKSAMSPDVAKSAAET-
SAQHAEKDSQMKPKLERIIEVHIEKGPQSPCE.

SEQ ID NO: 2 EE-RR:
LEIEAAFLEQENTALETEVAELEQEVQRLENIVSQYETRYGPLGSLEIRAAFLRRRNTA LRTRVAELRQRVQRLRNIVSQYETRYGPL.

SEQ ID NO: 3 AcidP1-BaseP1:
AQLEKELQALEKENAQLEWELQALEKELAQGSGSAQLKKKLQALKKKNAQLKWKL QALKKKLAQ.

SEQ ID NO: 4 nullsfGFP (mutation to abolish the fluorescence of the original sfGFP is underlined)
MSKGEELFTGVVPILVELDGDVNGHKFSVRGEGEGDATNGKLTLKFICTTGKLPVPW PTLVTTLTGGVQCFSRYPDHMKRHDFFKSAMPEGYVQERTISFKDDGTYKTRAEVK FEGDTLVNRIELKGIDFKEDGNILGHKLEYNFNSHNVYITADKQKNGIKANFKIRHNV EDGSVQLADHYQQNTPIGDGPVLLPDNHYLSTQSVLSKDPNEKRDHMVLLEFVTAA GITHGMDELYK.

SEQ ID NO: 5 NLS
RKRPSDLVHVFSPPRKK.

SEQ ID NO: 6 KGC
KSRITSEGEYIPLDQIDINV.

SEQ ID NO: 7 ER2
FCYENEV.

SEQ ID NO: 8 nullCoChR (mutation to abolish photocurrent of the original CoChR is underlined)
MLGNGSAIVPIDQCFCLAWTDSLGSDTEQLVANILQWFAFGFSILILMFYAYQTWRA TCGWEEVYVCCVELTKVIIEFFHEFDDPSMLYLANGHRVQWLRYAEWLLTCPVILIH LSNLTGLKDDYSKRTMRLLVSDVGTIVWGATSAMSTGYVKVIFFVLGCIYGANTFFH AAKVYIESYHVVPKGRPRTVVRIMAWLFFLSWGMFPVLFVVGPEGFDAISVYGSTIG HTIIDLMSANCWGLLGHYLRVLIHQHIIIYGDIRKKTKINVAGEEMEVETMVDQEDEE TV.

SEQ ID NO: 9 KA2 (1-150)
MPAELLLLLIVAFANPSCQVLSSLRMAAILDDQTVCGRGERLALALAREQINGIIEVP AKARVEVDIFELQRDSQYETTDTMCQILPKGVVSVLGPSSSPASASTVSHICGEKEIPH IKVGPEETPRLQYLRFASVSLYPSNEDVSLAVS.

SEQ ID NO: 10 KA2 (1-150)-Y76A
MPAELLLLLIVAFANPSCQVLSSLRMAAILDDQTVCGRGERLALALAREQINGIIEVP AKARVEVDIFELQRDSQAETTDTMCQILPKGVVSVLGPSSSPASASTVSHICGEKEIPH IKVGPEETPRLQYLRFASVSLYPSNEDVSLAVS.

SEQ ID NO: 11 KA2 (1-100)
MPAELLLLLIVAFANPSCQVLSSLRMAAILDDQTVCGRGERLALALAREQINGIIEVP AKARVEVDIFELQRDSQYETTDTMCQILPKGVVSVLGPSSSP.

SEQ ID NO: 12 Ank (1-334) (AnkyrinG (1-334))
MAHAASQLKKNRDLEINAEEETEKKKKHRKRSRDRKKKSDANASYLRAARAGHLE KALDYIKNGVDVNICNQNGLNALHLASKEGHVEVVSELLQREANVDAATKKGNTA LHIASLAGQAEVVKVLVTNGANVNAQSQNGFTPLYMAAQENHLEVVRFLLDNGAS QSLATEDGFTPLAVALQQGHDQVVSLLLENDTKGKVRLPALHIAARKDDTKAAALL LQNDTNADIESKMVVNRATESGFTSLHIAAHYGNINVATLLLNRAAAVDFTARNDIT PLHVASKRG-
NANMVKLLLDRGAKIDAKTRDGLTPLHCGARSGHEQVVEMLLDRAA P.

SEQ ID NO: 13 AnkCT-motif (AnkyrinG (2334-2622))
RTDIRMAIVADHLGLSWTELARELNFSVDEINQIRVENPNSLISQSFMLLKKWVTRDG KNATTDALTSVLTKINRIDIVTLLEGPIFDYGNISGTRSFADENNVFHDPVDGWQNET PSGSLESPAQARRLTGGLLDRLDDSSDQARDSITSYLTGEPGKIEANGNHTAEVIPEA KAKPYFPESQNDIGKQSIKENLKPKTHGCGRTEEPVSPLTAYQKSLEETSKLVIEDAP KPCVPVGMKKMTRTTADGKARLNLQEEEGSTRSEPKQGEGYKVKTKKEIRNVEKK TH.

SEQ ID NO: 14 AnkMB-motif (Ankyrin$_G$ (1-800))
MAHAASQLKKNRDLEINAEEETEKKRKHRKRSRDRKKKSDANASYLRAARAGHLE KALDYIKNGVDVNICNQNGLNALHLASKEGHVEVVSELLQREANVDAATKKGNTA LHIASLAGQAEVVKVLVTNGANVNAQSQNGFTPLYMAAQENHLEVVRFLLDNGAS QSLATEDGFTPLAVALQQGHDQVVSLLLENDTKGKVRLPALHIAARKDDTKAAALL LQNDTNADVESKSGFTPLHIAAHYGNINVATLLLNRAAAVDFTARNDITPLHVASKR GNANMVKLLLDRGAKIDAKTRDGLTPLHCGARSGHEQVVEMLLDRSAPILSKTKNG LSPLHMATQGDHLNCVQLLLQHNVPVDDVTNDYLTALHVAAHCGHYKVAKVLLD KKASPNAKALNGFTPLHIACKKNRIRVMELLLKHGASIQAVTESGLTPIHVAAFMGH VNIVSQLMHHGASPNTTNVRGETALHMAARSGQAEVVRYLVQDGAQVEAKAKDD QTPLHISARLGKADIVQQLLQQGASPNAATTSGYTPLHLAAREGHEDVAAFLLDHGA SLSITTKKGFTPLHVAAKYGKLEVASLLLQKSASPDAAGKSGLTPLHVAAHYDNQK VALLLLDQGASPHAAAKNGYTPLHIAAKKNQMDIATSLLEYGADANAVTRQGIASV HLAAQEGHVDMVSLLLSRNANVNLSNKSGLTPLHLAAQEDRVNVAEVLVNQGAHV DAQTKMGYTPLHVGCHYGNIKIVNFLLQHSAKVNAKTKNGYTALHQAAQQGHTHII NVLLQNNASPNELTVNGNTAL.

SEQ ID NO: 15 AnkSB-motif (AnkyrinG (801-1521))
AIARRLGYISVVDTLKVVTEEIMTTTTITEKHKMNVPETMNEVLDMSDDEVRKASAP EKLSDGEYISDGEEGEDAITGDTDKYLGPQDLKELGDDSLPAEGYVGFSLGARSASL RSFSSDRSYTLNRSSYARDSMMIEELLVPSKEQHLTFTREFDSDSLRHYSWAADTLD NVNLVSSPVHSGFLVSFMVDARGGSMRGSRHHGMRIIIPPRKCTAPTRITCRLVKRH KLANPPPMVEGEGLASRLVEMGPAGAQFLGPVIVEIPHFGSMRGKERELIVLRSENG ETWKEHQFDSKNEDLAELLNGMDEELDSPEELGTKRICRIITKDFPQYFAVVSRIKQE SNQIGPEGGILSSTTVPLVQASFPEGALTKRIRVGLQAQPVPEETVKKILGNKATFSPIV TVEPRRRKFHKPITMTIPVPPPSGEGVSNGYKGDATPNLRLLCSITGGTSPAQWEDITG TTPLTFIKDCVSFTTNVSARFWLADCHQVLETVGLASQLYRELICVPYMAKFVVFAK TNDPVESSLRCFCMTDDRVDKTLEQQENFEEVARSKDIEVLEGKPIYVDCYGNLAPL TKGGQQLVFNFYSFKENRLPFSIKIRDTSQEPCGRLSFLKEPKTTKGLPQTAVCNLNIT LPAHKKETESDQDDAEKADRRQSFASLALRKRY-

SYLTEPSMKTVERSSGTARSLPTT YSHKPFF-STRPYQSWTTAPITVPGPAKSGSLSSSPSNTPSA.

SEQ ID NO: 16 AnkSR-motif (AnkyrinG (1534-1933))
SPLKSIWSVSTPSPIKSTLGASTTSSVKSIS-DVASPIRSFRTVSSPIKTVVSPSPYNPQVAS GTLGRVP-TITEATPIKGLAPNSTFSSRTSPVTTAGSLLERS-SITMTPPASPKSNITMYSSS LPFKSIITSATPLISSPLKSVVSPTKSAADVISTAKAT-MASSLSSPLKQMSGHAEVALV NGSVSPLKYPSSSAL-INGCKATATLQDKISTATNAVSSVVSAASDTVEKAL-STTTAMP FSPLRSYVSAAPSAFQSLRTPSASALYTSLGS-SIAATTSSVTSSIITVPVYSVVNVLPEP ALKKLPDSNSFTKSAAALLSPIKTLTTET-RPQPHFNRTSSPVKSSLFLASSALKPSVPSS LSSSQEILKDVAEMKEDLMRM-TAILQTDVPEEKPFQTDLP.

SEQ ID NO: 17 KV2.1-motif (KV2.1 (536-600))
QSQPILNTKEMAPQSKPPEELEMSSMPSPVAPL-PARTEGVIDMRSMSSIDSFISCATDF PEATRF.

SEQ ID NO: 18 rSK1-tail (rSK1 (351-411))
QAQKLRTVKIEQGKVNDQANTLADLAKAQ-SIAYEVVSELQAQQEELEARLAALESR LDVL-GASLQALPSLIAQAICPLPPPWPGPSHLT-TAAQSPQSHWLPTTASDCG.

SEQ ID NO: 19 NaV1.6 (II-III)
TVRVPIAVGESDFENLNTEDVSSESDP.

SEQ ID NO: 20 NaV1.2 (I-II)
YEEQNQATLEEAEQKEAEFQQMLEQLKKQQEEA-QAAAAAASAESRDFSGAGGIGVF SESSSVASK-LSSKSEKELKNRRKKKKQKEQAGEEEKE-DAVRKSASEDSIRKKGFQFS LEGSRLTYEKRFSSPHQSLLSIRGSLFSPRRN-SRASLFNFKGRVKDIGSENDFADDEHS TFEDNDSRRDSLFVPHRHGERRPSNVSQASRASR-GIPTLPMNGKMHSAVDCNGVVSL VGGPSALT-SPVGQLLPEGTTTETEIRKRRSSSYHVSMDLLEDPS-RQRAMSMASILTNT MEELEESRQKCPPCWYK-FANMCLIWDCCKPWLKVKHVVN.

SEQ ID NO: 21 a linker sequence referred to herein as "12"
ggsggtggsggt.

SEQ ID NO: 22 a linker sequence referred to herein as "24"
ggsggtggsggtggsggtggsggt.

SEQ ID NO: 23 a linker sequence referred to herein as "27"
ggsggsggtggsggsggtggsggsggt.

SEQ ID NO: 24 a linker sequence referred to herein as "48"
ggsggtggsggtggsggtggsggtggsggtggsggtggsggtggsggt.

SEQ ID NO: 25 a linker sequence referred to herein as "96"
ggsggtggsggtggsggtggsggtggsggtggsggtggsggtggsggtgg-sggtggsggtggsggtggsggtggsggtggsggt ggsggtggsggt.

SEQ ID NO: 26 a linker sequence referred to herein as "192"
ggsggtggsggtggsggtggsggtggsggtggsggtggsggtggsggtgg-sggtggsggtggsggtggsggtggsggtggsggt ggsggtggsggtggsggtggsggtggsggtggsggtggsggtggsggtggs-gtggsggtggsggtggsggtggsggtggsggt ggsggtggsggtggsggtggsggt.

SEQ ID NO: 27: a linker sequence
ggsggt.

DETAILED DESCRIPTION

Methods for one-photon fluorescent imaging of calcium dynamics in vivo are popular due to their ability to simultaneously capture the dynamics of hundreds of neurons across large fields of view, at a low equipment complexity and cost. In contrast to two-photon methods, however, one-photon methods suffer from higher levels of crosstalk between cell bodies and the surrounding neuropil, resulting in decreased signal-to-noise and artifactual correlations of neural activity. Methods and compositions of the invention now permit engineering cell body-targeted variants of the fluorescent calcium indicators GCaMP6f and GCaMP7f. Fusion of GCaMP6f or GCaMP7f to both natural as well as engineered peptides have been prepared, and fusions that localized GCaMP6f to within approximately 50 microns of the cell body of neurons in live mice and larval zebrafish have been identified. One-photon imaging of soma-targeted GCaMP6f and soma-targeted GCaMP7f in dense neural circuits have been determined to have fewer artifactual spikes from neuropil, increased signal-to-noise ratio, and decreased artifactual correlation across neurons. Thus, soma-targeting of fluorescent calcium indicators as described herein increases neuronal signal fidelity and may facilitate even greater usage of simple, powerful, one-photon methods of population imaging of neural calcium dynamics.

The invention, in part, relates to molecules and compounds that can be used to target the cell body of cells in which they are present and surprisingly, expressing the targeting peptides in conjunction with sensor polypeptides, such as but not limited to calcium indicator polypeptides. The invention, in part, also relates to methods of imaging expressed sensors in cells, tissues, and subjects. Such methods comprise expressing fusion proteins in cells in a subject, wherein a fusion protein expressed in one or more cells in the subject comprise a targeting polypeptide of the invention and a sensor polypeptide of interest.

The invention, in part, relates to soma-targeted sensor molecules that are selectively expressed in the cell body and weakly expressed elsewhere in cells, thereby effectively eliminating crosstalk, or signal overlap, of multiple expressed sensor molecules. A number of soma-targeting polypeptides have now been identified and used in methods described herein. In a non-limiting example, it has now been demonstrated that an EE-RR polypeptide or a functional variant thereof or an AnkTail Motif polypeptide or a functional variant thereof, can be expressed with a sensor polypeptide, for example, though not intended to be limiting, an encoded fluorescent calcium indicator GCaMP6f and GCaMP7f, and used in methods to selectively deliver the sensor polypeptide to the cell body of neurons in a subject.

Other soma-targeting polypeptides that can be used in certain embodiments of methods of the invention have now been identified, some of which are: Nav1.6, Nav1.2, rSK1-tail, Ankyrin$_G$, Kv2.1, KA2, AnkG, AnkCT-motif, AnkMB-motif, AnkSB-motif, AnkSR-motif, and AcidP1-BaseP1. Details, sequences, and information on each of the listed soma-targeting polypeptides are provided elsewhere herein, including for example Table 1. In certain aspects of the invention, one of the polypeptides in the forgoing list is fused with a fluorescent calcium indicator GCaMP6f or GCaMP7f, and used in methods to selectively deliver the sensor polypeptide to the cell body of cells, such as but not limited to, neurons in a subject.

Certain embodiments of methods and compositions of the invention can be used in combination with imaging means and stimulation means to image and detect activity in the soma of a cell in which the targeting polypeptide and the sensor polypeptide are expressed in a method of the invention. Fusion proteins of the invention that comprise an sensor polypeptide and a soma-targeting polypeptide of the invention, for example an EE-RR targeting polypeptide, an AnkTail Motif polypeptide, or certain other polypeptides disclosed herein can be used in methods for detecting and imaging an activity in a single cell or in a plurality of cells in mammalian brain slices, with millisecond temporal resolution, effectively without cross-talk imaging of activity of nearby cells. The term: "EE-RR polypeptide of the invention" used herein in reference to targeting polypeptides, includes the EE-RR polypeptide set forth as SEQ ID NO: 2 and polypeptides that are functional variants of the EE-RR polypeptide of SEQ ID NO: 2.

The term "AnkTail motif polypeptide of the invention" as used herein in reference to targeting polypeptides, includes the polypeptide set forth as SEQ ID NO: 1 and polypeptides that are functional variants of the AnkTail motif polypeptide of SEQ ID NO: 1.

As used herein the term "parent" polypeptide means the initial sequence form which a variant is derived. For example SEQ ID NO: 3 is a parent sequence of a functional variant of derived from that EE-RR polypeptide and SEQ ID NO: 1 is the parent sequence of a functional variant derived from that AnkTail motif polypeptide.

In some aspects of the invention, polypeptides in a fusion peptide may be connected to adjacent polypeptides and amino acid sequences with a linker amino acid sequence. An example of a linker amino acid sequence is; GSG and additional linker sequences are known and routinely used in the art and are suitable for use in compositions and methods of the invention. Linker sequences are also referred to as "spacer" sequences. In some aspects of compositions and methods of the invention, no linker is present between two polypeptides in a fusion protein, and in certain embodiments of the invention a linker between two polypeptides in a fusion protein may be: G, GS, GSGS, GGSGGT, or other suitable linker sequence, see sequences provided including, but not limited to: SEQ ID NOs: 21-27. Various linker sequences lengths can be used that include from 1 through 192 or more amino acids, including all integers between. Methods to prepare linker sequences are known in the fusion-protein arts can be used in methods of the invention.

A fusion protein of the invention may, in some aspects, comprise a sensor polypeptide and an AnkTail motif targeting polypeptide set forth herein as SEQ ID NO: 1 or a functional variant thereof, an EE-RR targeting polypeptide set forth herein as SEQ ID NO: 2, or a functional variant thereof. A non-limiting example of a fusion protein of the invention comprises a calcium indicator polypeptide, such as but not limited to: GCaMP6f or GCaMP7f, and a soma-targeting polypeptide of the invention, such as but not limited to an EE-RR polypeptide or functional variant thereof. A non-limiting example of a fusion protein of the invention is called: GCaMP6f-27-EE-RR, which includes a linker-referred to as "27" which corresponds to the linker sequence: ggsggsggtggsggsggtggsggsggt (SEQ ID NO: 23).

The invention also includes, in some aspects, use of optimized 2P optics with a fusion protein of the invention comprising a soma-targeting polypeptide of the invention, such as, but not limited to: an AnkTail motif targeting polypeptide set forth as SEQ ID NO: 1, or a functional variant thereof, and a calcium channel sensor polypeptide, which can permit a diverse set of neural codes and computations to be probed in systems and circuit neuroscience. As used herein components of a fusion protein, such as, but not limited to: one or more of an AnkTail motif polypeptide, an EE-RR polypeptide, or another soma-targeting polypeptide described herein, an ion channel activity sensor, an additional targeting polypeptide, and a detectable label polypeptide, may be referred to being "fused" to each other. For example, when referring to an AnkTail motif polypeptide and a sensor polypeptide that are part of a fusion protein, the AnkTail motif polypeptide may be referred to as being "fused" to the sensor polypeptide. As used herein, the term "and functional variant thereof" in used a phrase such as, but not limited to: "AnkTail motif polypeptide and/or EE-RR polypeptide and functional variants thereof" is intended to encompass: functional variants of the parent AnkTail motif polypeptide and functional variants of the parent EE-RR polypeptide.

In some aspects of the invention, one or more additional polypeptides of interest to express in a cell can be directed by a soma-targeting polypeptide of the invention, such as an AnkTail motif polypeptide, an EE-RR polypeptide, or other soma-targeting polypeptide of the invention, functional variants thereof, to the cell body of the cell in which they are expressed. As used herein, the term "directed" used in reference to a polypeptide of interest that is part of a fusion protein that also includes a soma-targeting polypeptide of the invention such as an AnkTail motif polypeptide, an EE-RR polypeptide, another soma-targeting polypeptide disclosed herein—or functional variant thereof of the invention, means the expressed polypeptide of interest is localized in the cell body of the cell in which the fusion protein is expressed, due to the function of the soma-targeting polypeptide. As herein, the term "directed" and "directing" are used interchangeably with the terms "targeted" and "targeting". A soma-targeting polypeptide of the invention, such as an AnkTail motif polypeptide, an EE-RR polypeptide, another soma-targeting polypeptide disclosed herein directs the localization of the expressed polypeptide of interest to the soma of the cell in which it is expressed. The ability to direct the location of the expressed polypeptide of interest to a specific cell region, the soma, results in improved efficiencies of specific delivery and localization of sensor polypeptides of interest in cells. A soma-targeting polypeptide of the invention, such as an AnkTail motif polypeptide, an EE-RR polypeptide, another soma-targeting polypeptide disclosed herein, or functional variants thereof may be used in embodiments of the invention for directed delivery of a membrane polypeptide of interest such as a sensor polypeptide in a cell. In certain aspects of the invention, a sensor polypeptide of interest is a calcium sensor.

A soma-targeting polypeptide of the invention may be used with a cargo polypeptide, a non-limiting example of which is a sensor polypeptide to result in the location of the expressed cargo polypeptide within a stated distance of the soma of a host cell. As used herein the term "host cell" means a cell in which the soma-targeting polypeptide and sensor polypeptide are expressed. It will be understood that a statement that a polypeptide is within a given distance of the soma of a host cell, includes instances when the cargo polypeptide is in the soma of the cell. In some embodiments of the invention, a cargo polypeptide is positioned within 60 microns, 50 microns, 40 microns, 30 microns, 20 microns, 10 microns, or 5 microns of the cell soma of the host cell. In some embodiments of the invention, the sensor polypeptide is in the soma and in certain embodiments of the invention the sensor polypeptide is outside of the soma and is within about 60, 59, 58, 57, 56, 55, 54, 53, 52, 51, 50, 49, 48, 47, 46, 45, 44, 43, 42, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 micron from an edge of the soma. The targeted GCaMP of the invention that is present in a host cell exhibits s a statistically significant preference to be in soma, compared to a GCaMP that is not targeted using a soma-targeting polypeptide or method of the invention.

Compositions of the invention may include a soma-targeting molecule of the invention, such as an AnkTail motif polypeptide, an EE-RR polypeptide, another soma-targeting polypeptide disclosed herein or a functional variant thereof, a sensor molecule, and one or more additional molecules. In some embodiments of the invention, a soma-targeting molecule of the invention, such as an AnkTail motif polypeptide, an EE-RR polypeptide, another soma-targeting polypeptide disclosed herein or functional variant thereof is a polypeptide. Certain embodiments of the invention, include a polynucleotide sequence that encodes an AnkTail motif polypeptide, an EE-RR polypeptide, another soma-targeting polypeptide disclosed herein or functional variant thereof.

Methods that can be used to prepare and express a fusion protein of the invention in a cell and in a subject, are well known in the art. In some aspects of the invention, one or more soma-targeting polypeptides of the invention may be used to direct one or more independently selected sensors expressed in a cell and/or subject. In certain implementations, the invention comprises methods for preparing and using genes encoding sensor polypeptides in vectors that also include a nucleic acid molecule that encodes a soma-targeting polypeptide of the invention. The invention, in part, also includes polynucleotides comprising nucleic acid sequences that encode a soma-targeting polypeptide of the invention as well as vectors and constructs that comprise such nucleic acid sequences. In some embodiments the invention includes expression in cells, tissues, and subjects of polypeptides encoded by the nucleic acid sequences.

Sequences and Functional Variants

As used herein the term "targeting sequence" means a soma-targeting sequence of the invention, such as an AnkTail motif polypeptide, an EE-RR polypeptide, another soma-targeting polypeptide disclosed herein or their encoding nucleic acid molecule or functional variants thereof. As used herein the term "a soma-targeting molecule of the invention" means a sequence such as the amino acid or encoding polynucleotide sequence of: an EE-RR polypeptide, an AnkTail motif polypeptide, functional variants of an EE-RR polypeptide, and functional variants of an AnkTail motif polypeptide. A soma-targeting molecule of the invention may also be another of the soma-targeting molecules disclosed herein such as: Nav1.6, Nav1.2, rSK1-tail, Ankyrin$_G$, Kv2.1, KA2, AnkG, AnkCT-motif, AnkMB-motif, AnkSB-motif, AnkSR-motif, and AcidP1-BaseP1, and functional variants thereof.

The term "variant" as used herein in the context of polypeptide molecules and/or polynucleotide molecules, describes a molecule with one or more of the following characteristics: (1) the variant differs in sequence from the molecule of which it is a variant (also referred to herein as a "parent molecule"), (2) the variant is a fragment of the molecule of which it is a variant and is identical in sequence to the fragment of which it is a variant, and/or (3) the variant is a fragment and differs in sequence from the fragment of the molecule of which it is a variant. As used herein, the term "parent" in reference to a sequence means a sequence from which a variant originates. For example, though not intended to be limiting: SEQ ID NO: 1 is the parent sequence for an AnkTail motif polypeptide functional variant of the invention.

A soma-targeting polypeptide of the invention may have the amino acid sequence set forth herein. As a non-limiting example, an AnkTail motif targeting polypeptide of the invention may have the amino acid sequence set forth herein as SEQ ID NO: 1, or may be a functional variant of the AnkTail motif targeting polypeptide that has a sequence that is modified from that of SEQ ID NO: 1. As another non-limiting example, an EE-RR targeting polypeptide of the invention may be a parent EE-RR polypeptide as described herein, or may be a functional variant of the parent EE-RR targeting polypeptide that has a sequence that is modified from that of its parent.

As used herein the term "modified" or "modification" in reference to a polypeptide sequence or a polynucleotide sequence refers to a change of 1, 2, 3, 4, 5, 6, 7, 8, 9, 10, 11, 12, 13, 14, 15, 16, 17, 18, 18, 20, 21, 22, 23, 24, 25, or more amino acids or nucleic acids, respectively in the sequence as compared to the parent soma-targeting polypeptide, or encoding nucleic acid sequence. As used herein, a sequence change or modification may be one or more of a substitution, deletion, insertion or a combination thereof. For example, though not intended to be limiting: the amino acid sequence of a functional variant EE-RR polypeptide may be identical to the EE-RR sequence set forth as SEQ ID NO: 2 except that it has one, two, three, four, five, or more amino acid substitutions, deletions, insertions, or combinations thereof.

The invention, in some aspects includes soma-targeting polypeptides of the invention and their encoding nucleic acid molecules, that have one or more substitutions or other modifications from molecules described herein, while retaining at least a portion of the function of the parent molecule of which they are a variant. For example, a soma-targeting polypeptides of the invention can be modified with one or more substitutions, deletions, insertions, combinations thereof, or other modifications and can be tested using methods described herein for characteristics including, but not limited to: expression, cell localization, targeting of one or more polypeptides of interest to the soma of a cell in which they are expressed, and the ability to direct a sensor polypeptide (co-expressed as part of a fusion protein) to the cell body (soma) of the cell in which the fusion protein comprising the soma-targeting polypeptide variant and the sensor polypeptide are expressed. A functional variant will have at least a portion of the targeting function of soma-targeting polypeptide from which it was derived, which is also referred to herein as its "parent sequence." In certain aspects of the invention, a functional variant of an EE-RR parent polypeptide, a functional variant of a parent AnkTail motif polypeptide, or other functional variant of another parent soma-targeting polypeptide of the invention has at least 5%, 10%, 15%, 20%, 25%, 30%, 35%, 40%, 45%, 50%, 55%, 60%, 65%, 70%, 75%, 80%, 85%, 90%, 95%, 100%, 105%, 110%, 120%, 130%, 140%, 150%, 160%, 170%, 180%, 190%, or 200% (including all integers in the stated range) of a level of function of its respective parent polypeptide from which it was derived. In some aspects of the invention, a functional variant of a soma-targeting polypeptide of the invention has more than 200% of the function of its parent polypeptide.

It will be understood that in some embodiments of the invention, a functional variant of a soma-targeting polypeptide of the invention may have an amino acid sequence that corresponds to the amino acid sequence of its parent polypeptide, or a variant thereof, but without 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74 amino acids corresponding to the amino acid sequence of the parent polypeptide. In some aspects of the invention, a functional variant of a soma-targeting polypeptide of the invention may be a fragment of the parent polypeptide set forth herein wherein the fragment has at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the region of the amino acid sequence of the parent sequence which it aligns. As a non-limiting example, a functional variant of an AnkTail motif polypeptide set forth herein as SEQ ID NO:1, may be a fragment of SEQ ID NO; I wherein the fragment has at least 75%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity to the region of the amino acid sequence of SEQ ID NO: 1 which it aligns.

In certain aspects of the invention a functional variant of a soma-targeting polypeptides of the invention, non-limiting examples of which are an AnkTail motif polypeptide, an EE-RR polypeptide comprises a sequence set forth as SEQ ID NO: 1, and SEQ ID NO: 2, respectively or a fragment thereof that includes one or more additional amino acids. For example, though not intended to be limiting, a functional variant may include one or more additional amino acids at the C terminus and/or N terminus that are not present in SEQ ID NO: 1, the parent sequence.

In invention in certain aspects, includes compositions and methods comprising a soma-targeting polypeptide of the invention, such as an AnkTail motif polypeptide or an EE-RR polypeptide that is a fragment of the amino acid sequence set forth as SEQ ID NO: 1, SEQ ID NO: 2, respectively, or is greater in length than SEQ ID NO: 1, or SEQ ID NO: 2 respectively, and retains at least a portion of the targeting function of the SEQ ID NO: 1, and SEQ ID NO: 2, respectively, to direct a sensor polypeptide to the soma of a cell in which a fusion protein comprising the AnkTail motif or EE-RR polypeptide variant and the sensor polypeptide is expressed. A functional variant of the soma-targeting polypeptide of the invention that is a fragment of a soma-targeting polypeptide of the invention, may be shorter or longer than its parent sequence.

A variant polypeptide (also referred to herein as a "modified" polypeptide) may include one or more deletions, point mutations, truncations, amino acid substitutions and/or additions of amino acids or non-amino acid moieties. Modifications of a polypeptide of the invention, such as soma-targeting polypeptide of the invention, may be made in certain aspects of the invention by modification of the nucleic acid sequence that encodes the polypeptide. Modifications of the molecules of the invention also embrace fusion proteins comprising all or part of the amino acid sequence of the parent soma-targeting polypeptide of the invention or a functional variant thereof.

In certain embodiments of the invention, a polypeptide variant may be a polypeptide that is modified specifically to alter a feature of the polypeptide that may be, but need not be related to its physiological activity. For example, though not intended to be limiting, one or more amino acid residues may substituted, deleted, or added to a soma-targeting polypeptide of the invention and result in a polypeptide variant having one or more of: increased stability, increased targeting efficiency: a least a portion of the targeting efficiency of the parent soma-targeting polypeptide. As used herein the term "targeting efficiency" when used in relation to a soma-targeting polypeptide of the invention, or functional variant thereof means the ability of the polypeptide to direct one or more additional polypeptides, for example though not intended to be limiting: a sensor polypeptide, a detectable label polypeptide, etc. to the cell body (soma) of a cell in which the soma-targeting polypeptide and the one or more additional polypeptides are expressed. In conjunction with teaching provided herein, a skilled artisan can use art-known methods to envision, prepare, and utilize additional functional variants of a soma-targeting polypeptide of the invention, but that includes one, two, three, four, or more amino acid substitutions, deletions, additions, or combinations thereof.

Polypeptides suitable for use in methods of the invention can be synthesized with modifications and/or modifications can be made in a polypeptide by selecting and introducing an amino acid substitution, deletion, or addition. Modified polypeptides then can be tested for one or more activities [e.g., delivery of one or more additional polypeptides, (for example: delivery of a sensor polypeptide); stability; accurate direction of the soma-targeting polypeptide of the invention and the additional polypeptide, (for example: directing a sensor polypeptide co-expressed in a fusion protein with the soma-targeting polypeptide) to the soma of a cell in which the molecules are expressed, etc.] to determine which modification provides a modified polypeptide with the desired properties and function.

The skilled artisan will also realize that conservative amino acid substitutions may be made in a soma-targeting polypeptide of the invention to result in a functional variant polypeptide of the parent polypeptide that retains at least a portion of the functional capability of the parent polypeptide. As used herein, a "conservative amino acid substitution" refers to an amino acid substitution that does not alter the relative charge or size characteristics of the polypeptide in which the amino acid substitution is made. Conservative substitutions of amino acids may, in some embodiments of the invention, include substitutions made amongst amino acids within the following groups: (a) M, I, L, V; (b) F, Y, W; (c) K, R, H; (d) A, G; (e) S, T; (f) Q, N; and (g) E. D. Polypeptide variants can be prepared according to methods for altering polypeptide sequence and known to one of ordinary skill in the art such. Non-limiting examples of functional variants of a soma-targeting polypeptide of the invention, are polypeptides comprising conservative amino acid substitutions of the AnkTail-motif polypeptide, EE-RR polypeptide, and other soma-targeting polypeptides of the invention disclosed herein.

The invention, in part, includes functional variants of a nucleic acid sequences that encode soma-targeting polypeptides of the invention as set forth herein. In some aspects of the invention, a functional variant of a soma-targeting polypeptide-encoding nucleic acid sequence of the invention has at least 75%, 80%, 81%, 82%, 83%, 84%, 85%, 86%, 87%, 88%, 89%, 90%, 91%, 92%, 93%, 94%, 95%, 96%, 97%, 98%, or 99% identity to the nucleic acid sequence that encodes the parent polypeptide, and the nucleic acid sequence of the functional variant encodes a polypeptide that is a functional variant of a soma-targeting polypeptide of the invention. In certain embodiments of the invention, a functional variant of a polynucleotide has at least 85%, 86%, 87%, 88%, 89%, 90%, 91%, 92%, 93%, 94%, 95%, 96%, 97%, 98%, 99%, or 100% nucleic acid sequence identity to the polynucleotide sequence of which it is a variant.

Sequence identity can be determined using standard techniques known in the art. To determine the percent identity (similarity) of two amino acid sequences the sequences are aligned for optimal comparison purposes (e.g., gaps may be introduced in the sequence of one protein for optimal alignment with the other protein). The amino acid residues at corresponding amino acid positions are then compared.

When a position in one sequence is occupied by the same amino acid residue as the corresponding position in the other sequence, then the molecules have identity/similarity at that position. The percent identity or percent similarity between the two sequences is a function of the number of identical positions shared by the sequences (i.e., % identity or % similarity=number of identical positions/total number of positions×100). Such an alignment can be performed using any one of a number of well-known computer algorithms designed and used in the art for such a purpose. Similarly, percent identity/similarity of polynucleotide sequences encoding a polypeptide of the invention can be determined using art-known alignment and comparison methods for nucleic acid molecules.

Standard art-known methods can be used to prepare variants of the soma-targeting polypeptide of the invention and their respective encoding nucleic acid sequences. A site or region for introducing an amino acid sequence modification may be predetermined, and the mutation per se need not be predetermined. For example, to optimize the performance of a mutation at a given site, random mutagenesis may be conducted at the target codon or region and the expressed polypeptide screened for the level of desired function or activity. Techniques for making substitution mutations at predetermined sites in DNA having a known sequence are well known, for example, M13 primer mutagenesis and PCR mutagenesis. Variant sequences may in some embodiments of the invention be prepared by site specific mutagenesis of nucleic acids in the DNA encoding a polypeptide of the invention, using cassette or PCR mutagenesis or other techniques known in the art, to produce DNA encoding the polypeptide. In certain embodiments of the invention, activity of variant or fragment of a polynucleotide or polypeptide can be tested by cloning the gene encoding the altered polypeptide into a bacterial or mammalian expression vector, introducing the vector into an appropriate host cell, expressing the altered polypeptide, and testing for a functional capability of the polypeptide as disclosed herein. Additional methods for generating recombinant polypeptides are known in the art may include use of prokaryotic and eukaryotic expression systems including but not limited to bacterial and mammalian expression systems.

It is understood in the art that the codon systems in different organisms can be slightly different, and that therefore where the expression of a given protein from a given organism is desired, the nucleic acid sequence can be modified for expression within that organism. Thus, in some embodiments, a targeting polypeptide and/or fusion protein of the invention is encoded by a mammalian-codon-optimized nucleic acid sequence, which may in some embodiments be a human-codon optimized nucleic acid sequence. In certain aspects of the invention, a nucleic acid sequence is optimized for expression in a human cell.

As used herein, the terms "protein" and "polypeptide" are used interchangeably and thus the term polypeptide may be used to refer to a full-length protein and may also be used to refer to a fragment of a full-length protein, and/or functional variants thereof. As used herein, the terms "polynucleotide" and "nucleic acid sequence" may be used interchangeably and may comprise genetic material including, but not limited to: RNA, DNA, mRNA, cDNA, etc., which may include full length sequences, functional variants, and/or fragments thereof.

Targeted Molecules

Molecules that can be targeted to a specific location in a cell, such as the cell body, include, but are not limited to: sensor polypeptides, detectable label polypeptides, fluorescent polypeptides, additional trafficking polypeptides, etc. As used herein a polypeptide that is targeted to a location using a soma-targeting polypeptide of the invention may also be referred to as a "cargo" polypeptide. In some embodiments of the invention, a cargo polypeptide comprises a sensor polypeptide molecule. In some embodiments of the invention a cargo polypeptide comprises a calcium indicator polypeptide. In certain embodiments of the invention a cargo polypeptide comprises a CGaMP6f polypeptide, or functional variant thereof. In some aspects of the invention a cargo polypeptide comprises any variant of the GCaMP family, including, but not limited to: CGaMP6f, CGaMP6m, CGaMP6s GCaMP7, GCaMP7f, or a functional variant thereof. In some aspects of the invention a cargo polypeptide comprises any variant of the red emitting calcium sensors, such, but not limited to, RCaMP1, R-GECO, R-CaMP2, RCaMP1, R-GECO1, jRCaMP1a, jRCaMP1b, and mApple-based jRGECO1a or a functional variant thereof. Additional calcium sensor molecules are known in the art and can be used in embodiments of methods of the invention, see for example: Horikawa, K. J. Med. Invest, 2015, Vol. 62, 24-28; Chen, T., et al. Nature. 2013 Jul. 18; 499 (7458): 295-300; and Dana et al. eLife 2016;5:e12727; the content of each of which is incorporated by reference herein.

Non-limiting examples of detectable label cargo polypeptides include: green fluorescent protein (GFP): enhanced green fluorescent protein (EGFP), red fluorescent protein (RFP): yellow fluorescent protein (YFP), dtTomato, mCherry, DsRed, mRuby, cyan fluorescent protein (CFP): far red fluorescent proteins, etc. Numerous fluorescent proteins and their encoding nucleic acid sequences are known in the art and routine methods can be used to include such sequences in fusion proteins and vectors, respectively, of the invention.

Additional sequences that may be included in a fusion protein of the invention are trafficking sequences, including, but not limited to: Kir2.1 sequences and functional variants thereof, KGC sequences, ER2 sequences, etc. Additional trafficking polypeptides and their encoding nucleic acid sequences are known in the art and routine methods can be used to include and use such sequences in fusion proteins and vectors, respectively, of the invention.

Another type of cargo molecule that may be included in compositions and used in methods of the invention is a sensor molecule. As used herein, the term "sensor" means a molecule that when expressed in a cell functions as sensor and reacts in a detectable manner to changes in ion flow across a membrane and/or in cell. A non-limiting example of a sensor is a calcium indicator, such as GCaMP6f and/or GCaMP7f. As used herein the term "sensor" may include a sensor having a sequence that is one or more of: a wild type sensor sequence, a modified sensor sequence, a mutated sensor sequence, a chimeric sensor sequence, a synthetic sensor sequence, a functional fragment of a sensor sequence that may include one or more additions, deletions, substitutions, or other modifications to the sequence of the parent sensor sequence from which the variant sensor sequence originates, and a functional variant of a sensor sequence that may include one or more additions, deletions, substitutions, or other modifications to the sequence of the parent sensor sequence from which the variant sequence originates.

Methods of preparing and using sensor molecules and functional variants thereof are well known in the art and such sensor molecules may be used in aspects of the invention. Additional sensor polypeptides and their encoding nucleic acid sequences are known in the art and routine methods can be used to include and use such sequences and functional variants thereof in fusion proteins and vectors, respectively, of the invention.

In some embodiments of the invention, an activity of a cell may be one or more of: an action potential, a pH change, release of a neurotransmitter, etc. Methods and compositions of the invention can be used to assess electrical activity and ion flux activity and changes and modulation of such activities upon stimulation and activation of a host cell or a cell that is in communication with a host cell. Methods and compositions of the invention permit imaging, such as but not limited to one-photon imaging of soma-targeted sensor in dense neural circuits with fewer artifactual spikes from neuropil, increased signal—to noise ratio, and decreased artifactual correlation across neurons. Thus, methods and compositions of the invention permit soma-targeting of sensor molecules that results in increased neuronal signal fidelity and are able to facilitate higher efficacy of imaging means such as, but not limited to, one-photon methods of cell population imaging of neural dynamics. It will be understood that an activity in a host cell may result from direct or indirect stimulation of the host cell. For example a host cell may be directly contacted with a stimulus or it may receive a stimulus that originated in a second cell, one that is upstream from the host cell that when stimulated transmits a stimulus to the host cell via an action potential, transmitter, etc.

Delivery of Targeting and Other Polypeptides

Delivery of a targeting molecule to a cell and/or expression of a targeting polypeptide and its cargo in a cell can be done using art-known delivery means. In some embodiments of the invention a soma-targeting polypeptide and sensor polypeptide of the invention are included in a fusion protein. It is well known in the art how to prepare and utilize fusion proteins that comprise one or more polypeptide sequences. In certain embodiments of the invention, a fusion protein can be used to deliver a targeting polypeptide, such as a soma-targeting polypeptide of the invention such as, but not limited to: an EE-RR polypeptide, AnkTail motif polypeptide, or a functional variant thereof of the invention to a cell and may, in some embodiments, be used to deliver a cargo polypeptide such as a sensor polypeptide to the soma of a host cell in which the fusion protein is expressed. A fusion protein of the invention can be expressed in a specific cell type, tissue type, organ type, and/or region in a subject, or in vitro, for example in culture, in a slice preparation, etc. Preparation, delivery, and use of a fusion protein and its encoding nucleic acid sequences are well known in the art. Routine methods can be used in conjunction with teaching herein to express a soma-targeting polypeptide, a sensor polypeptide, and optionally additional polypeptides, in a desired cell, tissue, or region in vitro or in a subject.

It is an aspect of the invention to provide a sensor polypeptide that is non-toxic, or substantially non-toxic in cells in which it is expressed. A sensor polypeptide of the invention does not significantly alter cell health, ion flow, or electrical activity in the cell in which it is expressed. In some embodiments of the invention, a sensor polypeptide of the invention is genetically introduced into a cell, and reagents and methods are provided herein for genetically targeted expression of sensor polypeptides. Genetic targeting using a soma-targeting polypeptide of the invention can be used to deliver a sensor polypeptide to specific cell types, to specific cell subtypes, to specific spatial regions within an organism, and to sub-cellular regions within a cell, such as the soma of a cell. Routine genetic procedures can also be used to control parameters of expression, such as but not limited to: the amount of a sensor polypeptide expressed, the timing of the expression, etc.

In some embodiments of the invention a reagent for genetically targeted expression of a sensor polypeptide is a vector comprising a gene encoding a soma-targeting polypeptide of the invention and gene encoding a sensor polypeptide. As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert a sensor polypeptide and a soma-targeting polypeptide of the invention into dividing and non-dividing cells and can insert a sensor polypeptide and a soma-targeting polypeptide of the invention into a cell that is an in vivo, in vitro, or ex vivo cell.

Vectors useful in methods of the invention may include additional sequences including, but not limited to, one or more signal sequences and/or promoter sequences, or a combination thereof. In certain embodiments of the invention, a vector may be a lentivirus, adenovirus, adeno-associated virus, or other vector that comprises a gene encoding a sensor polypeptide and a gene encoding a soma-targeting polypeptide of the invention. An adeno-associated virus (AAV) such as AAV8, AAV1, AAV2, AAV4, AAV5, AAV9, are non-limiting examples of vectors that may be used to express a fusion protein of the invention in a cell and/or subject. Expression vectors and methods of their preparation and use are well known in the art. Non-limiting examples of suitable expression vectors and methods for their use are provided herein.

Promoters that may be used in methods and vectors of the invention include, but are not limited to, cell-specific promoters or general promoters. Non-limiting examples promoters that can be used in vectors of the invention are: ubiquitous promoters, such as, but not limited to: CMV, CAG, CBA, and EF1a promoters; and tissue-specific promoters, such as but not limited to: Synapsin, CamKIIa, GFAP, RPE, ALB, TBG, MBP, MCK, TNT, and aMHC promoters. Methods to select and use ubiquitous promoters and tissue-specific promoters are well known in the art. A non-limiting example of a tissue-specific promoter that can be used to express a sensor polypeptide in a cell such as a neuron is a synapsin promoter, which can be used to express a sensor polypeptide and soma-targeting polypeptide of the invention in embodiments of methods of the invention. Additional tissue-specific promoters and general promoters are well known in the art and, in addition to those provided herein, may be suitable for use in compositions and methods of the invention.

Imaging

According to principles of this invention, a soma-targeting polypeptide of the invention, can be used to target a polypeptide such as, but not limited to, a sensor polypeptide, to the soma of a cell. The activity of the sensor polypeptide in the soma of a host cell can be determined using art-known detection means. Non-limiting examples of detection means are provided herein, including in the Examples. Examples of a cell in which a fusion protein comprising a soma-targeting polypeptide of the invention can be delivered with a sensor polypeptide, for detection using the sensor include but are not limited to: a single isolated cell, a cell in culture, an in vitro cell, an in vivo cell, an ex vivo cell, a cell in a tissue, a cell in a subject, a cell in an organ, a cell in a cultured tissue, a cell in a neural network, a cell in a brain slice, a neuron, etc.

A soma-targeting polypeptide of the invention expressed as part of a fusion protein that also includes one or more of a sensor polypeptide, a fluorescent polypeptide, a detectable label polypeptide, etc. permits detection and imaging of the ion movement and activity in the cell in which the fusion protein is expressed. In some aspects of the invention, imaging methods include detection of activity in one or more cells with millisecond temporal resolution, without statistically significant cross-talk activation of nearby cells. Expression of a fusion protein of the invention in a cell results in delivery and localization of the cargo polypeptide in the cell body of the cell. Because little or no delivery of the sensor polypeptide occurs outside of the cell body of a cell in which a fusion protein of the invention is expressed, it is possible to detect activity in the host cell, even in the presence of other cells, with sub-millisecond precision. Certain embodiments of imaging methods of the invention are described herein, and certain means for optimizing such methods are provided in the Examples section. It will also be understood that alternative detection and imaging tools and methods may be compatible with compositions and methods of the invention.

Targeting polypeptides of the invention, such as a soma-targeting polypeptide of the invention are well suited for directing one or more cargo polypeptides that are expressed in a fusion protein with the targeting polypeptide, to the soma of a host cell in which the fusion protein is expressed. Expression of the sensor in the cell body can be used to detect ion movement and ion localization changes in the host cell. Embodiments of compositions and methods of the invention result in specific targeting of the expressed cargo to the soma of the host cell, and thus can be used to selectively detect activity in a single cell in which a fusion protein of the invention is expressed. It will be understood that the type and amount of a sensor expressed in a host cell will determine the type of ion flux that can be detected in the host cell. Art-known methods can be used to select suitable sensor parameters such as type of ions to be detected, activity to be detected, etc. for use with compositions and methods of the invention expressed in host cells and membranes.

Certain aspects of the invention include methods for detecting one or more characteristics of a cell, such as, but not limited to: ion flux across a cell membrane. Compositions and methods of the invention can be used in a cell and/or a subject as a means with which to: detect ion flux across a membrane of a cell, assess changes in cells resulting from a candidate treatment of a disease or condition in a cell or subject, to assess activity and identify a candidate agent that alters ion flux in a manner detected by a sensor of a fusion protein of the invention expressed in a host cell, etc. Various methods useful to detect changes in activity (or output) of one or more sensor polypeptides expressed in a host cell and/or a host subject are known in the art and the compositions and methods of the invention may be used in conjunction with such methods to enhance selective imaging of a cell.

Methods and compositions of the invention permit selective expression of a sensor polypeptide in a cell body and determination of ion flux based on detection of changes in the sensor, with little or no cross-talk from other cells. As used herein the term "cross-talk" when used in the context of sensing means ion flux in one or more cells whose processes physically touch the cell in which a fusion protein of the invention is expressed. A soma-targeting polypeptide and sensor polypeptide of the invention, when expressed in a cell results in selective targeting of the sensor polypeptide to the cell body of the cell in which it is expressed. Selective targeting by the soma-targeting polypeptide of the invention directs a sensor polypeptide to a host cell soma and permits imaging of sensor activity in single cells even within a plurality of cells and/or in cellular networks without cross-talk. Methods and compositions of the invention provide an efficient and selective means to localize and image activity of sensor polypeptides that are expressed in fusion proteins of the invention, and the activity of the sensor polypeptide reflects ion flux and concentration changes in the cell.

Working operation of a prototype of this invention has been demonstrated in vitro and in vivo, by genetically expressing a fusion protein comprising a sensor polypeptide and a soma-targeting polypeptide of the invention in cells, detecting ion changes evidenced by the sensor, and demonstrating that the methods of the invention can be used to detect changes in ion flux in the host cell. Depending on the particular implementation, methods of the invention allow directed localization of a sensor in the soma of a cell and precise detection of ion flux in host cells in vivo, ex vivo, and in vitro.

Cells and Subjects

A cell used in methods and with sequences of the invention may be an excitable cell or a non-excitable cell. A cell in which a fusion protein comprising a sensor polypeptide and a soma-targeting polypeptide of the invention may be expressed and may be used in methods of the invention include prokaryotic and eukaryotic cells. Useful cells include, but are not limited to, vertebrate cells, which in some embodiments of the invention may be mammalian cells. Examples of cells in which a fusion protein comprising a sensor polypeptide and a soma-targeting polypeptide of the invention may be expressed are excitable cells, which include cells able to produce and respond to electrical signals. Examples of excitable cell types include, but are not limited to neurons, muscles, cardiac cells, and secretory cells (such as pancreatic cells, adrenal medulla cells, pituitary cells, etc.). A cell in which a fusion protein of the invention is expressed may be a single cell, an isolated cell, a cell that is one of a plurality of cells, aa cell that is one in a network of two or more interconnected cells, a cell that is one of two or more cells that are in physical contact with each other, etc.

Non-limiting examples of cells that may be used in methods of the invention include: nervous system cells, cardiac cells, circulatory system cells, visual system cells, auditory system cells, secretory cells, endocrine cells, and muscle cells. In some embodiments, a cell used in conjunction with the invention may be a healthy normal cell, which is not known to have a disease, disorder or abnormal condition. In some embodiments, a cell used in conjunction with methods and compositions of the invention may be an abnormal cell, for example, a cell obtained from a subject diagnosed as having a disorder, disease, or condition, including, but not limited to a degenerative cell, a neurological disease-bearing cell, a cell model of a disease or condition, an injured cell, etc. In some embodiments of the invention, a cell may be a control cell. In some aspects of the invention a cell can be a model cell for a disease or condition.

A fusion protein comprising a sensor polypeptide and a soma-targeting polypeptide of the invention may be expressed in one or more cells from culture, cells in solution, cells obtained from subjects, and/or cells in a subject (in vivo cells). Sensor polypeptides in fusion proteins of the invention may be expressed in cultured cells, cultured tissues (e.g., brain slice preparations, etc.), and in living subjects, etc. As used herein, the term "subject" may refer to a: human, non-human primate, cow, horse, pig, sheep, goat, dog, cat, rodent, fly or other host organism. As used herein the term "host" means the subject or cell in which a fusion protein of the invention is expressed. In some aspects of the invention a host is a vertebrate subject. In certain embodiments of the invention, a host is a mammal. In certain aspects of the invention a host is an invertebrate subject.

Controls and Candidate Compound Testing

Using certain embodiments of compositions and methods of the invention, one or more sensor polypeptides can be expressed in a localized region of a cell, for example the soma, and methods to image ion flux and changes in the cell, for example in response to external stimulation of the host cell, can be utilized to assess changes in cells, tissues, and subjects in which they are expressed. Some embodiments of the invention include directed delivery of one or more sensor polypeptides to the soma of a cell to identify effects of one or more candidate compounds on the cell, tissue, and/or subject in which the sensor is expressed. Results of testing one or more changes in ion flux using a sensor polypeptide of the invention can be advantageously compared to a control.

As used herein a control may be a predetermined value, which can take a variety of forms. It can be a single cut-off value, such as a median or mean. It can be established based upon comparative groups, such as cells or tissues that include the sensor and receive an external stimulation and cells or tissues that include the sensor that are not contacted with the external stimulation. In some embodiments, a host cell that includes a sensor may be contacted with a candidate compound and the effect on the ion flux determined by detecting the sensor. This effect can be compared to a control host cell that includes the sensor, but is not contacted with the candidate compound. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention Candidate-compound identification methods of the invention may be carried out in a cell in a subject or in cultured or in vitro cells. Non-limiting examples of candidate-compound identification methods of the invention in a subject may include expressing a fusion protein comprising a sensor polypeptide and a soma-targeting polypeptide of the invention, providing an external stimulation or activation of the host cell, and administering to the subject a candidate compound. The subject is then monitored to determine whether any change occurs that differs from a control effect in a subject. Candidate-compound identification methods of the invention that are performed in vitro may include expressing a fusion protein comprising a sensor polypeptide and a soma-targeting polypeptide of the invention in a cell, which may or may not be a cultured cell, providing an external stimulation or activation of the host cell, and administering to the subject a candidate compound and determining whether there is a change in the sensor output resulting from the contacting the host cell, or an upstream cell in communication with the host cell, with a candidate compound. The host cell is monitored to determine whether any change occurs that differs from a control effect in a substantially similar cell that is not contacted with the candidate compound.

Methods of identifying effects of candidate compounds using fusion proteins of the invention may also include additional steps and assays to further characterizing an identified activity change in the cell, tissue, or subject when the host cell comprising a sensor is exposed to stimulation or is activated. In some embodiments of the invention, testing in a cell, tissue, or subject can also include testing one or more cells that each comprises one or more independently selected sensors polypeptides, and in some aspects of the invention two or more different sensor polypeptides are expressed in two or more cells that may be in close spatial proximity with each other, may be in physical contact with each other, or may be spatially distant from each other.

In a non-limiting example of a candidate drug identification method of the invention, cells in which a fusion protein comprising a sensor polypeptide and soma-targeting polypeptide of the invention are exposed to a stimulation or are activated and changes in the host cell are determined by detecting changes in the output of the sensor. A candidate therapeutic compound can then be applied to determine if they modulate the response of the host cell to depolarization (determined for example using patch clamping methods or other suitable art-known means). These and other methods enable therapeutic compound screening using detection of the output of a sensor polypeptide using methods of the invention, is localized in the cell body of the host cell in which it is expressed.

In some embodiments of the invention, a fusion protein comprising a sensor polypeptide and soma-targeting polypeptide of the invention can be used in test systems and assays for assessing membrane protein trafficking and physiological function in cells and subjects and the use of use of a sensor polypeptide that is located in the soma of a host cell can determine ion changes in the host cell. Implementation of fusion proteins comprising a soma-targeting polypeptide and a sensor in a host cell and determining changes in output of the expressed sensor in the host cell under various conditions, such as depolarization, APs, ion flux, hyperpolarization etc. are included in certain aspects of the invention. In certain aspects of the invention, a fusion protein comprising a sensor polypeptide and soma-targeting polypeptide of the invention can be expressed in a host cell and/or subject and used to assess or diagnose a disease or condition in the subject—that impacts the host cell with altered ion flux or activity that results in a change in output of the sensor.

Methods of Administration

Methods of the invention may include administering to a subject, an effective amount of a vector encoding a fusion protein comprising a sensor polypeptide and a soma-targeting polypeptide of the invention, to assess one or more activities in a host cell. In certain aspects of the invention, an effective amount of a host cell comprising a fusion protein of the invention may be administered to a subject in a method of the invention. An embodiment of a method of the invention may be used to assess the stage or status of a disorder, disease, or condition that results in a change in ion flux or an activity of a host cell.

In certain aspects of the invention, a means of expressing in a cell of a subject, a fusion protein comprising a soma-targeting polypeptide of the invention and a sensor polypeptide may comprise: administering to a cell a vector that encodes a fusion protein comprising the sensor polypeptide and a soma-targeting polypeptide of the invention: administering to a subject a cell in which a fusion protein of the invention is present: or administering a fusion protein of the invention to a subject. Delivery or administration of a fusion protein of the invention may include administration of a pharmaceutical composition that comprises cell, wherein the cell expresses the sensor polypeptide fused to a soma-targeting polypeptide of the invention. Administration of a sensor polypeptide and soma-targeting polypeptide of the invention may, in some aspects of the invention, include administration of a pharmaceutical composition comprising a vector, wherein the vector comprises a nucleic acid sequence encoding a sensor polypeptide and a soma-targeting polypeptide of the invention, wherein the administration of the vector results in expression of a fusion protein comprising the sensor polypeptide and the soma-targeting polypeptide of the invention in one or more cells in the subject. In some aspects of the invention, targeted expression of a sensor polypeptide in the soma of a cell may be referred to as "increasing" expression of that sensor polypeptide in the soma of the cell. It will be understood that in some aspects of the invention, the starting level of expression of the sensor in the soma of a cell may be zero and a method of the invention may be used to increase that level above zero. In certain aspects of the invention, for example in a subsequent delivery of a fusion protein of the invention to a cell and/or subject, a level of expression of the sensor polypeptide the soma of a cell may be greater than zero, with one or more of the sensor polypeptides present in the soma, and a method of the invention may be used to increase the expression level of the sensor polypeptide in the cell soma.

An effective amount of a sensor polypeptide and a soma-targeting polypeptide of the invention is an amount that results in expression of the sensor polypeptide in the cell body of a host cell, in a tissue or subject at a level or amount that permits determining the sensor output. An effective amount may also be determined by assessing the ability to detect the sensor output under different conditions. Other assays to determine activity of the sensor will be known to a skilled artisan and can be employed for measuring a level of a response. The amount of a sensor expressed in a host cell may be varied for example by increasing or decreasing the amount of the targeted sensor polypeptide administered, by changing the composition in which the sensor polypeptide is administered, by changing the route of administration, by changing the dosage timing, by changing expression conditions of a fusion protein of the invention, by changing the activation amounts and parameters of a sensor polypeptide of the invention, and so on. An effective amount will vary with the particular intended use and means of detection of the output of the sensor polypeptide, the location and condition of the cells in which the sensor polypeptide is to be expressed, the duration of the detection of the sensor, the specific route of administration, and the like factors within the knowledge and expertise of a practitioner. In a non-limiting example, an effective amount may depend upon the location and number of cells in the subject in which the sensor polypeptide and targeting EE-RR polypeptide or functional variant thereof of the invention, is to be expressed. An effective amount may also depend on the location of the cell that is to be the host cell. Factors useful to determine an effective amount of a delivered agent are well known to those of ordinary skill in the art and can be addressed with no more than routine experimentation.

A sensor polypeptide and targeting soma-targeting polypeptide of the invention may be administered using art-known methods. The manner and dosage administered may be adjusted by the individual practitioner. The absolute amount administered will depend upon a variety of factors, including the material selected for administration, whether the administration is in single or multiple doses, and individual subject parameters including age, physical condition, size, weight, etc. These factors are well known to those of ordinary skill in the art and can be addressed with no more than routine experimentation.

Pharmaceutical compositions that deliver a fusion protein comprising a sensor polypeptide and a soma-targeting polypeptide of the invention may be administered alone, in combination with each other, and/or in combination with other agents that are administered to subjects. A pharmaceutical composition used in the foregoing methods may contain an effective amount of a compound that will increase the level of a desired sensor polypeptide to a level that produces the desired response in a unit of weight or volume suitable for administration to a subject. In some embodiments of the invention, a pharmaceutical composition of the invention may include a pharmaceutically acceptable carrier.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. In certain embodiments of the invention, such preparations may contain salt, buffering agents, preservatives, compatible carriers, aqueous solutions, water, etc. When used in medicine, the salts may be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

One or more of a sensor polypeptide or encoding polynucleotide thereof of the invention, or a cell or vector comprising a nucleic acid sequence encoding a sensor polypeptide and a soma-targeting polypeptide of the invention may be administered, for example in a pharmaceutical composition, directly to a tissue. Direct tissue administration may be achieved by direct injection, and such administration may be done once, or alternatively a plurality of times. If administered multiple times, the polypeptides, polynucleotides, cells, and/or vectors may be administered via different routes. For example, the first (or the first few) administrations may be made directly into the affected tissue while later administrations may be systemic.

A dose of a composition of the invention that is administered to a subject to increase the level of a desired sensor polypeptide in one or more cells of the subject can be chosen in accordance with different parameters, in particular in accordance with the mode of administration used and the state of the subject. In the event that the ability to detect output of an expressed sensor in a subject is insufficient at the initial doses applied, higher doses (or effectively higher doses by a different, more localized delivery route) may be employed to the extent that patient tolerance permits. The amount and timing of activity detected from an expressed sensor polypeptide that has been delivered using a targeting a soma-targeting polypeptide of the invention can also be adjusted based on efficacy of the expression and activity in a particular subject.

Various modes of administration known to the skilled artisan can be used to effectively deliver a pharmaceutical composition to increase the level of a sensor polypeptide in the soma of a desired cell in a tissue or body region of a subject. Methods for administering such a composition or pharmaceutical compound of the invention may be topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., Remington, The Science and Practice of Pharmacy, 2012, Editor: Allen, Loyd V., Jr, $22^{nd}$ Edition) provide modes of administration and formulations for delivery of various pharmaceutical preparations and formulations in pharmaceutical carriers. Other protocols which are useful for the administration of a composition of the invention will be known to a skilled artisan, in which the dose amount, schedule of administration, sites of administration, mode of administration (e.g., intra-organ) and the like vary from those presented herein.

Administration of a cell or vector to increase expression of a sensor polypeptide in the soma of one or more cells in a mammal other than a human; and administration and use of a targeted sensor polypeptide using a soma-targeting polypeptide of the invention, e.g. for testing purposes or veterinary therapeutic purposes, may be carried out under substantially the same conditions as described above. It will be understood that embodiments of the invention are applicable to both human and animals. Thus this invention is intended to be used in husbandry and veterinary practice as well as in human embodiments.

EXAMPLES

Example 1

Both two-photon (Chen et al., 2013; Helmchen and Denk, 2005; Raichle et al., 1998) and one-photon imaging modalities have resolution limits that will typically mix signals from cell bodies with those from closely passing axons and dendrites, resulting in artifactual correlations of measured neural activity (FIG. 1A-1B). This crosstalk between neuropil signals and cell body signals can be somewhat mitigated in two-photon microscopy by restricting measurements to the interiors of cell bodies: the crosstalk problem is worse for one-photon epifluorescent methods, where contamination of somatic signals by neuropil signals may be impossible to overcome (Chen et al., 2013: Harris et al., 2016; Peron et al., 2015).

As a result, many studies use computational methods to attempt to clean up the in vivo calcium signals, algorithmically correcting somatic signals for the neuropil contribution (Andilla and Hamprecht, 2014: Mukamel et al., 2009; Pinto and Dan, 2015; Pneumatikakis et al., 2014, 2016). Although such algorithms are widely used in two-photon calcium imaging, one-photon calcium imaging is subject to higher neuropil contamination levels, which remains an open problem for ongoing computational research (Zhou et al., 2016). Furthermore, the contribution of neuropil to observations of a given cell body of interest is only estimated, not exactly measured, through such computational strategies. Accordingly, a second strategy has emerged, namely localizing genetically encoded calcium indicators to the nucleus by fusing them to well-known nuclear localization sequences (NLSs) or histones (H2B), which effectively eliminates the neuropil signal (Bengtson et al., 2010; Kim et al., 2014; Nguyen et al., 2016; Schrödel et al., 2013: Vladimirov et al., 2014). While such nuclear localized calcium indicators do indeed enable low crosstalk imaging of neural populations, even in one-photon microscopy settings, there is a concern that the requirement for calcium to enter the nucleus greatly slows the temporal precision of such imaging, compared to classical cytosolic calcium imaging.

It has now been confirmed that nuclear localized versions of the popular genetically encoded fluorescent calcium indicator such as GCaMP6f and GCaMP7f exhibit, in cultured mouse neurons, on and off time constants 3-5× slower than those of cytoplasmic GCaMP6f. Studies were performed to test to see if a genetically encoded calcium indicator such as GCaMP6f could be localized to the cytosol near the cell body, and it if would greatly reduce neuropil fluorescence, similar to the effect of nuclear localized GCaMP6f, while not sacrificing kinetics as occurs with nuclear localization. While soma-targeting of membrane proteins such as optogenetic actuators has been done for many years (Baker et al. 2016; Forli et al., 2018; Greenberg et al., 2011; Pégard et al., 2017; Shemesh et al., 2017; Wu et al., 2013a) to decrease crosstalk in the context of single-cell precision optogenetics, this strategy has not been adapted for genetically encoded calcium indicators. A diversity of peptides, both natural and engineered, were screened and two such small motifs were identified that when fused to GCaMP6f, enabled it to express primarily within 50 microns of the cell body. The kinetics of response were similar to those mediated by conventional GCaMP6f. It was determined that in intact brain circuits, such as in living larval zebrafish and mice, these soma-targeted GCaMP6f molecules were able to greatly reduce the number of neuropil contamination spikes mistakenly attributed to a given neural cell body. Because of these effects, use of soma-targeted GCaMP6f and GCaMP7f greatly reduced artifactual correlations between nearby neurons in live zebrafish and mouse brain. Thus soma targeted calcium indicators may be useful in a diversity of situations where high speed one-photon calcium population is desired.

Methods

Experimental Model and Subject Details

Procedures involving animals were in accordance with the National Institutes of Health Guide for the care and use of laboratory animals and approved by the Massachusetts Institute of Technology Animal Care and Use Committee. Zebrafish experiments at Janelia were conducted according to protocols approved by the Institutional Animal Care and Use Committee of the Howard Hughes Medical Institute, Janelia Research Campus. Zebrafish experiments at MIT were conducted according to protocols approved by the Institutional Animal Care and Use Committee of MIT. Hippocampal neuron culture was prepared from postnatal day 0 or day 1 Swiss Webster (Taconic) mice as previously described (Klapoetke et al., 2014). In-utero electroporation and subsequent slice work was performed on female Swiss Webster mice (Taconic).

Zebrafish Animals and Transgenesis

For FIG. 4, previously published transgenic zebrafish line expressing GCaMP6f in the cytosol Tg(elavl3: GCaMP6f) jf1 (Freeman et al., 2014), was used. The soma-localized GCaMP6f fish was generated as previously described (Freeman et al., 2014) using the Tol2 transposon system, in which indicators were subcloned into a Tol2 vector that contained the zebrafish elavl3 promoter. The transgene construct and transposase RNA were injected into 1-2-cell-stage embryos, and the transgenic lines were isolated by the high expression of bright green fluorescence in the central nervous system in the next generation. The larvae were reared in 14:10 light-dark cycles according to a standard protocol at 28.5° C., in a solution containing Instant Ocean salt from Carolina Biological Supply Company (65 mg/L Instant Ocean, 30 mg/L Sodium bicarbonate). Experiments were performed on animals 5-7 day's post fertilization (dpf) at room temperature. Fish lines and DNA constructs for elavl3:SomaGCaMP6f1 available upon request.

Neuronal Culture, Transfection, and AAV Transduction

For neuronal expression of GCaMP6f fusions with trafficking sequences during the screen for soma targeting sequences (e.g., FIG. 1C-N), and for neuronal expression of mCardinal (e.g., FIG. 1C-N), primary mouse hippocampal neurons were transfected at 4 days in vitro (DIV) with a commercial calcium phosphate kit (Invitrogen). An additional washing step with acidic MEM buffer (pH 6.8-6.9) after calcium phosphate precipitate incubation was added to completely re-suspend residual precipitates (Jiang and Chen, 2006). 1 μg of DNA was used. Neurons were imaged 14-18 DIV (days in vitro: 10-14 days post-transfection). For neuronal expression of GCaMP6f, GCaMP6f-NLS, SomaGCaMP6f1, SomaGCaMP6f2, and/or mCherry for electrophysiology, antibody staining, and membrane staining in FIG. 2A-F, FIG. 8A-H, FIG. 9A-D, and FIG. 10A-C, we transduced primary mouse hippocampal neurons at DIV 7-9 with the corresponding AAV(s) with a DJ serotype under CAG or Syn promoter (UNC vector core).

Gene Synthesis

All genes were synthesized (by Epoch Life Science) with mammalian codon optimization and subcloned into pAAV backbone under CAG or Syn promoter, see Tables 1, 2 and sequences set forth elsewhere herein for descriptions and amino acid sequences. Briefly, for the final selected variants, 1200 bp from the tail region of the human Ankyrin$_G$ protein (Zhang and Bennett, 1998) (AnkTail-motif) were cloned followed by the ER2 (Hofherr et al., 2005) trafficking sequence from the potassium channel Kir2.1, with the resulting molecule being GCaMP6f-27-AnkTail-motif-ER2, named SomaGCaMP6f1, and 264 bp of a de novo designed coiled-coil peptide EE-RR fused to the C-terminus of GCaMP6f via a 27 amino acid flexible linker, named SomaGCaMP6f2. A nuclear localization sequence (NLS) was synthesized based on a sequence found in the literature (Kosugi et al., 2009).

Image Analysis

Analysis of GCaMP variant brightness and red fluorescent protein brightness along neurites, and calculation of green-to-red ratio as a function of position in brain slices and zebrafish brains.

Images for this analysis were taken for fixed brain slices prepared as described below using mice at P12-P24 (FIG. 3A, FIG. 3B, FIG. 3D, and FIG. 11), and for fixed zebrafish larvae at 5-7 dpf (FIG. 4B-C). Images in the red channel (representing mScarlet in mouse brain slices or mCherry in zebrafish) and in the green channel (representing GCaMP6f variants) were collected using a spinning disk CSUWI confocal unit (Yokogawa, Tokyo, Japan). The neurons were using the same parameters for GCaMP6f, SomaGCaMP6f1 and SomaGCaMP6f2. It was decided to image native GCaMP6f, as it represented the natural state of the protein, and presented any brightness differences between the three variants (GCaMP6f, SomaGCaMP6f1 and SomaGCaMP6f2), while not fluctuating in time due to neural activity since the samples were fixed. The image analysis was performed in ImageJ as follows: the images in the red channel were used in order to trace neurons. This was because the SomaGCaMP variant signal decreased from the cell body as one entered the neurites, while mCherry or mScarlet was not somatically targeted. For each neuron the boundaries of the soma were first defined. To that end, a 20 μm diameter circle was drawn 5-20 μm away from the soma, inside which there was no apparent fluorescence from the soma or from neurites. Then, the average fluorescence in the circle was defined as the background fluorescence for this neuron, focusing on the red channel. Pixels with fluorescence intensity of at least 10% above background levels were considered as part of the soma or processes, and the boundary between soma and its processes was defined manually by examining the cell morphology. Then, polygon with 5-15 sides was drawn along the soma boundary and the average fluorescence inside of it was measured, and the previously calculated background value was subtracted. The resulting value was considered to be the soma fluorescence in the red channel. This analysis was repeated in the green channel, using the boundaries previously defined by the analysis of the red channel. The resulting value was considered the soma fluorescence in the green channel. To measure fluorescence intensities along neurites, 1 μm$^2$ rectangles were defined along the neurite that were up to 150 μm away from the soma at increments of 10 μm in the red channel. (For some neurons only up to 140 μm could be measured because after that the neurites became very dim and/or not traceable with the distal neurites from multiple neurons packed together. As a result, the majority of neurons were measured up to 150 μm, while some cells were only measured up to 140 μm.) The distance between each rectangle and the soma was measured along the respective neurites (not the minimal linear distance from the soma, since neurites were curved). It was ensured that the pixel intensity values at the boundaries of each rectangle were at least 10% above the background fluorescence defined above, to be considered inside the neurite. The fluorescence intensity in each rectangle was averaged, then the background fluorescence was subtracted, then it was divided by the average soma fluorescence and the resulting ratio was plotted with respect to distance along the neurite. The ratios for each distance were averaged across neurites and data was plotted (using Matlab) as average and standard error of the mean. This analysis was repeated in the green channel, using the boundaries defined by the red channel. In summary, these analyses yielded the dendrite/soma ratios out to 140-150 μm in increments of 10 μm, in both the green and the red channels. The values in the green channel were divided by the corresponding values in the red channels. The green/red ratio values were normalized to the green/red value at the soma, to achieve the final measure of green to red fluorescence ratio. Importantly, dendrites were chosen by traceability: if a dendrite was crossing other dendrites and thereby it was not possible to determine its continuity, it was excluded from the analysis.

Analysis of GCaMP Brightness Along Neurites, in Cultured Neurons.

Images for this analysis were taken for cultured neurons (FIG. 1L-M) at 14-18 DIV (10-14 days post-transfection). The image analysis was performed in ImageJ. For each neuron the first step was to define the boundaries of the soma. To that end, a 20 μm diameter circle near the soma was drawn, inside which there was no apparent fluorescence from the soma or from neurites. The average fluorescence in the circle was defined as background fluorescence. Pixels with fluorescence intensity of at least 10% above background levels were considered as part of the soma and processes, and the boundary between soma and its processes was defined by the apparent cell morphology. Then, a polygon along the defined soma boundary and measured the average fluorescence inside of it, and subtracted the previously calculated background value. The resulting value was considered soma fluorescence. To measure fluorescence intensities along neurites, 1 µm$^2$ rectangles along the neurite were defined that were up to 100 µm away from soma at increments of 10 µm. The distance between each rectangle and the soma was measured along the neurites (not the minimal linear distance from the soma, since neurites were curved). Then the background value was defined exactly as described above for the soma. It was ensured that the pixel intensity values at the boundaries of the rectangle were at least 10% above background levels, to be considered inside the neurite. The fluorescence intensity in each rectangle was averaged, then the background was subtracted, and the result divided by the average soma fluorescence and the resulting ratio was plotted with respect to distance along the neurite. The ratios for each distance were averaged across neurites and data was plotted (using Matlab) as average and standard error of the mean.

Analysis of Ion Channel and Scaffold Protein Distribution in Cultured Neurons.

Primary mouse hippocampal neurons (FIG. 9A-D) were transduced with either GCaMP6f+mCherry, SomaGCaMP6f1+mCherry or SomaGCaMP6f2+mCherry. Images for this analysis were taken from neurons fixed at 14-18 DIV (10-14 days post-transduction). Following fixation, we stained the proteins as described below; Images in the red channel (representing mCherry), in the green channel (representing GCaMP6f variants), and in the near-infrared channel (representing protein staining) were collected using a spinning disk CSUWI confocal (Yokogawa, Tokyo, Japan). The neurons were imaged using the same parameters for GCaMP6f, SomaGCaMP6f1 and SomaGCaMP6f2. The image analysis was performed in ImageJ as follows: the images in the red channel were used in order to trace neurons. This was because the SomaGCaMP variant signal decreased from the cell body and into the neurites, while mCherry was non-targeted. For each neuron, first the boundaries of the soma were defined using the red channel as described in the previous sections. Then, it was switched to the near-infrared channel, and the background value for this neuron was calculated as described above. Next a polygon was drawn along the defined soma boundary and the average fluorescence inside of it was measured, and the previously calculated background value was then subtracted. The resulting value was considered soma fluorescence in the near-infrared channel. To measure fluorescence intensities along neurites, 1 µm$^2$ rectangles were defined along the neurite that were up to 100 µm away from soma at increments of 10 µm in the red channel. The distance between each rectangle and the soma was measured along the neurites (not the minimal linear distance from the soma, since neurites were curved). It was decided to trace the neurite which had the highest intensity for each neuron, meaning it was the axon. This was based on past reports showing that the highest labeling for Kv2.1 (Jensen et al., 2017), Nav1.2 (Tian et al., 2014), Ankyrin$_G$ (Zhang and Bennett, 1998) and Cav2.1 (Yu et al., 2010) is along the axon. The fluorescence intensity in the near-infrared channel was averaged for each rectangle, then the background value of this neuron was subtracted, and the result divided by the average soma fluorescence and the resulting ratio plotted with respect to distance along the neurite. The ratios for each distance were averaged across neurites and data was plotted (using Matlab) as average and standard error of the mean.

Analysis of Membrane Distribution in Cultured Neurons.

Primary mouse hippocampal neurons (FIG. 10A-C) were transduced with either GCaMP+mCherry, SomaGCaMP6f1+mCherry or SomaGCaMP6f2+mCherry. Images for this analysis were taken from neurons fixed at 14-18 DIV (10-14 days post-transduction). Following fixation, the membrane was stained as described below. Images in the red channel (representing mCherry) and in the green channel (representing GCaMP6f variants) and a near infrared channel (representing the membrane staining) were collected using a spinning disk CSUWI confocal (Yokogawa. Tokyo, Japan). The neurons were imaged using the same parameters for GCaMP6f, SomaGCaMP6f1 and SomaGCaMP6f2. The image analysis was performed on single confocal z slices in ImageJ as follows: first boundaries of the soma were defined using the red channel as described above. Then, it was switched to the near-infrared channel (membrane staining) and the green channel (GCaMP6f variant), and the background values were calculated for each channel as described above. Next a rectangle was drawn with a width of 32 microns and a height of 1 micron that went through the cell body from side to side. This width was chosen because the diameter of cell bodies is smaller than 32 µm, and therefore it was possible to analyze the fluorescence from one side of the cell body to the other. The fluorescence was then measured along the wide dimension of the rectangle, at increments of 0).3 µm, in both the green (GCaMP6f variant) and the near infrared channel (membrane staining), the background for each channel was subtracted and the results plotted along the same x-axis. It was noticed that in several cases the nucleus was included in the rectangle and in some not, however the focus was on the plasma membrane and its relation to the GCaMP6f variants, and it was found, as discussed in the results that the membrane staining fluorescent signal was starting to rise further away from the center of the cell body compared to the GCaMP fluorescent signal.

Analyzing brightness, df/f$_0$, signal-to-noise ratio (SNR), fluorescent rise-time and fluorescence decay time following I action potential in-vitro For FIG. 2, hippocampal cells expressing the GCaMP6f trafficking variants were bathed with synaptic blockers (0.01 mM NBQX and 0.01 mM GABAzine) and patched (in current clamp), and at the same time images were acquired with a Hamamatsu Orca Flash 4.0 with an exposure of 20 ms. An action potential was elicited in the neuron using a 10 ms, 50-200 pA current injection, and the resulting fluorescence change was recorded for a period of 20) seconds, to allow the GCaMP6f fluorescence to return to baseline. To avoid sampling bias, the first 2-3 cells detected according to the GCaMP fluorescence brightness in each plate were imaged and patched. To calculate the GCaMP6f brightness at the soma of each cell, the boundary of the soma was defined by the apparent cell morphology in the image and subtracted the background fluorescence (as defined above) from the average fluorescence inside the soma boundary. To calculate df/f$_0$ baseline fluorescence was first calculated. Baseline fluorescence was defined as the average fluorescence during the 1-second period right before the beginning of fluorescence response. df/f$_0$ was calculated by dividing the maximum fluorescence change by baseline fluorescence. To calculate the signal to noise ratio (SNR) the maximum fluorescence change was divided by the standard deviation of baseline fluorescence during the 1-second period right before the onset of a GCaMP-spike. The Ton was calculated by extracting the time constant from the exponential fit of the rising segment of the fluorescence response. The $\tau_{off}$ was calculated by extracting the time constant from the exponential fit of the falling segment of the fluorescence.

Measuring Df/f$_0$ and Soma—to Neuropil Ratio in Acute Brain Slices for SomaGCaMP Variant Screening For FIG. 7A-L, regions of interest (ROIs) denoting cell bodies and neuropil were determined manually on a projection of the standard deviation of the fluorescence per pixel in the movies using ImageJ: twenty cells and one neuropil section were traced by hand using ImageJ's freehand selection and ROI manager tools, from which 21 time histories of average fluorescence values F were extracted of length 2000 frames (40 seconds at 50 Hz). The baseline fluorescence was defined as a 4-second time window with no apparent action potentials, from which B was defined as the mean value in the baseline. For each neuron the df/f$_0$ was defined as $$\frac{\Delta F}{F} = \frac{\max(F) - B}{B},$$

next the soma to neuropil $df/f_0$ ratio was calculated by dividing the soma df/f$_0$ by the neuropil df/f$_0$.

Manually Tracing Cell Bodies in Slice Patching and Imaging Crosstalk Experiments in Mouse Brain Slices When tracing the cells (FIG. 3, FIG. 9), a region of interest was chosen that was inside the cell body. Steps were taken to avoid choosing the ROI as the entire cell body, since that ROI may contain GCaMP6f filled processes originating from neighboring cells. A cell body was defined by the apparent cell morphology as was done as in the in vitro current clamp experiments. An ROI inside the cell body was then chosen that was approximately 1 µm from the cell body's apparent boundaries.

Analyzing Brightness, Df/f0 and Signal-to-Noise Ratio (SNR) in Acute Slice Patching Experiments of GCaMP6f or SomaGCaMPf1

For FIG. 3 and FIG. 9, the boundary of the soma was defined by the apparent cell morphology from the movies recorded in slice patching experiments, and the average fluorescence inside the soma boundary in each frame was measured. To calculate df/f (baseline fluorescence was first calculated. Baseline fluorescence was defined as the average fluorescence during the 100 to 500 ms period right before the beginning of fluorescence response. df/f0 was calculated by dividing the maximum fluorescence changes over baseline fluorescence in each cell body. To calculate the signal to noise ratio (SNR) the maximum fluorescence change was divided by the standard deviation of baseline fluorescence during the 100 to 500 ms period right before the onset of GCaMP-spikes.

Measuring the Fluorescent Signals from Cell Bodies in Slice Patching and Imaging Crosstalk Experiments in Mouse Brain Slices When choosing a region of interest (FIG. 3G-J, FIG. 13A-D), an area was chosen that was inside the cell body. Choosing the ROI as the entire cell body was avoided, because that ROI may contain GCaMP6f filled processes originating from neighboring cells. A cell body was defined by the apparent cell morphology as was done as in the in vitro current clamp experiments. An ROI inside the cell body was then chosen, approximately 1 µm from the cell body's apparent boundaries.

Analyzing Brightness, Df/f$_0$ and SNR in Acute Slice Patching Experiments of GCaMP6f or SomaGCaMPf1

For FIG. 3E, F and FIG. 13A, the boundary of the soma was defined by the apparent cell morphology from the movies recorded in slice patching experiments, and the average fluorescence inside the soma boundary in each frame was measured. To calculate df/f$_0$. first the baseline fluorescence was calculated. Baseline fluorescence was defined as the average fluorescence during the 100 to 500 ms period right before the beginning of fluorescence response. df/f$_0$ was calculated by dividing the maximum fluorescence changes over baseline fluorescence in each cell body. To calculate the SNR the maximum fluorescence change was divided by the standard deviation of baseline fluorescence during the 100 to 500 ms period right before the onset of GCaMP-spikes.

Analyzing Brightness, Df/f$_0$. SNR and Correlations in Zebrafish Larvae with Either Transient Expression or Stable Pan-Neuronal Expression of GCaMP6f or SomaGCaMPf1

The movies recorded from zebrafish larvae with stable pan-neuronal expression using a lightsheet microscope (FIG. 4H-M) were first motion corrected using NormCorre (Pnevmatikakis and Giovanucci 2017). The movies recorded from zebrafish larvae with transient expression using a 2-photon microscope (FIG. 4D-G) were not motion corrected because little motion was observed. The boundary of the soma was defined by the apparent cell morphology from the movies, and the average fluorescence inside the soma boundary in each frame was measured. To calculate df/f$_0$ baseline fluorescence was first calculated. Baseline fluorescence was defined as the average fluorescence during the 1-second period right before the beginning of a fluorescence transient. df/f$_0$ was calculated by dividing the maximum fluorescence change by baseline fluorescence in each cell body. To calculate the SNR the maximum fluorescence change was divided by the standard deviation of baseline fluorescence during the 1-second period right before the onset of a GCaMP-spike. To calculate correlation-coefficients between neuronal pairs in zebrafish larvae with stable pan-neuronal expression of GCaMP6f or SomaGCaMPf1, the motion corrected movies were processed with CalmAn (Pneumatikakis et al 2016) to segment all putative neurons in the field of view, then the fluorescence traces were denoised and deconvolved. An additional manual review was done for each candidate neuron from CalmAn to examine the spatial footprint and temporal characteristics to confirm it was a neuron. These filtered sets of neurons were then used for pairwise correlations (FIG. 4N, FIG. 4O) of the denoised time signal and pairwise distance measurements using the centroid of the spatial footprints.

Analysis of In Vivo Calcium Imaging Data in Live Mice (for FIG. 5A-G)

a) Motion Correction

Sessions varied between 5 and 12 minutes in length and imaging sessions were analyzed from four SomaGCaMP6f2 mice and six GCaMP6f expressing mice. Motion correction was performed with a custom python script. For each imaging session, a reference image was generated by projecting the mean values of every pixel in the first 2047 frames of the recording session. The reference image and each frame of the video underwent a series of image processing steps to enhance the contrast and the character of the image. First the image was high-pass filtered with a Gaussian filter (python SciPy package, ndimage.gaussian_ filter, sigma=50) to remove any potential non-uniform background. Then the edges of the high intensity areas were enhanced by sharpening the image as described in www.scipy-lectures.org/advanced/image processing/. In brief, the image was consecutively low-pass filtered with Gaussian filters at two levels (sigma=2 and 1). The differences in the two images, which represent the edges of high intensity areas, were multiplied by 100 and added back to the first low-pass filtered image, resulting in a sharpened image. Finally, to compensate for potential bleaching that may affect the overall intensity of the whole image, the intensity of each image was normalized by shifting the mean intensity to zero and divided by the standard deviation of the intensity. Then the cross-correlations between the enhanced reference image and each frame was calculated to obtain the displacement between the location of max correlation coefficient and the center of the image. The shift that countered the displacement was then applied to the original, unenhanced image to complete the motion correction.

b) Identification of Regions of Interest from Mouse In-Vivo Experiments:

To identify the regions of interest (ROIs) that represent neurons, first time-collapsed images were generated by subtracting the average intensity value of each pixel over all videos from its maximum intensity. Then ACSAT (Shen et al., 2018) was applied to generate ROIs with the following parameters: iteration=2, minimum size=50 pixels, and maximum size=300 pixels. In brief, ACSAT is a threshold-based ROI segmentation algorithm that adaptively adjusts the threshold at both global and local levels to capture ROIs with various intensities. Due to the shifting process during motion correction, the time-collapsed image often contains high intensity strips at the edge, which cause false-positive ROIs in ACSAT. Therefore, any ROIs within 10 pixels of the edge were excluded. Also, ROIs that were identified which were exceedingly large or small in size (less than 50 pixels or greater than 500 pixels) were excluded. Centroids were then identified for each ROI using the MATLAB command "regionprops" with the "centroid" argument.

c) Trace Interpolation for Mouse In-Vivo Experiments:

While SomaGCaMP6f2 sessions were recorded at a constant rate of 20 Hz by the camera, the sampling frequency for GCaMP6f sessions was triggered by a MATLAB script which accidentally introduced an unintentional slight variability within the sampling rate (21.31+/−0.02 Hz (+/−s.d)). Therefore, traces for GCaMP6 were interpolated between the first and last time point in each 4-video sequence given by the time stamps of the corresponding Tiff files. Interpolation was performed with a constant sampling interval of 50 ms (20 Hz) using linear interpolation ("interp1" in MATLAB).

d) Computation of $Df/f_0$ and Linear Detrending for Mouse In-Vivo Experiments:

After interpolating the traces from GCaMP6f sessions, $df/f_0$ values were computed for each trace by subtracting its mean and dividing by its initial fluorescence. Each trace was then subject to a linear detrending using the MATLAB command "detrend". Following this step, traces were each manually inspected to ensure that they had a dynamic nature and represented actual neurons. Traces that didn't meet these qualifications were excluded from further analysis (n=12 SomaGCaMP6f2 and n=15 GCaMP6f cells).

e) Identification of Homologous Subregions from GCaMP6f Session for Mouse In-Vivo Experiments:

To equalize the number of neurons recorded from each session and to keep the range of distances between cells consistent from different imaging sessions, only a portion of the full field was analyzed from each recording session. To do so, subregions from each GCaMP6f session were highlighted for further analysis. First, the visible brain region in each GCaMP6f session was characterized by computing a bounding box around the area of cell labeling, and computed the total number of neurons in each bounding box. These computations were performed as follows:

First, an ROI mask was constructed for each session. Each mask was then morphologically closed using the MATLAB function imclose (*,strel), with "strel" a structuring element, in this case set to the shape of a disk with a radius of 30 pixels (strel (disk',30)). Second, this image was morphologically eroded using the MATLAB command "imerode", again using a "disk"-type structuring element but in this case with a radius of 10 pixels. Finally, the image was morphologically dilated using the MATLAB command "imdilate", and a structuring element of a disk with radius 20 pixels. This produced an image with an opaque region encompassing the region of the image most densely laden with ROIs. Following these procedures, a bounding box around this region was computed using the command "regionprops" with a second argument of "boundingbox" Finally, the number of ROIs with centroids in this bounding box was computed for each session. Limits of the bounding box used for calculating relative positions of the centroids were computed by rounding the coordinates of the x and y starting points of the bounding box, and taking those points between these values through the values (extent of x=round (x+width−1), extent of y=round (y+height−1)), where height and width are the properties of the bounding box returned by MATLAB. Centroids were rounded to their nearest whole pixel values for this analysis.

To compute the factors necessary to identify a bounding box across all other sessions, summary statistics of these bounding boxes were computed for each GCaMP6f session. To identify the height of our bounding box, the height of each bounding box was divided by the bounding box's area, averaged these quantities, and then they were multiplied by the average area across all bounding boxes. An analogous procedure was performed to find a suitable bounding box width. Lastly, the number of ROIs identified in each bounding box were averaged to find a target number of neurons. In summary, the target region had a height of approximately 396 μm, a width of approximately 804 μm, yielding an area of $3.1856e+05$ μm$^2$, with approximately 177 neurons in this region. The SomaGCaMP6f2 data had an average bounding box height of approximately 373 μm, a width of approximately 715 μm, and an average area of $2.64e05$ μm$^2$.

To locate an area that fulfilled these requirements, the height and width estimated were first both rounded to whole numbers. Then, first by vertical pixels and then by horizontal pixels, areas constituting the required widths and heights were searched and the number of neurons with (rounded) centroids within these areas were counted. After all rectangles with these characteristics were searched, the region identified that had a number of neurons closest to the average number of neurons in bounding boxes from all other sessions was used as the region for analysis. If multiple regions had the same number of ROIs or were equally close in number, the first region that was identified was used. For the remainder of these analyses (peak characteristic comparison and pairwise-correlation analysis), only the identified ROIs within this region were used.

f) Event Identification for Mouse In-Vivo Experiments:

Spectral frequency analysis has been shown to be a reliable tool for estimating calcium fluorescence events as it is less influenced by drifts in baseline activity (Deneux et al., 2016; Patel et al., 2015; Ruffinatti et al., 2013). Within the generated data is was noticed that the onsets of Ca events could be detected using Fourier analysis where event onset coincided with increasing low frequency power (power-event). To take advantage of this observation, first the spectrogram was calculated from traces (Matlab chronux, mtspecgramc with tapers= [23] and window= [10.05]), and averaged the power below 2 Hz. To detect any significant increase in power, the change in the power at each time point (powerdiff) was calculated, and the outliers (3 median absolute deviations away from the median power) in powerdiff (Matlab function isoutlier) identified. For outliers that occurred at consecutive time points, only the first outliner was kept, which represented the start of the change. In addition, the outliers with positive powerdiff were selected because they were indicators for the increase in the power. After identifying the time points of the significant increase, the end of powerevent was determined by identifying the first time point where the power decreased.

To obtain the peaks and start points of Ca events, first the end point of powerevent Was extended to the second time point with decreased Ca signal. After extension, the peak was defined as the time point within powerevent where the maximum Ca signal occurred, and the start point was defined as the time point with minimum Ca signal between the peak and the start of powerevent. To ensure the quality of Ca events, any Ca event with amplitude (the signal difference between the peak and the onset) less than 4 standard deviations of the trace in the 20 second time window prior to Ca event onset was excluded. At the end of this process, some Ca events were found to overlap. To address this issue, the final set of Ca events was set to be the union of all of the identified Ca events, and the peak amplitude of each new event was defined as the maximum of the event minus the minimum of the event.

g) Computation of Peak Characteristics for Mouse In-Vivo Experiments:

Once peaks were identified, their waveforms were determined. Waveforms were defined as 10 seconds flanking (5 seconds before and 5 seconds following) an event peak. Once identified, we subtracted the minimum value off the waveform. Then, event rate, rise time and decay times were computed as follows. To compute the event rate for a particular session, the number of waveforms identified over the course of the session were totaled for each region of interest, and this number was then divided by the total length of the session. Next, rise times were computed using the mean post-minimum subtracted peak waveform taken across all waveforms for a given ROI. These waveforms are aligned naturally because each is centered around its peak. To obtain the rise and decay time for each ROI, first a threshold was calculated as follows: all events were averaged together, centered around their peak maxima, and the following equation was used to determine a threshold value:

$$\text{Threshold} = \frac{\max(\text{avg } waveform) - \text{mean}(\text{avg } waveform)}{2} + \text{mean}(\text{avg } waveform)$$

For rise time, the number of data points between the maximum of each identified event and the first point prior to the event where the trace fell to less than or equal to a significance threshold were computed. Falling times were computed by determining the number of data points between the maximum of an event and the first point following this maximum whose value dropped to a value less than or equal to the significance threshold. Any trace that lacked either an identified rise time or decay time, or both, was excluded from statistical analyses, and were also excluded from the computation of pairwise correlations. Event rates, fall times, and rise times computed ROI-wise from SomaGCaMP6f2 mice were compared with the respective values from ROIs in GCaMP6f mice via a Wilcoxon rank-sum test.

h) Pairwise-Correlation Analysis for Mouse In-Vivo Experiments:

Following application of the CNMF algorithm, traces for each region of interest were truncated into 50 time point (2.5 second) segments in order to reduce the risk of non-stationarity of the df/$f_0$ time traces, and correlation coefficients were computed pairwise over the course of each session. Pairwise correlation coefficients were then averaged over all of the segments of each session for each pair of ROIs. For statistical analysis, the average pairwise correlation coefficient across all ROI pairs for each recording session was computed, and results from GCaMP6f and SomaGCaMP6f2 animals were compared using a Wilcoxon rank-sum test.

Image Processing and Analysis for Mice In Vivo Endoscopic Recordings

Image preprocessing of endoscope data (FIG. 6C-H, FIG. 18A-B) was accomplished using Mosaic software (v. 1.1.2., Inscopix). Raw videos were pre-processed by applying ×4 spatial downsampling to reduce file size and processing time. Lateral movement was corrected for by using a portion of a single reference frame (typically a window surrounding a constellation of neurons) as previously described (Vander Weele et al., 2018). Images were cropped to remove post-registration borders and sections in which cells were not observed.

After motion correction and cropping, extracted fluorescence activity traces from single cells were used either as they were (FIG. 18a-B, upper panels) or by using a modified version of the constrained non-negative matrix factorization algorithm optimized for micro-endoscopic imaging (CNMF-E) developed by Zhou and colleagues (2016) (FIG. 18a-B, bottom panels). As described previously (Vander Weele et al., 2018), the analysis differed from CNMF-E (Zhou et al., 2016) in that cells were identified manually by hand-selecting seeding pixels, based on visual inspection of the video and an image generated by plotting the peak-to-noise ratio for each pixel over the length of the video.

Simulation of Calcium Imaging in Densely Labeled Tissue in Mouse and Zebrafish with GCaMP6f and SomaGCaMP Variants To simulate calcium imaging in densely labeled tissue in mouse and zebrafish with GCaMP6f and SomaGCaMP variants (FIG. 14), the simulation software from Yoon et al 2019 was used. Briefly, a given number of neuron cell bodies are generated randomly in space of a specified volume. Neuronal processes are created as a random walk of specified length starting from the cell bodies, and the trafficking of calcium indicator is modeled by parameters observed experimentally (see table below). The optics of a given microscope are then modeled: in this case the population of neurons was modeled as it would be viewed through a 1-photon microscope, under the following resolution: 1 micron×1 micron×2 microns. For a 25 s duration, ground truth activity was randomly generated per neuron and a video of the optical calcium dynamics was simulated, as if it were taken from a microscope. Then CNMF was applied to the data and the correlation in time between the ground truth neuron activity and the observed simulated neuron activity was calculated. To simulate densely labeled tissue in mouse, 30 neurons in a 64×64×64 μm volume was used as the neuronal density and 20 neuronal processes per neuron. To simulate densely labeled tissue in zebrafish, 120 neurons in a 64×64×64 μm volume was used as the neuronal density and 5 neuronal processes per neuron.

TABLE 1

Parameter table:

|  | Mouse | Zebrafish |
| --- | --- | --- |
| Number of neurons per 64 × 64 × 64 um volume | 30 | 120 |
| Number of neural processes per neuron | 20 | 5 |
| Length of GCaMP6f fluorescent signal process (in microns) | 50 | 50 |
| Length of SomaGCaMP6f variant fluorescent signal in process (in microns) | 5 | 5 |

Antibody and Membrane Staining of Fixed Neuron Culture

Primary mouse hippocampal neurons were fixed at 14-21 days in vitro with 1× phosphate-buffered saline (PBS)+4% paraformaldehyde for 10 min at room temperature (RT), quenched with 1×PBS+100 mM glycine for 5 min at RT, and washed twice in 1× PBS for 5 min at RT. Fixed neurons were permeabilized in 1×PBS+0).1% Triton X-100 for 15 min at RT, and then blocked in the BLOTTO-T solution, which was made by adding 0.1% Triton X-100 into the commercially available BLOTTO solution (#37530), Thermo Fisher Scientific), for 45 min at RT with gentle shaking. Fixed neurons were incubated in primary antibodies in BLOTTO-T for 45 min at RT with gentle shaking, and then washed in BLOTTO-T for 3 times for 5 min each at RT with gentle shaking. Fixed neurons were incubated in secondary antibodies in BLOTTO-T for 45 min at RT with gentle shaking, and then washed in 1× PBS for 3 times for 5 min each at RT with gentle shaking. For samples stained with mouse monoclonal primary antibodies (including anti-Nav1.2 and anti-Kv2.1), anti-mouse-IgG-subclass specific secondary antibodies were used (anti-mouse-IgG2a and anti-mouse-IgG1, respectively).

Primary and secondary antibodies and concentrations used:

Anti-Ankyrin$_G$, Santa Cruz Biotechnology (sc-12719) at 1:50; anti-mouse IgG (H+L) Alexa 647 (A-21235) at 1:200. Anti-Nav1.2, NeuroMab (75-0) 24) at 1:1000; anti-mouse IgG2a Alexa 647 (A-21241) at 1:1500. Anti-Kv2.1, NeuroMab (75-014) at 1:1000; anti-mouse IgG1 Alexa 647 (A-21240)) at 1:1500. Anti-Cav2.1, Alomone (ACC-001) at 1:250; anti-rabbit IgG (H+L) Alexa 647 (A-21245) at 1:1000. Anti-mCherry, Kerafast (EMU106) at 1:1000; anti-rabbit IgG (H+L) Alexa 546 (A-11035) at 1:300. Anti-mCherry, Thermo Fisher Scientific (M11217) at 1:1000; anti-rat IgG (H+L) Alexa 546 (A-11081) at 1:300.

Membrane staining was performed with fluorophore-conjugated wheat germ agglutinin (#W32466, Thermo Fisher Scientific) following the manufacturer's protocol. Briefly, neurons were fixed in the same way as described above, but without the permeabilization and blocking procedures. Fixed neurons were washed 3 times in Hank's Balanced Salt Solution (HBSS) for 5 min each at RT, and then incubated with Alexa Fluor 647-conjugated wheat germ agglutinin in HBSS at 5 μg/mL for 10 min at RT. Neurons were then washed twice in HBSS and once in 1×PBS, for 5 min each at RT.

Electrophysiology

Current and Voltage Clamp Recordings of Cultured Neurons

Whole cell patch clamp recordings in culture (for FIG. 2A-F and FIG. 8a-H) were made using Axopatch 200B or Multiclamp 700B amplifiers, a Digidata 1440 digitizer, and a PC running pClamp (Molecular Devices). For in vitro current-clamp recordings, neurons were patched 14-18 DIV (7-11 days after AAV transduction) to allow for sodium channel maturation. Neurons were bathed in room temperature Tyrode containing 125 mM NaCl, 2 mM KCl, 3 mM CaCl$_2$), 1 mM MgCl$_2$, 10 mM HEPES, 30 mM glucose and the synaptic blockers 0.01 mM NBQX and 0.01 mM GABAzine. The Tyrode pH was adjusted to 7.3 with NaOH and the osmolarity was adjusted to 300 mOsm with sucrose. For in vitro voltage-clamp recordings, neurons were patched 19-21 DIV (17-20 days post-transfection) and were done under similar conditions as current-clamp recordings, except the Tyrode also contained 1 μM tetrodotoxin (TTX, Tocris Bioscience). For recordings, borosilicate glass pipettes (Warner Instruments) with an outer diameter of 1.2 mm and a wall thickness of 0.255 mm were pulled to a resistance of 5-10 MΩ with a P-97 Flaming/Brown micropipette puller (Sutter Instruments) and filled with a solution containing 155 mM K-gluconate, 8 mM NaCl, 0.1 mM CaCl$_2$), 0.6 mM MgCl2, 10 mM HEPES, 4 mM Mg-ATP, and 0.4 mM Na-GTP. The pipette solution pH was adjusted to 7.3 with KOH and the osmolarity was adjusted to 298 mOsm with sucrose.

Electrophysiology and Calcium Imaging in Acute Brain Slice for Cross Talk Analysis and Assessment of Sensitivity for Spike Number Individual living slices (FIG. 3A-J and FIG. 13A-D) were transferred to a recording chamber mounted on an upright microscope (Olympus BX51WI) and continuously superfused (2-3 ml/min) with artificial cerebrospinal fluid (ACSF) (124 mM NaCl, 2.5 mM KCl, 1.2 mM NaH2PO4, 24 mM NaHCO$_3$, 5 mM HEPES, 12.5 mM glucose, 2 mM MgSO4, 2 mM CaCl2 with the pH adjusted to 7.3-7.4 with NaOH or HCl and the osmolarity adjusted to 300-310 mOsm with glucose) at room temperature. Cells were visualized through a 40× NA0.8 water-immersion objective to identify GCaMP6f-positive cells. Whole-cell current-clamp recordings were obtained from GCaMP6f-positive pyramidal neurons in layer 2/3 of motor cortex, using an Axopatch 700B amplifier (Molecular Devices) and Digidata 1440) digitizer (Molecular Devices). For recordings, borosilicate glass pipettes (Warner Instruments) with an outer diameter of 1.2 mm and a wall thickness of 0.255 mm were pulled to a resistance of 3-5 MΩ with a P-97 Flaming/Brown micropipette puller (Sutter Instruments) and filled with a solution containing 155 mM K-gluconate, 8 mM NaCl, 0.1 mM CaCl$_2$), 0.6 mM MgCl2, 10 mM HEPES, 4 mM Mg-ATP, and 0.4 mM Na-GTP. The pipette solution pH was adjusted to 7.3 with KOH and the osmolarity was adjusted to 298 mOsm with sucrose. GCaMP fluorescence was excited by a SPECTRA X light engine (Lumencor) with 470/24 nm excitation filter (Semrock). To perform fair comparison of GCaMP6f1 and SomaGCaMP6f1 for FIG. 3A-J and FIG. 13A-D, excitation light power was adjusted on a cell-to-cell basis, in the range of 0.5 to 20 mW/mm$^2$, to achieve similar intensity of fluorescence baseline between the two constructs. Fluorescence was collected through the same objective through a 525/50 nm emission filter and imaged onto an sCMOS camera (Andor Zyla5.5 or Hamamatsu Orca-Flash4.0 V2) at 50 Hz acquisition frequency. For assessing the sensitivity of the GCaMP6f variants to action potential number using whole-cell patch clamp (FIG. 13A) we performed 500 pA current injections (50 Hz current injections, 5 ms, in trains of 5, 10, or 20 pulses). For assessing crosstalk we performed the imaging as described above while stimulating cells in the slice with 0.1 mM 4-aminopyridine, aimed at producing low spike rates (as seen in FIG. 3I).

Imaging

Imaging GCaMP Targeting Variants in Culture

GCaMP6f trafficking variants that were found to localize predominantly in the soma of cultured neurons (FIG. 1C-V, FIG. 2A-D, and FIG. 19A-D) were imaged with an LED (X-Cite XLEDI, Excelitas Tecnologies) mounted on a microscope for wide-field illumination (Leica 3000B), through a Leica HCX APO L 40× objective (air, NA=0.6). Imaging was performed with a Hamamatsu Orca Flash 4.0 camera using a 480 nm LED and GFP-3035D filter cube (Semrock) for GFP fluorescence (power, 34.84 mW/mm$^2$).

Calcium Imaging in Acute Brain Slices for Screening of Somatic GCaMP6f Variants

For FIG. 7A-M, individual slices were transferred to a recording chamber mounted on an inverted epifluorescence microscope (Nikon Eclipse Ti inverted microscope equipped with 10× NA 0.3 objective lens, a SPECTRA X light engine (Lumencor) with 475/28 nm exciter (Semrock), and a 5.5 Zyla camera (Andor), controlled by NIS-Elements AR software) and continuously superfused (2-3 ml/min) with ACSF at room temperature. Cells were visualized through a 10× objective to identify GCaMP6f-positive cells under excitation light power in the range from 0.5 to 4 mW/mm$^2$ adjusted to achieve comparable levels of baseline fluorescence for all screened constructs. 4-aminopyridine at a final concentration of 1 mM was added to induce neuronal activity.

Imaging GCaMP and SomaGCaMP6f1 in zebrafish

For FIG. 4D-G, individual zebrafish larvae at 4-5 dpf expressing either GCaMP6f or SomaGCaMP6f1 were exposed to the paralytic agent alpha-bungarotoxin (Sigma Aldrich) for 30-45 seconds, at a concentration of 1 mg/ml. Then, the paralyzed fish were embedded in 1.5% ultralow-melting agarose (Sigma Aldrich) prepared in E3 medium, and imaged using a custom built 2-photon microscope. A forward moving grating was used as a stimulus as GCaMP6f or SomaGCaMP6f1 expressing cells were imaged at 15 Hz: for GCaMP6f experiments, 20s on/20s off stimulus periods were used; for SomaGCaMP6f1, 10s on/10s off (the difference in frequencies between GCaMP6f and SomaGCaMP6f1 was inadvertent).

For FIG. 4H-M and FIG. 15, individual zebrafish larvae at 4-5 dpf expressing either GCaMP6f or SomaGCaMP6f1 were exposed to the paralytic agent pancuronium bromide (Sigma Aldrich) for 30-45 seconds, at a concentration of 0.20 mg/ml. The fish were under visual inspection until they stopped swimming. Then, the paralyzed fish were embedded in 1.5% ultralow-melting agarose (Sigma Aldrich) prepared in E3 medium. The embedded larvae were mounted in an imaging chamber flooded with E3 medium, in a Lightsheet Z. 1 microscope (Zeiss). For imaging, the fish were illuminated with an excitation laser line at 488 nm with maximum power of 50 mW, through 10×/0.2NA illumination optics, and imaged through a 20×/1.0NA water dipping detection objective. Because the baseline fluorescence of SomaGCaMP6f1 was approximately 4.7 fold lower compared to GCaMP6f, the percentage of light power for GCaMP6f imaging was 5% while the light power for SomaGCaMP6f1 imaging was 22.5-25%. The fish were imaged at 25 Hz, downsampled to 1 Hz, for periods of 10-20 minutes, while incubated with 1 mM 4-aminopyridine to induce spiking.

In Vivo Mouse Imaging in the Striatum:

For FIG. 5 and FIG. 16, animals were positioned underneath a microscope, and imaged while freely locomoting on a spherical treadmill. For each animal, full session recordings (5-12 min) were performed while monitoring GCaMP fluorescence using the specifications noted below. Image acquisition occurred via a custom microscope equipped with a scientific CMOS (sCMOS) camera (ORCA-Flash4.0 LT Digital CMOS camera C11440-42U; Hamamatsu, Boston, MA). GCaMP was excited using a 5W LED (LZ1-00B200, 460 nm; LedEngin, San Jose CA). The custom microscope included a Leica N Plan 10× 0.25 PHI microscope objective lens, a dual band excitation filter (FF01-468/553-25), a dichroic mirror (FF493/574-Di01-25x36), and a dual band emission filter (FF01-512/630-25: Semrock, Rochester, NY). Image acquisition was performed using HC Image Live (HC Image Live: Hamamatsu; Boston, MA). The exact sampling intervals varied based on demands of the Windows 7 operating system but was approximately 20 Hz. For each image frame, exposure time was fixed at 20 ms. Image data were stored as multi-page tagged image file format (mp-TIFF's).

For FIG. 6, animals were gently restrained and connected with the miniaturized microscope (single channel epifluorescence, 475-nm blue LED, Inscopix) via the baseplate and secured with a small screw on the baseplate. After adjustments were made to optimize the focus, animals were placed into an operant conditioning chamber (Med Associates). Grayscale images were collected at 20 frames per second on an Inscopix miniaturized microscope (nVista HD V2).

Animal Surgery, Training and Behavior

Mouse Surgery and Virus Injection in the Striatum (FIG. 5 and FIG. 16);

All animal procedures were approved by the Boston University Institutional Animal Care and Use Committee. Breeding pairs were obtained from Jackson Laboratory (Maine). A total of 11 mice (PV-cre mice; B6; 129P2-Pvalb$^{tm1(cre)Arbr}$/J: the Cre function was not used in these experiments), 8-12 weeks old at the start of the experiments, were used in these experiments. Both male and female mice were used in this study. Animals first underwent viral injection surgery targeting the left striatum under stereotaxic conditions (AP: +0.5, ML: −1.8 mm, DV: −1.6). Mice were injected with 500 nL of either (AAV8-Syn-GCaMP6f; n=7; titer: 6.6 e12 GC/ml) or 500 nL AAVDJ-Syn-SomaGCaMP6f2; n=1; titer: 5.6e12 GC/ml or 500 nL AAVDJ-CAG-SomaGCaMP6f2; n=3; titer: 2.4e12 GC/ml. AAV8 GCaMP6f was used due to its availability. DJ was used for all new constructs including the somatic GCaMP6f.

AAV8-Syn-GCaMP6f was obtained from the University of Pennsylvania Vector Core and AAVDJ-CAG-SomaGCaMP6f2 and AAVDJ-Syn-SomaGCaMP6f2 were obtained from the University of North Carolina Vector Core. All injections were made via pulled glass pipettes (diameter: 1.2 mm) pulled to a sharp point and then broken at the tip to a final inner diameter of ~20 μm. Virus was delivered via slow pressure ejection (10-15 psi, 15-20 ms pulses delivered at 0.5 Hz). The pipette was lowered over 3 min and allowed to remain in place for 3 min before infusion began. The rate of the infusion was 100 nL/min. At the conclusion of the infusion, the pipette remained in place for 10 min before slowly being withdrawn over 2-3 minutes. Upon complete recovery (7+days after virus injection, mice underwent a second procedure for the implantation of a sterilized custom imaging cannula (OD: 0.317 cm, ID: 0.236 cm, height, 2 mm diameter), fitted with a circular coverslip (size 0; OD: 3 mm) adhered using a UV-curable optical adhesive (Norland Products). To access the dorsal striatum, the cortical tissue overlying the striatum was carefully aspirated away to expose the corpus callosum. The white matter was then thinned until the underlying striatal tissue could be visualized through the surgical microscope. The window was then placed and centered above the striatum. During the same surgery, a custom aluminum head-plate was attached to the skull, anterior to the imaging cannula.

Mouse Training (FIG. 5 and FIG. 16);

Following surgery for virus infusion and window implantation (typically about 21-28 days), mice were handled for several days before being headfixed to the treadmill/imaging apparatus. Mice then were habituated to running on the spherical treadmill while headfixed, 3-4 days per week, over the next two weeks at the same time of day as subsequent recordings. Each animal received at least 6 habituation sessions prior to the first recording day. Habituation was performed in the dark with the imaging LED illuminated to the same intensity as it would be for recording sessions.

Movement Data Acquisition (FIG. 5 and FIG. 16):

The spherical treadmill was constructed similar to that previously described by Dombeck et al. Neuron. 2007 Oct. 4: 56 (1): 43-57. Briefly, the treadmill consisted of a 3D printed plastic housing and a Styrofoam ball supported with air. Movement was monitored using two computer USB mouse sensors affixed to the plastic housing at the midline of the Styrofoam ball. Each mouse sensor was mounted 3-4 mm away from the surface of the ball to prevent interference with ball movement. The LED sensors projected on the ball surface 78 degrees apart. The x- and y-surface displacement measured by each mouse was acquired using a separate computer running a Linux OS (minimal CentOS 6), and a simple multi-threaded python script that asynchronously read and accumulated mouse motion events, and sent packaged <dx,dy> data at 100 Hz to the image acquisition computer via a RS232 serial link. Packaged motion data were received on the imaging computer using a Matlab script that stored the accumulated motion between frame triggers synchronized to each acquired frame.

Subjects and Surgery in the mPFC (FIG. 6A-H)

Male wild-type C57BL/6J mice were group-housed (2-4 subjects per cage) on a 12:12 h reverse light:dark cycle (lights off at 09.00) with ad libitum access to food and water. Subjects were prepared for in vivo epifluorescent calcium imaging as previously described (Vander Weele et al., 2018). Briefly, viral vectors carrying either AAVDJ-CAG-SomaGCaMP6f2 or AAVDJ-CAG-GCaMP6f (UNC Vector Core, titers were matched at $2.4 \times 10^{12}$) were injected into the medial prefrontal cortex (mPFC) (from bregma in mm: AP: +1.8, ML: +0.3, DV: −2.75 and −2.4) (300 nL each, at 100 nL/minute) using a beveled microinjection needle (33 gauge for mice) with a 10 μl microsyringe (Nanofil; WPI) and pump (UMP3 and Micro4; WPI). The most ventral injection (DV: −2.75) was completed first and the injection needle was immediately raised to the more dorsal location (DV: −2.4) for the next injection. After completion of the second injection, 10 min were allowed to pass before the needle was raised another 0).1 mm and allowed to rest another 5 minutes before being slowly withdrawn.

After virus infusions, the craniotomy was enlarged to >1 mm in diameter, dura removed, and surface of the tissue was perforated with a 30 gauge beveled needle, but no tissue was aspirated. A 1 mm diameter, ~4 mm length gradient refractive index lens (GRIN lens; GLP-1040, Inscopix) was held by vacuum on the tip of a blunted needle surrounded by plastic tubing for stability and was lowered stereotaxically through the craniotomy under constant saline perfusion to minimize tissue/blood desiccation. Lenses were implanted slightly posterior and lateral of the needle track for virus infusions to avoid tissue damage in the imaging plane, and were lowered to the mPFC (AP: −1.77, ML: −0.4, DV: −2.32, mm from bregma). Lens implants were secured to the skull with a thin layer of adhesive cement (C&B Metabond; Parkell), followed by black cranioplastic cement (Ortho-Jet; Lang). Lenses were covered with the top of an eppendorf tube and cemented in place with cranioplastic cement for protection during the virus incubation period (at least 3 weeks). Following virus incubation, mice were again anaesthetized with isoflurane, stereotaxically secured, and baseplates (Inscopix) were cemented around the lens to support the connection of the miniaturized microscope for freely moving imaging.

In Utero Electroporation (FIG. 3 and FIG. 7)

Embryonic day (E) 15.5 timed-pregnant female Swiss Webster mice (Taconic) were deeply anesthetized with 2% isoflurane. Uterine horns were exposed and periodically rinsed with warm sterile phosphate buffered saline (PBS). A plasmid encoding GCaMP6f or SomaGCaMP6f variants under control of CAG promoter at final concentration 1-2 μg/μl diluted with PBS was injected into the lateral ventricle of the right cerebral hemisphere. Five voltage pulses (40) V, 50 ms duration, 1 Hz) were delivered using 5 mm round plate electrodes (ECM™ 830 Electroporation Generator, Harvard Apparatus). Injected embryos were placed back into the dam, and allowed to mature to delivery. All experimental manipulations were performed in accordance with protocols approved by the Massachusetts Institute of Technology Committee on Animal Care and were in accordance with the National Institutes of Health Guide for the Care and Use of Laboratory Animals.

Acute Brain Slice Preparation

Acute brain sections for cross talk analysis, and spike number sensitivity assessment (FIG. 3 and FIG. 13 respectively) were prepared using in utero electroporated mice at P12-P24, as described above. Mice were used without regard for sex. Mice were anaesthetized by isoflurane inhalation, euthanized, and cerebral hemispheres were removed, placed in ice cold choline-based cutting solution consisting of (in mM): 110 choline chloride, 25 $NaHCO_3$, 2.5 KCl, 7 $MgCl_2$, 0.5 $CaCl_2$), 1.25 $NaH_2PO_4$, 25 glucose, 11.6 ascorbic acid, and 3.1 pyruvic acid (339-341 mOsm/kg; pH 7.75 adjusted with NaOH), blocked and transferred into a slicing chamber containing ice-cold choline-based cutting solution. Coronal slices (300 μm thick) were cut with a Compresstome VF-300 slicing machine, transferred to a holding chamber with ACSF, and recovered for 10 min at 34° C., followed by another 50 min at room temperature. Slices were subsequently maintained at room temperature until use. Both cutting solution and ACSF were constantly bubbled with 95% $O_2$/5% $CO_2$.

Histological Analysis of GCMP6f and SomaGCaMP6f1 in the Mouse Brain

Deeply anesthetized mice were perfused transcardially with 4% paraformaldehyde in 0.1 M phosphate buffer (pH 7.3) and brains were postfixed for 4 h at 4° C. 50 μm sections were cut with a Leica VT1000s vibratome and imaged using an inverted Nikon Eclipse Ti microscope equipped with a spinning disk sCSUW1 confocal scanner unit (Yokogawa, Tokyo, Japan), 642 nm solid state laser, a 40×, NA 1.15 objective (Nikon), and a 4.2 PLUS Zyla camera (Andor), controlled by NIS-Elements AR software.

Results

Designing and Screening Cell-Body Targeted GCaMP6f Variants

As a test case to realize the strategy of cell body targeting of genetically encoded calcium indicators, it was decided to use GCaMP6f, which is currently popular due to its high calcium sensitivity and ability to report single action potentials (Chen et al., 2013). First, the literature was searched for proteins known to express somatically. We chose 6 such proteins were chosen (see FIG. 19 for a list of the proteins, as well as the various fragments and fusions, and Table 17 for the sequences of the fragments) for further consideration. These were the kainate receptor subunit KA2 (Shemesh et al . . . 2017: Valluru et al., 2005), the potassium channel Kv2.1 (Lim et al., 2000), the sodium channels Nav1.2 and Nav1.6 (Garrido et al., 2003), the adaptor protein Ankyrin$_G$ (Zhang and Bennett, 1998), and the rat small conductance calcium-activated potassium channel rSK1 (Bowden et al., 2001). In addition, de novo designed coiled-coil proteins that self-assemble into complexes were explored, to determine if their mutual binding could potentially slow their diffusion from the cell body; interestingly, two of these self-assembling protein fragments, EE-RR (Moll et al., 2001; Selgrade et al., 2013) and AcidP1-BaseP1 (Oakley and Kim, 1998), did indeed (see below) result in somatic localization, suggesting that such fundamental protein engineering building blocks might find applicability in neuroengineering.

For the known soma-restricted proteins, earlier work analyzed cell body expression by fusing the full-length proteins to reporters-specifically, Nav1.2, Nav1.6, Ankyrin$_G$, and rSK1 were fused to fluorescent proteins (FPs) (Garrido et al., 2003: Moruno Manchon et al., 2015: Schäfer et al., 2010; Zhang and Bennett, 1998), KA2 to a Myc-tag (Valluru et al., 2005), and Kv2.1 to an HA-tag (Lim et al., 2000). In some cases, earlier work showed that key fragments were sufficient to cause soma targeting of a reporter (FIG. 19). For Nav1.2 and Nav1.6, 326- and 27-amino acid segments within intracellular loops between transmembrane domains, termed Nav1.2 (I-II) and Nav1.6 (II-III) respectively (see Table 17 for sequences), were sufficient for somatic localization (Garrido et al., 2001, 2003). For Kv2.1, a 65-amino acid segment within the intracellular loop between transmembrane domains IV and V (Kv2.1-motif, see Table 17 for sequences) sufficed (Lim et al., 2000; Wu et al., 2013b). For rSK1, the tail region (rSK1-tail, see Table 17 for sequences) sufficed (Fletcher et al., 2003). For Ankyrin$_G$ it was found that the spectrin-binding domain (AnkSB-motif, see Table 17 for all Ankyrin subsequences), the tail domain (AnkTail-motif), the membrane-binding domain (AnkMB-motif), the COOH-terminal domain (AnkCT-motif) and the serine-rich domain (AnkSR-motif) were all targeted to the axon and the cell body of neurons (Zhang and Bennett, 1998).

```
AnkTail-motif (Ankyrin_G (1934-2333)):
                                                  SEQ ID NO: 1
REGRIDDEEPFKIVEKVKEDLVKVSEILKKDVCVESKGPPKSPKSDKGHSPEDDWTEFS
SEEIREARQAAASHAPSLPERVHGKANLTRVIDYLTNDIGSSSLTNLKYKFEEAKKDGE
ERQKRILKPAMALQEHKLKMPPASMRPSTSEKELCKMADSFFGADAILESPDDFSQHD
QDKSPLSDSGFETRSEKTPSAPQSAESTGPKPLFHEVPIPPVITETRTEVVHVIRSYEPSSG
EIPQSQPEDPVSPKPSPTFMELEPKPTTSSIKEKVKAFQMKASSEEEDHSRVLSKGMRV
KEETHITTTTRMVYHSPPGGECASERIEETMSVHDIMKAFQSGRDPSKELAGLFEHKSA
MSPDVAKSAAETSAQHAEKDSQMKPKLERIIEVHIEKGPQSPCE.

EE-RR:
                                                  SEQ ID NO: 2
LEIEAAFLEQENTALETEVAELEQEVQRLENIVSQYETRYGPLGSLEIRAAFLRRRNTAL
RTRVAELRQRVQRLRNIVSQYETRYGPL.

AcidP1-BaseP1:
                                                  SEQ ID NO: 3
AQLEKELQALEKENAQLEWELQALEKELAQGSGSAQLKKKLQALKKKNAQLKWKLQ
ALKKKLAQ.
nullsfGFP (mutation to abolish the fluorescence of the origi-
nal
sfGFP is underlined)
                                                  SEQ ID NO: 4
MSKGEELFTGVVPILVELDGDVNGHKFSVRGEGEGDATNGKLTLKFICTTGKLPVPWP
TLVTTLTGGVQCFSRYPDHMKRHDFFKSAMPEGYVQERTISFKDDGTYKTRAEVKFE
GDTLVNRIELKGIDFKEDGNILGHKLEYNFNSHNVYITADKQKNGIKANFKIRHNVED
GSVQLADHYQQNTPIGDGPVLLPDNHYLSTQSVLSKDPNEKRDHMVLLEFVTAAGITH
GMDELYK.

NLS
                                                  SEQ ID NO: 5
RKRPSDLVHVFSPPRKK.

KGC
                                                  SEQ ID NO: 6
KSRITSEGEYIPLDQIDINV.

ER2
                                                  SEQ ID NO: 7
FCYENEV.

nullCoChR (mutation to abolish photocurrent of the original
CoChR is underlined)
                                                  SEQ ID NO: 8
MLGNGSAIVPIDQCFCLAWTDSLGSDTEQLVANILQWFAFGFSILILMFYAYQTWRAT
CGWEEVYVCCVELTKVIIEFFHEFDDPSMLYLANGHRVQWLRYAEWLLTCPVILIHLS
```

-continued
```
NLTGLKDDYSKRTMRLLVSDVGTIVWGATSAMSTGYVKVIFFVLGCIYGANTFFHAA
KVYIESYHVVPKGRPRTVVRIMAWLFFLSWGMFPVLFVVGPEGFDAISVYGSTIGHTII
DLMSANCWGLLGHYLRVLIHQHIIIYGDIRKKTKINVAGEEMEVETMVDQEDEETV.
```

KA2(1-150)  
SEQ ID NO: 9
```
MPAELLLLLIVAFANPSCQVLSSLRMAAILDDQTVCGRGERLALALAREQINGIIEVPA
KARVEVDIFELQRDSQYETTDTMCQILPKGVVSVLGPSSSPASASTVSHICGEKEIPHIK
VGPEETPRLQYLRFASVSLYPSNEDVSLAVS.
```

KA2(1-150)-Y76A  
SEQ ID NO: 10
```
MPAELLLLLIVAFANPSCQVLSSLRMAAILDDQTVCGRGERLALALAREQINGIIEVPA
KARVEVDIFELQRDSQAETTDTMCQILPKGVVSVLGPSSSPASASTVSHICGEKEIPHIK
VGPEETPRLQYLRFASVSLYPSNEDVSLAVS.
```

KA2(1-100)  
SEQ ID NO: 11
```
MPAELLLLLIVAFANPSCQVLSSLRMAAILDDQTVCGRGERLALALAREQINGIIEVPA
KARVEVDIFELQRDSQYETTDTMCQILPKGVVSVLGPSSSP.
```

Ank(1-334) (Ankyrin$_G$ (1-334))  
SEQ ID NO: 12
```
MAHAASQLKKNRDLEINAEEETEKKKHRKRSRDKKKSDANASYLRAARAGHLEK
ALDYIKNGVDVNICNQNGLNALHLASKEGHVEVVSELLQREANVDAATKKGNTALH
IASLAGQAEVVKVLVTNGANVNAQSQNGFTPLYMAAQENHLEVVRFLLDNGASQSL
ATEDGFTPLAVALQQGHDQVVSLLLENDTKGKVRLPALHIAARKDDTKAAALLLQN
DTNADIESKMVVNRATESGFTSLHIAAHYGNINVATLLLNRAAAVDFTARNDITPLHV
ASKRGNANMVKLLLDRGAKIDAKTRDGLTPLHCGARSGHEQVVEMLLDRAAP.
```

AnkCT-motif (Ankyrin$_G$ (2334-2622))  
SEQ ID NO: 13
```
RTDIRMAIVADHLGLSWTELARELNFSVDEINQIRVENPNSLISQSFMLLKKWVTRDG
KNATTDALTSVLTKINRIDIVTLLEGPIFDYGNISGTRSFADENNVFHDPVDGWQNETP
SGSLESPAQARRLTGGLLDRLDDSSDQARDSITSYLTGEPGKIEANGNHTAEVIPEAKA
KPYFPESQNDIGKQSIKENLKPKTHGCGRTEEPVSPLTAYQKSLEETSKLVIEDAPKPC
VPVGMKKMTRTTADGKARLNLQEEEGSTRSEPKQGEGYKVKTKKEIRNVEKKTH.
```

AnkMB-motif (Ankyrin$_G$ (1-800))  
SEQ ID NO: 14
```
MAHAASQLKKNRDLEINAEEETEKKRKHRKRSRDKKKSDANASYLRAARAGHLEK
ALDYIKNGVDVNICNQNGLNALHLASKEGHVEVVSELLQREANVDAATKKGNTALHI
ASLAGQAEVVKVLVTNGANVNAQSQNGFTPLYMAAQENHLEVVRFLLDNGASQSLA
TEDGFTPLAVALQQGHDQVVSLLLENDTKGKVRLPALHIAARKDDTKAAALLLQNDT
NADVESKSGFTPLHIAAHYGNINVATLLLNRAAAVDFTARNDITPLHVASKRGNANM
VKLLLDRGAKIDAKTRDGLTPLHCGARSGHEQVVEMLLDRSAPILSKTKNGLSPLHM
ATQGDHLNCVQLLLQHNVPVDDVTNDYLTALHVAAHCGHYKVAKVLLDKKASPNA
KALNGFTPLHIACKKNRIRVMELLLKHGASIQAVTESGLTPIHVAAFMGHVNIVSQLM
HHGASPNTTNVRGETALHMAARSGQAEVVRYLVQDGAQVEAKAKDDQTPLHISARL
GKADIVQQLLQQGASPNAATTSGYTPLHLAAREGHEDVAAFLLDHGASLSITTKKGFT
PLHVAAKYGKLEVASLLLQKSASPDAAGKSGLTPLHVAAHYDNQKVALLLLDQGASP
HAAAKNGYTPLHIAAKKNQMDIATSLLEYGADANAVTRQGIASVHLAAQEGHVDMV
SLLLSRNANVNLSNKSGLTPLHLAAQEDRVNVAEVLVNQGAHVDAQTKMGYTPLHV
GCHYGNIKIVNFLLQHSAKVNAKTKNGYTALHQAAQQGHTHIINVLLQNNASPNELT
VNGNTAL.
```

AnkSB-motif (Ankyrin$_G$ (801-1521))  
SEQ ID NO: 15
```
AIARRLGYISVVDTLKVVTEEIMTTTTITEKHKMNVPETMNEVLDMSDDEVRKASAPE
KLSDGEYISDGEEGEDAITGDTDKYLGPQDLKELGDDSLPAEGYVGFSLGARSASLRSF
SSDRSYTLNRSSYARDSMMIEELLVPSKEQHLTFTREFDSDSLRHYSWAADTLDNVNL
VSSPVHSGFLVSFMVDARGGSMRGSRHHGMRIIIPPRKCTAPTRITCRLVKRHKLANPP
PMVEGEGLASRLVEMGPAGAQFLGPVIVEIPHFGSMRGKERELIVLRSENGETWKEHQ
FDSKNEDLAELLNGMDEELDSPEELGTKRICRIITKDFPQYFAVVSRIKQESNQIGPEGG
ILSSTTVPLVQASFPEGALTKRIRVGLQAQPVPEETVKKILGNKATFSPIVTVEPRRRKF
HKPITMTIPVPPPSGEGVSNGYKGDATPNLRLLCSITGGTSPAQWEDITGTTPLTFIKDC
VSFTTNVSARFWLADCHQVLETVGLASQLYRELICVPYMAKFVVFAKTNDPVESSLRC
FCMTDDRVDKTLEQQENFEEVARSKDIEVLEGKPIYVDCYGNLAPLTKGGQQLVFNF
YSFKENRLPFSIKIRDTSQEPCGRLSFLKEPKTTKGLPQTAVCNLNITLPAHKKETESDQ
DDAEKADRRQSFASLALRKRYSYLTEPSMKTVERSSGTARSLPTTYSHKPFFSTRPYQS
WTTAPITVPGPAKSGSLSSSPSNTPSA.
```

AnkSR-motif (Ankyrin$_G$ (1534-1933))  
SEQ ID NO: 16
```
SPLKSIWSVSTPSPIKSTLGASTTSSVKSISDVASPIRSFRTVSSPIKTVVSPSPYNPQVASG
TLGRVPTITEATPIKGLAPNSTFSSRTSPVTTAGSLLERSSITMTPPASPKSNITMYSSSLP
FKSIITSATPLISSPLKSVVSPTKSAADVISTAKATMASSLSSPLKQMSGHAEVALVNGS
VSPLKYPSSSALINGCKATATLQDKISTATNAVSSVVSAASDTVEKALSTTTAMPFSPL
RSYVSAAPSAFQSLRTPSASALYTSLGSSIAATTSSVTSSIITVPVYSVVNVLPEPALKKL
PDSNSFTKSAALLSPIKTLTTETRPQPHFNRTSSPVKSSLFLASSALKPSVPSSLSSSQEI
LKDVAEMKEDLMRMTAILQTDVPEEKPFQTDLP.
```

-continued

```
Kv2.1-motif (K_v2.1(536-600))
                                                    SEQ ID NO: 17
QSQPILNTKEMAPQSKPPEELEMSSMPSPVAPLPARTEGVIDMRSMSSIDSFISCATDFP
EATRF.

rSK1-tail (rSK1(351-411))
                                                    SEQ ID NO: 18
QAQKLRTVKIEQGKVNDQANTLADLAKAQSIAYEVVSELQAQQEELEARLAALESRL
DVLGASLQALPSLIAQAICPLPPPWPGPSHLTTAAQSPQSHWLPTTASDCG.

Na_v1.6(II-III)
                                                    SEQ ID NO: 19
TVRVPIAVGESDFENLNTEDVSSESDP.

Na_v1.2(I-II)
                                                    SEQ ID NO: 20
YEEQNQATLEEAEQKEAEFQQMLEQLKKQQEEAQAAAAAASAESRDFSGAGGIGVFS
ESSSVASKLSSKSEKELKNRRKKKKQKEQAGEEEKEDAVRKSASEDSIRKKGFQFSLE
GSRLTYEKRFSSPHQSLLSIRGSLFSPRRNSRASLFNFKGRVKDIGSENDFADDEHSTFE
DNDSRRDSLFVPHRHGERRPSNVSQASRASRGIPTLPMNGKMHSAVDCNGVVSLVGG
PSALTSPVGQLLPEGTTTETEIRKRRSSSYHVSMDLLEDPSRQRAMSMASILTNTMEEL
EESRQKCPPCWYKFANMCLIWDCCKPWLKVKHVVN.
```

Over 30 fusions between GCaMP6f and the protein fragments reported above were made (see the different fusions screened in Table 2 and the sequences of localization fragments in Table 17). For Nav1.2, Nav1.6, Kv2.1, and rSK1 we performed fusions in which the previously characterized localization fragment was attached to the C-terminus of GCaMP6f. In a recent study (Shemesh et al., 2017), the channelrhodopsin CoChR (Klapoetke et al., 2014) was fused to the first 150 amino acids of the KA2 receptor subunit (KA2 (1-150)) thereby creating a somatic CoChR. Because both N and C terminal fusions of KA2 (1-150) with CoChR caused somatic localization, similar upstream and downstream fusions of this fragment were made with GCaMP6f (Table 2). In the present study, it was also found that the first 100 amino acids of KA2 (KA2 (1-100)) were sufficient to introduce somatic localization of GCaMP6f, therefore additional upstream and downstream fusions of KA2 (1-100) with GCaMP6f (Table 2) were made. Because the length of the linker between parts of a fusion protein can affect the ultimate function of the fusion, the effect of different linker lengths between GCaMP6f and trafficking sequences on soma localization (Table 2) were tested. In some cases, a superfolder GFP (sfGFP (P?delacq et al., 2006), which contains three mutations to EGFP in order to enhance folding), was inserted into the construct, with a mutation to abolish its fluorescence (here called nullsfGFP, see Methods for the full sequence of nullsfGFP; Table 2). This was done to explore whether better folding, facilitated by sfGFP, might help improve expression of the final fusion protein. For Ankyrin$_G$ fragments, fusions both upstream and downstream of GCaMP6f (Table 2) were made. For de-novo coiled-coil proteins, only downstream fusions were made.

Each of these GCaMP6f fusion proteins was expressed in cultured mouse hippocampal neurons (Table 2). Using wide-field fluorescence microscopy a preliminary screen was performed to sort through the fusions and prioritize them for more detailed characterizations. In this screen, the following were assessed: the expression level (fluorescence under baseline conditions), the somatic localization of the GCaMP6f fluorescence, the toxicity (assessed as the percentage of dead fluorescent cells out of all expressing cells), and whether there was a fluorescent change over the baseline fluorescence (termed here df/f$_0$, see Methods for explanation of calculation) in response to spontaneous neural activity. It was found that five constructs did not result in obvious toxicity, exhibited somatic localization, and displayed dynamic activity with a df/f$_0$ similar to that of GCaMP6f (Table 2). These were GCaMP6f fused to the fragments mentioned below (integers in the construct names denote the length of the linker; see Table 2 for fusions tested and for the sequences of different linkers); Nav1.2 (I-II) (GCaMP6f-27-Nav1.2 (I-II)-ER2); GCaMP6f fused upstream to nullsfGFP and to KA2 (1-100) (GCaMP6f-24-nullsfGFP-24-KA2 (1-100)-ER2); GCaMP6f fused downstream to a zero-photocurrent CoChR mutant called nullCoChR followed by the Kv2.1-motif (nullCoChR-12-GCaMP6f-Kv2.1-motif); GCaMP6f fused to AnkTail-motif (GCaMP6f-27-AnkTail-motif-ER2); and finally GCaMP6f fused to the coiled-coil peptide set EE-RR (GCaMP6f-27-EE-RR).

TABLE 2

GCaMP6f fusion proteins that were screened in cultured hippocampal neurons in this project

| Serial # | Full name | Expressed? | Caused cell death? If yes, percentage of dead cells? | Somatic? | Spontaneous fluorescent spikes detected? | Baseline brightness compared to GCaMP6f: Lower, similar, higher? |
|---|---|---|---|---|---|---|
| 1 | KA2(1-00)-1192-GCaMP6f-ER2 | Yes | Yes, ~50% dead | Yes | Yes | Similar |
| 2 | GCaMP6f-27-Nav1.2(I-II)-ER2 | Yes | No | Yes | Yes | Similar |
| 3 | nullsfGFP-24-KA2(1-100)-48-GCaMP6f-ER2 | Yes | Yes, ~50% dead | Yes | No | Similar |

TABLE 2-continued

GCaMP6f fusion proteins that were
screened in cultured hippocampal neurons in this project

| Serial # | Full name | Expressed? | Caused cell death? If yes, percentage of dead cells? | Somatic? | Spontaneous fluorescent spikes detected? | Baseline brightness compared to GCaMP6f: Lower, similar, higher? |
|---|---|---|---|---|---|---|
| 4 | KA2(1-100)-192-GCaMP6f | Yes | Yes, ~50% dead | Yes | No | Similar |
| 5 | KA2(1-100)-24-nullsfGFP-48-GCaMP6f-ER2 | Yes | Yes, ~90% dead | N/A, due to toxicity. | N/A, due to toxicity. | N/A, due to toxicity. |
| 6 | GCaMP6f-96-KA2(1-100) | Yes | No | Yes | No | Lower |
| 7 | GCaMP6f-24-nullsfGFP-24-KA2(1-100) | Yes | No | Yes | Yes | Lower |
| 8 | GCaMP6f-96-KA2(1-100)-ER2 | Yes | No | Yes | Yes | Similar |
| 9 | GCaMP6f-24-nullsfGFP24-KA2(1-100)-ER2 | Yes | Yes, ~90% dead | Yes | Yes | N/A, due to toxicity. |
| 10 | KA2(1-100)-48-GCaMP6f-ER2 | Yes | No | Yes | Yes | Similar |
| 11 | KA2(1-100)-48-KGC-12-GCaMP6f-ER2 | Yes | No | Yes | No | Similar |
| 12 | KA2(1-100)-48-ER2-12-GCaMP6f-KGC | Yes | No | Yes | No | Similar |
| 13 | KA2(1-150)-48-KA2(1-150)-48-GCaMP6f-ER2 | Yes | No | Yes, the most somatic (no more than 10 um from soma) | No | Similar |
| 14 | KA2(1-150)-48-GCaMP6f-48-KA2(1-150) | Yes | Yes, ~50% dead | Yes | No | Similar |
| 15 | KA2(1-150)-Y76A-48-GCaMP6f | Yes | Yes, ~90% dead | Yes | Yes | N/A, due to toxicity |
| 16 | KA2(1-150)-Y76A-48-GCaMP6f-ER2 | Yes | No | Yes | Yes | Similar |
| 17 | nullCoChR-12-KA2-(1-150)-GCaMP6f-ER2 | Yes | Yes, ~90% dead | N/A, due to toxicity | N/A, due to toxicity | N/A, due to toxicity |
| 18 | KA2-(1-150)-12-nullCoChR-GCaMP6f-ER2 | Yes | Yes, ~90% dead | Yes | Yes | Similar |
| 19 | nullCoChR-12-KA2-(1-150)-GCaMP6f-Ky2.1-motif | Yes | No | Yes | Yes | Lower |
| 20 | nullCoChR-Ank(1-334)-GCaMP6f | Yes | Yes, ~90% dead | Yes | N/A, due to toxicity | N/A, due to toxicity |
| 21 | GCaMP6f-AnkCT-motif-ER2 | Yes | No | No | Yes | Similar |
| 22 | GCaMP6f-AnkMB-motif-ER2 | Yes | No | No | No | Similar |
| 23 | GCaMP6f-AnkSB-motif-ER2 | Yes | No | No, somato-dendritic | Yes | Similar |
| 24 | GCaMP6f-AnkSR-motif-ER2 | No | No | No | Yes | Similar |
| 25 | GCaMP6f-27-AnkTail-motif-ER2 | Yes | No | Yes | Yes | Similar |
| 26 | AnkTail-motif-27-GCaMP6f-ER2 | Yes | No | Yes | Yes, but with a low df/f$_0$. | Similar |
| 27 | GCaMP6f-27-Nav1.6(II-III)-ER2 | Yes | No | No, somato-dendritic | Yes | Similar |
| 28 | GCaMP6f-27-Ky2.1-motif-ER2 | Yes | No | No | Yes | Similar |
| 29 | GCaMP6f-rSK1-tail-ER2 | Yes | No | Yes | Yes | Lower |
| 30 | nullCoChR-12-GCaMP6f-Kv2.1-motif | Yes | No | Yes | Yes | Similar |

TABLE 2-continued

GCaMP6f fusion proteins that were
screened in cultured hippocampal neurons in this project

| Serial # | Full name | Expressed? | Caused cell death? If yes, percentage of dead cells? | Somatic? | Spontaneous fluorescent spikes detected? | Baseline brightness compared to GCaMP6f: Lower, similar, higher? |
|---|---|---|---|---|---|---|
| 31 | KA2(1-150)-12-GCaMP6f-ER2 | Yes | No | Yes | Yes, but with a low df/f₀. | Similar |
| 32 | GCaMP6f-27-EE-RR | Yes | No | Yes | Yes | Similar |
| 33 | GCaMP6f-KGC-27-EE-RR | Yes | No | Yes, but less somatic than GCaMP6f-27-EE-RR | Yes | Similar |
| 34 | GCaMP6f-27-AcidP1-BaseP1 | Yes | No | Yes, but less somatic than GCaMP6f-27-EE-RR | Yes | Similar |

The number inside the construct name is an abbreviation for the linker size: 12=ggsggtggsggt (SEQ ID NO: 21), 24=ggsggtggsggtggsggtggsggt (SEQ ID NO: 22), 27=ggsggsggtggsggsggtggsggsggt (SEQ ID NO: 23), 48=ggsggtggsggtggsggtggsggtggsggtggsggtggsggtggsggt (SEQ ID NO: 24), 96=ggsggtggsggtggsggtggsggtggsggtggsggtggsggtggsggtggsggtggsggtggsggtggsggtggsggtggsggt ggsggtggsggt (SEQ ID NO: 25), 192=10 ggsggtggsggtggsggtggsggtggsggtggsggtggsggtggsggtggsggtggsggtggsggtggsggt ggsggtggsggtggsggt ggsggtggsggtggsggtggsggtggsggtggsggtggsggtggsggtggsggtggsggtggsggtggsggt ggsggtggsggtggsggtggsggt (SEQ ID NO: 26), KGC (Ma et al., 2001) and ER2 (Hofherr et al., 2005) are trafficking sequences from the potassium channel Kir2.1. KA2 (150)-Y76A is a mutant of KA2 (1-150), in which the amino acid known for dimerization of KA2 (Kumar et al., 2011) was mutated to alanine (see Table 17 for sequences). All the results in table 2 are from cultured mouse hippocampal neurons (see Methods). For amino acid sequences corresponding to the acronyms used, see Table 17.

These five somatic GCaMP6f candidates were screened for expression in mouse brain circuitry, incubating mouse cortical slices expressing these five candidates with 4-aminopyridine (4-AP) to induce spiking as a screen for physiological function. 1 mM 4-AP resulted in approximately 5-20 GCaMP fluorescent transients occurring per minute (FIG. 7), which is referred to herein as GCaMP-spikes; essentially no GCaMP-spikes were seen in slices not exposed to 4-AP. For each somatic GCaMP6f candidate, the df/f₀, was assessed by calculating the ratio between the df/f₀ at the cell body and the df/f₀ in the neuropil (see Methods for how somata vs. neuropil in mouse brain slices was determined). The screen criteria was set so that a good somatic GCaMP6f would have a df/f₀ similar to or larger than conventional GCaMP6f at the soma, and also exhibit a ratio of soma df/f₀ to neuropil df/f₀ larger than non-targeted GCaMP6f. The latter ratio was used as a measure, during this screen, of soma-localization, as it was reasoned that for a soma-localized GCaMP6f, the neuropil df/f₀ would begin to get lost in the noise; while not precise, the intention at this phase of the project was simply to do a fast screen in brain slices, as measuring exact falloff of fluorescence along neurites is hard to measure without actually tracing the neurites. It was found that GCaMP6f-24-nullsfGFP-24-KA2 (1-100)-ER2 expressed in the neurites of pyramidal neurons in the cortex, indicating impaired somatic localization when tested in an in vivo context, and this construct was not further pursued in FIG. 7 or beyond. The remaining four constructs had a similar df/f₀ compared to GCaMP6f (FIG. 7 and Table 7), while all four variants had a soma df/f₀ to neuropil df/f₀ ratio significantly higher than that of GCaMP6f (FIG. 7 and Table 7). Among the somatic variants GCaMP6f-27-AnkTail-motif-ER2 and GCaMP6f-27-EE-RR had the highest baseline brightness (FIG. 7 and Table 7), which is important for in-vivo experiments. Therefore, a decision was made to investigate GCaMP6f-27-AnkTail-motif-ER2 and GCaMP6f-27-EE-RR for more detailed characterization. These two constructs were named: SomaGCaMP6f1 and SomaGCaMP6f2, respectively.

TABLE 7

Statistical analysis for FIG. 7.

FIG. 7K-df/f₀ of different GCaMP6f targeting variants.
(n = 20 cells from 2 slices from 2 mice for each variant).
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f-27-Nav1.2(I-II)-ER2 | 20 | 1171.00 | 1010.00 | 58.5500 | 1.383 |
| nullCoChR-12-GCaMP6f-Kv2.1-motif | 20 | 579.000 | 1010.00 | 28.9500 | −3.710 |

TABLE 7-continued

Statistical analysis for FIG. 7.

| | | | | | |
|---|---|---|---|---|---|
| GCaMP6f-27-AnkTail-motif-ER2 | 20 | 1288.00 | 1010.00 | 64.4000 | 2.391 |
| GCaMP6f-27-EE-RR | 20 | 1107.00 | 1010.00 | 55.3500 | 0.832 |
| GCaMP6f | 20 | 905.000 | 1010.00 | 45.2500 | −0.901 |

1-Way Test, ChiSquare Approximation

| ChiSquare | DF | Prob > ChiSq |
|---|---|---|
| 18.3802 | 4 | 0.0010 |

Nonparametric Comparisons with Control Using Steel Method
Control Group = GCaMP6f

| q* | Alpha |
|---|---|
| 2.44177 | 0.05 |

| Molecule | Control | Score Mean Difference | Std Err Dif | Z | p-Value |
|---|---|---|---|---|---|
| nullCoChR-12-GCaMP6f-Kv2.1-motif | GCaMP6f | 6.15000 | 3.696846 | 1.66358 | 0.2781 |
| GCaMP6f-27-Nav1.2(I-II)-ER2 | GCaMP6f | −5.55000 | 3.696846 | −1.50128 | 0.3671 |
| GCaMP6f-27-AnkTail-motif-ER2 | GCaMP6f | −7.35000 | 3.696846 | −1.98818 | 0.1467 |
| GCaMP6f-27-EE-RR | GCaMP6f | −3.65000 | 3.696846 | −0.98733 | 0.7195 |

FIG. 7L-the ratio between $df/f_0$ of the cell body and $df/f_0$ of the neuropil for different GCaMP6f targeting variants. (n = 20 cells from 2 slices from 2 mice for each variant). Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f-27-Nav1.2(I-II)-ER2 | 20 | 1409.00 | 1010.00 | 70.4500 | 3.434 |
| nullCoChR-12-GCaMP6f-Kv2.1-motif | 20 | 1546.00 | 1010.00 | 77.3000 | 4.615 |
| GCaMP6f-27-AnkTail-motif-ER2 | 20 | 1005.00 | 1010.00 | 50.2500 | −0.039 |
| GCaMP6f-27-EE-RR | 20 | 738.000 | 1010.00 | 36.9000 | −2.340 |
| GCaMP6f | 20 | 352.000 | 1010.00 | 17.6000 | −5.666 |

1-Way Test, ChiSquare Approximation

| ChiSquare | DF | Prob > ChiSq |
|---|---|---|
| 56.6418 | 4 | <.0001 |

Nonparametric Comparisons with Control Using Steel Method
Control Group = GCaMP6f

| q* | Alpha |
|---|---|
| 2.44177 | 0.05 |

| Molecule | Control | Score Mean Difference | Std Err Dif | Z | p-Value |
|---|---|---|---|---|---|
| GCaMP6f-27-AnkTail-motif-ER2 | GCaMP6f | −17.1500 | 3.696846 | −4.63909 | <.0001 |

TABLE 7-continued

Statistical analysis for FIG. 7.

| | | | | | |
|---|---|---|---|---|---|
| nullCoChR-12-GCaMP6f-Kv2.1-motif | GCaMP6f | −19.3500 | 3.696846 | −5.23419 | <.0001 |
| GCaMP6f-27-EE-RR | GCaMP6f | −9.1500 | 3.696846 | −2.47508 | 0.0458 |
| GCaMP6f-27-Nav1.2(I-II)-ER2 | GCaMP6f | −19.9500 | 3.696846 | −5.39649 | <.0001 |

Characterization of SomaGCaMP6f and SomaGCaMP7f Variants in Mouse Hippocampal Cultures GCaMP6f, GCaMP6f-27-AnkTail-motif-ER2 (SomaGCaMP6f1) or GCaMP6f-27-EE-RR (SomaGCaMP6f2) were co-expressed with the red fluorescent protein mCardinal to serve as a cellular tracer, using cultured mouse hippocampal neurons (FIG. 1C-K). In cultured neurons, the number of transfected neurons was sparse (approximately one transfected neuron per 200 non-transfected neurons) and therefore it was possible to trace single neurites. Thus, neurites were traced and fluorescence observed as a function of distance down each neurite in individual cells. It was found that the fluorescence decreased at a higher rate along the neurites in SomaGCaMP6f1 (FIG. 1R-S) and SomaGCaMP6f2 (FIG. 1R, FIG. 1T) expressing cells compared to GCaMP6f expressing cells (see Table 3 for full statistics). Based on the success in creating a GCaMP6f based somatic variants, a GCaMP7 (Dana et al., 2019) somatic variant was created. GCaMP7f was fused to the EE-RR sequence to yield GCaMP7f-27-EE-RR, termed SomaGCaMP7f. It was determined that the fluorescence decreased at a higher rate along the neurites in SomaGCaMP7f (FIG. 1U-V) expressing cells compared to GCaMP7f expressing cells (see Table 3 for full statistics).

TABLE 3

Statistical analysis for FIG. 1.

Figure 1R:
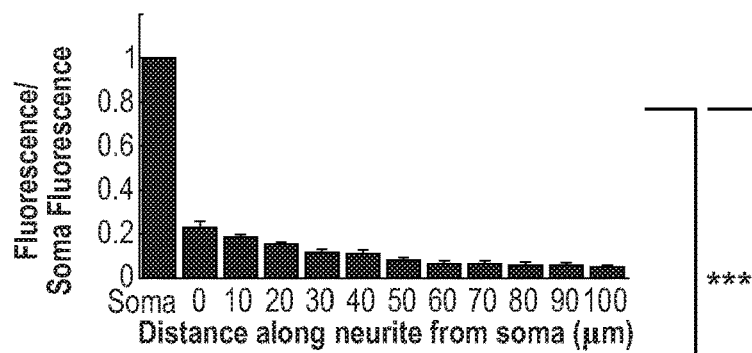
FIG. 1R is a bar plot of GCaMP6f brightness versus position along a neurite, normalized to GCaMP6f brightness at the soma, extracted from neurites of cultured hippocampal neurons expressing GCaMP6f (n=8 neurites from 8 cells from 3 cultures).
Figure 1S:
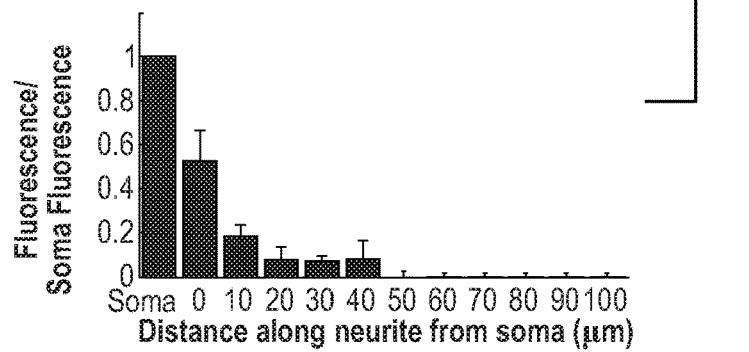
FIG. 1S, as in FIG. 1R, except for neurons expressing GCaMP6f-27-AnkTail-motif-ER2 (SomaGCaMP6f1: n=5 neurites from 5 cells from 2 cultures). * P<0).001, Kruskal-Wallis analysis of variance of neurite brightness followed by post-hoc test via Steel's test with GCaMP6f as a control group: see Table 3 for full statistics for FIG. 1).
Figure 1T:
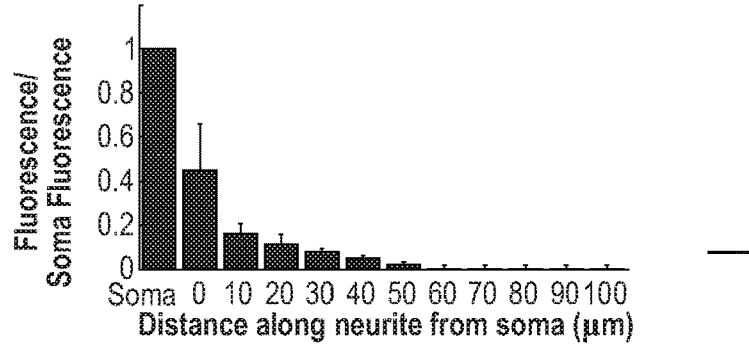
FIG. 1T, as in FIG. 1R, but for neurons expressing GCaMP6f-27-EE-RR (SomaGCaMP6f2; n=5 neurites from 5 cells from 3 cultures). * P<0).001, Kruskal-Wallis analysis of variance of neurite brightness followed by post-hoc test via Steel's test with GCaMP6f as a control group: see Table 3 for full statistics for FIG. 1).

For: FIG. 1R-T- Brightness versus position along a neurite of GCaMP6f variants, normalized to GCaMP brightness at the soma.
Kruskal-Wallis analysis of variance of neurite brightness followed by post-hoc test via Steel's test with GCaMP6f as a control group. For GCaMP6f, n = 8 neurites from 8 cells from 3 cultures. For SomaGCaMP6f1, n = 5 neurites from 5 cells from 2 cultures. For SomaGCaMP6f2, n = 5 neurites from 5 cells from 3 cultures.
Wilcoxon/Kruskal-Wallis Tests (Rank Sums)

| Molecule | Cell Count | Score Sum | Expected Score | Score Mean | (Mean-Mean0)/Std0 |
|---|---|---|---|---|---|
| GCaMP6f | 8 | 10930.0 | 8613.00 | 125.632 | 5.830 |
| SomaGcaMP6f1 | 5 | 4321.00 | 5445.00 | 78.564 | −3.130 |
| SomaGcaMP6f2 | 5 | 4252.00 | 5445.00 | 77.309 | −3.322 |

1-Way Test, ChiSquare Approximation

| ChiSquare | DF | Prob > ChiSq |
|---|---|---|
| 34.0115 | 2 | <.0001 |

Nonparametric Comparisons with Control Using Steel Method
Control Group = GCaMP6f

| q* | Alpha |
|---|---|
| 2.22275 | 0.05 |

| Molecule | Control | Score Mean Difference | Std Err Dif | Z | p-Value |
|---|---|---|---|---|---|
| SomaGcaMP6f1 | GCaMP6f | −32.4359 | 7.086385 | −4.57722 | <.0001 |
| SomaGcaMP6f2 | GCaMP6f | −36.2938 | 7.086385 | −5.12163 | <.0001 |

TABLE 3-continued

Statistical analysis for FIG. 1.

Figure 1U:
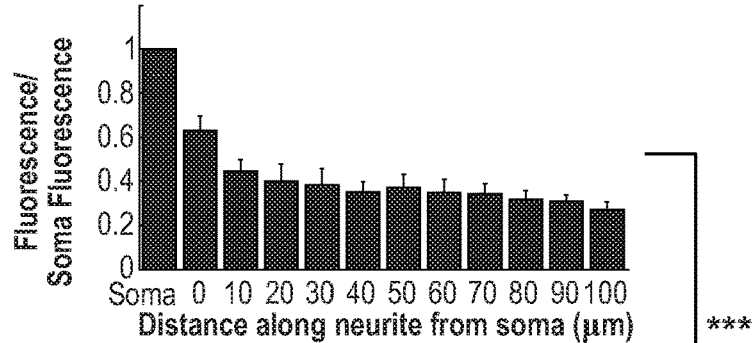
FIG. 1U, as in FIG. 1R, for neurons expressing GCaMP7f (n=6 neurites from 6 cells from 2 cultures).
Figure 1V:
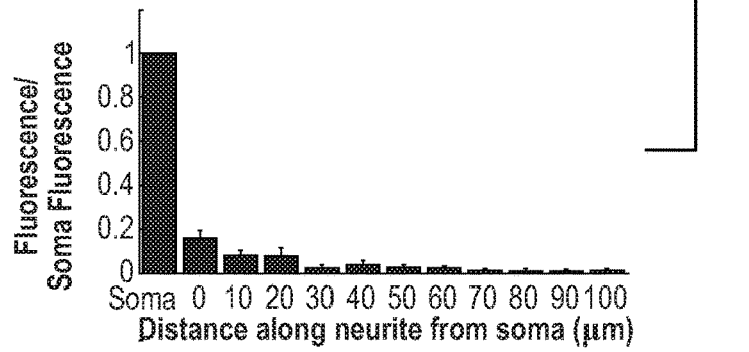

For FIG. 1U-V-Brightness versus position along a neurite of
GCaMP7f variants, normalized to GCaMP brightness at the soma
Wilcoxon rank sum test of the neurite brightness between neurons expressing
GCaMP7f (n = 6 neurites from 6 cells from 2 cultures) and SomaGCaMP7f
(n = 6 neurites from 6 cells from 2 cultures).

| | |
|---|---|
| P-value | 4.0870e−22 |
| zval | −9.6689 |
| Rank sum test statistic | 2264 |

The baseline fluorescence of GCaMP6f, SomaGCaMP6f1, and SomaGCaMP6f2 expressing cells in culture were all similar to each other, and to that of the nuclear-localized GCaMP6f-NLS (FIG. 2A, see Table 17 and Methods for the nuclear localization sequence). The baseline fluorescence of GCaMP7f and SomaGCaMP7f expressing cells in culture were all similar to each other (FIG. 2A, see Table 17 and Methods for the nuclear localization sequence). Next, the fluorescent response of each molecule to a single action potential in cultured hippocampal neurons (FIG. 2B) were compared, which indicated comparable responses (FIG. 2C; see Table 4 for full statistics). It was found that SomaGCaMP6f1 and SomaGCaMP6f2 had SNRs (defined as the magnitude of the fluorescence change caused by a single action potential divided by the standard deviation of the baseline fluorescence) similar to GCaMP6f, whereas GCaMP6f-NLS had an SNR significantly lower than that of GCaMP6f (FIG. 2D; see Table 4 for full statistics). It was found that SomaGCaMP7f an SNR similar to GCaMP7f, (FIG. 2D; see Table 4 for full statistics). It was found that SomaGCaMP6f1 and SomaGCaMP6f2 had rise (Ton) and decay ($T_{off}$) times, for a single action potential, similar to those of GCaMP6f, and that, as expected from previous work, GCaMP6f-NLS had rise and decay times significantly slower than those of GCaMP6f (FIG. 2E-F and Table 4 for full statistics). It was found that SomaGCaMP7f had rise (Ton) and decay ($T_{off}$) times, for a single action potential, similar to those of GCaMP7f (FIG. 2E-F and Table 4 for full statistics).

TABLE 4

Statistical analysis for FIG. 2.

For FIG. 2A-brightness among GCaMP6f, GCaMP6f-NLS,
SomaGCaMP6f1 and SomaGCaMP6f2
Brightness values for GCaMP6f, GCaMP6f-NLS, SomaGCaMP6f1
and SomaGCaMP6f2 (n = 8 cells from 2 cultures for GCaMP6f;
n = 7 cells from 2 cultures for SomaGCaMP6f1;
n = 5 cells from 2 cultures for SomaGCaMP6f2;
n = 7 cells from 2 cultures for GCaMP6f-NLS).
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 8 | 111.000 | 112.000 | 13.8750 | −0.027 |
| GCaMP6f-NLS | 7 | 129.000 | 98.000 | 18.4286 | 1.688 |
| SomaGCaMP6f1 | 7 | 76.000 | 98.000 | 10.8571 | −1.190 |
| SomaGCaMP6f2 | 5 | 62.000 | 70.000 | 12.4000 | −0.468 |

1-Way Test, ChiSquare Approximation

| ChiSquare | DF | Prob > ChiSq |
|---|---|---|
| 3.4818 | 3 | 0.3231 |

Nonparametric Comparisons With Control Using Steel Method
Control Group = GCaMP6f

| q* | Alpha |
|---|---|
| 2.35898 | 0.05 |

| Molecule | Control | Score Mean Difference | Std Err Dif | Z | p-Value |
|---|---|---|---|---|---|
| GCaMP6f-NLS | GCaMP6f | 2.54464 | 2.314550 | 1.09941 | 0.5684 |
| SomaGCaMP6f2 | GCaMP6f | −0.81250 | 2.220173 | −0.36596 | 0.9704 |
| SomaGCaMP6f1 | GCaMP6f | −1.47321 | 2.314550 | −0.63650 | 0.8689 |

TABLE 4-continued

Statistical analysis for FIG. 2.

For FIG. 2A-brightness between GCaMP7f and SomaGCaMP7f
Wilcoxon rank sum test between GCaMP7f and SomaGCaMP7f (n = 6 cells
from 2 cultures for GCaMP7f; n = 7 cells from 3 cultures for SomaGCaMP7).

| | |
|---|---|
| P-value | 0.5338 |
| Rank sum test statistic | 47 |

For FIG. 2C-df/$f_0$ among GCaMP6f, GCaMP6f-NLS, SomaGCaMP6f1
and SomaGCaMP6f2 df/$f_0$ for GCaMP6f, GCaMP6f-NLS, SomaGCaMP6f1
and SomaGCaMP6f2 (n = 8 cells from 2 cultures for GCaMP6f;
n = 5 cells from 2 cultures for SomaGCaMP6f1;
n = 7 cells from 2 cultures for SomaGCaMP6f2;
n = 8 cells from 2 cultures for GCaMP6f-NLS).
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 8 | 103.000 | 116.000 | 12.8750 | −0.636 |
| GCaMP6f-NLS | 8 | 80.000 | 116.000 | 10.0000 | −1.805 |
| SomaGCaMP6f1 | 5 | 119.000 | 72.500 | 23.8000 | 2.759 |
| SomaGCaMP6f2 | 7 | 104.000 | 101.500 | 14.8571 | 0.106 |

1-Way Test, ChiSquare Approximation

| ChiSquare | DF | Prob > ChiSq |
|---|---|---|
| 9.1104 | 3 | 0.0279 |

Nonparametric Comparisons with Control Using Steel Method
Control Group = GCaMP6f

| q* | Alpha |
|---|---|
| 2.35735 | 0.05 |

| Molecule | Control | Score Mean Difference | Std Err Dif | Z | p-Value |
|---|---|---|---|---|---|
| SomaGCaMP6f1 | GCaMP6f | 4.71250 | 2.220173 | 2.12258 | 0.0891 |
| SomaGCaMP6f2 | GCaMP6f | 0.93750 | 2.314550 | 0.40505 | 0.9602 |
| GCaMP6f-NLS | GCaMP6f | −1.37500 | 2.380476 | −0.57762 | 0.8965 |

For FIG. 2C-df/$f_0$ between GCaMP7f and SomaGCaMP7f
Wilcoxon rank sum test between GCaMP7f and SomaGCaMP7f (n = 6 cells
from 2 cultures for GCaMP7f; n = 7 cells from 3 cultures for SomaGCaMP7).

| | |
|---|---|
| P-value | 0.9452 |
| Rank sum test statistic | 41 |

For FIG. 2D-SNR among GCaMP6f, GCaMP6f-NLS,
SomaGCaMP6f1 and SomaGCaMP6f2
SNR for GCaMP6f, GCaMP6f-NLS, SomaGCaMP6f1 and
SomaGCaMP6f2 (n = 8 cells from 2 cultures for GCaMP6f;
n = 5 cells from 2 cultures for SomaGCaMP6f1;
n = 7 cells from 2 cultures for SomaGCaMP6f2;
n = 8 cells from 2 cultures for GCaMP6f-NLS).
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 8 | 134.000 | 116.000 | 16.7500 | 0.890 |
| GCaMP6f-NLS | 8 | 40.000 | 116.000 | 5.0000 | −3.840 |

TABLE 4-continued

Statistical analysis for FIG. 2.

| | | | | | |
|---|---|---|---|---|---|
| SomaGCaMP6f1 | 5 | 99.000 | 72.500 | 19.8000 | 1.560 |
| SomaGCaMP6f2 | 7 | 133.000 | 101.500 | 19.0000 | 1.645 |

1-Way Test, ChiSquare Approximation

| ChiSquare | DF | Prob > ChiSq |
|---|---|---|
| 15.4389 | 3 | 0.0015 |

Nonparametric Comparisons with Control Using Steel Method
Control Group = GCaMP6f

| $q^*$ | Alpha |
|---|---|
| 2.35735 | 0.05 |

| Molecule | Control | Score Mean Difference | Std Err Dif | Z | p-Value |
|---|---|---|---|---|---|
| SomaGCaMP6f2 | GCaMP6f | 1.74107 | 2.314550 | 0.75223 | 0.8019 |
| SomaGCaMP6f1 | GCaMP6f | 1.46250 | 2.220173 | 0.65873 | 0.8558 |
| GCaMP6f-NLS | GCaMP6f | −7.37500 | 2.380476 | −3.09812 | 0.0056 |

FIG. 2D-SNR between GCaMP7f and SomaGCaMP7f
Wilcoxon rank sum test between GCaMP7f and SomaGCaMP7f (n = 6 cells
from 2 cultures for GCaMP7f; n = 7 cells from 3 cultures for SomaGCaMP7).

| P-value | 0.8357 |
|---|---|
| Rank sum test statistic | 40 |

For FIG. 2E-$T_{on}$ among GCaMP6f, GCaMP6f-NLS,
SomaGCaMP6f1 and SomaGCaMP6f2
Time constant for signal rise (Ton) for GCaMP6f,
GCaMP6f-NLS, SomaGCaMP6f1 and SomaGCaMP6f2
(n = 8 cells from 2 cultures for GCaMP6f;
n = 5 cells from 2 cultures for SomaGCaMP6f1;
n = 6 cells from 2 cultures for SomaGCaMP6f2;
n = 8 cells from 2 cultures for GCaMP6f-NLS).
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 8 | 89.000 | 112.000 | 11.1250 | −1.195 |
| GCaMP6f-NLS | 8 | 188.000 | 112.000 | 23.5000 | 4.010 |
| SomaGCaMP6f1 | 5 | 48.000 | 70.000 | 9.6000 | −1.342 |
| SomaGCaMP6f2 | 6 | 53.000 | 84.000 | 8.8333 | −1.779 |

1-Way Test, ChiSquare Approximation

| ChiSquare | DF | Prob > ChiSq |
|---|---|---|
| 16.5938 | 3 | 0.0009 |

TABLE 4-continued

Statistical analysis for FIG. 2.

Nonparametric Comparisons with Control Using Steel Method
Control Group = GCaMP6f

| q* | Alpha |
|---|---|
| 2.35926 | 0.05 |

| Molecule | Control | Score Mean Difference | Std Err Dif | Z | p-Value |
|---|---|---|---|---|---|
| GCaMP6f-NLS | GCaMP6f | 7.87500 | 2.378725 | 3.31060 | 0.0027 |
| SomaGCaMP6f1 | GCaMP6f | −0.81250 | 2.217121 | −0.36647 | 0.9703 |
| SomaGCaMP6f2 | GCaMP6f | −1.60417 | 2.256756 | −0.71083 | 0.8285 |

For FIG. 2E-$T_{on}$ between GCaMP7f and SomaGCaMP7f
Wilcoxon rank sum test between GCaMP7f and SomaGCaMP7f
(n = 6 cells from 2 cultures for GCaMP7f;
n = 7 cells from 3 cultures for SomaGCaMP7).

| P-value | 0.2949 |
|---|---|
| Rank sum test statistic | 34 |

For FIG. 2F-$T_{off}$ among GCaMP6f, GCaMP6f-NLS,
SomaGCaMP6f1 and SomaGCaMP6f2
Time constant for signal decay ($T_{off}$) for
GCaMP6f, GCaMP6f-NLS, SomaGCaMP6f1 and
SomaGCaMP6f2 (n = 7 cells from 2 cultures for GCaMP6f;
n = 5 cells from 2 cultures for SomaGCaMP6f1;
n = 7 cells from 2 cultures for SomaGCaMP6f2;
n = 8 cells from 2 cultures for GCaMP6f-NLS).
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 7 | 98.000 | 98.000 | 14.0000 | 0.000 |
| GCaMP6f-NLS | 8 | 179.000 | 112.000 | 22.3750 | 3.531 |
| SomaGCaMP6f1 | 5 | 24.000 | 70.000 | 4.8000 | −2.840 |
| SomaGCaMP6f2 | 7 | 77.000 | 98.000 | 11.0000 | −1.134 |

1-Way Test, ChiSquare Approximation

| ChiSquare | DF | Prob > ChiSq |
|---|---|---|
| 16.6242 | 3 | 0.0008 |

Nonparametric Comparisons with Control Using Steel Method
Control Group = GCaMP6f

| q* | Alpha |
|---|---|
| 2.35201 | 0.05 |

| Molecule | Control | Score Mean Difference | Std Err Dif | Z | p-Value |
|---|---|---|---|---|---|
| GCaMP6f-NLS | GCaMP6f | 5.75893 | 2.314550 | 2.48814 | 0.0349 |
| SomaGCaMP6f2 | GCaMP6f | −2.28571 | 2.236068 | −1.02220 | 0.6128 |
| SomaGCaMP6f1 | GCaMP6f | −4.45714 | 2.111195 | −2.11119 | 0.0901 |

For FIG. 2F-$T_{off}$ between GCaMP7f and SomaGCaMP7f
Wilcoxon rank sum test between GCaMP7f and SomaGCaMP7f
(n = 6 cells from 2 cultures for GCaMP7f;
n = 7 cells from 3 cultures for SomaGCaMP7).

| P-value | 0.2949 |
|---|---|
| Rank sum test statistic | 50 |

The resting potential, membrane capacitance, holding current, and membrane resistance of cultured hippocampal neurons were analyzed next and it was determined that they did not differ for cells expressing SomaGCaMP6f1 or SomaGCaMP6f2 vs. GCaMP6f (FIG. 8). In addition, the resting potential, membrane capacitance, holding current, and membrane resistance of cultured hippocampal neurons expressing GCaMP7f and SomaGCaMP7f did not differ (FIG. 8).

TABLE 8

Statistical analysis for FIG. 8-membrane and action potential properties.

For FIG. 8A
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 6 | 72.500 | 60.000 | 12.0833 | 1.053 |
| SomaGCaMP6f1 | 7 | 59.000 | 70.000 | 8.4286 | −0.888 |
| SomaGCaMP6f2 | 6 | 58.500 | 60.000 | 9.7500 | −0.088 |

1-Way Test, ChiSquare Approximation

| ChiSquare | DF | Prob > ChiSq |
|---|---|---|
| 1.3825 | 2 | 0.5009 |

Nonparametric Comparisons with Control Using Steel Method
Control Group = GCaMP6f

| q* | Alpha |
|---|---|
| 2.20992 | 0.05 |

| Molecule | Control | Score Mean Difference | Std Err Dif | Z | p-Value |
|---|---|---|---|---|---|
| SomaGCaMP6f2 | GCaMP6f | −1.50000 | 2.081666 | −0.72058 | 0.6896 |
| SomaGCaMP6f1 | GCaMP6f | −2.16667 | 2.163688 | −1.00138 | 0.4984 |

For FIG. 8B
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 5 | 37.000 | 45.000 | 7.4000 | −0.791 |
| SomaGCaMP6f1 | 6 | 52.000 | 54.000 | 8.6667 | −0.151 |
| SomaGCaMP6f2 | 6 | 64.000 | 54.000 | 10.6667 | 0.955 |

1-Way Test, ChiSquare Approximation

| ChiSquare | DF | Prob > ChiSq |
|---|---|---|
| 1.1817 | 2 | 0.5539 |

Small sample sizes. Refer to statistical tables for tests,
rather than large-sample approximations.
Nonparametric Comparisons with Control Using Steel Method
Control Group = GCaMP6f

| q* | Alpha |
|---|---|
| 2.20658 | 0.05 |

| Molecule | Control | Score Mean Difference | Std Err Dif | Z | p-Value |
|---|---|---|---|---|---|
| SomaGCaMP6f2 | GCaMP6f | 1.650000 | 2.008316 | 0.8215838 | 0.6158 |
| SomaGCaMP6f1 | GCaMP6f | 0.916667 | 2.008316 | 0.4564355 | 0.8562 |

TABLE 8-continued

Statistical analysis for FIG. 8-membrane and action potential properties.

For FIG. 8C
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 5 | 33.500 | 45.000 | 6.7000 | −1.160 |
| SomaGCaMP6f1 | 6 | 59.500 | 54.000 | 9.9167 | 0.503 |
| SomaGCaMP6f2 | 6 | 60.000 | 54.000 | 10.0000 | 0.553 |

1-Way Test, ChiSquare Approximation

| ChiSquare | DF | Prob > ChiSq |
|---|---|---|
| 1.4721 | 2 | 0.4790 |

Small sample sizes. Refer to statistical tables for tests,
rather than large-sample approximations.
Nonparametric Comparisons with Control Using Steel Method
Control Group = GCaMP6f

| q* | Alpha |
|---|---|
| 2.20658 | 0.05 |

| Molecule | Control | Score Mean Difference | Std Err Dif | Z | p-Value |
|---|---|---|---|---|---|
| SomaGCaMP6f2 | GCaMP6f | 2.016667 | 2.008316 | 1.004158 | 0.4926 |
| SomaGCaMP6f1 | GCaMP6f | 1.833333 | 2.003746 | 0.914953 | 0.5519 |

For FIG. 8D
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 5 | 37.000 | 45.000 | 7.4000 | −0.791 |
| SomaGCaMP6f1 | 6 | 34.000 | 54.000 | 5.6667 | −1.960 |
| SomaGCaMP6f2 | 6 | 82.000 | 54.000 | 13.6667 | 2.764 |

1-Way Test, ChiSquare Approximation

| ChiSquare | DF | Prob > ChiSq |
|---|---|---|
| 8.2405 | 2 | 0.0162 |

Small sample sizes. Refer to statistical tables for tests,
rather than large-sample a pproximations.
Nonparametric Comparisons with Control Using Steel Method
Control Group = GCaMP6f

| q* | Alpha |
|---|---|
| 2.20658 | 0.05 |

| Molecule | Control | Score Mean Difference | Std Err Dif | Z | p-Value |
|---|---|---|---|---|---|
| SomaGCaMP6f2 | GCaMP6f | 4.21667 | 2.008316 | 2.09960 | 0.0648 |
| SomaGCaMP6f1 | GCaMP6f | −1.28333 | 2.008316 | −0.63901 | 0.7414 |

TABLE 8-continued

Statistical analysis for FIG. 8-membrane and action potential properties.

For FIG. 8F-Action potential width
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 12 | 269.000 | 222.000 | 22.4167 | 1.560 |
| SomaGCaMP6f1 | 12 | 175.000 | 222.000 | 14.5833 | −1.560 |
| SomaGCaMP6f2 | 12 | 222.000 | 222.000 | 18.5000 | 0.000 |

1-Way Test, ChiSquare Approximation

| ChiSquare | DF | Prob > ChiSq |
|---|---|---|
| 3.3168 | 2 | 0.1904 |

Nonparametric Comparisons with Control Using Steel Method
Control Group = GCaMP6f

| q* | Alpha |
|---|---|
| 2.21213 | 0.05 |

| Molecule | Control | Score Mean Difference | Std Err Dif | Z | p-Value |
|---|---|---|---|---|---|
| SomaGCaMP6f2 | GCaMP6f | −2.41667 | 2.886751 | −0.83716 | 0.6119 |
| SomaGCaMP6f1 | GCaMP6f | −5.25000 | 2.886751 | −1.81865 | 0.1234 |

For FIG. 8G-Action potential amplitude
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 12 | 212.000 | 222.000 | 17.6667 | −0.319 |
| SomaGCaMP6f1 | 12 | 192.000 | 222.000 | 16.0000 | −0.990 |
| SomaGCaMP6f2 | 12 | 262.000 | 222.000 | 21.8333 | 1.326 |

1-Way Test, ChiSquare Approximation

| ChiSquare | DF | Prob > ChiSq |
|---|---|---|
| 1.9520 | 2 | 0.3768 |

Nonparametric Comparisons with Control Using Steel Method
Control Group = GCaMP6f

| q* | Alpha |
|---|---|
| 2.21213 | 0.05 |

| Molecule | Control | Score Mean Difference | Std Err Dif | Z | p-Value |
|---|---|---|---|---|---|
| SomaGCaMP6f2 | GCaMP6f | 2.41667 | 2.886751 | 0.837158 | 0.6119 |
| SomaGCaMP6f1 | GCaMP6f | −0.75000 | 2.886751 | −0.259808 | 0.9518 |

For FIG. 8H-Action potential threshold
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 12 | 214.000 | 222.000 | 17.8333 | −0.252 |
| SomaGCaMP6f1 | 12 | 190.000 | 222.000 | 15.8333 | −1.058 |

TABLE 8-continued

Statistical analysis for FIG. 8-membrane and action potential properties.

| SomaGCaMP6f2 | 12 | 262.000 | 222.000 | 21.8333 | 1.326 |
|---|---|---|---|---|---|

1-Way Test, ChiSquare Approximation

| ChiSquare | DF | Prob > ChiSq |
|---|---|---|
| 2.0198 | 2 | 0.3642 |

Nonparametric Comparisons with Control Using Steel Method
Control Group = GCaMP6f

| $q^*$ | Alpha |
|---|---|
| 2.21213 | 0.05 |

| Molecule | Control | Score Mean Difference | Std Err Dif | Z | p-Value |
|---|---|---|---|---|---|
| SomaGCaMP6f2 | GCaMP6f | 2.50000 | 2.886124 | 0.866214 | 0.5919 |
| SomaGCaMP6f1 | GCaMP6f | −1.16667 | 2.885496 | −0.404321 | 0.8881 |

Action potential width, amplitude, and threshold in cultured hippocampal neurons, were analyzed next and it was found that they did not statistically differ for cells expressing SomaGCaMP6f1 or SomaGCaMP6f2 vs. GCaMP6f (FIG. 8). Similarly, it was found that action potential width, amplitude, and threshold in cultured hippocampal neurons did not statistically differ for cells expressing SomaGCaMP7f vs. GCaMP6f (FIG. 8). In addition, the distribution of native proteins along axons was quantified (see methods) and no statistically significant differences were found in the locations of all endogenous proteins assessed (the potassium channel Kv2.1, the sodium channel Nav1.2, and the calcium channel Cav2.1) as well as the scaffolding protein AnkG, between GCaMP6f-, SomaGCaMP6f1-, and SomaGCaMP6f2-expressing neurons (FIG. 9). To test whether somatic GCaMP6f variants were cytosolic, as GCaMP6f is known to be, the cellular plasma membrane were stained with fluorescently conjugated wheat germ agglutinin (WGA-647, see methods). It was found that for neurons expressing GCaMP6f, SomaGCaMP6f1 and SomaGCaMP6f2, the membrane fluorescent signal, which defines the boundaries of neurons, started to rise further away from the center of the cell body compared to the GCaMP fluorescent signal. This quantitatively implies that the GCaMP was primarily found in the cytosol (FIG. 1O).

TABLE 9

Statistical analysis for FIG. 9 - Distribution of ion channels and AnkyrinG in neurons expressing GCaMP6f, SomaGCaMP6f1 or SomaGCaMP6f2

For FIG. 9A - Fluorescent profiles of immunostained Kv2.1 in cultured neurons
Bonferroni-corrected Kruskal-Wallis analysis of variance of fluorescent profiles of immunostained Kv2.1 in cultured neurons (n = 6 GCaMP6f expressing neurons from 3 cultures; n = 6 SomaGCaMP6f1 expressing neurons from 2 cultures; n = 6 SomaGCaMP6f2 expressing neurons from 4 cultures). The overall significance level $\alpha$ was set to 0.05, and the significance level of each individual Kruskal-Wallis analysis of variance was $\alpha/11 = 0.0045$.

| Distance along neurite from soma (um) | 0 | 10 | 20 | 30 | 40 | 50 |
|---|---|---|---|---|---|---|
| P value | 0.926795 | 0.644941 | 0.675831 | 0.84896 | 0.691826 | 0.504488 |
| Distance along neurite from soma (um) | 60 | 70 | 80 | 90 | 100 | — |
| P value | 0.926795 | 0.277842 | 0.580503 | 0.044551 | 0.587333 | — |

For FIG. 9B - Fluorescent profiles of immunostained NaV1.2 in cultured neurons
Bonferroni-corrected Kruskal-Wallis analysis of variance of fluorescent profiles of immunostained NaV1.2 in cultured neurons (n = 6 GCaMP6f expressing neurons from 3 cultures; n = 6 SomaGCaMP6f1 expressing neurons from 4 cultures; n = 6 SomaGCaMP6f2 expressing neurons from 2 cultures). The overall significance level $\alpha$ was set to 0.05, and the significance level of each individual Kruskal-Wallis analysis of variance was $\alpha/11 = 0.0045$.

| Distance along neurite from soma (um) | 0 | 10 | 20 | 30 | 40 | 50 |
|---|---|---|---|---|---|---|

TABLE 9-continued

Statistical analysis for FIG. 9 - Distribution of ion channels and
AnkyrinG in neurons expressing GCaMP6f, SomaGCaMP6f1 or SomaGCaMP6f2

| P value | 0.420842 | 0.459426 | 0.834196 | 0.75085 | 0.85394 | 0.587333 |
|---|---|---|---|---|---|---|
| Distance along neurite from soma (um) | 60 | 70 | 80 | 90 | 100 | — |
| P value | 0.547529 | 0.385499 | 0.250082 | 0.522504 | 0.271418 | — |

For FIG. 9C - Fluorescent profiles of immunostained Ankyring in cultured neurons
Bonferroni-corrected Kruskal-Wallis analysis of variance of fluorescent profiles of
immunostained AnkyrinG in cultured neurons (n = 6 GCaMP6f expressing neurons from 4
cultures; n = 5 SomaGCaMP6fl expressing neurons from 2 cultures; n = 6 SomaGCaMP6f2
expressing neurons from 2 cultures). The overall significance level α was set to 0.05, and the
significance level of each individual Kruskal-Wallis analysis of variance was α/11 = 0.0045.

| Distance along neurite from soma (um) | 0 | 10 | 20 | 30 | 40 | 50 |
|---|---|---|---|---|---|---|
| P value | 0.198365 | 0.824099 | 0.240705 | 0.21723 | 0.993485 | 0.031078 |
| Distance along neurite from soma (um) | 60 | 70 | 80 | 90 | 100 | — |
| P value | 0.355122 | 0.320908 | 0.30218 | 0.558948 | 0.636587 | — |

For FIG. 9D - Fluorescent profiles of immunostained CaV2.1 in cultured neurons
Bonferroni-corrected Kruskal-Wallis analysis of variance of fluorescent profiles of
immunostained CaV2.1 in cultured neurons (n = 5 GCaMP6f expressing neurons from 2
cultures; n = 5 SomaGCaMP6fl expressing neurons from 2 cultures; n = 5 SomaGCaMP6f2
expressing neurons from 5 cultures). The overall significance level α was set to 0.05, and the
significance level of each individual Kruskal-Wallis analysis of variance was α/11 = 0.0045.

| Distance along neurite from soma (um) | 0 | 10 | 20 | 30 | 40 | 50 |
|---|---|---|---|---|---|---|
| P value | 0.18452 | 0.357007 | 0.444858 | 0.264477 | 0.612626 | 0.062662 |
| Distance along neurite from soma (um) | 60 | 70 | 80 | 90 | 100 | — |
| P value | 0.878095 | 0.878095 | 0.173774 | 0.511709 | 0.357007 | — |

Characterization of SomaGCaMP Variants in Brain Slices

The localization experiments of FIG. 1 were repeated in neurons in brain slices. GCaMP variants were co-expressed with a red fluorescent protein (mScarlet) in layer⅔ neurons of mouse cortex. mScarlet was used to manually trace cell bodies and neural processes and quantified fluorescence brightness along the processes for the various GCaMP6f variants (FIG. 3A). The fluorescence in the green channel (GCaMP6f variants) was characterized by the fluorescence in the red channel (mScarlet) as a way to control for the varying size and shape of neural processes. It was found that along the first 140 μm of neural process coming out of the soma, the green fluorescence in GCaMP6f expressing cells decreased to 25.1+5.1%, while it decreased to 3.2+1.1% and 2.8+1.0% in SomaGCaMP6f1 and SomaGCaMP6f2 expressing cells, respectively (FIG. 3B, green fluorescence along neural processes; FIG. 11, green and red fluorescence along neural processes).

TABLE 10

Statistical analysis for FIG. 11-Fluorescent profiles of GCaMP6f,
SomaGCaMP6f1 and SomaGCaMP6f2 in fixed brain slices For FIG. 11A
Kolmogorov-Smirnov test of neurite fluorescence between
GCaMP6f and mScarlet (n = 5 neurons from 2 mice).

| P-value | 9.8965e−10 |
|---|---|
| KS test statistic | 0.5128 |

For FIG. 11B
Kolmogorov-Smirnov test of neurite fluorescence between
SomaGCaMP6f1 and mScarlet (n = 9 neurons from 2 mice).

| P-value | 1.1020e−15 |
|---|---|
| KS test statistic | 0.5076 |

For FIG. 11C
Kolmogorov-Smirnov test of neurite fluorescence between
SomaGCaMP6f2 and mScarlet (n = 6 neurons from 2 mice).

| P-value | 3.9771e−17 |
|---|---|
| KS test statistic | 0.6477 |

A preliminary assessment was performed to determine whether soma targeting of GCaMP6f could reduce neuropil contamination through a brain slice experiment, comparing patch-reported spikes to GCaMP-reported spikes. Since the focus in these studies was on the live brain, SomaGCaMP6f1 was chosen for this preliminary brain slice experiment: the rest of the studies focused on the validation and exploration of SomaGCaMP6f1 and SomaGCaMP6f2 in living brain (see below). The preliminary study was designed to patch cells in brain slices and electrophysiologically record from them while simultaneously imaging the cell bodies in order to count how many fluorescent GCaMP6f-reported spikes were detected in the cell body in the absence of corresponding patch-reported action potentials, and thus were the result of neuropil contamination. It was found that the baseline brightness of the cell body of SomaGCaMP6f1-expressing neurons was about 5-fold lower than that of GCaMP6f-expressing neurons in live brain slices (FIG. 12 and Table 11 for full statistics), indicating a potential difference in level of expression between the in vitro (FIG. 2) and in vivo (FIG. 3) contexts, not uncommon for genetically encoded reagents given the different transfection protocols, gene dosages, and cellular contexts.

TABLE 11

Statistical analysis for FIG. 12-baseline brightness in mouse brain slice Wilcoxon rank sum test of baseline brightness in slice between GCaMP6f and SomaGCaMP6f1 (n = 42 neurons from 4 slices from 2 GCaMP6f mice; n = 43 neurons from 8 slices from 3 SomaGCaMP6f1 mice).

| | |
|---|---|
| P-value | 3.7642e-15 |
| Rank sum test statistic | 2701 |
| Z-statistic | 7.8625 |

Using identical imaging parameters for histological analysis (see Methods), the density of labeled cells was measured. Although SomaGCaMP6f1 is dimmer than GCaMP6f in the living brain (see below), it was possible to easily identify the cells with expression and count them. It was found that slices expressing either GCaMP6f or SomaGCaMP6f1 contained cells expressing the indicators at a density of 18±7 cells per $10^6$ $\mu m^3$ and 21±5 cells per $10^6$ $\mu m^3$, respectively (mean±standard error of the mean; n=3 slices from 3 mice for GCaMP6f; n=3 slices from 3 mice for SomaGCaMP6f1; Table 5 for full statistics). Thus, in order to compare GCaMP6f and SomaGCaMP6f1 to each other fairly, in terms of change in fluorescence ($df/f_0$), SNR, and crosstalk, the excitation light power in SomaGCaMP6f1 experiments was increased to match the baseline brightness to GCaMP6f slices (FIG. 3C and Table 5 for full statistics), for all further experiments reported in FIG. 3. In such conditions, it was found that despite similar brightness of cell bodies, fluorescence in the neurites decreased significantly faster along the neurite for SomaGCaMP6f1 than for GCaMP6f (FIG. 3D).

TABLE 5 shows statistical analysis for FIG. 3.

Wilcoxon rank sum test for the expression density (number of expressing cells per $um^3$) in the visual cortex of the slices from in utero electroporation between GCaMP6f and SomaGCaMP6f1 (n = 3 slices from 3 mice for GCaMP6f; n = 3 slices from 3 mice for SomaGCaMP6f1).

| | |
|---|---|
| P-value | 0.7000 |
| Rank sum test statistic | 9 |

For FIG. 3B
Ratio of GCaMP brightness and mScarlet brightness at the neurites, normalized to the ratio at the soma, for GCaMP6f (n = 5 neurons from 2 mice), SomaGCaMP6f1 (n = 9 neurons from 2 mice), and SomaGCaMP6f2 (n = 6 neurons from 2 mice).
Wilcoxon/Kruskal-Wallis Tests (Rank Sums)

| Molecule | Count (neurite ROIs) | Score Sum | Expected Score | Score Mean | (Mean-Mean0)/Std0 |
|---|---|---|---|---|---|
| GCaMP6f | 57 | 10512.0 | 6726.00 | 184.421 | 8.474 |
| SomaGCaMP6f1 | 106 | 10265.0 | 12508.0 | 96.840 | -4.324 |
| SomaGCaMP6f2 | 72 | 6953.00 | 8496.00 | 96.569 | -3.211 |

1-Way Test, ChiSquare Approximation

| ChiSquare | DF | Prob > ChiSq |
|---|---|---|
| 71.8356 | 2 | <.0001 |

Nonparametric Comparisons with Control Using Steel Method
Control Group = GCaMP6f

| q* | Alpha |
|---|---|
| 2.19833 | 0.05 |

| Molecule | Control | Score Mean Difference | Std Err Dif | Z | p-Value |
|---|---|---|---|---|---|
| SomaGCaMP6f2 | GCaMP6f | -49.4594 | 6.627765 | -7.46246 | <.0001 |
| SomaGCaMP6f1 | GCaMP6f | -59.6615 | 7.752264 | -7.69600 | <.0001 |

For FIG. 3C Wilcoxon rank sum test for the brightness of neurons in slices between GCaMP6f and SomaGCaMP6f1 (for GCaMP6f, n = 5 neurons 4 slices from 2 mice; for SomaGCaMP6f1, n = 9 neurons 4 slices from 2 mice), with light power adjusted to make them equal.

| | |
|---|---|
| P-value | 0.7023 |
| Rank sum test statistic | 338 |
| Z-statistic | 0.3822 |

TABLE 5-continued shows statistical analysis for FIG. 3.

For FIG. 3D GCaMP brightness at the neurites, normalized to the ratio at the soma, for GCaMP6f (n = 5 neurons from 2 mice), SomaGCaMP6f1 (n = 9 neurons from 2 mice), and SomaGCaMP6f2 (n = 6 neurons from 2 mice).
Wilcoxon/Kruskal-Wallis Tests (Rank Sums)

| Molecule | Count | Score Sum | Expected Score | Score Mean | (Mean-Mean0)/ Std0 |
|---|---|---|---|---|---|
| GCaMP6f | 78 | 17518.0 | 11661.0 | 224.590 | 8.956 |
| SomaGCaMP6f1 | 132 | 15520.0 | 19734.0 | 117.576 | −5.702 |
| SomaGCaMP6f2 | 88 | 11513.0 | 13156.0 | 130.830 | −2.421 |

1-Way Test, ChiSquare Approximation

| ChiSquare | DF | Prob > Chi Sq |
|---|---|---|
| 81.4803 | 2 | <.0001* |

Nonparametric Comparisons With Control Using Steel Method
Control Group = GCaMP6f

| q* | Alpha |
|---|---|
| 2.20217 | 0.05 |

| Molecule | Molecule | Score Mean Difference | Std Err Dif | Z | p-Value |
|---|---|---|---|---|---|
| SomaGCaMP6f2 | GCaMP6f | −52.9512 | 7.474585 | −7.08417 | <.0001* |
| SomaGCaMP6f1 | GCaMP6f | −74.7829 | 8.678319 | −8.61721 | <.0001* |

For FIG. 3E Wilcoxon rank sum test for the df/f$_0$ of somata of neurons in slices between GCaMP6f and SomaGCaMP6f1 following an action potential (n = 14 APs from 3 neurons from 3 slices from 2 mice for GCaMP6f; n = 6 APs from 3 neurons from 3 slices from 3 mice for SomaGCaMP6f1).

| P-value | 0.3429 |
|---|---|
| Rank sum test statistic | 51 |
| Z-statistic | −0.9485 |

For FIG. 3F Wilcoxon rank sum test for the SNR of somata of neurons in slices between GCaMP6f and SomaGCaMP6f1 following an action potential (n = 14 APs from 3 neurons from 3 slices from 2 mice for GCaMP6f; n = 6 APs from 3 neurons from 3 slices from 3 mice for SomaGCaMP6f1).

| P-value | 0.2317 |
|---|---|
| Rank sum test statistic | 132 |
| Z-statistic | −1.1959 |

For FIG. 3I Wilcoxon rank sum test for the number of action potentials per minute in neurons in slices between GCaMP6f and SomaGCaMP6f1 following an action potential (n = 8 neurons from 8 slices for GCaMP6f from 4 mice; n = 6 neurons from 6 slices for SomaGCaMP6f1 from 3 mice).

| P-value | 0.7770 |
|---|---|
| Rank sum test statistic | 71 |

For FIG. 3J Wilcoxon rank sum test for the number of erroneous GCaMP-spikes per minute in neurons expressing either GCaMP6f or SomaGCaMP6f1 in slice (n = 8 neurons from 8 slices from 4 mice for GCaMP6f; n = 6 neurons from 6 slices from 3 mice for SomaGCaMP6f1).

| P-value | 0.0168 |
|---|---|
| Rank sum test statistic | 90.5 |

It was found that df/f$_0$ of transients per single patch-reported spikes observed during 4-AP evoked activity was similar between GCaMP6f and SomaGCaMP6f1 expressing cells in such slices (FIG. 3E and Table 5 for full statistics), while the df/f$_0$ of the transient driven by a burst (50 Hz current injections of 500 pA, 5 ms, in trains of 5, 10, or 20 pulses) was significantly higher in SomaGCaMP6f1 vs. GCaMP6f expressing cells (FIG. 13 and Table 12 for full statistics). The SNR for imaged action potentials was also comparable between GCaMP6f- and SomaGCaMP6f1-expressing neurons in the slice (FIG. 3F and Table 5 for full statistics). The amount of crosstalk was then compared, as indicated by the number of fluorescent GCaMP-reported spikes that lack an associated patch-reported spike (termed here 'erroneous GCaMP spike') in brain slices expressing GCaMP6f vs. SomaGCaMP6f1. Since neurons in slice had a very low level of spontaneous activity, stimulating neurons near to a patched neuron with an extracellular electrode was attempted but it was found that the electrical stimulation of neighboring cells often resulted in electrical stimulation of the patched cell. Therefore, it was not possible to discriminate erroneous GCaMP spikes from actual GCaMP spikes with this method. Because GCaMP is blue light excited, and blue light causes excitation of all opsins to some extent, optogenetics was not used. Because for crosstalk analysis it was desired to have the cells to spike non-homogeneously, the slices were exposed to 0.1 mM 4-AP (FIG. 3G vs. FIG. 3H, respectively). The 4-AP concentration was empirically adjusted to elicit a low spiking frequency (≤1 Hz), and therefore have a higher resolution in time to identify erroneous GCaMP spikes. Patch-reported spike rates were similar between GCaMP6f- and SomaGCaMP6f1-expressing cells in slices under the low-frequency spiking induced by 4-AP (FIG. 3I and Table 5 for full statistics). Low-frequency spiking allowed a detailed counting of spikes in the fluorescence vs. patch-reported traces. It was found under such conditions that neurons in the GCaMP6f slices exhibited a roughly 2:3 ratio of erroneous spikes to actual spikes, meaning that for every three GCaMP-spikes that were corroborated by patch-reported APs, there were two erroneous GCaMP6f spikes. In contrast, in SomaGCaMP6f1 slices, the ratio was reduced to 1:6 (FIG. 3J), a 75% decrease in artifact ratio.

The decay times of the fluorescent GCaMP spikes were measured, using two different stimulation protocols. In the first, current was electrophysiologically injected into GCaMP6f- or SomaGCaMP6f1-expressing cells to induce single action potentials in single cells in brain slices. In the second stimulation protocol, 0.1 mM 4-AP was used to induce action potentials throughout the slice. The $T_{off}$ was similar for GCaMP6f and SomaGCaMP6f1 for single action potentials evoked by electrophysiology (FIG. 13B and Table 12 for full statistics). For 4-AP evoked APs, GCaMP6f-expressing cells showed increased $T_{off}$ compared to SomaGCaMP6f1 expressing cells (FIG. 13C). The difference in $T_{off}$ between electrophysiology evoked action potentials and 4-AP evoked action potentials may be due to potassium channel blocking induced by 4-AP in GCaMP6f expressing neurites, which could slow the calcium transients in the neurites, which in turn result in crosstalk into the imaged cell bodies.

It was found that a number of calcium spikes/min in CGaMP6f expressing neurons was 10.4±2.2 GCaMP-spikes per minute (FIG. 13D). This number is similar to the number of electrophysiology derived action potentials in GCaMP6f expressing neurons (FIG. 3I, 6.2+/−1.3), plus the number of erroneous spikes in GCaMP6f-expressing neurons (FIG. 3J, 3.9+/−1.4). For SomaGCaMP6f1 expressing neurons, we found that the number of calcium spikes/min was 6.7±3.0 (FIG. 13D). This number is similar to the number of electrophysiology derived action potentials in SomaGCaMP6f1 expressing neurons (FIG. 3I, 6.0+/−2.4), plus the number of erroneous spikes in SomaGCaMP6f1 expressing neurons (FIG. 3J, 0.65+/−0.3).

TABLE 12

Statistical analysis for FIG. 13-sensitivity for multiple action potentials, temporal dynamics and event rate for GCaMP6f and SomaGCaMP6f1.

Fog FIG. 13A
Bonferroni-corrected Wilcoxon rank sum test of the df/f$_0$ between GCaMP6f (n = 7 neurons from 5 slices from 2 mice) and SomaGCaMP6f1 (n = 5 neurons from 3 slices from 2 mice) expressing neurons. The overall significance level α was set to 0.05, and the significance level of each individual Wilcoxon rank sum test was α/4 = 0.0125. P values less than 0.0125 are highlighted in bold.

| Number of action potentials | 1 | 5 | 10 | 20 |
|---|---|---|---|---|
| P-value | 0.0200 | 7.9920e−04 | 3.9960e−04 | 3.9960e−04 |
| Rank sum test statistic | 41.5 | 46 | 45 | 45 |

For FIG. 13B
Wilcoxon rank sum test of the $\pi_{off}$ of calcium spikes in slice during electrophysiological inducement of single action potentials between GCaMP6f and SomaGCaMP6f1(n = 3 neurons from 3 slices from 3 mice for GCaMP6f; n = 3 neurons from 3 slices from 3 mice for SomaGCaMP6f1).

| | |
|---|---|
| P-value | 1.000 |
| Rank sum test statistic | 11 |

For FIG. 13C
Wilcoxon rank sum test the $\pi_{off}$ of calcium spikes in slice during 4-aminopyridine inducement of single action potentials between GCaMP6f and SomaGCaMP6f1 (n = 5 neurons from 5 slices from 4 mice for GCaMP6f; n = 5 neurons from 4 slices from 3 mice for SomaGCaMP6f1).

| | |
|---|---|
| P-value | 0.0317 |
| Rank sum test statistic | 38 |

For FIG. 13D
Wilcoxon rank sum test of the event rate of calcium spikes per minute in slice between GCaMP6f and SomaGCaMP6f1 (n = 8 neurons from 8 slices for GCaMP6f from 4 mice; n = 6 neurons from 6 slices from 3 mice for SomaGCaMP6f1).

| | |
|---|---|
| P-value | 0.2455 |
| Rank sum test statistic | 79.5 |

Simulating the Benefits of SomaGCaMP Reduction of Neuropil Contamination Vs. Post-Hoc Computational Reduction of Neuropil Contamination Algorithms for neuropil contamination reduction for one-photon calcium imaging have been developed for neuroscience use. Studies were performed using both simulation and experimentation to permit comparison of the neuropil contamination reduction enabled by SomaGCaMP variants to that enabled by algorithmic cleanup. A popular algorithm is the constrained nonnegative matrix factorization (CNMF) framework (Pnevmatikakis et al., 2016), which enables identification of GCaMP-expressing neurons with subsequent demixing and deconvolution of their fluorescence spikes. Calcium transients were stimulated (see methods elsewhere herein) mouse (FIG. 14A-C) and larval zebrafish (FIG. 14D-F) brain, to help understand the impact of SomaGCaMP vs. CNMF on mouse and fish live brain imaging experiments (see below). The "ground truth" spikes were simulated in the cell bodies (FIG. 14A, 14D) as well as how the data would look in isolated volumes, imaged through a lightsheet microscope (chosen due to its high spatial resolution compared to other one-photon microscopes in this paper), reported by GCaMP6f (FIGS. 14B and 14E) vs. SomaGCaAMP6f variants (FIGS. 14C and 14F). In order to study the difference in crosstalk of visible neurons between SomaGCaMP6f and GCaMP6f, in-plane and out-of-plane artifacts of neuropil driven by the point-spread-function of the microscope were simulated. The correlation between the simulated ground truth spiking of each neuron and the microscope-observed spiking that would be observed from each neuron, when expressing GCaMP6f vs. SomaGCaMP6f variants was calculated.

It was found that for both mice (FIG. 14G) and fish (FIG. 14H), the correlation between the simulated ground truth spiking and the microscope-observed spiking reported by SomaGCaMP variants were significantly higher than when the microscope-observed spiking was reported by GCaMP6f (see Table 13 for full statistics). CNMF, in contrast, did not increase the correlation between simulated ground truth spiking and the microscope-observed spiking, reported by either GCaMP6f or SomaGCaMP variants. These simulations indicated that even following computational neuropil contamination mitigation, SomaGCaMP6f1 and SomaGCaMP6f2 have the capability to report calcium spikes with a higher accuracy compared to GCaMP6f. Furthermore, computational approaches such as CNMF, while able to reduce correlations between neural activity may not be increasing the accuracy of the data, and perhaps some of the reduction of correlation is removal of actual biological signal, at least as explored in simulations.

TABLE 13

Statistical analysis for FIG. 14

For FIG. 14G Two-way analysis of variance (ANOVA) of the correlation coefficient between the ground-truth calcium dynamics and recorded calcium dynamics in the simulations for mouse, followed by post-hoc Tukey's HSD test.
Factor 1, molecules: SomaGCaMP6f2 vs GCaMP6f.
Factor 2, demixing: with CMNF vs without CMNF.
n = 300 neurons from 10 simulations for SomaGCaMP6f2; n = 300 neurons from 10 simulations for GCaMP6f.
Two-way ANOVA table:

| Source | SS | df | MS | F | Prob > F |
|---|---|---|---|---|---|
| Molecules | 6.2098 | 1 | 6.2098 | 40.5516 | 2.72E−10 |
| Demixing | 0.0981 | 1 | 0.0981 | 0.6408 | 0.4236 |
| Interaction | 0.1592 | 1 | 0.1592 | 1.0394 | 0.3082 |
| Error | 183.1481 | 1196 | 0.1531 | — | — |
| Total | 189.6152 | 1199 | — | — | — |

Post-hoc Tukey's HSD test on Factor 1, molecules (SomaGCaMP6f2 vs GCaMP6f): P = 2.9646e−10

For FIG. 14H Two-way analysis of variance (ANOVA) of the correlation coefficient between the ground-truth calcium dynamics and recorded calcium dynamics in the simulations for zebrafish, followed by post-hoc Tukey's HSD test.
Factor 1, molecules: SomaGCaMP6f1 vs GCaMP6f.
Factor 2, demixing: with CMNF vs without CMNF.
n = 1200 neurons from 10 simulations for SomaGCaMP6f1; n = 1200 neurons from 10 simulations for GCaMP6f.
Two-way ANOVA table:

| Source | SS | df | MS | F | Prob > F |
|---|---|---|---|---|---|
| Molecules | 24.4007 | 1 | 24.4007 | 260.8343 | 3.76E−57 |
| Demixing | 0.2303 | 1 | 0.2303 | 2.4618 | 0.1167 |
| Interaction | 0.2002 | 1 | 0.2002 | 2.1397 | 0.1436 |
| Error | 441.1751 | 4716 | 0.0935 | — | — |
| Total | 466.0063 | 4719 | — | — | — |

Post-hoc Tukey's HSD test on Factor 1, molecules (SomaGCaMP6f1 vs GCaMP6f): P=1.0597e−10

SomaGCaMP6f1 reduces crosstalk between neurons in larval zebrafish brain Studies were performed to experimentally assess the utility of SomaGCaMP variants in vivo. First, GCaMP6f, SomaGCaMP6f1, SomaGCaMP6f2, GCaMP7f and SomaGCaMP7f were transiently and sparsely expressed in the brains of larval zebrafish by DNA injection into embryos at 1-2 cell stages (FIG. 4A). Transient expression of SomaGCaMP6f2 was observed in the injected fish, but it was decided to focus the studies on comparing GCaMP6f vs. SomaGCaMP6f1 in zebrafish because the SomaGCaMP6f1 fish transgenic line was ready for experimentation. First, neurons expressing either GCaMP6f and mCherry or SomaGCaMP6f1 and mCherry were imaged and compared using confocal microscopy under identical imaging conditions (FIG. 4B, top panels). Neurons expressing either GCaMP7f and mCherry or SomaGCaMP7f and mCherry were also imaged and compared using confocal microscopy under identical imaging conditions (FIG. 4B, bottom panels). The green-to-red ratio along the neurites of zebrafish neurons was measured. It was found that along the first 140 μm of the neural process coming out of the soma, the neurite green-to-red ratio in SomaGCaMP6f1 expressing cells decreased to 3.5±1.4% of that in GCaMP6f expressing cells (FIG. 4C, top). It was found that along the first 140 μm of the neural process coming out of the soma, the neurite green-to-red ratio in SomaGCaMP7f expressing cells decreased to 4.0±1.0% of that in GCaMP7f expressing cells (FIG. 4C, bottom).

The tectum of the fish brain was imaged with a two-photon microscope while presenting a visual stimulus consisting of a moving grating (FIG. 4D), using similar powers for both GCaMP and SomaGCaMP6f1, and it was found that cells expressing GCaMP6f or SomaGCaMP6f1 exhibited fluorescence transients during the presentation of the visual stimulus (FIG. 4E), and that the df/f$_0$ and SNR measured at the cell bodies were similar in GCaMP6f and SomaGCaMP6f1-expressing fish (FIG. 4F-G). For the following experiments, stably expressing fish lines (see Methods) expressing pan-neuronally were generated. These fish were imaged with a one-photon lightsheet microscope (FIG. 4H), and it was found that in GCaMP6f-expressing fish, GCaMP6f-filled neurites abutted GCaMP6f-filled cell bodies, resulting in the kind of situation that could result in crosstalk, but in SomGCaMP6f1 fish this phenomenon was less pronounced when both were evaluated for the same region of interest and analyzed with the same software package (Pnevmatatakis et al 2016) (FIG. 4I). In these fish lines, as in mice (see above), it was found that the baseline fluorescence of SomaGCaMP1-expressing cells was approximately 5-fold lower compared to GCaMP6f (n=25 cells from 5 GCaMP6f fish, n=25 cells from 5 SomaGCaMP6f1 fish, see Table 6 for values and statistics). For this reason, the laser power was increased approximately 4.5-5 fold in SomaGCaMP6f1 experiments to cause similar brightness as GCaMP6f, for the remaining experiments in FIG. 4. To induce neural spiking, the fish were immersed in 1 mM 4-AP and their brains imaged over 10-minute-long periods. The df/f$_0$ for GCaMP6f and SomaGCaMP6f1 cells in the forebrain were similar, and the SNR for SomaGCaMP6f1 was twice that of GCaMP6f (FIG. 4J-K). The number of GCaMP spikes in GCaMP6f, SomaGCaMP6f1 fish, H2B-GCaMP6f fish, were counted and approximately 3 times more GCaMP spikes were detected in SomaGCaMP6f1 fish or in H2B-GCaMP6f fish (which express GCaMP6f in nuclei) compared to non-targeted GCaMP6f fish (FIG. 15 and Table 14 for full statistics), suggesting a general utility in somatic targeting for increasing spike count accuracy. However, it was found that GCaMP6f and SomaGCaMP6f1 fish had GCaMP-spikes with similar $\tau_{on}$ and $\tau_{off}$ values, while H2B-GCaMP6f fish had GCaMP spikes that were approximately twice as slow compared to GCaMP6f fish (FIG. 4L-M and Table 6 for full statistics), highlighting the improved kinetics associated with somatic vs. nuclear targeting.

TABLE 14

Statistical analysis for FIG. 15-calcium spike count for GCaMP6f and SomaGCaMP6f1 fish.

For FIG. 15A
n = 101 neurons from 5 fishes for GCaMP6f; n = 146 neurons from 4 fishes for SomaGCaMP6f1; n = 513 neurons from 6 fishes for H2B-GCaMP6f.
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 101 | 12273.5 | 38430.5 | 121.520 | −12.973 |
| SomaGCaMP6f1 | 146 | 47495.5 | 55553.0 | 325.312 | −3.443 |
| H2B-GCaMP6f | 513 | 229411 | 195197 | 447.195 | 12.298 |

1-Way Test, ChiSquare Approximation

| ChiSquare | DF | Prob > ChiSq |
|---|---|---|
| 204.6652 | 2 | <.0001* |

Nonparametric Comparisons for All Pairs Using Steel-Dwass Method

| q* | Alpha |
|---|---|
| 2.34370 | 0.05 |

| Molecule | Molecule | Score Mean Difference | Std Err Dif | Z | p-Value |
|---|---|---|---|---|---|
| H2B-GCaMP6f | GCaMP6f | 273.6236 | 18.62811 | 14.68875 | <.0001* |

TABLE 14-continued

Statistical analysis for FIG. 15-calcium spike count for GCaMP6f and SomaGCaMP6f1 fish.

| | | | | | |
|---|---|---|---|---|---|
| H2B-GCaMP6f | SomaGCaMP6f1 | 97.8716 | 17.35290 | 5.64007 | <.0001* |
| SomaGCaMP6f1 | GCaMP6f | 51.3564 | 9.21019 | 5.57604 | <.0001* |

For FIG. 15B-Pearson correlation coefficient (raw data and after CMNF) between cell pairs in the larval zebrafish forebrain expressing either GCaMP6f, SomaGCaMP6f1 or H2B-GCaMP6f (n = 426 neurons from 5 fishes for GCaMP6f; n = 340 neurons from 4 fishes for SomaGCaMP6f1; n = 676 neurons from 6 fishes for H2B-GCaMP6f).
Kruskal-Wallis analysis of variance followed by post-hoc Tukey's HSD test among all groups.
Kruskal-Wallis analysis of variance

| 'Source' | 'SS' | 'df' | 'MS' | 'Chi-sq' | 'Prob > Chi-sq' |
|---|---|---|---|---|---|
| 'Groups' | 2.61E+12 | 5 | 5.23E+11 | 5523.719 | 0 |
| 'Error' | 3.3E+13 | 75342 | 4.38E+08 | [] | [] |
| 'Total' | 3.56E+13 | 75347 | [] | [] | [] |

Tukey's HSD test
P = 0.8055 between 'SomaGCaMP6f1, raw data' and 'GCaMP6f, CNMF'.
P < 1e–4 for all other pairs of groups.

For FIG. 15C-Pearson correlation coefficient (raw data) between cell pairs in the larval zebrafish forebrain expressing either GCaMP6f, SomaGCaMP6f1 or H2B-GCaMP6f, in three distance ranges from the soma: 0-50 μm, 50-100 μm and 100-300 μm (n = 426 neurons from 5 fishes for GCaMP6f; n = 340 neurons from 4 fishes for SomaGCaMP6f1; n = 676 neurons from 6 fishes for H2B-GCaMP6f).
Kruskal-Wallis analysis of variance followed by post-hoc Tukey's HSD test among different distance ranges in either GCaMP6f, SomaGCaMP6f1 or H2B-GCaMP6f.
Kruskal-Wallis analysis of variance for GCaMP6f

| 'Source' | 'SS' | 'df' | 'MS' | 'Chi-sq' | 'Prob > Chi-sq' |
|---|---|---|---|---|---|
| 'Groups' | 8.35E+10 | 2 | 4.18E+10 | 1598.023 | 0 |
| 'Error' | 1.23E+12 | 25041 | 48937482 | [] | [] |
| 'Total' | 1.31E+12 | 25043 | [] | [] | [] |

Tukey's HSD test for GCaMP6f

| Distance 1 | Distance 2 | P-value |
|---|---|---|
| 0-50 μm | 50-100 μm | 9.56E–10 |
| 0-50 μm | 100-300 μm | 9.56E–10 |
| 50-100 μm | 100-300 μm | 9.56E–10 |

Kruskal-Wallis analysis of variance for SomaGCaMP6f1

| 'Source' | 'SS' | 'df' | 'MS' | 'Chi-sq' | 'Prob > Chi-sq' |
|---|---|---|---|---|---|
| 'Groups' | 9.81E+09 | 2 | 4.91E+09 | 757.3684 | 3.46E-165 |
| 'Error' | 1.52E+11 | 12465 | 12170211 | [] | [] |
| 'Total' | 1.62E+11 | 12467 | [] | [] | [] |

Tukey's HSD test for SomaGCaMP6f1

| Distance 1 | Distance 2 | P-value |
|---|---|---|
| 0-50 μm | 50-100 μm | 9.56E–10 |
| 0-50 μm | 100-300 μm | 9.56E–10 |
| 50-100 μm | 100-300 μm | 9.56E–10 |

Kruskal-Wallis analysis of variance for H2B-GCaMP6f

| 'Source' | 'SS' | 'df' | 'MS' | 'Chi-sq' | 'Prob > Chi-sq' |
|---|---|---|---|---|---|
| 'Groups' | 3.88E+09 | 2 | 1.94E+09 | 294.2756 | 1.26E–64 |
| 'Error' | 1.62E+11 | 12573 | 12874294 | [] | [] |
| 'Total' | 1.66E+11 | 12575 | [] | [] | [] |

TABLE 14-continued

Statistical analysis for FIG. 15-calcium spike count for GCaMP6f and SomaGCaMP6f1 fish.

Tukey's HSD test for H2B-GCaMP6f

| Distance 1 | Distance 2 | P-value |
|---|---|---|
| 0-50 μm | 50-100 μm | 9.56E−10 |
| 0-50 μm | 100-300 μm | 9.56E−10 |
| 50-100 μm | 100-300 μm | 3.35E−07 |

For FIG. 15D-Pearson correlation coefficient (after CNMF) between cell pairs in the larval zebrafish forebrain expressing either GCaMP6f, SomaGCaMP6f1 or H2B-GCaMP6f, in three distance ranges from the soma: 0-50 μm, 50-100 μm and 100-300 μm (n = 426 neurons from 5 fishes for GCaMP6f; n = 340 neurons from 4 fishes for SomaGCaMP6f1; n = 676 neurons from 6 fishes for H2B-GCaMP6f).
Kruskal-Wallis analysis of variance followed by post-hoc Tukey's HSD test among different distance ranges in either GCaMP6f, SomaGCaMP6f1 or H2B-GCaMP6f.

Kruskal-Wallis analysis of variance for GCaMP6f

| 'Source' | 'SS' | 'df' | 'MS' | 'Chi-sq' | 'Prob > Chi-sq' |
|---|---|---|---|---|---|
| 'Groups' | 4.64E+10 | 2 | 2.32E+10 | 880.5684 | 6.12E−192 |
| 'Error' | 1.28E+12 | 25149 | 50878916 | [] | [] |
| 'Total' | 1.33E+12 | 25151 | [] | [] | [] |

Tukey's HSD test for GCaMP6f

| Distance 1 | Distance 2 | P-value |
|---|---|---|
| 0-50 μm | 50-100 μm | 9.56E−10 |
| 0-50 μm | 100-300 μm | 9.56E−10 |
| 50-100 μm | 100-300 μm | 9.56E−10 |

Kruskal-Wallis analysis of variance for SomaGCaMP6f1

| 'Source' | 'SS' | 'df' | 'MS' | 'Chi-sq' | 'Prob > Chi-sq' |
|---|---|---|---|---|---|
| 'Groups' | 4.58E+09 | 2 | 2.29E+09 | 347.2199 | 4.00E−76 |
| 'Error' | 1.61E+11 | 12573 | 12818790 | [] | [] |
| 'Total' | 1.66E+11 | 12575 | [] | [] | [] |

Tukey's HSD test for SomaGCaMP6f1

| Distance 1 | Distance 2 | P-value |
|---|---|---|
| 0-50 μm | 50-100 μm | 9.56E−10 |
| 0-50 μm | 100-300 μm | 9.56E−10 |
| 50-100 μm | 100-300 μm | 0.2846 |

Kruskal-Wallis analysis of variance for H2B-GCaMP6f

| 'Source' | 'SS' | 'df' | 'MS' | 'Chi-sq' | 'Prob > Chi-sq' |
|---|---|---|---|---|---|
| 'Groups' | 1.86E+09 | 2 | 9.3E+08 | 141.0621 | 2.34E−31 |
| 'Error' | 1.64E+11 | 12573 | 13034913 | [] | [] |
| 'Total' | 1.66E+11 | 12575 | [] | [] | [] |

Tukey's HSD test for H2B-GCaMP6f

| Distance 1 | Distance 2 | P-value |
|---|---|---|
| 0-50 μm | 50-100 μm | 9.56E−10 |
| 0-50 μm | 100-300 μm | 9.56E−10 |
| 50-100 μm | 100-300 μm | 0.0091 |

TABLE 6

Statistical analysis for fish and mouse in vivo experiments (which include FIGS. 4, 5, 6).

Baseline brightness in zebrafish neurons in vivo, expressing GCaMP6f or SomaGCaMP6f1

| Baseline brightness (A.U.) | GCaMP6f | SomaGCaMP6f1 |
|---|---|---|
| Average | 4434 | 938 |
| Standard error of mean | 696 | 100 |

Wilcoxon rank sum test of baseline brightness between GCaMP6f (n = 25 neurons from 5 fishes) and SomaGCaMP6f1 (n = 25 neurons from 5 fishes):

| | |
|---|---|
| P-value | 1.3079e−08 |
| Z-statistic | 5.6850 |
| Rank sum test statistic | 931 |

For FIG. 4C-Normalized brightness ratio between GCaMP6f (or SomaGCaMP6f1) and mCherry at neurites in zebrafish neurons
Wilcoxon rank sum test of the normalized brightness ratio between GCaMP6f (or SomaGCaMP6f1) and mCherry at neurites in zebrafish neurons (for GCaMP6f, n = 8 neurons from 4 fishes; for SomaGCaMP6f1, n = 7 neurons from 6 fishes):

| | |
|---|---|
| P-value | 9.5194e−22 |
| Z-statistic | 9.5820 |
| Rank sum test statistic | 19011 |

For FIG. 4F-df/$f_0$ of somata of neurons in the visual area of zebrafish expressing GCaMP6f or SomaGCaMP6f1 in response to the moving grating
Wilcoxon rank sum test of df/$f_0$ between GCaMP6f (n = 6 neurons from 3 fishes) and SomaGCaMP6f1 (n = 5 neurons from 3 fishes):

| | |
|---|---|
| P-value | 0.6623 |
| Rank sum test statistic | 33 |

For FIG. 4G-SNR of somata of neurons in the visual area of zebrafish expressing GCaMP6f or SomaGCaMP6f1 in response to the moving grating
Wilcoxon rank sum test of SNR between GCaMP6f (n = 6 neurons from 3 fishes) and SomaGCaMP6f1 (n = 5 neurons from 3 fishes):

| | |
|---|---|
| P-value | 0.0823 |
| Rank sum test statistic | 26 |

For FIG. 4J-df/$f_0$ of somata of zebrafish neurons expressing GCaMP6f or SomaGCaMP6f1 and stimulated with 4AP
Wilcoxon rank sum test of df/$f_0$ between GCaMP6f (n = 5 neurons from 2 fishes) and SomaGCaMP6f1 (n = 5 neurons from 2 fishes):

| | |
|---|---|
| P-value | 0.0952 |
| Rank sum test statistic | 36 |

For FIG. 4K-SNR of somata of zebrafish neurons expressing GCaMP6f or SomaGCaMP6f1 and stimulated with 4AP
Wilcoxon rank sum test of SNR between GCaMP6f (n = 5 neurons from 2 fishes) and SomaGCaMP6f1 (n = 5 neurons from 2 fishes):

| | |
|---|---|
| P-value | 0.0317 |
| Rank sum test statistic | 17 |

For FIG. 4L-Ton of somata of zebrafish neurons expressing GCaMP6f or SomaGCaMP6f1 or H2B-GCaMP6f and stimulated with 4AP
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 101 | 22581.0 | 38430.5 | 223.574 | −7.747 |
| SomaGCaMP6f1 | 146 | 29620.0 | 55553.0 | 202.877 | −10.922 |
| H2B-GCaMP6f | 513 | 236979 | 195197 | 461.947 | 14.802 |

TABLE 6-continued

Statistical analysis for fish and mouse in vivo experiments (which include FIGS. 4, 5, 6).

1-Way Test, ChiSquare Approximation

| ChiSquare | DF | Prob > ChiSq |
|---|---|---|
| 219.6277 | 2 | <.0001* |

Nonparametric Comparisons for All Pairs Using Steel-Dwass Method

| q* | Alpha |
|---|---|
| 2.34370 | 0.05 |

| Molecule | Molecule | Score Mean Difference | Std Err Dif | Z | p-Value |
|---|---|---|---|---|---|
| H2B-GCaMP6f | SomaGCaMP6f1 | 223.397 | 17.80458 | 12.5472 | <.0001* |
| H2B-GCaMP6f | GCaMP6f | 194.244 | 19.24531 | 10.0931 | <.0001* |
| SomaGCaMP6f1 | GCaMP6f | −9.079 | 8.64376 | −1.0503 | 0.5451 |

For FIG. 4M-$T_{off}$ of somata of zebrafish neurons expressing GCaMP6f or SomaGCaMP6f1 or H2B-GCaMP6f and stimulated with 4AP
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 101 | 24000.0 | 38430.5 | 237.624 | −7.041 |
| SomaGCaMP6f1 | 146 | 26905.0 | 55553.0 | 184.281 | −12.044 |
| H2B-GCaMP6f | 513 | 238275 | 195197 | 464.474 | 15.233 |

1-Way Test, ChiSquare Approximation

| ChiSquare | DF | Prob > ChiSq |
|---|---|---|
| 235.5982 | 2 | <.0001* |

Nonparametric Comparisons for All Pairs Using Steel-Dwass Method

| q* | Alpha |
|---|---|
| 2.34370 | 0.05 |

| Molecule | Molecule | Score Mean Difference | Std Err Dif | Z | p-Value |
|---|---|---|---|---|---|
| H2B-GCaMP6f | SomaGCaMP6f1 | 245.926 | 17.82138 | 13.7995 | <.0001* |
| H2B-GCaMP6f | GCaMP6f | 179.260 | 19.26898 | 9.3030 | <.0001* |
| SomaGCaMP6f1 | GCaMP6f | −11.667 | 8.99113 | −1.2976 | 0.3965 |

For FIG. 4O-correlations between cell pairs as a function of distance, between zebrafish neurons expressing GCaMP6f or SomaGCaMP6f1 and stimulated with 4AP
Two-dimensional Kolmogorov-Smirnov test between GCaMP6f (n = 426 cells from 5 fishes) and SomaGCaMP6f1 (n = 340 cells from 4 fishes).
For raw data:

| P-value | 0 |
|---|---|
| K-S test statistic | 0.2848 |

For data after CNMF:

| P-value | 1.8946e−46 |
|---|---|
| K-S test statistic | 0.080301 |

TABLE 6-continued

Statistical analysis for fish and mouse in vivo experiments (which include FIGS. 4, 5, 6).

Two-dimensional Kolmogorov-Smirnov test between GCaMP6f (n = 426 cells from 5 fishes) and H2B-GCaMP6f (n = 676 cells from 6 fishes).
For raw data:

| | |
|---|---|
| P-value | 0 |
| K-S test statistic | 0.413281 |

For data after CNMF:

| | |
|---|---|
| P-value | 0 |
| K-S test statistic | 0.287532 |

For FIG. 5I Kruskal-Wallis analysis of variance followed by post-hoc test via Dunn's test for GCaMP-spike rates for neurons expressing either SomaGCaMP6f2, or GCaMP6f, or GCaMP7f, or SomaGCaMP7f (n = 594 neurons from 4 mice expressing SomaGCaMP6f2, n = 930 neurons from 6 GCaMP6f mice, n = 1098 neurons from 5 mice expressing SomaGCaMP7f, n = 634 neurons from 4 GCaMP7f mice).

Kruskal-Wallis test

| | |
|---|---|
| P value | <0.0001 |
| Kruskal-Wallis statistic | 2191 |

| Dunn's multiple comparisons test | Mean rank diff. | Adjusted P Value |
|---|---|---|
| GCaMP6f vs. SomaGCaMP6f | −224.4 | <0.0001 |
| GCaMP6f vs. GCaMP7f | −1609 | <0.0001 |
| GCaMP6f vs. SomaGCaMP7f | −1633 | <0.0001 |
| SomaGCaMP6f vs. GCaMP7f | −1384 | <0.0001 |
| SomaGCaMP6f vs. SomaGCaMP7f | −1409 | <0.0001 |
| GCaMP7f vs. SomaGCaMP7f | −24.26 | >0.9999 |

For FIG. 5J Two-dimensional Kolmogorov-Smirnov test between GCaMP6f and SomaGCaMP6f2 (n = 44890 cell-pairs from 4 SomaGCaMP6f2 mice; n = 67795 cell-pairs from 6 GCaMP6f mice).
For raw data:

| | |
|---|---|
| P-value | 0 |
| K-S test statistic | 0.535433 |

For data after CNMF:

| | |
|---|---|
| P-value | 1.2550e−13 |
| K-S test statistic | 0.099351 |

For FIG. 5K Two-dimensional Kolmogorov-Smirnov test between GCaMP7f and SomaGCaMP7f (n = 10420 cell-pairs from 5 SomaGCaMP7f mice; n = 12582 cell-pairs from 4 GCaMP7f mice).
For raw data:

| | |
|---|---|
| P-value | 0 |
| K-S test statistic | 0.3583 |

For data after CNMF:

| | |
|---|---|
| P-value | 5.7349e−21 |
| K-S test statistic | 0.0710 |

For FIG. 5L Kruskal-Wallis analysis of variance followed by post-hoc test via Dunn's test for the Pearson correlation coefficients from all cell-pairs fromSomaGCaMP6f2, or GCaMP6f or SomaGCaMP7f or GCaMP7f mice (n = 44890 cell-pairs from 4 SomaGCaMP6f2 mice; n = 67795 cell-pairs from 6 GCaMP6f mice, n = 10420 cell-pairs from 5 SomaGCaMP7f mice; n = 12582 cell-pairs from 4 GCaMP7f mice).
Raw data:

Kruskal-Wallis test

| | |
|---|---|
| P value | <0.0001 |
| Kruskal-Wallis statistic | 16453 |

| Dunn's multiple comparisons test | Mean rank diff. | Adjusted P Value |
|---|---|---|
| GCaMP6f vs. SomaGCaMP6f2 | 18034 | <0.0001 |
| GCaMP6f vs. GCaMP7f | 11462 | <0.0001 |
| GCaMP6f vs. SomaGCaMP7f | 20706 | <0.0001 |

TABLE 6-continued

Statistical analysis for fish and mouse in vivo experiments (which include FIGS. 4, 5, 6).

| | | |
|---|---|---|
| SomaGCaMP6f2 vs. GCaMP7f | −6573 | <0.0001 |
| SomaGCaMP6f2 vs. SomaGCaMP7f | 2672 | <0.0001 |
| GCaMP7f vs. SomaGCaMP7f | 9245 | <0.0001 |

After CNMF:

Kruskal-Wallis test

| | |
|---|---|
| P value | <0.0001 |
| Kruskal-Wallis statistic | 314.0 |

| Dunn's multiple comparisons test | Mean rank diff. | Adjusted P Value |
|---|---|---|
| GCaMP6f vs. SomaGCaMP6f2 | 1056 | 0.0126 |
| GCaMP6f vs. GCaMP7f | 1302 | <0.0001 |
| GCaMP6f vs. SomaGCaMP7f | 3052 | <0.0001 |
| SomaGCaMP6f2 vs. GCaMP7f | 245.9 | >0.9999 |
| SomaGCaMP6f2 vs. SomaGCaMP7f | 1996 | <0.0001 |
| GCaMP7f vs. SomaGCaMP7f | 1750 | <0.0001 |

For FIG. 6E Wilcoxon rank sum test of the SNR for neurons expressing either SomaGCaMP6f2 or GCaMP6f (n = 222 neurons from 4 mice expressing SomaGCaMP6f2, n = 107 neurons from 2 GCaMP6f mice).

| | |
|---|---|
| P-value | 5.9432e−10 |
| Rank sum test statistic | 12650 |
| Z-statistic | −6.1919 |

For FIG. 6F Wilcoxon rank sum test of the GCaMP-spike rates for neurons expressing either SomaGCaMP6f2 or GCaMP6f (n = 222 neurons from 4 mice expressing SomaGCaMP6f2, n = 107 neurons from 2 GCaMP6f mice).

| | |
|---|---|
| P-value | 7.1827e−17 |
| Rank sum test statistic | 10911 |
| Z-statistic | −8.3440 |

For FIG. 6G Wilcoxon rank sum test of the fluorescence rise time (Ton) from all SomaGCaMP6f2 orGCaMP6f expressing cells (n = 222 cell from 4 SomaGCaMP6f2 expressing mice; n = 107 cell-pairs from 2 GCaMP6f expressing mice).

| | |
|---|---|
| P-value | 3.9157e−12 |
| Rank sum test statistic | 23180 |
| Z-statistic | 6.9402 |

For FIG. 6H Wilcoxon rank sum test of the fluorescence rise time (Toff) from all SomaGCaMP6f2 or GCaMP6f expressing cells (n = 222 cell from 4 SomaGCaMP6f2 expressing mice; n = 107 cell-pairs from 2 GCaMP6f expressing mice).

| | |
|---|---|
| P-value | 9.6810e−15 |
| Rank sum test statistic | 2.3869e+04 |
| Z-statistic | 7.7434 |

Density of GCaMP variants expressing cells in zebrafish, mouse striatum, and mouse medial prefrontal cortex
Wilcoxon rank sum test of the density of the GCaMP variants expressing cells in zebrafish (n = 5 fishes for GCaMP6; n = 4 fishes for SomaGCaMP6f1).

| | |
|---|---|
| P-value | 0.9048 |
| Rank sum test statistic | 24 |

Wilcoxon rank sum test of the density of the GCaMP variants expressing cells in mouse striatum (n = 7 mice for GCaMP6f; n = 4 mice for SomaGCaMP6f2).

| | |
|---|---|
| P-value | 0.3152 |
| Rank sum test statistic | 36 |

Wilcoxon rank sum test of the density of the GCaMP variants expressing cells in mouse medial prefrontal cortex (n = 5 mice for GCaMP6f; n = 4 mice for SomaGCaMP6f2).

| | |
|---|---|
| P-value | 0.9048 |
| Rank sum test statistic | 26 |

TABLE 6-continued

Statistical analysis for fish and mouse in vivo experiments (which include FIGS. 4, 5, 6).

Wilcoxon rank sum test of the density of the GCaMP variants expressing cells in zebrafish
(n = 9 fishes) and mouse striatum (n = 11 mice).

| | |
|---|---|
| P-value | 0.0049 |
| Rank sum test statistic | 132 |
| zval | 2.8110 |

Wilcoxon rank sum test of the density of the GCaMP variants expressing cells in zebrafish
(n = 9 fishes) and mouse medial prefrontal cortex (n = 9 mice).

| | |
|---|---|
| P-value | 8.2271e−05 |
| Rank sum test statistic | 125 |

Wilcoxon rank sum test of the density of the GCaMP variants expressing cells in mouse
striatum (n = 11 mice) and mouse medial prefrontal cortex (n = 9 mice).

| | |
|---|---|
| P-value | 0.0039 |
| Rank sum test statistic | 154 |
| zval | 2.8870 |

Pearson correlation coefficients between all the possible neuron pairs in the field of view (FIG. 4N) were calculated and plotted against the distance between these neural pairs (FIG. 4O, top panels), to see whether crosstalk was more pronounced for nearby neurons in the GCaMP6f case than in the SomaGCaMP6f1 case. It was found that in GCaMP6f, SomaGCaMP6f1 and H2B-GCaMP6f expressing brains, the shorter the distance between neuron pairs, the higher the correlation between their GCaMP-spikes (FIG. 15C). However, the mean correlation coefficient in the GCaMP6f case was approximately twice that of the SomaGCaMP6f1 case and approximately three times higher than that of the H2B-GCaMP6f case (FIG. 4O top panels, FIG. 15B; Tables 6 and 14 for full statistics). This suggested that the contamination of cell body signals by neuropil signals could manifest as an artifactual increase in correlation between neural activity patterns, which could lead in turn to artifactual conclusions about neural connectivity, oscillatory dynamics, synchrony, and neural codes.

Post hoc cleanup with CNMF (FIG. 4O, bottom panels; Table 6 for full statistics) was applied, and it was found that CNMF decreased the mean correlation coefficient between nearby neurons for all three GCaMP6f variants (FIG. 15B), but the mean correlation coefficient was still twice and thrice higher in the GCaMP6f case compared to the SomaGCaMP6f1 and H2B-GCaMP6f cases respectively. Thus, even with CNMF usage, soma-targeting still offered reduced neuron-neuron correlations in the dense larval zebrafish brain.

It was noted that the mean correlation mediated by pre-CNMF SomaGCaMP6f1 (FIG. 15) was similar to that mediated by post-CNMF GCaMP6f. Of course, somatic targeting of GCaMP6f and application of CNMF post-experiment are not equivalent; recall that CNMF does not improve the accuracy of reconstruction of ground truth GCaMP spiking at least in simulation (FIG. 14), raising the question of whether at least part of the improvement seen with CNMF utilization (FIG. 15B, Table 14) may represent an erroneous decrease in real correlations between neurons.

SomaGCaMP6f2 Reduces Crosstalk, Increases SNR and Enables Detecting More GCaMP Spikes in Brains of Behaving Mice For in vivo mouse experiments, the two SomaGCaMP6f variants were expressed in the dorsal striatum of mice. The striatum contains densely packed medium spiny neurons, whose cell bodies are accessible to fluorescence imaging. The dorsal striatum was chosen because recently it has been suggested that medium spiny neurons form populations of clustered cells with highly correlated neural activity (Barbera et al., 2016), although the relative strength of this correlation remains controversial—in part due to questions about neuropil contamination (Klaus et al., 2017). SomaGCaMP6f1 and SomaGCaMP6f2 were expressed in the dorsal striatum of the living mouse brain, and both were imaged using a conventional wide-field imaging system, as described before (Mohammed et al., 2016a). Consistent with the zebrafish and mice cortical slices experiments, it was found that the brightness of SomaGCaMP6f1 in vivo was approximately 5 times lower compared than that of GCaMP6f (FIG. 16 and Table 15 for full statistics). SomaGCaMP6f2, in contrast, had a similar brightness compared to GCaMP6f (FIG. 16 and Table 15 for full statistics), therefore studies focused on SomaGCaMP6f2 in the live mouse brain. Imaged calcium activity patterns within the dorsal striatum were compared between GCaMP6f-vs. SomaGCaMP6f2-expressing mice, or GCaMP7f-vs. SomaGCaMP7f-expressing mice, voluntarily running on a spherical treadmill (FIG. 5A-D). In SomaGCaMP6f2-expressing mice, a substantial reduction in neuropil fluorescence was noted as compared to GCaMP6f (FIG. 5A-B). In SomaGCaMP7f-expressing mice, a substantial reduction in neuropil fluorescence was noted as compared to GCaMP7f (FIG. 5C-D). SomaGCaMP6f2 decay times were faster than GCaMP6f decay times (FIG. 16). SomaGCaMP6f2 reported approximately 20% more calcium events than GCaMP6f, while SomaGCaMP7 reported a similar number of calcium events compared to GCaMP7f (FIG. 5I).

TABLE 15

Statistical analysis for FIG. 16

For FIG. 16A
Baseline fluorescence in vivo in the dorsal striatum for GCaMP6f, SomaGCaMP6f1 and SomaGCaMP6f2. Kruskal-Wallis analysis of variance followed by post-hoc test via Steel's test with GCaMP6f as control group (n = 75 neurons from 5 mice for GCaMP6f; n = 50 neurons from 2 mice for SomaGCaMP6f1; n = 80 neurons from 4 mice for SomaGCaMP6f2).
Wilcoxon/Kruskal-Wallis Tests (Rank Sums)

| Molecule | Count | Score Sum | Expected Score | Score Mean | (Mean-Mean0)/Std0 |
|---|---|---|---|---|---|
| GCaMP6f | 75 | 9471.00 | 7725.00 | 126.280 | 4.267 |
| SomaGCaMP6f1 | 50 | 1384.00 | 5150.00 | 27.680 | −10.324 |
| SomaGCaMP6f2 | 80 | 10260.0 | 8240.00 | 128.250 | 4.874 |

1-Way Test, ChiSquare Approximation

| ChiSquare | DF | Prob>ChiSq |
|---|---|---|
| 106.6466 | 2 | <.0001 |

Nonparametric Comparisons with Control Using Steel Method
Control Group = GCaMP6f

| q* | Alpha |
|---|---|
| 2.21692 | 0.05 |

| Molecule | Control | Score Mean Difference | Std Err Dif | Z | p-Value |
|---|---|---|---|---|---|
| SomaGCaMP6f2 | GCaMP6f | 1.8471 | 7.214857 | 0.25601 | 0.9544 |
| SomaGCaMP6f1 | GCaMP6f | −60.5833 | 6.614378 | −9.15934 | <.0001 |

For FIG. 16B Wilcoxon rank sum tests comparing the rising times and the decay times between GCaMP6f and SomaGCaMP6f2 calcium signals for all detected calcium events (n = 930 neurons from 6 GCaMP6f mice; n = 594 neurons from 4 SomaGCaMP6f2 mice).
Rising times:

| | |
|---|---|
| P-value | 0.890 |
| Rank sum test statistic | 710259 |
| z-statistic | 0.137 |

Decay times:

| | |
|---|---|
| P-value | 5.657e−11 |
| Rank sum test statistic | 763719 |
| z-statistic | 6.553 |

For FIG. 16C-Pearson correlation coefficient (raw data) between cell pairs in the mouse striatum expressing either GCaMP6f (white) or SomaGCaMP6f2 (gray), in three distance ranges from the soma: 0-50 μm, 50-100 μm and 100-300 μm (n = 860 neurons from 6 mice for GCaMP6f; n = 149 neurons from 4 mice for SomaGCaMP6f2).
Kruskal-Wallis analysis of variance followed by post-hoc Tukey's HSD test among different distance ranges in either GCaMP6f or SomaGCaMP6f2.
Kruskal-Wallis analysis of variance for GCaMP6f

| 'Source' | 'SS' | 'df' | 'MS' | 'Chi-sq' | 'Prob>Chi-sq' |
|---|---|---|---|---|---|
| 'Groups' | 2016203 | 2 | 1008102 | 39.11275 | 3.21E−09 |
| 'Error' | 38449369 | 783 | 49105.2 | [] | [] |
| 'Total' | 40465573 | 785 | [] | [] | [] |

Tukey's HSD test for GCaMP6f

| Distance 1 | Distance 2 | P-value |
|---|---|---|
| 0-50 μm | 50-100 μm | 0.00083 |
| 0-50 μm | 100-300 μm | 2.38E−09 |
| 50-100 μm | 100-300 μm | 0.0256 |

TABLE 15-continued

Statistical analysis for FIG. 16

Kruskal-Wallis analysis of variance for SomaGCaMP6f2

| 'Source' | 'SS' | 'df' | 'MS' | 'Chi-sq' | 'Prob> Chi-sq' |
|---|---|---|---|---|---|
| 'Groups' | 539114.5 | 2 | 269557.2 | 41.78049 | 8.46E−10 |
| 'Error' | 4519058 | 390 | 11587.33 | [] | [] |
| 'Total' | 5058172 | 392 | [] | [] | [] |

Tukey's HSD test for SomaGCaMP6f2

| Distance 1 | Distance 2 | P-value |
|---|---|---|
| 0-50 μm | 50-100 μm | 0.00038 |
| 0-50 μm | 100-300 μm | 1.35E−09 |
| 50-100 μm | 100-300 μm | 0.0254 |

For FIG. 16D-Pearson correlation coefficient (after CMNF) between cell pairs in the mouse striatum expressing either GCaMP6f (white) or SomaGCaMP6f2 (gray), in three distance ranges from the soma: 0-50 μm, 50-100 μm and 100-300 μm (n = 860 neurons from 6 mice for GCaMP6f; n = 149 neurons from 4 mice for SomaGCaMP6f2). Kruskal-Wallis analysis of variance followed by post-hoc Tukey's HSD test among different distance ranges in either GCaMP6f or SomaGCaMP6f2.

Kruskal-Wallis analysis of variance for GCaMP6f

| 'Source' | 'SS' | 'df' | 'MS' | 'Chi-sq' | 'Prob> Chi-sq' |
|---|---|---|---|---|---|
| 'Groups' | 4845262 | 2 | 2422631 | 93.99424 | 3.89E−21 |
| 'Error' | 35620310 | 783 | 45492.09 | [] | [] |
| 'Total' | 40465573 | 785 | [] | [] | [] |

Tukey's HSD test for GCaMP6f

| Distance 1 | Distance 2 | P-value |
|---|---|---|
| 0-50 μm | 50-100 μm | 3.31E−07 |
| 0-50 μm | 100-300 μm | 9.56E−10 |
| 50-100 μm | 100-300 μm | 3.68E−05 |

Kruskal-Wallis analysis of variance for SomaGCaMP6f2

| 'Source' | 'SS' | 'df' | 'MS' | 'Chi-sq' | 'Prob> Chi-sq' |
|---|---|---|---|---|---|
| 'Groups' | 561676.2 | 2 | 280838.1 | 43.52898 | 3.53E−10 |
| 'Error' | 4496496 | 390 | 11529.48 | [] | [] |
| 'Total' | 5058172 | 392 | [] | [] | [] |

Tukey's HSD test for SomaGCaMP6f2

| Distance 1 | Distance 2 | P-value |
|---|---|---|
| 0-50 μm | 50-100 μm | 1.98E−05 |
| 0-50 μm | 100-300 μm | 1.34E−09 |
| 50-100 μm | 100-300 μm | 0.132 |

The Pearson correlation coefficients between all the possible neuron pairs within the imaging field were calculated. Correlograms from mice expressing either GCaMP6f or SomaGCaMP6f2 are shown in FIG. 5F (top panels). Within the striatum of GCaMP6f-expressing mice, high correlations were identified for nearby cells that fell off with increasing distance. In contrast, SomaGCaMP6f2-expressing mice had far lower correlations across the board (FIG. 5J, top panels: Table 6); results even identified instances of strong negative correlations that were not present in GCaMP6f mice. Similar to the analysis performed on the zebrafish GCaMP spike data, the mean correlation coefficient for three distance ranges (0-50 μm, 50-150 μm, 100-300 μm) was analyzed it is was found that there was a dependency of the correlation on the distance, for both GCaMP6f and SomaGCaMP6f2 expressing neurons (FIG. 16). However, across the population, the mean correlation coefficient was approximately 2× lower when expressing SomaGCaMP6f2 then with GCaMP6f (FIG. 5L, top). Following CNMF application, the pairwise correlations in GCaMP6f brains decreased, almost to the level mediated by SomaGCaMP6f2 (FIG. 5L, bottom panels; FIG. 5J, bottom). However, as noted above herein, the simulations that were performed raises the question of whether the CNMF-mediated correlation decrease might not actually be increasing accuracy of the data, and might delete real biological correlations as well as spurious ones (FIG. 14). Correlograms from mice expressing either GCaMP7f or SomaGCaMP7f2 are shown in FIG. 5K (top panels). Within the striatum of GCaMP6f-expressing mice, high correlations were identified for nearby cells that fell off with increasing distance. In contrast, SomaGCaMP7f-expressing mice had far lower correlations across the board (FIG. 5K, top panels:

Table 6). Across the population, the mean correlation coefficient was approximately 2× lower when expressing SomaGCaMP7f than with GCaMP7f (FIG. 5L, top). Following CNMF application, the pairwise correlations in GCaMP6f brains decreased, almost to the level mediated by SomaGCaMP6f2 (FIG. 5L, bottom panels; FIG. 5K, bottom).

The difference between results obtained in zebrafish and the results obtained in mice might result from the density of the GCaMP-expressing neurons. In fish, the neural density was $0.00028+/-0.00006$ cells per $\mu m^3$ for GCaMP6f expressing neurons and $0.00030+/-0.00008$ cells per $\mu m^3$ for SomaGCaMP6f1 expressing neurons. In mice, the neural density was severalfold lower, at $0.00010+/-0.00002$ cells per $\mu m^3$ for GCaMP6f and $0.00016+/-0.00004$ cells per $\mu m^3$ for SomaGCaMP6f2 (see Table 6 for full statistics). One possibility is that as a neural network becomes denser in labeling, the ability of CNMF to reduce correlations (whether real or spurious) is decreased.

In addition to wide-field imaging, the advent of gradient-refractive index (GRIN) lenses and miniature head-mounted microscopes has allowed for cellular-resolution calcium imaging in deep regions of the rodent brain during naturalistic behaviors (Flusberg et al., 2008). This has rapidly seen widespread use in many subfields of behavioral neuroscience such as memory (Cai et al., 2016; Grewe et al., 2017), spatial navigation (Sun et al., 2015: Ziv et al., 2013) motivation and learning (Jennings et al., 2015: Pinto and Dan, 2015), and addiction (Xia et al., 2017). While the ability to visualize neuronal activity during free behavior has opened new frontiers in the calcium imaging field, miniaturized microscopes suffer from the poor axial resolution which can result in exacerbation of neuropil contamination and crosstalk. Therefore, extracting activity from microendoscopic videos with confidence is an ongoing challenge in the field, and the optimal methods for addressing this issue is a highly debated topic (Resendez et al., 2016; Siciliano and Tye, 2019). To test whether soma-targeting can help with increasing the precision and confidence in imaging calcium spikes, GCaMP6f or SomaGCaMP6f2 were expressed in the medial prefrontal cortex of mice (FIG. 6A-D) and optical access was gained via a chronically implanted GRIN lens. Both GCaMP6f and SomaGCaMP6f2 were imaged using the same imaging parameters (FIG. 17) and it was found that the SNR of the GCaMP spikes was 1.4 times higher in SomaGCaMP6f2 expressing mice compared to mice expressing GCaMP6f (FIG. 6E). In addition, SomaGCaMP6f2 reported approximately 92% more calcium events than GCaMP6f (FIG. 6F). SomaGCaMP6f2 rise and decay times were faster than GCaMP6f decay times reminiscent of that observed in zebrafish larvae (FIG. 6G-H).

The pairwise correlograms were plotted for the microendoscopic data (FIG. 18), which was taken over a much smaller field of view (~9× smaller in area) than the zebrafish and mouse striatum data. In addition, the neural density was quite low for both GCaMP expressing mice ($0.000072+/-0.000006$ cells per $\mu m^3$) and in SomaGCaMP6f2 expressing mice ($0.000076+/-0.000008$ cells per $\mu m^3$) (see Table 6 for full statistics). It was found that overall pairwise correlations were quite high, and similar between GCaMP6f and SomaGCaMP6f2 (FIG. 18A-C), and similar across different distances taken from the small field of view (FIG. 18D); CNMF decreased all these correlations by a huge factor (FIG. 18C) compared to the other CNMF analyses described above, possibly because of the low density of expression in this experiment and the high magnitude of background signal present in microendoscope data.

TABLE 16

Statistical analysis for FIG. 18

For FIGS. 18A and 18B-Correlograms denoting the relationship of distance to the strength of correlated fluorescence between cell pairs from mice expressing GCaMP6f (n = 107 neurons from 2 mice) or SomaGCaMP6f2 (n = 222 neurons from 4 mice).

Two-dimensional Kolmogorov-Smirnov test of the strength of correlated fluorescence between cell pairs from mice expressing GCaMP6f before CNMF (n = 107 cells from 2 mice) and SomaGCaMP6f2 before CNMF (n = 222 cells from 4 mice).

| P-value | 3.3999e−53 |
| --- | --- |

Two-dimensional Kolmogorov-Smirnov test of the strength of correlated fluorescence between cell pairs from mice expressing GCaMP6f after CNMF (n = 107 cells from 2 mice) and SomaGCaMP6f2 after CNMF (n = 222 cells from 4 mice).

| P-value | 4.6904e−4 |
| --- | --- |

Two-dimensional Kolmogorov-Smirnov test of the strength of correlated fluorescence between cell pairs from mice expressing GCaMP6f before CNMF (n = 107 cells from 2 mice) and GCaMP6f after CNMF (n = 107 cells from 2 mice).

| P-value | 1.1314e−221 |
| --- | --- |

Two-dimensional Kolmogorov-Smirnov test of the strength of correlated fluorescence between cell pairs from mice expressing SomaGCaMP6f2 before CNMF (n = 222 cells from 4 mice) and SomaGCaMP6f2 after CNMF (n = 222 cells from 4 mice).

| P-value | 0 |
| --- | --- |

TABLE 16-continued

For FIG. 18C-Pearson correlation coefficient (raw data and after CMNF) between cell pairs in the mouse medial prefrontal cortex expressing either GCaMP6f or SomaGCaMP6f2 (n = 107 neurons from 2 mice for GCaMP6f; n = 222 neurons from 4 mice for SomaGCaMP6f2). Kruskal-Wallis analysis of variance followed by post-hoc Tukey's HSD test among all groups.

Kruskal-Wallis analysis of variance

| 'Source' | 'SS' | 'df' | 'MS' | 'Chi-sq' | 'Prob> Chi-sq' |
|---|---|---|---|---|---|
| 'Groups' | 73996226 | 3 | 24665409 | 795.5217 | 4.05E−172 |
| 'Error' | 24135627 | 1052 | 22942.61 | [] | [] |
| 'Total' | 98131854 | 1055 | [] | [] | [] |

Tukey's HSD
P = 0.9945 between 'SomaGCaMP6f1, CNMF' and 'GCaMP6f, CNMF'.
P < 1e−4 for all other pairs of groups.

For FIG. 18D-Pearson correlation coefficient (raw data) between cell pairs in the mouse medial prefrontal cortex expressing either GCaMP6f or SomaGCaMP6f2, in three distance ranges from the soma: 0-25 μm, 25-50 μm and 50-100 μm (n = 107 neurons from 2 mice for GCaMP6f; n = 222 neurons from 4 mice for SomaGCaMP6f2). Kruskal-Wallis analysis of variance followed by post-hoc Tukey's HSD test among different distance ranges in either GCaMP6f or SomaGCaMP6f2.

Kruskal-Wallis analysis of variance for GCaMP6f

| 'Source' | 'SS' | 'df' | 'MS' | 'Chi-sq' | 'Prob> Chi-sq' |
|---|---|---|---|---|---|
| 'Groups' | 1145344 | 2 | 572672 | 49.20711 | 2.06E−11 |
| 'Error' | 11121099 | 525 | 21183.05 | [] | [] |
| 'Total' | 12266443 | 527 | [] | [] | [] |

Tukey's HSD test for GCaMP6f

| Distance 1 | Distance 2 | P-value |
|---|---|---|
| 0-25 μm | 25-50 μm | 4.61E−07 |
| 0-25 μm | 50-100 μm | 1.04E−09 |
| 25-50 μm | 50-100 μm | 0.3373 |

Kruskal-Wallis analysis of variance for SomaGCaMP6f2

| 'Source' | 'SS' | 'df' | 'MS' | 'Chi-sq' | 'Prob> Chi-sq' |
|---|---|---|---|---|---|
| 'Groups' | 200260.4 | 2 | 100130.2 | 34.34999 | 3.48E−08 |
| 'Error' | 1333030 | 26 | 5107.393 | [] | [] |
| 'Total' | 1533290 | 263 | [] | [] | [] |

Tukey's HSD test for SomaGCaMP6f2

| Distance 1 | Distance 2 | P-value |
|---|---|---|
| 0-25 μm | 25-50 μm | 7.54E−06 |
| 0-25 μm | 50-100 μm | 2.26E−07 |
| 25-50 μm | 50-100 μm | 0.7796 |

For FIG. 18E-Pearson correlation coefficient (after CMNF) between cell pairs in the mouse medial prefrontal cortex expressing either GCaMP6f or SomaGCaMP6f2, in three distance ranges from the soma: 0-25 μm, 25-50 μm and 50-100 μm (n = 107 neurons from 2 mice for GCaMP6f; n = 222 neurons from 4 mice for SomaGCaMP6f2). Kruskal-Wallis analysis of variance followed by post-hoc Tukey's HSD test among different distance ranges in either GCaMP6f or SomaGCaMP6f2.

Kruskal-Wallis analysis of variance for GCaMP6f

| 'Source' | 'SS' | 'df' | 'MS' | 'Chi-sq' | 'Prob> Chi-sq' |
|---|---|---|---|---|---|
| 'Groups' | 171210 | 2 | 85605.02 | 7.355657 | 2.53E−02 |
| 'Error' | 12095224 | 525 | 23038.52 | [] | [] |
| 'Total' | 12266435 | 527 | [] | [] | [] |

TABLE 16-continued

| Tukey's HSD test for GCaMP6f | | |
|---|---|---|
| Distance 1 | Distance 2 | P-value |
| 0-25 µm | 25-50 µm | 0.7442 |
| 0-25 µm | 50-100 µm | 0.1400 |
| 25-50 µm | 50-100 µm | 0.0234 |

| Kruskal-Wallis analysis of variance for SomaGCaMP6f2 | | | | | |
|---|---|---|---|---|---|
| 'Source' | 'SS' | 'df' | 'MS' | 'Chi-sq' | 'Prob>Chi-sq' |
| 'Groups' | 12004.84 | 2 | 6002.42 | 2.059149 | 3.57E−01 |
| 'Error' | 1521285 | 26 | 5828.679 | [] | [] |
| 'Total' | 1533290 | 263 | [] | [] | [] |

| Tukey's HSD test for SomaGCaMP6f2 | | |
|---|---|---|
| Distance 1 | Distance 2 | P-value |
| 0-25 µm | 25-50 µm | 0.9994 |
| 0-25 µm | 50-100 µm | 0.4377 |
| 25-50 µm | 50-100 µm | 0.4187 |

DISCUSSION

Results of the studies described herein demonstrate it is possible to target genetically encoded calcium sensors to cell bodies in multiple species in vivo. The variants that were focused on for further characterization and validation, SomaGCaMP6f1, SomaGCaMP6f2 and SomaGCaMP7f, demonstrated satisfactory brightness (with that of SomaGCaMP6f2 comparable to that of conventional GCaMP6f; and SomaGCaMP7f comparable to that of conventional GCaMP7f; SomaGCaMP6f1 was dimmer than conventional GCaMP6f), sensitivity, and kinetics in mouse and zebrafish brains. Decreased crosstalk was observed, as reflected by lower numbers of artifactual (e.g., not detectable via patch pipette) spikes, and reduced artifactual correlation between neurons that are nearby, in both zebrafish and mouse brain. Although nuclear-localized GCaMP can also achieve isolation between neurons, the slow speed has given pause to potential users; soma-targeting results in several-fold higher SNR and several-fold faster kinetics, compared to nuclear GCaMP. In addition, computational cleanup of non-targeted GCaMP via application of CNMF decreased correlations between nearby neurons, but in a fashion that may not actually improve the accurate reconstruction of spikes (at least when probed by simulations), a problem avoided by somatic GCaMP that improves the direct reporting of neural activity from individual neurons.

Having fewer artifactual spikes will increase the accuracy of the assessment of neural codes in the living brain. Many studies examine neural activity using one-photon single cell resolution calcium imaging, including in the hippocampus of mice (Berdyyeva et al., 2014, 2016; Mohammed et al., 2016b; Ziv et al., 2013), in the visual cortex of mice (Kim et al., 2016), in the dorsal horn of mice (Sekiguchi et al., 2016), in the enthorinal cortex of mice (Kitamura et al., 2015), in the hypothalamus of mice (Jennings et al., 2015), in the prefrontal cortex of mice (Pinto and Dan, 2015) and in the entire brain of zebrafish (Ahrens et al., 2013). SomaGCaMP6f or SomaGCaMP7f variants can be useful in such experiments, since eliminating erroneous spikes could help experimenters better determine which neurons are contributing to a behavior, and how.

Reducing artifactual correlation may also help with studies of functional connectivity, where correlated neural activity has been used to infer functional connectivity in the retina (Greschner et al., 2011), cortex (Alonso and Martinez, 1998), and many other systems. Single-photon calcium imaging has a speed advantage compared to two-photon imaging, and wide-field calcium imaging is simple, feasible and robust. The advantage of SomaGCaMP6f or SomaGCaMP7f in performing single-photon imaging in these model systems is that they may enable separation of bona-fide physiological correlation from non-physiological correlation, something that post hoc computational methods cannot guarantee. Examples of such experiments include: in *Drosophila melanogaster*, different compounds that decrease synchrony between cells were tested by calcium imaging in neurons (Streit et al., 2016); in experiments performed in the spinal cord of mice, pairwise correlations between neurons were observed and analyzed (Sekiguchi et al., 2016); in the striatum of mice, medium spiny neurons exhibited correlated neural activity (Barbera et al., 2016), and ensembles of spiny projection neurons that were more correlated were analyzed for spatial patterns (Klaus et al., 2017); in zebrafish, GCaMP3 expressing neurons were clustered using pairwise correlations as the metric (Romano et al., 2017). SomaGCaMP6f could help such studies by improving confidence in the correlations observed.

REFERENCES

Ahrens, M. B., et al. Orger, M. B., Robson, D. N., Li, J. M., and Keller, P. J. (2013). Whole-brain functional imaging at cellular resolution using light-sheet microscopy. Nat. Methods 10, 413-420.

Alivisatos, A. P., Andrews, A. M., Boyden, E. S., Chun, M., Church, G. M., Deisseroth, K., Donoghue, J. P., Fraser, S. E., Lippincott-Schwartz, J., Looger, L. L., et al. (2013). Nanotools for Neuroscience and Brain Activity Mapping. ACS Nano 7, 1850-1866.

Alonso, J.-M., and Martinez, L. M. (1998). Functional connectivity between simple cells and complex cells in cat striate cortex. Nat. Neurosci. 1, 395-403.

Andilla, F. D., and Hamprecht, F. A. (2014). Sparse Space-Time Deconvolution for Calcium Image Analysis. 64-72.

Baker, C. A., Elyada, Y. M., Parra, A., and Bolton, M. M. (2016). Cellular resolution circuit mapping with temporal-focused excitation of soma-targeted channelrhodopsin. Elife 5.

Barbera, G., Liang, B., Zhang, L., Gerfen, C. R., Culurciello, E., Chen, R., Li, Y., and Lin, D.-T. (2016). Spatially Compact Neural Clusters in the Dorsal Striatum Encode Locomotion Relevant Information. Neuron 92, 202-213.

Bengtson, C. P., Freitag, H. E., Weislogel, J.-M., and Bading, H. (2010). Nuclear Calcium Sensors Reveal that Repetition of Trains of Synaptic Stimuli Boosts Nuclear Calcium Signaling in CAI Pyramidal Neurons. Biophys. J. 99, 4066-4077.

Berdyyeva, T., Otte, S., Aluisio, L., Ziv, Y., Burns, L. D., Dugovic, C., Yun, S., Ghosh, K. K., Schnitzer, M. J., Lovenberg, T., et al. (2014). Zolpidem Reduces Hippocampal Neuronal Activity in Freely Behaving Mice: A Large Scale Calcium Imaging Study with Miniaturized Fluorescence Microscope. PLOS One 9, e1 12068.

Berdyyeva, T. K., Frady, E. P., Nassi, J. J., Aluisio, L., Cherkas, Y., Otte, S., Wyatt, R. M., Dugovic, C., Ghosh, K. K., Schnitzer, M. J., et al. (2016). Direct Imaging of Hippocampal Epileptiform Calcium Motifs Following Kainic Acid Administration in Freely Behaving Mice. Front. Neurosci. 10, 53.

Bowden, S. E. H., Fletcher, S., Loane, D. J., and Marrion, N. V. (2001). Somatic Colocalization of Rat SKI and D class (Cav 1.2) L-type Calcium Channels in Rat CAI Hippocampal Pyramidal Neurons. J. Neurosci. 21.

Cai, D. J., Aharoni, D., Shuman, T., Shobe, J., Biane, J., Song, W., Wei, B., Veshkini, M., La-Vu, M., Lou, J., et al. (2016). A shared neural ensemble links distinct contextual memories encoded close in time. Nature 534, 115-118.

Chen, T.-W., Wardill, T. J., Sun, Y., Pulver, S. R., Renninger, S. L., Baohan, A., Schreiter, E. R., Kerr, R. A., Orger, M. B., Jayaraman, V., et al. (2013). Ultrasensitive fluorescent proteins for imaging neuronal activity. Nature 499, 295-300.

Dana, H., Sun, Y., Mohar, B., Hulse, B. K., Kerlin, A. M., Hasseman, J. P., Tsegaye, G., Tsang, A., Wong, A., Patel, R., et al. (2019). High-performance calcium sensors for imaging activity in neuronal populations and microcompartments. Nat. Methods 16, 649-657.

Deneux, T., Kaszas, A., Szalay, G., Katona, G., Lakner, T., Grinvald, A., Rózsa, B., and Vanzetta, I. (2016). Accurate spike estimation from noisy calcium signals for ultrafast three-dimensional imaging of large neuronal populations in vivo. Nat. Commun. 7, 12190.

Dunn, T. W., Mu, Y., Narayan, S., Randlett, O., Naumann, E. A., Yang, C.-T., Schier, A. F., Freeman, J., Engert, F., and Ahrens, M. B. (2016). Brain-wide mapping of neural activity controlling zebrafish exploratory locomotion. Elife 5, e12741.

Fletcher, S., Bowden, S. E. H., and Marrion, N. V. (2003). False interaction of syntaxin 1A with a Ca2+-activated K+channel revealed by co-immunoprecipitation and pull-down assays; implications for identification of protein-protein interactions. Neuropharmacology 44, 817-827.

Flusberg, B. A., Nimmerjahn, A., Cocker, E. D., Mukamel, E. A., Barretto, R. P. J., Ko, T. H., Burns, L. D., Jung, J. C., and Schnitzer, M. J. (2008). High-speed, miniaturized fluorescence microscopy in freely moving mice. Nat. Methods 5, 935-938.

Forli, A., Vecchia, D., Binini, N., Succol, F., Bovetti, S., Moretti, C., Nespoli, F., Mahn, M., Baker, C. A., Bolton, M. M., et al. (2018). Two-Photon Bidirectional Control and Imaging of Neuronal Excitability with High Spatial Resolution In Vivo. Cell Rep. 22, 3087-3098.

Freeman, J., Vladimirov, N., Kawashima, T., Mu, Y., Sofroniew, N.J., Bennett, D. V, Rosen, J., Yang, C.-T., Looger, L. L., and Ahrens, M. B. (2014). Mapping brain activity at scale with cluster computing. Nat. Methods 11, 941-950.

Garrido, J. J., Fernandes, F., Giraud, P., Mouret, I., Pasqualini, E., Fache, M. P., Jullien, F., and Dargent, B. (2001). Identification of an axonal determinant in the C-terminus of the sodium channel Na (v) 1.2. EMBO J. 20, 5950-5961.

Garrido, J. J., Giraud, P., Carlier, E., Fernandes, F., Moussif, A., Fache, M.-P., Debanne, D., and Dargent, B. (2003). A targeting motif involved in sodium channel clustering at the axonal initial segment. Science 300, 2091-2094.

Greenberg, K. P., Pham, A., and Werblin, F. S. (2011). Differential targeting of optical neuromodulators to ganglion cell soma and dendrites allows dynamic control of center-surround antagonism. Neuron 69, 713-720.

Greschner, M., Shlens, J., Bakolitsa, C., Field, G. D., Gauthier, J. L., Jepson, L. H., Sher, A., Litke, A. M., and Chichilnisky, E. J. (2011). Correlated firing among major ganglion cell types in primate retina. J. Physiol. 589, 75-86.

Grewe, B. F., Gründemann, J., Kitch, L. J., Lecoq, J. A., Parker, J. G., Marshall, J. D., Larkin, M. C., Jercog, P. E., Grenier, F., Li, J. Z., et al. (2017). Neural ensemble dynamics underlying a long-term associative memory. Nature 543, 670-675.

Grienberger, C., and Konnerth, A. (2012). Imaging Calcium in Neurons. Neuron 73, 862-885.

Grubb, M. S., and Burrone, J. (2010). Channelrhodopsin-2 localised to the axon initial segment. PLOS One 5, e13761.

Harris, K. D., Quiroga, R. Q., Freeman, J., and Smith, S. L. (2016). Improving data quality in neuronal population recordings. Nat. Neurosci. 19, 1165-1174.

Helmchen, F., and Denk, W. (2005). Deep tissue two-photon microscopy. Nat. Methods 2, 932-940.

Hofherr, A., Fakler, B., and Klöcker, N. (2005). Selective Golgi export of Kir2.1 controls the stoichiometry of functional Kir2.x channel heteromers. J. Cell Sci. 118, 1935-1943.

Jennings, J. H., Ung, R. L., Resendez, S. L., Stamatakis, A. M., Taylor, J. G., Huang, J., Veleta, K., Kantak, P. A., Aita, M., Shilling-Scrivo, K., et al. (2015). Visualizing Hypothalamic Network Dynamics for Appetitive and Consummatory Behaviors. Cell 160, 516-527.

Jensen, C. S., Watanabe, S., Stas, J. I., Klaphaak, J., Yamane, A., Schmitt, N., Olesen, S.-P., Trimmer, J. S., Rasmussen, H. B., and Misonou, H. (2017). Trafficking of Kv2.1 Channels to the Axon Initial Segment by a Novel Nonconventional Secretory Pathway. J. Neurosci. 37, 11523-11536.

Jiang, M., and Chen, G. (2006). High Ca2+-phosphate transfection efficiency in low-density neuronal cultures. Nat. Protoc. 1, 695-700.

Keller, P. J., Ahrens, M. B., and Freeman, J. (2015). Light-sheet imaging for systems neuroscience. Nat. Methods 12, 27-29.

Kim, C. K., Miri, A., Leung, L. C., Berndt, A., Mourrain, P., Tank, D. W., and Burdine, R. D. (2014). Prolonged, brain-wide expression of nuclear-localized GCaMP3 for functional circuit mapping. Front. Neural Circuits 8, 138.

Kim, T. H., Zhang, Y., Lecoq, J., Jung, J. C., Li, J., Zeng, H., Niell, C. M., and Schnitzer, M. J. (2016). Long-Term Optical Access to an Estimated One Million Neurons in the Live Mouse Cortex. Cell Rep. 17, 3385-3394.

Kitamura, T., Sun, C., Martin, J., Kitch, L. J., Schnitzer, M. J., and Tonegawa, S. (2015). Entorhinal Cortical Ocean Cells Encode Specific Contexts and Drive Context-Specific Fear Memory. Neuron 87, 1317-1331.

Klapoetke, N.C., Murata, Y., Kim, S. S., Pulver, S. R., Birdsey-Benson, A., Cho, Y. K., Morimoto, T. K., Chuong, A. S., Carpenter, E. J., Tian, Z., et al. (2014). Independent optical excitation of distinct neural populations. Nat. Methods 11, 338-346.

Klaus, A., Martins, G. J., Paixao, V. B., Zhou, P., Paninski, L., and Costa, R. M. (2017). The Spatiotemporal Organization of the Striatum Encodes Action Space. Neuron 96, 949.

Kosugi, S., Hasebe, M., Matsumura, N., Takashima, H., Miyamoto-Sato, E., Tomita, M., and Yanagawa, H. (2009). Six classes of nuclear localization signals specific to different binding grooves of importin alpha. J. Biol. Chem. 284, 478-485.

Kumar, J., Schuck, P., and Mayer, M. L. (2011). Structure and assembly mechanism for heteromeric kainate receptors. Neuron 71, 319-331.

Lim, S. T., Antonucci, D. E., Scannevin, R. H., and Trimmer, J. S. (2000). A Novel Targeting Signal for Proximal Clustering of the Kv2.1 K+Channel in Hippocampal Neurons. Neuron 25, 385-397.

Ma, D., Zerangue, N., Lin, Y. F., Collins, A., Yu, M., Jan, Y. N., and Jan, L. Y. (2001). Role of ER export signals in controlling surface potassium channel numbers. Science 291, 316-319.

Mohammed, A. I., Gritton, H. J., Tseng, H., Bucklin, M. E., Yao, Z., and Han, X. (2016a). An integrative approach for analyzing hundreds of neurons in task performing mice using wide-field calcium imaging. Sci. Rep. 6, 20986.

Mohammed, A. I., Gritton, H. J., Tseng, H., Bucklin, M. E., Yao, Z., and Han, X. (2016b). An integrative approach for analyzing hundreds of neurons in task performing mice using wide-field calcium imaging. Sci. Rep. 6, 20986.

Moll, J. R., Ruvinov, S. B., Pastan, I., and Vinson, C. (2001). Designed heterodimerizing leucine zippers with a ranger of pIs and stabilities up to 10-15 M. Protein Sci. 10, 649-655.

Moruno Manchon, J. F., Uzor, N.-E., Dabaghian, Y., Furr-Stimming, E. E., Finkbeiner, S., and Tsvetkov, A. S. (2015). Cytoplasmic sphingosine-1-phosphate pathway modulates neuronal autophagy. Sci. Rep. 5, 15213.

Mukamel, E. A., Nimmerjahn, A., and Schnitzer, M. J. (2009). Automated analysis of cellular signals from large-scale calcium imaging data. Neuron 63, 747-760.

Nguyen, J. P., Shipley, F. B., Linder, A. N., Plummer, G. S., Liu, M., Setru, S. U., Shaevitz, J. W., and Leifer, A. M. (2016). Whole-brain calcium imaging with cellular resolution in freely behaving Caenorhabditis elegans. Proc. Natl. Acad. Sci. 113, E1074-E1081.

Oakley, M. G., and Kim, P. S. (1998). A buried polar interaction can direct the relative orientation of helices in a coiled coil. Biochemistry 37, 12603-12610.

P?delacq, J.-D., Cabantous, S., Tran, T., Terwilliger, T. C., and Waldo, G. S. (2006). Engineering and characterization of a superfolder green fluorescent protein. Nat. Biotechnol. 24, 79-88.

Patel, T. P., Man, K., Firestein, B. L., and Meaney, D. F. (2015). Automated quantification of neuronal networks and single-cell calcium dynamics using calcium imaging. J. Neurosci. Methods 243, 26-38.

Pégard, N. C., Mardinly, A. R., Oldenburg, I. A., Sridharan, S., Waller, L., and Adesnik, H. (2017). Three-dimensional scanless holographic optogenetics with temporal focusing (3D-SHOT). Nat. Commun. 8, 1228.

Peron, S. P., Freeman, J., Iyer, V., Guo, C., and Svoboda, K. (2015). A Cellular Resolution Map of Barrel Cortex Activity during Tactile Behavior. Neuron 86, 783-799.

Pinto, L., and Dan, Y. (2015). Cell-Type-Specific Activity in Prefrontal Cortex during Goal-Directed Behavior. Neuron 87, 437-450.

Pnevmatikakis, E. A., Gao, Y., Soudry, D., Pfau, D., Lacefield, C., Poskanzer, K., Bruno, R., Yuste, R., and Paninski, L. (2014). A structured matrix factorization framework for large scale calcium imaging data analysis.

Pneumatikakis, E. A., Soudry, D., Gao, Y., Machado, T. A., Merel, J., Pfau, D., Reardon, T., Mu, Y., Lacefield, C., Yang, W., et al. (2016). Simultaneous Denoising, Deconvolution, and Demixing of Calcium Imaging Data. Neuron 89, 285-299.

Raichle, M. E., Garaschuk, O., Holthoff, K., and Konnerth, A. (1998). Behind the scenes of functional brain imaging: a historical and physiological perspective. Proc. Natl. Acad. Sci. U. S. A. 95, 765-772.

Ramírez, O. A., Härtel, S., and Couve, A. (2011). Location matters: the endoplasmic reticulum and protein trafficking in dendrites. Biol. Res. 44, 17-23.

Resendez, S. L., Jennings, J. H., Ung, R. L., Namboodiri, V. M. K., Zhou, Z. C., Otis, J. M., Nomura, H., McHenry, J. A., Kosyk, O., and Stuber, G. D. (2016). Visualization of cortical, subcortical and deep brain neural circuit dynamics during naturalistic mammalian behavior with head-mounted microscopes and chronically implanted lenses. Nat. Protoc. 11, 566-597.

Romano, S. A., Perez-Schuster, V., Jouary, A., Boulanger-Weill, J., Candeo, A., Pietri, T., and Sumbre, G. (2017). An integrated calcium imaging processing toolbox for the analysis of neuronal population dynamics. PLOS Comput. Biol. 13, e1005526.

Ruffinatti, F. A., Gilardino, A., Lovisolo, D., and Ferraro, M. (2013). Spatial Wavelet Analysis of Calcium Oscillations in Developing Neurons. PLOS One 8, e75986.

Schäfer, M. K. E., Nam, Y.-C., Moumen, A., Keglowich, L., Bouché, E., Küffner, M., Bock, H. H., Rathjen, F. G., Raoul, C., and Frotscher, M. (2010). L1 syndrome mutations impair neuronal L1 function at different levels by divergent mechanisms. Neurobiol. Dis. 40, 222-237.

Schrödel, T., Prevedel, R., Aumayr, K., Zimmer, M., and Vaziri, A. (2013). Brain-wide 3D imaging of neuronal activity in Caenorhabditis elegans with sculpted light. Nat. Methods 10, 1013-1020.

Sekiguchi, K. J., Shekhtmeyster, P., Merten, K., Arena, A., Cook, D., Hoffman, E., Ngo, A., and Nimmerjahn, A. (2016). Imaging large-scale cellular activity in spinal cord of freely behaving mice. Nat. Commun. 7, 11450.

Selgrade, D. F., Lohmueller, J. J., Lienert, F., and Silver, P. A. (2013). Protein scaffold-activated protein trans-splicing in mammalian cells. J. Am. Chem. Soc. 135, 7713-7719.

Shemesh, O. A., Tanese, D., Zampini, V., Linghu, C., Piatkevich, K., Ronzitti, E., Papagiakoumou, E., Boyden, E. S., and Emiliani, V. (2017). Temporally precise single-cell-resolution optogenetics. Nat. Neurosci. 20, 1796-1806.

Shen, S. P., Tseng, H., Hansen, K. R., Wu, R., Gritton, H., Si, J., and Han, X. (2018). Automatic Cell Segmentation by Adaptive Thresholding (ACSAT) for large scale calcium imaging datasets. bioRxiv 260075.

Siciliano, C. A., and Tye, K. M. (2019). Leveraging calcium imaging to illuminate circuit dysfunction in addiction. Alcohol 74, 47-63.

Streit, A. K., Fan, Y. N., Masullo, L., and Baines, R. A. (2016). Calcium Imaging of Neuronal Activity in *Drosophila* Can Identify Anticonvulsive Compounds. PLOS One 11, e0148461.

Sun, C., Kitamura, T., Yamamoto, J., Martin, J., Pignatelli, M., Kitch, L. J., Schnitzer, M. J., and Tonegawa, S. (2015). Distinct speed dependence of entorhinal island and ocean cells, including respective grid cells. Proc. Natl. Acad. Sci. 112, 9466-9471.

Tian, C., Wang, K., Ke, W., Guo, H., and Shu, Y. (2014). Molecular identity of axonal sodium channels in human cortical pyramidal cells. Front. Cell. Neurosci. 8, 297.

Valluru, L., Xu, J., Zhu, Y., Yan, S., Contractor, A., and Swanson, G. T. (2005). Ligand binding is a critical requirement for plasma membrane expression of heteromeric kainate receptors. J. Biol. Chem. 280, 6085-6093.

Vladimirov, N., Mu, Y., Kawashima, T., Bennett, D. V, Yang, C.-T., Looger, L. L., Keller, P. J., Freeman, J., and Ahrens, M. B. (2014). Light-sheet functional imaging in fictively behaving zebrafish. Nat. Methods 11, 883-884.

Vander Weele, C. M., Siciliano, C. A., Matthews, G. A., Namburi, P., Izadmehr, E. M., Espinel, I. C., Nieh, E. H., Schut, E. H. S., Padilla-Coreano, N., Burgos-Robles, A., et al. (2018). Dopamine enhances signal-to-noise ratio in cortical-brainstem encoding of aversive stimuli. Nature 563, 397-401.

Wu, C., Ivanova, E., Zhang, Y., and Pan, Z.-H. (2013a). rAAV-mediated subcellular targeting of optogenetic tools in retinal ganglion cells in vivo. PLOS One 8, e66332.

Wu, C., Ivanova, E., Zhang, Y., and Pan, Z.-H. (2013b). rAAV-mediated subcellular targeting of optogenetic tools in retinal ganglion cells in vivo. PLOS One 8, e66332.

Xia, L., Nygard, S. K., Sobczak, G. G., Hourguettes, N.J., and Bruchas, M. R. (2017). Dorsal-CAI Hippocampal Neuronal Ensembles Encode Nicotine-Reward Contextual Associations. Cell Rep. 19, 2143-2156.

Yu, Y., Maureira, C., Liu, X., and McCormick, D. (2010). P/Q and N channels control baseline and spike-triggered calcium levels in neocortical axons and synaptic boutons. J. Neurosci. 30, 11858-11869.

Zhang, X., and Bennett, V. (1998). Restriction of 480/270-KD ankyrin G to axon proximal segments requires multiple ankyrin G-specific domains. J. Cell Biol. 142, 1571-1581.

Zhou, P., Resendez, S. L., Rodriguez-Romaguera, J., Jimenez, J. C., Neufeld, S. Q., Stuber, G. D., Hen, R., Kheirbek, M. A., Sabatini, B. L., Kass, R. E., et al. (2016). Efficient and accurate extraction of in vivo calcium signals from microendoscopic video data.

Ziv, Y., Burns, L. D., Cocker, E. D., Hamel, E. O., Ghosh, K. K., Kitch, L. J., El Gamal, A., and Schnitzer, M. J. (2013). Long-term dynamics of CA1 hippocampal place codes. Nat. Neurosci. 16, 264-266.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein.

What is claimed is:

1. A composition comprising a soma-targeting polypeptide fusion protein, wherein the soma-targeting polypeptide fusion protein comprises an EE-RR polypeptide or functional variant thereof; and an Anktail motif polypeptide or functional variant thereof, wherein the EE-RR polypeptide comprises the amino acid sequence of SEQ ID NO: 2; the functional variant of the EE-RR polypeptide has at least 90% sequence identity to SEQ ID NO: 2; the Anktail motif polypeptide comprises the amino acid sequence of SEQ ID NO: 1; and the functional variant of the Anktail motif polypeptide has at least 90% sequence identity to SEQ ID NO: 1.

2. The composition of claim 1, wherein the soma-targeting polypeptide fusion protein further comprises a cargo polypeptide.

3. The composition of claim 2, wherein the cargo polypeptide comprises a cell-activity sensor polypeptide.

4. The composition of claim 1, wherein the soma-targeting polypeptide fusion protein comprises an EE-RR polypeptide having the amino acid sequence set forth as SEQ ID NO: 2.

5. The composition of claim 1, wherein the soma-targeting polypeptide fusion protein comprises an Anktail motif polypeptide having the amino acid sequence set forth as SEQ ID NO: 1.

6. The composition of claim 1, wherein the composition is a pharmaceutical composition and comprises a pharmaceutically acceptable carrier.

7. A nucleic acid molecule comprising a sequence encoding a soma-targeting polypeptide fusion protein, wherein the soma-targeting polypeptide fusion protein comprises an EE-RR polypeptide or functional variant thereof; and an Anktail motif polypeptide or functional variant thereof, wherein the EE-RR polypeptide comprises the amino acid sequence of SEQ ID NO: 2; the functional variant of the EE-RR polypeptide has at least 90% sequence identity to SEQ ID NO: 2; the Anktail motif polypeptide comprises the amino acid sequence of SEQ ID NO: 1; and the functional variant of the Anktail motif polypeptide has at least 90% sequence identity to SEQ ID NO: 1.

8. The nucleic acid molecule of claim 7, further comprising, a nucleic acid sequence encoding a cargo polypeptide, optionally wherein the cargo polypeptide comprises a cell-activity sensor an indicator polypeptide.

* * * * *

UNITED STATES PATENT AND TRADEMARK OFFICE
CERTIFICATE OF CORRECTION

| | | |
|---|---|---|
| PATENT NO. | : 12,351,615 B2 | Page 1 of 1 |
| APPLICATION NO. | : 17/312445 | |
| DATED | : July 8, 2025 | |
| INVENTOR(S) | : Shemesh et al. | |

It is certified that error appears in the above-identified patent and that said Letters Patent is hereby corrected as shown below:

In the Claims

Column 161 In Claim 8, Line 4, replace "activity sensor an indicator polypeptide" with --activity sensor polypeptide--.

Signed and Sealed this
Twenty-sixth Day of August, 2025

Coke Morgan Stewart
*Acting Director of the United States Patent and Trademark Office*